(12) United States Patent
Shirley et al.

(10) Patent No.: US 7,795,415 B2
(45) Date of Patent: Sep. 14, 2010

(54) CASEIN KINASE STRESS-RELATED POLYPEPTIDES AND METHODS OF USE IN PLANTS

(75) Inventors: Amber Shirley, Durham, NC (US); Oswaldo da Costa e Silva, Neustadt (DE); Ruoying Chen, Duluth, GA (US); Nocha van Thielen, Durham, NC (US); Damian Allen, Urbana, IL (US); Lori V. Mills, Cary, NC (US)

(73) Assignee: BASF Plant Science GmbH (DE)

( * ) Notice: Subject to any disclaimer, the term of this patent is extended or adjusted under 35 U.S.C. 154(b) by 0 days.

(21) Appl. No.: 12/472,651

(22) Filed: May 27, 2009

(65) Prior Publication Data

US 2009/0282580 A1  Nov. 12, 2009

Related U.S. Application Data

(62) Division of application No. 11/667,820, filed as application No. PCT/US2005/041522 on Nov. 17, 2005, now abandoned.

(51) Int. Cl.
*C07H 21/04* (2006.01)

(52) U.S. Cl. .................... 536/23.6; 536/23.1

(58) Field of Classification Search ............ None
See application file for complete search history.

(56) References Cited

OTHER PUBLICATIONS

Kearney et al. (Biochem. Biophys. Res. Commun., 203:231-236, 1994).*
Ngo et al., (The Protein Folding Problem and Tertiary Structure Prediction, K. Merz., and S. Le Grand (eds.) pp. 492-495,1994).*
Guo et al. (PNAS, 101: 9205-9210, 2004).*
Bork et al. (TIG, 12:425-427, 1996).*
Smith et al. (Nature Biotechnology, 15:1222-1223, 1997).*
Doerks et al., (TIG, 14:248-250, 1998).*
Wells, (Biochemistry 29:8509-8517, 1990).*
Hanks et al. (Science, 241: 42-52, 1988).*

* cited by examiner

*Primary Examiner*—Vinod Kumar
(74) *Attorney, Agent, or Firm*—Patricia A. McDaniels

(57) ABSTRACT

A transgenic plant transformed by a casein kinase Stress-Related Polypeptide (CKSRP) coding nucleic acid, wherein expression of the nucleic acid sequence in the plant results in increased tolerance to environmental stress as compared to a wild type variety of the plant. Also provided are agricultural products, including seeds, produced by the transgenic plants. Also provided are isolated CKSRPs, and isolated nucleic acid coding CKSRPs, and vectors and host cells containing the latter.

3 Claims, 14 Drawing Sheets

```
                      301                                                                                                   400
SEQ ID NO:10 (233)    RDELISLSHVFFFELRGSELWDE----------LKAPNNKLKYEKIGMTKQKLNPDDELLNNAIEYQFATYLKYARSEKEDEDEXDYEISLMDDDALRLNDLKDEGH
SEQ ID NO:47 (255)    RDELVGAICHVFFYELRGHELWDE----------LKAPNNKQKYEKIGEKKRSTNVYDEAQG--LEVQEGRYELEIVRSLSEECELEGYRKILLSVLDDLGETAEGQ
SEQ ID NO:48 (262)    RDEMVHAMCHVFFMELRGQELWDE----------LKAPNNKQKYEKIGEKKRLTNVYDEAQG--LEIQEGRYELEIVNTSEETEEEGYRMILLSVLDDLGETAEGQ
SEQ ID NO:2  (193)    RDELIALSLYILEMELRGSELWNC----------LKAGTKQKQKYEKISEKKMSTPIEVECKN--YESEFASYFHYCEREDDKEKAYLKRIFRDLEIREGFQFEYV
SEQ ID NO:4  (265)    RDELESLSYLMEMELRGNELWGS----------KGGQRLTDQKQHEYMHNKIEMNITVBFECDG--YESQFADELHHAESEHYEQEEYCYLRSLFRDLFIQKKEQLEHV
SEQ ID NO:6  (193)    RDELESLSYLMEMELRGSELWDS----------MKQGTKKQKYEKISEKKMSTPIEFECKA---YESFASYFHYCEREDDKEKAYLKRIFRDLEIREGFQFEYV
SEQ ID NO:49 (193)    RDELESLSYVMELNLGSELWGS----------LKAATKRQKYERISEKKMSTPIEVECKG---YESEESTYLNFCESRDDKEASKILQLFRNLEHRQGFSYEEYV
SEQ ID NO:50 (193)    RDELESLSYVMELNLGSELWGS----------LKAATKROKYERISEKKMSTPIEVECKG---YESEFATYLNEQESRDDKEASYTRQLFRNLEHRQGFSYELV
SEQ ID NO:51 (201)    RDELEALHMFMELNRTSELWQG----------LKAAJKKQKYEKISEKKMSTPVEVECKG---YEAEFAMYLNYCERFEEAEMYLROLFRILFRTLNHQYEMYT
SEQ ID NO:52 (229)    RDELISLSYLIMEYQKIGDTERATPIEVECEN--TE-EMATYIRYEREDEFEXREMEYERKIETDLEDRKGYMEFYE
SEQ ID NO:8  (265)    RDELISLSYLIMEMELRGNEITSELWQG----------QGGQRFTDQKQHEYMHNKIEMETTDDENCDG--YERQFADELHHAEREHGYEQEEYSYERSLFRDLEIQKKEQLEHV
SEQ ID NO:53 (193)    RDELLESLSYLMEMELRGSELWDG----------LKAGTKKQKYDKTSEKKMLTPVEVECKS---YEEEISYFHYCESREDEKEEDXESYELKRIFRDLEIREGYQLEYI 401                                                                                                   500
SEQ ID NO:10 (330)    YDEXMDENGGKGWNIKINRRANLHGYGNPNPRVNGNTARNNVN------TNSKTRNTTPVATPKQQ----AQ----------NSYNKDNSKSRISSN
SEQ ID NO:47 (350)    YESMKINDGRGWDLNINKKPNLHGYGHPNLHGYGHPNPNEKSRKHRNK------QLQMQQLQMQQLQQQQ----QQ----------QYAQKTEADMRNSQY
SEQ ID NO:48 (357)    YEEMVKINGGRGWDLSINKKPNLHGYGHPNLHGYGHPNPNEKSKRHRSKNHQYSSPDHHHHYNQQQQQQA---QA----------QAQAQAQAKVQQQQL
SEQ ID NO:2  (288)    FEETILKYQQSQISGG------SSTRLGASAGQTSGALGTGATGSRDLQRPTEMDPSRRRLPGGANGSVANALDSSKHKSPGLDESA-KDSALAVVSEP
SEQ ID NO:4  (363)    YESETVYTQ----------------------------------------------------------LPQNGSLQSVRS-------------ONSAASSHLQN
SEQ ID NO:6  (288)    FEETILKYQQTHFSGG---PLRPAAAAGGSSGAAAAAAAGIGTVPRDAQRAIEPTDVAARTRMVGATRSSGLNPLDASKHKSTSPDEAASKDIALSGLAEP
SEQ ID NO:49 (288)    FEENMLKFGAARNPED----------------------------VDRERERHERE----ERMGQLRGSAYTRALPPGPPTGA-------TANRLRSAAEP
SEQ ID NO:50 (288)    FEENMLKFGASRAADD----------------------------AERERR--DRE----ERLRHSRNPATRGLP----ST----------ASGRLRGTQEV
SEQ ID NO:51 (296)    FEYTMEKOKAAQQAAS---VG---------------------------SSGQGQ-----------QAQTPTGKQTDK-----------------TKSNMKGF---
SEQ ID NO:52 (323)    YEXMIGKQLPTP--VG------------------------------------------------AVQQDPALSSNRE---------AHQHRDKMQQSKNQS
SEQ ID NO:8  (363)    YEXTVYTQ--------------------------------------------------------------PPQNGSAQTVRS------PAAGPQTHLQS
SEQ ID NO:53 (288)    FEENTKQGSESNRLRSSGR---TSGLVGPSAERTERAAARQDVP------DRFSGTVDPFARRTGSGSHYG-----EHTKHRNILDSLLAPKTAVDLDKRRP
```

FIGURE 5C

```
                 501                                                                                                600
SEQ ID NO:10(406) PQSFTKQQHVLKKIEPNSKYIPETHSNLQRPIKSQSQTYDSISHTQNSPFVPYSSSKANPKRSNNEHNLPNHYTNLANKNINYQSQRNYEQENDAYSDDE
SEQ ID NO:47(425) KPKLDPTSYEAYQHQTQKYIQEQQK-RQQQQKLQEQLQEQOLQQQQQQQLRATGQPSQPQAQTQSQQFGARYQPQQPSAALRTPEQHPNDDNSS
SEQ ID NO:48(437) QQAQAQQQANRYQLQPDDSHYDEER----EASKLDPTSYEAYQQTQQKYAQQQQKQMQQKSKQFANTGANGQTNKYPYNAQPTANDEQNAKNAAQDRNS
SEQ ID NO:2 (382) ERMHTSSYATRGGSSSRHAVLSSSRPSGASAEVVDSSRTGSSKLGPTSLRSSAGMQRSSPVTSDPKRISSRHPQPPSANLRIYEAAIKGVESLSVEVDQS
SEQ ID NO:4 (394) RPSNVSYCPPLTKSEFRREVAAN-------------------------------------------------------------------------
SEQ ID NO:6 (386) ERTHASSFVR-GSSSSRHAVVGCARP-AGSTEAGDGTRVLAGKMGPTSLRTSAGMQRSSPVASTDPKRTGRDSYAG--NSGRNPSSSRNSKE------
SEQ ID NO:49(348) VASTPASRIQPAGNTSPRAISRVDRE---------------------------RKVSMRLHRGA-----PANVSSSDLTGRQEVSRIPASQTSVPFDHLGK----
SEQ ID NO:50(341) APPTPLPTSHTANTSPRPVSGMERE---------------------------RKVSMRLHRGA-----PVNISSSDLTGRQDTSRMSTSQIPGRVASSGLQSVVHR----
SEQ ID NO:51(338) ---------------------------------------------------------------------------------
SEQ ID NO:52(364) ADHRAAWDSQQANPHLLRAHTAADRHG----------G------SVQVVSSTNGELNTDDPTAGRSNAPITAPTEVEVMDETKCCCFFKRRKRKTIQRHK-
SEQ ID NO:8 (394) RPSNVSYCPPLTKPEFRREVAAN-------------------------------------------------------------------------
SEQ ID NO:53(376) ----TSSSRN-GSTSRKALISSSRP--SSGDPIDPNRS----NLIPTSSGSSRPS--TMQRLHQSTGLETRSSLTKTARNVHDDPTLRTFERLSISADRR 601          619
SEQ ID NO:10(506) NDTFCSKIYKYCCCCFCCC
SEQ ID NO:47(524) LAASHKGFFQKLGCC----
SEQ ID NO:48(533) NKSS-KGFFSKLGCC----
SEQ ID NO:2 (482) RYK----------------
SEQ ID NO:4 (418) -------------------
SEQ ID NO:6 (474) -------------------
SEQ ID NO:49(417) -------------------
SEQ ID NO:50(416) -------------------
SEQ ID NO:51(338) -------------------
SEQ ID NO:52(448) -------------------
SEQ ID NO:8 (418) -------------------
SEQ ID NO:53(463) K------------------
```

```
SEQ ID NO:73  (403)  --GKRSS-------TRKHMDSAEKGLETLQVS-SERFHHH------
SEQ ID NO:14  (400)  --RKRSS-------TRKQMDSARKGLETHHVS-DERYHHH------
SEQ ID NO:75  (426)  EAGKRSS-------SRRHMDSAEKGLDNLQVSSDDKFHHHH-----
SEQ ID NO:67  (247)  ATSLSRAVARG---SRDLPLHRSLELLSLG-GKRK-----------
SEQ ID NO:77  (441)  YESKKSSTLSRG--ARNTRGDPLRRSFELLSLRKS-----------
SEQ ID NO:12  (423)  YESKTASAFNRNRVAASR-ARDDALRSFELLSIRK-----------
SEQ ID NO:16  (447)  ARAAAAK-REEN------------RSFEFTLNRR------------
SEQ ID NO:65  (438)  TAGNRWGVVMS---RNSGLSDQVELGLFVP----KRWNT-------
SEQ ID NO:20  (494)  TAGNRWGVVMS---RNAGVSDQVVELDFLYPSEGLHRRWESGYRITSSAGTPDQAAFILSIPKRKPLDETQET
SEQ ID NO:55  (493)  TAGNLWIVMS----RNAGESEQVVELDFLYPSEGVHKRWDSGYRITAVAATWDQTALILSVPRRKPTDETQET
SEQ ID NO:61  (564)  TAGNLWIVMS----RNAGESEQVVELDFLYPSEGVHKRWDSGYRITAVAATWDQTALILSVPRRKPTDETQET
SEQ ID NO:10  (486)  INYQSQRN------YEQENDAYSDDENDTFCSKIYKYCCCCCFCCC-
SEQ ID NO:8   (418)  ----------------------------------------------
SEQ ID NO:4   (418)  ----------------------------------------------
SEQ ID NO:71  (410)  --SS----------LMSSEQHMSSAK--------------------
SEQ ID NO:2   (450)  SSRHPQPPS-----ANLRIMAAIKGMESLSVEVDQSRYK-------
SEQ ID NO:6   (452)  TGRDSYAG------NSGRNPSSSRNSKE------------------
SEQ ID NO:18  (433)  SENKK-SS------PSRGNTSVMNYESNLNKGIEGLHF--------
SEQ ID NO:59  (422)  VSSGRNAS------EVKNLDTARGMEGLQLENDERTHY--------
SEQ ID NO:63  (427)  --ARNES-------EVKNLTALKGHEGLQLENDEKAHY--------
SEQ ID NO:57  (441)  ISSGRNTS------NMKNLESTLRGLETLNFN-DERLQY-------
SEQ ID NO:69  (402)  ----------------TNKLETTKGMESLNFDDNKRVG--------

SEQ ID NO:73  (434)  ----------------------------------------------
SEQ ID NO:14  (431)  ----------------------------------------------
SEQ ID NO:75  (461)  ----------------------------------------------
SEQ ID NO:67  (247)  ----------------------------------------------
SEQ ID NO:77  (474)  ----------------------------------------------
SEQ ID NO:12  (456)  ----------------------------------------------
SEQ ID NO:16  (482)  ----------------------------------------------
SEQ ID NO:65  (462)  ----------------------------------------------
SEQ ID NO:20  (527)  LRTSAFPSNHVKEKWAKNLYIASICYGRTAC---------------
SEQ ID NO:55  (563)  LRTSAFPSQHVKEKWSKNLYLASVCYGRTVS---------------
SEQ ID NO:61  (634)  LRTSAFPSQHVKEKWSKNLYLASVCYGRTVS---------------
SEQ ID NO:10  (525)  ----------------------------------------------
SEQ ID NO:8   (418)  ----------------------------------------------
SEQ ID NO:4   (418)  ----------------------------------------------
SEQ ID NO:71  (424)  ----------------------------------------------
SEQ ID NO:2   (485)  ----------------------------------------------
SEQ ID NO:6   (474)  ----------------------------------------------
SEQ ID NO:18  (466)  ----------------------------------------------
SEQ ID NO:59  (455)  ----------------------------------------------
SEQ ID NO:63  (457)  ----------------------------------------------
SEQ ID NO:57  (473)  ----------------------------------------------
SEQ ID NO:69  (425)  ----------------------------------------------
```

| Gene name | EST | Functional Categories | Function | Assay | Relative WUE Data (% difference from controls) | | | | | | Drought Cycling Biomass (% difference from controls) | |
|---|---|---|---|---|---|---|---|---|---|---|---|---|
| | | | | | WUE vs SCO24 | WUE vs BPS C24 | DW vs SCO24 | DW vs BPS C24 | E vs SCO24 | E vs BPS C24 | Drought vs BPS C24 | Watered vs BPS C24 |
| PpPK-4 | 142 | Protein Kinase | protein kinase | E J P Y | 20 11 | 27 8 | 9 30 | 22 6 | -7 17 | -3 -3 | 23 24 | 22 14 |
| | 289 | Protein kinase | casein kinase | G J | 4 4 | 20 1 | 13 32 | 66 7 | 9 31 | 37 8 | | |
| PpCK-2 | 263 | Protein kinase | casein kinase | A T | -8 | 0 | -25 | 5 | -21 | 2 | 25 | 3.5 |
| PpCK-1 | 194 | Protein kinase | casein kinase | A D T | 8 -5 | 17 -17 | 6 12 | 47 -22 | -2 14 | 26 -5 | 78 | 43 |
| Mean for all genes | | | | | 5 | 8 | 11 | 19 | 6 | 9 | 37 | 21 |

SEQUENCE LISTING

```
<160> NUMBER OF SEQ ID NOS: 77

<210> SEQ ID NO 1
<211> LENGTH: 1942
<212> TYPE: DNA
<213> ORGANISM: Physcomitrella patens

<400> SEQUENCE: 1
atcccgggcg cagcatgtga ctcgtcacct gcagtttatt gaagaagaaa tccgtacaga      60
ataaaaggaa tacaacggcg tcgtcttcga tggaaccccg cgtcggcaac aagtatcgcc     120
ttggccggaa aattgggagt ggttcctttg gtgagatcta cctggggacc aatctcgtga     180
ctcatgagga ggtcggcatc aagctggaga gcatcaaggc caagcatcca caattgcttt     240
atgagtccaa gttgtaccgt attcttcaag gaggaactgg gattcccaac atcagatggt     300
acggaattga aggagactat aatgtgatgg ttcttgatct tctgggaccc agtcttgaag     360
atcttttcaa tttctgcagc cggaaattct ctttgaagac agttctcatg cttgccgacc     420
agctgatcaa tcgagtggag tatgtgcatg ccaagagttt cctccacagg gacataaagc     480
ctgacaattt cttgatgggg ctaggcaggc gagcaaatca ggtctatatg attgactttg     540
gtcttgcaaa gaagtatcgc gatcccacta ctcatcagca cattccttat agagagaaca     600
aaaatcttac tggaaccgct cgatatgcaa gtatcaacac tcatcttggt attgaacaaa     660
gcaggagaga tgatctggag tctcttggat atgttctcat gtatttcttg agaggcagcc     720
tgccttggca aggaatgaaa gcaggaacca agaagcagaa gtatgaaaaa atcagtgaga     780
aaaagatgtc caccccctata gagttccttt gtaaagctta cccgtctgag tttgcttcat     840
acttccacta ctgtcggtct cttcggttcg atgacaaacc ggactatgct tacctgaaga     900
gaattttccg agatctcttc attcgtgagg gttttcagtt tgattatgtt ttcgactgga     960
cgattttgaa gtatcagcaa acacattttt ctggtggtcc tctccgtcca gcggctgcgg    1020
cgggaggttc aagtggagca gcagcagcag cggcagcagg aattggtaca gtcccaagag    1080
acgcccagcg agcaattgag cctactgatg ttgccgctcg aactcgaatg gttggtgcga    1140
ctcgctctag tggattaaat ccactggacg cgtcaaagca taagagtact agcccagatg    1200
aagccgcttc taaggacata gcccttagcg gtcttgcaga accagagcgc acgcatgctt    1260
```

-continued

```
cttcgtttgt gcggggagc tcatcatcaa ggagagctgt tgttggatgt gctaggccag      1320
cagggtcaac agaggcggga gatggaacgc gggtgttggc tggcaaaatg ggccccacta      1380
gcctgcgcac atcagcagga atgcagagga gctctccggt ggcatctacg gatcccaagc      1440
ggacgggacg agattcttat gctggaaact ccggaagaaa tcctagttcc tctcgaaatt      1500
cgaaagagtg agcacattgg ttgaactggg tcctgcatct tgttcgaaga gcattacaac      1560
tgtatctggc cttggtatct gctgtggttt aggaatttgg ccttgtactt gatttgaaga      1620
acaggttcgt aagaaattga tcaaatttca atgtcgtggg cgtccagttc aggatatggt      1680
tggtggcttg tgatggatat attatctgtt tctatctttg aaggtgttgc ccccagccgt      1740
atagttttca tctttcatag cttgtagttg gcaaagccca ttgccatctg tcaatattca      1800
gagtgtggtt gagggagctg tttagccttc tagataagag atctggattg cgttctggat      1860
tgctgcacag accttgaaga tttgtggctg ttcgagatta tgaaatgaac agcttcctag      1920
agcaagtagt agctgttaac gc                                               1942
```

<210> SEQ ID NO 2
<211> LENGTH: 473
<212> TYPE: PRT
<213> ORGANISM: Physcomitrella patens

<400> SEQUENCE: 2

```
Met Glu Pro Arg Val Gly Asn Lys Tyr Arg Leu Gly Arg Lys Ile Gly
  1               5                  10                  15

Ser Gly Ser Phe Gly Glu Ile Tyr Leu Gly Thr Asn Leu Val Thr His
             20                  25                  30

Glu Glu Val Gly Ile Lys Leu Glu Ser Ile Lys Ala Lys His Pro Gln
         35                  40                  45

Leu Leu Tyr Glu Ser Lys Leu Tyr Arg Ile Leu Gln Gly Gly Thr Gly
     50                  55                  60

Ile Pro Asn Ile Arg Trp Tyr Gly Ile Glu Gly Asp Tyr Asn Val Met
 65                  70                  75                  80

Val Leu Asp Leu Leu Gly Pro Ser Leu Glu Asp Leu Phe Asn Phe Cys
                 85                  90                  95

Ser Arg Lys Phe Ser Leu Lys Thr Val Leu Met Leu Ala Asp Gln Leu
            100                 105                 110

Ile Asn Arg Val Glu Tyr Val His Ala Lys Ser Phe Leu His Arg Asp
        115                 120                 125

Ile Lys Pro Asp Asn Phe Leu Met Gly Leu Gly Arg Arg Ala Asn Gln
    130                 135                 140

Val Tyr Met Ile Asp Phe Gly Leu Ala Lys Lys Tyr Arg Asp Pro Thr
145                 150                 155                 160

Thr His Gln His Ile Pro Tyr Arg Glu Asn Lys Asn Leu Thr Gly Thr
                165                 170                 175

Ala Arg Tyr Ala Ser Ile Asn Thr His Leu Gly Ile Glu Gln Ser Arg
            180                 185                 190

Arg Asp Asp Leu Glu Ser Leu Gly Tyr Val Leu Met Tyr Phe Leu Arg
        195                 200                 205

Gly Ser Leu Pro Trp Gln Gly Met Lys Ala Gly Thr Lys Lys Gln Lys
    210                 215                 220

Tyr Glu Lys Ile Ser Glu Lys Lys Met Ser Thr Pro Ile Glu Phe Leu
225                 230                 235                 240

Cys Lys Ala Tyr Pro Ser Glu Phe Ala Ser Tyr Phe His Tyr Cys Arg
```

```
                    245                 250                 255
Ser Leu Arg Phe Asp Asp Lys Pro Asp Tyr Ala Tyr Leu Lys Arg Ile
                260                 265                 270

Phe Arg Asp Leu Phe Ile Arg Glu Gly Phe Gln Phe Asp Tyr Val Phe
            275                 280                 285

Asp Trp Thr Ile Leu Lys Tyr Gln Gln Thr His Phe Ser Gly Gly Pro
        290                 295                 300

Leu Arg Pro Ala Ala Ala Ala Gly Gly Ser Ser Gly Ala Ala Ala Ala
    305                 310                 315                 320

Ala Ala Ala Gly Ile Gly Thr Val Pro Arg Asp Ala Gln Arg Ala Ile
                325                 330                 335

Glu Pro Thr Asp Val Ala Ala Arg Thr Arg Met Val Gly Ala Thr Arg
            340                 345                 350

Ser Ser Gly Leu Asn Pro Leu Asp Ala Ser Lys His Lys Ser Thr Ser
        355                 360                 365

Pro Asp Glu Ala Ala Ser Lys Asp Ile Ala Leu Ser Gly Leu Ala Glu
    370                 375                 380

Pro Glu Arg Thr His Ala Ser Ser Phe Val Arg Gly Ser Ser Ser Ser
385                 390                 395                 400

Arg Arg Ala Val Val Gly Cys Ala Arg Pro Ala Gly Ser Thr Glu Ala
                405                 410                 415

Gly Asp Gly Thr Arg Val Leu Ala Gly Lys Met Gly Pro Thr Ser Leu
            420                 425                 430

Arg Thr Ser Ala Gly Met Gln Arg Ser Ser Pro Val Ala Ser Thr Asp
        435                 440                 445

Pro Lys Arg Thr Gly Arg Asp Ser Tyr Ala Gly Asn Ser Gly Arg Asn
    450                 455                 460

Pro Ser Ser Ser Arg Asn Ser Lys Glu
465                 470

<210> SEQ ID NO 3
<211> LENGTH: 1736
<212> TYPE: DNA
<213> ORGANISM: Physcomitrella patens

<400> SEQUENCE: 3
atcccgggct cacgtagtgc actgaactct gtctgaattt taggggatga gaggtagatt      60
tgaagaatac tggtgtctaa tttctgtta  atttttcacc cttgaggtag ctcatggatt    120
tgggaggtga tcgcatgaga gctcctcaga ggcagtctcg agaatatcaa tatagatcat    180
tggacgtctt cacagagcag cacgagcagt gcaaaagca  gcagcagcaa gatgagtatc    240
agagaacaga attgaagctc gagacactgc caaaaatgtt aagcaatgcg accgtgtcat    300
cttcccctcg aagcagtccg gatggacgta gactacgtac agtcgcgaat aagtatgctg    360
tggaaggtat ggttgggagt ggcgcattct gcaaggtgta tcagggctcc gatttgacga    420
accacgaggt tgtgggcatc aagctggagg atacgagaac tgagcacgct cagttaatgc    480
acgagtcgcg cttgtacaac atattgcggg gtgggaaggg agtgcccaac atgagatggt    540
tcggaaaaga gcaagactac aatgtgatgg tgctagacct attggggccg aacctgttgc    600
acctctttaa ggtgtgtggg ctaaggtttt cgttgaagac cgtgattatg ctcggttacc    660
aaatgattga ccgggtggaa tacgtgcatt ctcgagggct cgttcaccgt gacctgaagc    720
cggataactt cctcatgggc tgcggtcggc aaggaaacca agtgttcatt atagattttg    780
gcttggcaaa ggagtacatg gacccggcaa cacgaaggca tatcccttac cgagatagga    840
```

-continued

```
agagcttcac agggacggca cggtacgcta gtaggaatca gcacagagga atcgagcaca        900
gtagaagaga tgacatagaa tcacttggtt acattcttat gtactttcta agaggcaatt        960
tgccatggca agggaagggc gggcaacgcc tcactgacca gaagcaacac gagtacatgc       1020
acaacaaaat caagatgaac accactgtgg aggagctttg tgatgggtat cccagtcaat       1080
ttgccgactt tttgcaccac gcgcgaagtc taggtttcta cgagcagcct gactactgtt       1140
acctccgaag cttgttccgt gatcttttca ttcagaaaaa attccagctc gaccatgtgt       1200
acgactggac tgtgtatact caactccccc agaatggctc tctgcaatca gtgcgcagcc       1260
agaattccgc tgcttcgtcc catttgcaaa atcgaccttc gaatgtatca tattgtccac       1320
ccttgaccaa gtcggagttc cgtcgtgagg ttgttgcggc gaattagggc ttacgttggg       1380
aggactagtg gttcatcctc tgctctggta ctaaaatagc acaaggttgc ttactgtttc       1440
cctctctcaa gtcttacatg attgtgaatg ggggtttatg gagttgagga tgaggcaact       1500
aagcagagtg taggaaaaga gttgtagact ctctagtgtg tagtgtgtaa atcaaggctt       1560
ctagcattgt gtcggtagct tgtatggatc agactagaaa tgactttatc cattacaaga       1620
atttttactc ggaaagccca tgacggtgat gatttcaata cgttgcacaa gcaactttct       1680
tctgtaattg aaatagagga tctggtctga gtatgagaag atgggcatgt taacgc          1736
```

<210> SEQ ID NO 4
<211> LENGTH: 417
<212> TYPE: PRT
<213> ORGANISM: Physcomitrella patens

<400> SEQUENCE: 4

```
Met Asp Leu Gly Gly Asp Arg Met Arg Ala Pro Gln Arg Gln Ser Arg
 1               5                  10                  15

Glu Tyr Gln Tyr Arg Ser Leu Asp Val Phe Thr Glu Gln His Glu Gln
            20                  25                  30

Leu Gln Lys Gln Gln Gln Asp Glu Tyr Gln Arg Thr Glu Leu Lys
        35                  40                  45

Leu Glu Thr Leu Pro Lys Met Leu Ser Asn Ala Thr Val Ser Ser Ser
    50                  55                  60

Pro Arg Ser Ser Pro Asp Gly Arg Arg Leu Arg Thr Val Ala Asn Lys
65                  70                  75                  80

Tyr Ala Val Glu Gly Met Val Gly Ser Gly Ala Phe Cys Lys Val Tyr
                85                  90                  95

Gln Gly Ser Asp Leu Thr Asn His Glu Val Val Gly Ile Lys Leu Glu
            100                 105                 110

Asp Thr Arg Thr Glu His Ala Gln Leu Met His Glu Ser Arg Leu Tyr
        115                 120                 125

Asn Ile Leu Arg Gly Gly Lys Gly Val Pro Asn Met Arg Trp Phe Gly
    130                 135                 140

Lys Glu Gln Asp Tyr Asn Val Met Val Leu Asp Leu Leu Gly Pro Asn
145                 150                 155                 160

Leu Leu His Leu Phe Lys Val Cys Gly Leu Arg Phe Ser Leu Lys Thr
                165                 170                 175

Val Ile Met Leu Gly Tyr Gln Met Ile Asp Arg Val Glu Tyr Val His
            180                 185                 190

Ser Arg Gly Leu Val His Arg Asp Leu Lys Pro Asp Asn Phe Leu Met
        195                 200                 205

Gly Cys Gly Arg Gln Gly Asn Gln Val Phe Ile Ile Asp Phe Gly Leu
```

```
                210                 215                 220
Ala Lys Glu Tyr Met Asp Pro Ala Thr Arg Arg His Ile Pro Tyr Arg
225                 230                 235                 240

Asp Arg Lys Ser Phe Thr Gly Thr Ala Arg Tyr Ala Ser Arg Asn Gln
                245                 250                 255

His Arg Gly Ile Glu His Ser Arg Arg Asp Asp Ile Glu Ser Leu Gly
            260                 265                 270

Tyr Ile Leu Met Tyr Phe Leu Arg Gly Asn Leu Pro Trp Gln Gly Lys
        275                 280                 285

Gly Gly Gln Arg Leu Thr Asp Gln Lys Gln His Glu Tyr Met His Asn
    290                 295                 300

Lys Ile Lys Met Asn Thr Thr Val Glu Glu Leu Cys Asp Gly Tyr Pro
305                 310                 315                 320

Ser Gln Phe Ala Asp Phe Leu His His Ala Arg Ser Leu Gly Phe Tyr
                325                 330                 335

Glu Gln Pro Asp Tyr Cys Tyr Leu Arg Ser Leu Phe Arg Asp Leu Phe
            340                 345                 350

Ile Gln Lys Lys Phe Gln Leu Asp His Val Tyr Asp Trp Thr Val Tyr
        355                 360                 365

Thr Gln Leu Pro Gln Asn Gly Ser Leu Gln Ser Val Arg Ser Gln Asn
    370                 375                 380

Ser Ala Ala Ser Ser His Leu Gln Asn Arg Pro Ser Asn Val Ser Tyr
385                 390                 395                 400

Cys Pro Pro Leu Thr Lys Ser Glu Phe Arg Arg Glu Val Val Ala Ala
                405                 410                 415

Asn

<210> SEQ ID NO 5
<211> LENGTH: 1900
<212> TYPE: DNA
<213> ORGANISM: Physcomitrella patens

<400> SEQUENCE: 5
atcccgggtt gtcgaggacg gagagagaag agagagagag agagagagag aggtgttgtt        60
taggggaggc atgcgggagc aggattggtg ttaagttcgt aaggagaagg gagtacatgc       120
aagtgcgtgc ttgtcggata tcggacagct ggatttgtaa ataagcggag aggagggtcg       180
gtaatcaggg gcgtacatcg atggagccgc gtgtgggaaa caagtatcgg ctgggacgga       240
aaattgggag cggttccttt ggggagatct atcttggac caatgttcag accaatgagg        300
aggtcggaat aaagctggaa agcatcaaga cgaagcatcc acaattgctg tacgagtcca       360
agctctaccg gatactacaa ggaggaactg ggattcccaa tatcagatgg ttcgggatag       420
aaggagacta caatgtcttg gttctggatc tgttggggcc aagtctcgaa gacctttca       480 acttctgcag ccggaagttc tctttaaaga ctgttctcat gcttgctgac agctgatca       540 acagagtgga gtatgtgcat gcgaaaagct tcttcatag agacatcaag cctgataatt       600
ttctaatggg gcttggtagg cgagcaaacc aggtctacat tattgattt ggtcttgcca        660 agaagtaccg cgacccttcc acgcatcagc atattcccta cagggagaac aaaaatctga       720
cagggactgc tcggtatgca agcatcaaca ctcatcttgg tattgagcaa gcagacgag       780 atgatttgga atctcttgga tatgtgctca tgtacttcct gagaggcagt cttccatggc       840
aaggactgaa agcgggaacc aagaagcaga agtacgagaa gatcagtgag aaaaaaatgt       900
ccacgcccat tgaggtcctt tgtaaaaatt atccttcaga attcgcctcg tacttccact       960
```

```
actgccggtc cttgcgtttt gatgacaaac ccgactatgc atatttgaaa agaatcttcc     1020
gtgacctctt tattcgtgag ggttttcaat ttgactacgt ttttgactgg acaattctga     1080
agtaccagca gtcacaaatt tccggtggca gttcaactcg actgggtgct ctgcagggc     1140
aaaccagtgg tgcacttgga actggggcta caggaagccg agacctgcag cggcccaccg     1200
aaccaatgga tccttctcgg cgcaggcttc ctggaggagc aaatggctcc ggggtcgcaa     1260
atgctttgga ctcatctaag cacaaaagtc ctggacttga tgaatctgct aaggattctg     1320
ctcttgctgt tgtgtcagaa ccagagcgca tgcatacatc ttcgtatgca actcgggggg     1380
gttcttcctc caggcgagct gtcctatcta gcagcaggcc ctcagggggca tcagcagaag     1440
tcgtagattc ctctcgaaca gggagcagta agcttggtcc caccagctta cggtcgtcag     1500
cagggatgca gaggagctct ccagttactt cggacccaaa gcggatatct agccgccatc     1560
cacaaccgcc atctgccaac ttgaggattt acgaagccgc tatcaaggga gttgaatcac     1620
tttctgttga ggtggatcaa agccgttata agtaggccca ggcttgtggt tatatagccg     1680
ggctctgtct tctatcaaac cctcttgtta tgtagatgag agttgctcta catttggcaa     1740
cagcctgatt gaggggaaaa cggtggttct gtcctacaat ggtgctaaga ctacaggtct     1800
ctcatactta ggaatgaatg gatctctatc ttgttaccat caaaccattg tcagtgcttt     1860
gtgtggtagc tctctgccat acgattccta aggttaacgc                            1900
```

<210> SEQ ID NO 6
<211> LENGTH: 484
<212> TYPE: PRT
<213> ORGANISM: Physcomitrella patens

<400> SEQUENCE: 6

```
Met Glu Pro Arg Val Gly Asn Lys Tyr Arg Leu Gly Arg Lys Ile Gly
 1               5                  10                  15

Ser Gly Ser Phe Gly Glu Ile Tyr Leu Gly Thr Asn Val Gln Thr Asn
            20                  25                  30

Glu Glu Val Gly Ile Lys Leu Glu Ser Ile Lys Thr Lys His Pro Gln
        35                  40                  45

Leu Leu Tyr Glu Ser Lys Leu Tyr Arg Ile Leu Gln Gly Gly Thr Gly
    50                  55                  60

Ile Pro Asn Ile Arg Trp Phe Gly Ile Glu Gly Asp Tyr Asn Val Leu
65                  70                  75                  80

Val Leu Asp Leu Leu Gly Pro Ser Leu Glu Asp Leu Phe Asn Phe Cys
                85                  90                  95

Ser Arg Lys Phe Ser Leu Lys Thr Val Leu Met Leu Ala Asp Gln Leu
            100                 105                 110

Ile Asn Arg Val Glu Tyr Val His Ala Lys Ser Phe Leu His Arg Asp
        115                 120                 125

Ile Lys Pro Asp Asn Phe Leu Met Gly Leu Gly Arg Arg Ala Asn Gln
    130                 135                 140

Val Tyr Ile Ile Asp Phe Gly Leu Ala Lys Lys Tyr Arg Asp Pro Ser
145                 150                 155                 160

Thr His Gln His Ile Pro Tyr Arg Glu Asn Lys Asn Leu Thr Gly Thr
                165                 170                 175

Ala Arg Tyr Ala Ser Ile Asn Thr His Leu Gly Ile Glu Gln Ser Arg
            180                 185                 190

Arg Asp Asp Leu Glu Ser Leu Gly Tyr Val Leu Met Tyr Phe Leu Arg
        195                 200                 205
```

```
Gly Ser Leu Pro Trp Gln Gly Leu Lys Ala Gly Thr Lys Lys Gln Lys
    210                 215                 220

Tyr Glu Lys Ile Ser Glu Lys Lys Met Ser Thr Pro Ile Glu Val Leu
225                 230                 235                 240

Cys Lys Asn Tyr Pro Ser Glu Phe Ala Ser Tyr Phe His Tyr Cys Arg
                245                 250                 255

Ser Leu Arg Phe Asp Asp Lys Pro Asp Tyr Ala Tyr Leu Lys Arg Ile
            260                 265                 270

Phe Arg Asp Leu Phe Ile Arg Glu Gly Phe Gln Phe Asp Tyr Val Phe
        275                 280                 285

Asp Trp Thr Ile Leu Lys Tyr Gln Gln Ser Gln Ile Ser Gly Gly Ser
    290                 295                 300

Ser Thr Arg Leu Gly Ala Ser Ala Gly Gln Thr Ser Gly Ala Leu Gly
305                 310                 315                 320

Thr Gly Ala Thr Gly Ser Arg Asp Leu Gln Arg Pro Thr Glu Pro Met
                325                 330                 335

Asp Pro Ser Arg Arg Leu Pro Gly Gly Ala Asn Gly Ser Gly Val
            340                 345                 350

Ala Asn Ala Leu Asp Ser Ser Lys His Lys Ser Pro Gly Leu Asp Glu
        355                 360                 365

Ser Ala Lys Asp Ser Ala Leu Ala Val Val Ser Glu Pro Glu Arg Met
    370                 375                 380

His Thr Ser Ser Tyr Ala Thr Arg Gly Gly Ser Ser Arg Arg Ala
385                 390                 395                 400

Val Leu Ser Ser Arg Pro Ser Gly Ala Ser Ala Glu Val Val Asp
                405                 410                 415

Ser Ser Arg Thr Gly Ser Ser Lys Leu Gly Pro Thr Ser Leu Arg Ser
            420                 425                 430

Ser Ala Gly Met Gln Arg Ser Ser Pro Val Thr Ser Asp Pro Lys Arg
        435                 440                 445

Ile Ser Ser Arg His Pro Gln Pro Pro Ser Ala Asn Leu Arg Ile Tyr
    450                 455                 460

Glu Ala Ala Ile Lys Gly Val Glu Ser Leu Ser Val Glu Val Asp Gln
465                 470                 475                 480

Ser Arg Tyr Lys

<210> SEQ ID NO 7
<211> LENGTH: 1795
<212> TYPE: DNA
<213> ORGANISM: Physcomitrella patens

<400> SEQUENCE: 7
gcccttatcc cgggaggcat tgaactacct ggagtgagat ttttttggga atttgaaaga      60
gaattacata tatacaaggt tgaggctcac cgagaacaag tctgctgata gcttcttcac     120
tcttgaaata gatagttcat catggattca ggaggtgacc gcgtgcgagc tcctcagaag     180
cagtctcgcg aggaggatca gtaccgttca ttgaacattg ctacagagca tcgtcagcat     240
atacagaagc accaacaaca ccaacagcag ccggggactg gattggttgt tgaaacgctt     300
caaaaaacac tatgtaacgt gactgtgacc tcacctacaa gcagtccgga ggggggtaga     360
ttacgtactg ttgcgaacaa gtatgcagtg aaggaatgg tcggcagtgg cgcattttgc     420
aaggtgtacc agggttctga cttaaccaac catgaggttg tgggcatcaa gctcgaggat     480
acaagaacag agcacgcaca attgatgcac gagtcgcgat tatacaacat tttgcgggt      540
```

```
ggaaagggag tgcccaacat gagatggttt gggaaagagc aagactacaa tgtgatggtg      600
ctagatttgc tggggcctaa cctactgcac cttttcaagg tgtgtgggca agattttcg      660 ttgaagacgg tgatcatgtt ggggtaccaa atgatcgacc gggtggagta cgtgcactcg      720
cgaggtctag ttcatcgtga cttgaaacca gataatttcc tcatgggctg cggccggcaa      780
gggaaccaag tgttcattat tgactttggc ttggcaaaag agtacatcga ccccgcgaca      840
cgtagacaca ttccttaccg agatagaaag agctttacag aacagcgcg gtatgctagt      900 aggaatcagc acaaaggaat cgaacacagc aggagagatg acatagaatc acttggttac      960
attcttatgt actttcttag ggggaattta ccatggcaag gtcaagggg gcaacgtttc     1020 accgatcaga agcaacatga gtacatgcac aacaaaatta agatggagac taccatcgag     1080
gatctctgcg atgggtaccc cagacaattt gccgactttt acaccacgc gcgcgagttg     1140 ggattctatg agcagcctga ctactcgtac cttcgcagcc tgttccgtga tcttttcatt     1200
cagaagaaat ccagcttga ccatgtctac gactggacag tgtacactca acctcctcag     1260
aatggctctg cacaaacagt tcgaagcccg gctgccggtc acagactca cttacaaagt     1320 cgccccttcca atgtatcata ttgtccacct ctgactaaac cagagttccg gcgtgaggta     1380
gttgcggcga attagggttt acacaggaag agatgtggta agcatctca tcttcttcgt     1440 tctggtgcca aaatggtaca aggtcgtctg ctgtctcttt ctcgcaagcc ctcacatata     1500
gatgaaggtt tgtgaagtta gagatgcaac taccaagcaa aggctaggaa aagagctgta     1560
gactttctag tgtgtagtgt gtaaatcaag gcttctggca tggtatcggc agtcaggtgc     1620
atggagcaga atagaaatta cttcgtgcat gacaagattt ttttcttgc agagctctcg     1680 acggttctgc gatctcactt ctctacacaa ccagcgctcc tttaattgaa aagaggatct     1740
ggtacgagta tgataaagtt aacacagatt actagttcaa cgatatcgca agggc         1795
```

<210> SEQ ID NO 8
<211> LENGTH: 417
<212> TYPE: PRT
<213> ORGANISM: Physcomitrella patens

<400> SEQUENCE: 8

Met Asp Ser Gly Gly Asp Arg Val Arg Ala Pro Gln Lys Gln Ser Arg
 1               5                  10                  15

Glu Glu Asp Gln Tyr Arg Ser Leu Asn Ile Ala Thr Glu His Arg Gln
                20                  25                  30

His Ile Gln Lys His Gln Gln His Gln Gln Pro Gly Thr Gly Leu
            35                  40                  45

Val Val Glu Thr Leu Gln Lys Thr Leu Cys Asn Val Thr Val Thr Ser
        50                  55                  60

Pro Thr Ser Ser Pro Glu Gly Gly Arg Leu Arg Thr Val Ala Asn Lys
65                  70                  75                  80

Tyr Ala Val Glu Gly Met Val Gly Ser Gly Ala Phe Cys Lys Val Tyr
                85                  90                  95

Gln Gly Ser Asp Leu Thr Asn His Glu Val Val Gly Ile Lys Leu Glu
            100                 105                 110

Asp Thr Arg Thr Glu His Ala Gln Leu Met His Glu Ser Arg Leu Tyr
        115                 120                 125

Asn Ile Leu Arg Gly Gly Lys Gly Val Pro Asn Met Arg Trp Phe Gly
    130                 135                 140

Lys Glu Gln Asp Tyr Asn Val Met Val Leu Asp Leu Leu Gly Pro Asn

| | | | | 145 | | | | 150 | | | | 155 | | | | 160 |
|---|---|---|---|---|---|---|---|---|---|---|---|---|---|---|---|---|
Leu Leu His Leu Phe Lys Val Cys Gly Gln Arg Phe Ser Leu Lys Thr
                 165                    170                 175

Val Ile Met Leu Gly Tyr Gln Met Ile Asp Arg Val Glu Tyr Val His
           180                    185                 190

Ser Arg Gly Leu Val His Arg Asp Leu Lys Pro Asp Asn Phe Leu Met
        195                    200                205

Gly Cys Gly Arg Gln Gly Asn Gln Val Phe Ile Ile Asp Phe Gly Leu
      210                   215                 220

Ala Lys Glu Tyr Ile Asp Pro Ala Thr Arg Arg His Ile Pro Tyr Arg
225                 230                    235              240

Asp Arg Lys Ser Phe Thr Gly Thr Ala Arg Tyr Ala Ser Arg Asn Gln
            245                    250                255

His Lys Gly Ile Glu His Ser Arg Arg Asp Asp Ile Glu Ser Leu Gly
        260                    265                270

Tyr Ile Leu Met Tyr Phe Leu Arg Gly Asn Leu Pro Trp Gln Gly Gln
      275                 280                285

Gly Gly Gln Arg Phe Thr Asp Gln Lys Gln His Glu Tyr Met His Asn
    290                 295                300

Lys Ile Lys Met Glu Thr Thr Ile Glu Asp Leu Cys Asp Gly Tyr Pro
305                 310                    315              320

Arg Gln Phe Ala Asp Phe Leu His His Ala Arg Glu Leu Gly Phe Tyr
            325                    330                335

Glu Gln Pro Asp Tyr Ser Tyr Leu Arg Ser Leu Phe Arg Asp Leu Phe
        340                    345                350

Ile Gln Lys Lys Phe Gln Leu Asp His Val Tyr Asp Trp Thr Val Tyr
      355                 360                365

Thr Gln Pro Pro Gln Asn Gly Ser Ala Gln Thr Val Arg Ser Pro Ala
    370                 375                380

Ala Gly Pro Gln Thr His Leu Gln Ser Arg Pro Ser Asn Val Ser Tyr
385                 390                    395              400

Cys Pro Pro Leu Thr Lys Pro Glu Phe Arg Arg Glu Val Val Ala Ala
            405                    410              415

Asn

<210> SEQ ID NO 9
<211> LENGTH: 1575
<212> TYPE: DNA
<213> ORGANISM: Saccharomyces cerevisiae

<400> SEQUENCE: 9

```
atgtcccaac gatcttcaca acacattgta ggtattcatt atgctgtagg acctaagatt      60
ggcgaagggt ctttcggagt aatatttgag ggagagaaca ttcttcattc ttgtcaagcg     120
cagaccggta gcaagaggga ctctagtata ataatggcga acgagccagt cgcaattaaa     180
ttcgaaccgc gacattcgga cgcacccag ttgcgtgacg aatttagagc ctataggata      240
ttgaatggct gcgttggaat tccccatgct tattattttg gtcaagaagg tatgcacaac     300
atcttgatta tcgatttact agggccatca ttggaagatc tctttgagtg gtgtggtaga     360
aaattttcag tgaaacaac ctgtatggtt gccaagcaaa tgattgatag agttagagca      420
attcatgatc acgacttaat ctatcgcgat attaaaccg ataactttt aatttctcaa       480 tatcaaagaa tttcacctga aggaaaagtc attaaatcat gtgcctcctc ttctaataat     540
gatcccaatt taatatacat ggttgacttt ggtatggcaa acaatatag agatccaaga     600
```

-continued

```
acgaaacaac atataccata ccgtgaacga aaatcattga gcggtaccgc cagatatatg    660
tctattaata ctcattttgg aagagaacag tcacgtaggg atgatttaga atcgctaggt    720
cacgtttttt tttatttctt gagggatcc ttgccatggc aaggtttgaa agcaccaaac     780
aacaaactga agtatgaaaa gattggtatg actaaacaga aattgaatcc tgatgatctt    840
ttattgaata atgctattcc ttatcagttt gccacatatt taaatatgc acgttccttg     900 aagttcgacg aagatccgga ttatgactat ttaatctcgt taatggatga cgctttgaga    960
ttaaacgact taaggatga tggacactat gactggatgg atttgaatgg tggtaaaggc    1020
tggaatatca agattaatag aagagctaac ttgcatggtt acggaaatcc aaatccaaga   1080
gtcaatggca atactgcaag aaacaatgtg aatacgaatt caaagacacg aaatacaacg   1140
ccagttgcga cacctaagca acaagctcaa acagttata acaaggacaa ttcgaaatcc    1200
agaatttctt cgaacccgca gagctttact aaacaacaac acgtcttgaa aaaaatcgaa   1260
cccaatagta aatatattcc tgaaacacat tcaaatcttc aacggccaat taaaagtcaa   1320
agtcaaacgt acgactccat cagtcataca caaaattcac catttgtacc atattcaagt   1380
tctaaagcta accctaaaag aagtaataat gagcacaact taccaaacca ctacacaaac   1440
cttgcaaata agaatatcaa ttatcaaagt caacgaaatt acgaacaaga aaatgatgct   1500
tattctgatg acgagaatga tacattttgt tctaaaatat acaaatattg ttgttgctgt   1560
ttttgttgct gttga                                                    1575
```

<210> SEQ ID NO 10
<211> LENGTH: 524
<212> TYPE: PRT
<213> ORGANISM: Saccharomyces cerevisiae

<400> SEQUENCE: 10

```
Met Ser Gln Arg Ser Ser Gln His Ile Val Gly Ile His Tyr Ala Val
1               5                   10                  15

Gly Pro Lys Ile Gly Glu Gly Ser Phe Gly Val Ile Phe Glu Gly Glu
            20                  25                  30

Asn Ile Leu His Ser Cys Gln Ala Gln Thr Gly Ser Lys Arg Asp Ser
        35                  40                  45

Ser Ile Ile Met Ala Asn Glu Pro Val Ala Ile Lys Phe Glu Pro Arg
    50                  55                  60

His Ser Asp Ala Pro Gln Leu Arg Asp Glu Phe Arg Ala Tyr Arg Ile
65                  70                  75                  80

Leu Asn Gly Cys Val Gly Ile Pro His Ala Tyr Tyr Phe Gly Gln Glu
                85                  90                  95

Gly Met His Asn Ile Leu Ile Ile Asp Leu Leu Gly Pro Ser Leu Glu
            100                 105                 110

Asp Leu Phe Glu Trp Cys Gly Arg Lys Phe Ser Val Lys Thr Thr Cys
        115                 120                 125

Met Val Ala Lys Gln Met Ile Asp Arg Val Arg Ala Ile His Asp His
    130                 135                 140

Asp Leu Ile Tyr Arg Asp Ile Lys Pro Asp Asn Phe Leu Ile Ser Gln
145                 150                 155                 160

Tyr Gln Arg Ile Ser Pro Glu Gly Lys Val Ile Lys Ser Cys Ala Ser
                165                 170                 175

Ser Ser Asn Asn Asp Pro Asn Leu Ile Tyr Met Val Asp Phe Gly Met
            180                 185                 190
```

```
Ala Lys Gln Tyr Arg Asp Pro Arg Thr Lys Gln His Ile Pro Tyr Arg
        195                 200                 205

Glu Arg Lys Ser Leu Ser Gly Thr Ala Arg Tyr Met Ser Ile Asn Thr
    210                 215                 220

His Phe Gly Arg Glu Gln Ser Arg Arg Asp Asp Leu Glu Ser Leu Gly
225                 230                 235                 240

His Val Phe Phe Tyr Phe Leu Arg Gly Ser Leu Pro Trp Gln Gly Leu
                245                 250                 255

Lys Ala Pro Asn Asn Lys Leu Lys Tyr Glu Lys Ile Gly Met Thr Lys
            260                 265                 270

Gln Lys Leu Asn Pro Asp Asp Leu Leu Asn Asn Ala Ile Pro Tyr
        275                 280                 285

Gln Phe Ala Thr Tyr Leu Lys Tyr Ala Arg Ser Leu Lys Phe Asp Glu
    290                 295                 300

Asp Pro Asp Tyr Asp Tyr Leu Ile Ser Leu Met Asp Asp Ala Leu Arg
305                 310                 315                 320

Leu Asn Asp Leu Lys Asp Asp Gly His Tyr Asp Trp Met Asp Leu Asn
                325                 330                 335

Gly Gly Lys Gly Trp Asn Ile Lys Ile Asn Arg Arg Ala Asn Leu His
            340                 345                 350

Gly Tyr Gly Asn Pro Asn Pro Arg Val Asn Gly Asn Thr Ala Arg Asn
        355                 360                 365

Asn Val Asn Thr Asn Ser Lys Thr Arg Asn Thr Thr Pro Val Ala Thr
    370                 375                 380

Pro Lys Gln Gln Ala Gln Asn Ser Tyr Asn Lys Asp Asn Ser Lys Ser
385                 390                 395                 400

Arg Ile Ser Ser Asn Pro Gln Ser Phe Thr Lys Gln Gln His Val Leu
                405                 410                 415

Lys Lys Ile Glu Pro Asn Ser Lys Tyr Ile Pro Glu Thr His Ser Asn
            420                 425                 430

Leu Gln Arg Pro Ile Lys Ser Gln Ser Gln Thr Tyr Asp Ser Ile Ser
        435                 440                 445

His Thr Gln Asn Ser Pro Phe Val Pro Tyr Ser Ser Lys Ala Asn
    450                 455                 460

Pro Lys Arg Ser Asn Asn Glu His Asn Leu Pro Asn His Tyr Thr Asn
465                 470                 475                 480

Leu Ala Asn Lys Asn Ile Asn Tyr Gln Ser Gln Arg Asn Tyr Glu Gln
                485                 490                 495

Glu Asn Asp Ala Tyr Ser Asp Asp Glu Asn Asp Thr Phe Cys Ser Lys
            500                 505                 510

Ile Tyr Lys Tyr Cys Cys Cys Cys Phe Cys Cys Cys
        515                 520

<210> SEQ ID NO 11
<211> LENGTH: 1525
<212> TYPE: DNA
<213> ORGANISM: Brassica napus

<400> SEQUENCE: 11
agttgtctga atttgagaaa aaaagtctga gactttgttt tagagagaaa tcaatggatc      60
ttgtgattgg tgggaaattc aaacttggca gaaaaattgg cagtggatca tttggagagc     120
tctatcttgg tgtaaatgtc caaaccggag aagaagttgc tgttaagctg aatctgtca      180 agaccaagca tcctcagcta cactatgagt ccaaattgta tcgttgcttc caaggaggaa     240
```

-continued

```
gtggtattcc taacatcaag tggtatggag ttgatggaga atacaatgtt atggttattg      300
accttctagg tccaagtctt gaagacttgt tcaactactg caaccgaaaa ctctctttga      360
aaaccgttct catgcttgct gatcaactta ttaacagagt tgagtatatg cacactagag      420
gtttccttca ccgtgatatt aagcctgaca acttcttaat gggcctcggc cgcaaagcaa      480
accaggttta taattgat tttggattgg ggaagaaata cagagacctt cagactcaca        540
ggcacattcc ttacagagaa acaaaaacc tcactggaac agctcggtat gcaagtgtca       600
acacacacct tggagtagaa caaagtcgaa gggacgattt ggaagcagtt ggttatgtgc      660
ttatgtactt cctcaaagga agcttaccat ggcaggatt aaaagctggg acaaggaagc       720
agaagtatga cagaataagt gagaagaaag tctcaactcc tatagaggtc ttatgtagaa      780
accaaccgtc tgagtttgtt tcttacttcc gctactgccg gtctctacgg tttgatgaca     840
aacctgatta ctcttacctc aagaggctat tccgagactt gtttattaga aaggttatc      900
agtttgatta tgtatttgac tggaccgtct tgaagcatcc gcaaactggt tccagctcca     960
gttctagttc aagaacacgg gatcatacaa ctggaaaacc ggagttaact gctggaaaac    1020
cggagaggac tgctggcaat aggttatcag gtgcggttga agcttttca agaaggcatg     1080
caacaccacg tgatcggtct gcatcaagaa actctgatga tgtccctgtt ggtggtggtg    1140
agtcagaaag aagaggcagt tcgtcaagaa acggaagctc ttcaaggaga gcaatcgcct    1200
cgagctcacg tccaagttca gctggggtc ctagtgatag cagatcctct agccgtttgg     1260
tgacttcaag cggcggtggt ggaatgggat caacgagcca gagaatggga ccaggaggat    1320
atgagtcaaa gaagagttcg actctttccc gtggtgctag aaacactcgg ggagatccgt    1380
taaggaggag cttcgagctt ctttctcttc gtaaatcatg agaaacatac aaagaaagag    1440
attttataca aacgaaaatc tatatata tataagat atacaataca aacgattcat         1500
atacttcaaa aaaaaaaaa aaaaa                                            1525
```

```
<210> SEQ ID NO 12
<211> LENGTH: 455
<212> TYPE: PRT
<213> ORGANISM: Brassica napus

<400> SEQUENCE: 12
```

```
Met Asp Leu Val Ile Gly Gly Lys Phe Lys Leu Gly Arg Lys Ile Gly
  1               5                  10                  15

Ser Gly Ser Phe Gly Glu Leu Tyr Leu Gly Val Asn Val Gln Thr Gly
             20                  25                  30

Glu Glu Val Ala Val Lys Leu Glu Ser Val Lys Thr Lys His Pro Gln
         35                  40                  45

Leu His Tyr Glu Ser Lys Leu Tyr Thr Leu Leu Gln Gly Gly Ser Gly
     50                  55                  60

Ile Pro Asn Ile Lys Trp Tyr Gly Val Asp Gly Glu Tyr Asn Val Met
 65                  70                  75                  80

Val Ile Asp Leu Leu Gly Pro Ser Leu Glu Asp Leu Phe Asn Tyr Cys
                 85                  90                  95

Asn Arg Lys Leu Ser Leu Lys Thr Val Leu Met Leu Ala Asp Gln Leu
            100                 105                 110

Ile Asn Arg Val Glu Tyr Met His Thr Arg Gly Phe Leu His Arg Asp
        115                 120                 125

Ile Lys Pro Asp Asn Phe Leu Met Gly Leu Gly Arg Lys Ala Asn Gln
    130                 135                 140
```

```
Val Tyr Ile Ile Asp Phe Gly Leu Gly Lys Lys Tyr Arg Asp Leu Gln
145                 150                 155                 160

Thr His Arg His Ile Pro Tyr Arg Glu Asn Lys Asn Leu Thr Gly Thr
                165                 170                 175

Ala Arg Tyr Ala Ser Val Asn Thr His Leu Gly Val Glu Gln Ser Arg
            180                 185                 190

Arg Asp Asp Leu Glu Ala Val Gly Tyr Val Leu Met Tyr Phe Leu Lys
        195                 200                 205

Gly Ser Leu Pro Trp Gln Gly Leu Lys Ala Gly Thr Arg Lys Gln Lys
    210                 215                 220

Tyr Asp Arg Ile Ser Glu Lys Lys Val Ser Thr Pro Ile Glu Val Leu
225                 230                 235                 240

Cys Arg Asn Gln Pro Ser Glu Phe Val Ser Tyr Phe Arg Tyr Cys Arg
                245                 250                 255

Ser Leu Arg Phe Asp Asp Lys Pro Asp Tyr Ser Tyr Leu Lys Arg Leu
            260                 265                 270

Phe Arg Asp Leu Phe Ile Arg Glu Gly Tyr Gln Phe Asp Tyr Val Phe
        275                 280                 285

Asp Trp Thr Val Leu Lys His Pro Gln Thr Gly Ser Ser Ser Ser Ser
    290                 295                 300

Ser Ser Arg Thr Arg Asp His Thr Thr Gly Lys Pro Glu Leu Thr Ala
305                 310                 315                 320

Gly Lys Pro Glu Arg Thr Ala Gly Asn Arg Leu Ser Gly Ala Val Glu
                325                 330                 335

Ala Phe Ser Arg Arg His Ala Thr Pro Arg Asp Arg Ser Ala Ser Arg
            340                 345                 350

Asn Ser Asp Asp Val Pro Val Gly Gly Gly Glu Ser Gly Arg Arg Gly
        355                 360                 365

Ser Ser Ser Arg Asn Gly Ser Ser Ser Arg Arg Ala Ile Ala Ser Ser
    370                 375                 380

Ser Arg Pro Ser Ser Ala Gly Gly Pro Ser Asp Ser Arg Ser Ser Ser
385                 390                 395                 400

Arg Leu Val Thr Ser Ser Gly Gly Gly Gly Met Gly Ser Thr Ser Gln
                405                 410                 415

Arg Met Gly Pro Gly Gly Tyr Glu Ser Lys Lys Ser Ser Thr Leu Ser
            420                 425                 430

Arg Gly Ala Arg Asn Thr Arg Gly Asp Pro Leu Arg Arg Ser Phe Glu
        435                 440                 445

Leu Leu Ser Leu Arg Lys Ser
450                 455
```

<210> SEQ ID NO 13
<211> LENGTH: 1716
<212> TYPE: DNA
<213> ORGANISM: Brassica napus

<400> SEQUENCE: 13

```
gaaagagaga gataaagcaa aggagacaat ctacattcct ttttgttgtt cccccagatc    60
acgagaagaa ggagtctaga gagaaggtga ctatcgggtt cctctgtttt ccctgtttc   120 atcaacccta attccccaga aaattcaatc tttccttgct tctttccctg agacaatcct   180
gggtttgcgg ctctgactcc gttggattaa aaggtttctt caaagacgca ttttgctttc   240
gatagaggat aaaagtttcc tcttttaagt cggctttggg gttgatggag gctcgtgtgg   300
ggaacaagtt tcgtctcgga cgcaaaatcg ggagcggttc ttttggagag atccatctcg   360
```

```
gtactcatct tcaaacgaat gaagaagtcg ccatcaagct tgaaaatgcc aagacaaaac    420
atccacagct gctttatgaa tccaagttat acagacttct acagggagga actggtgttc    480
caaatctcaa gtggtttggt gttgaaggcg actacaatgt tctggtcatg gatttacttg    540
gacctagtct tgaagacttg ttcaatttct gtagcaggaa actttctctc aagtccgtcc    600
tcatgcttgc tgatcaaatg ataaaccgtg ttgagtattt ccattcgaaa tctttcctcc    660
accgagatct caagcctgac aacttcctca tggggttagg gagacgcgcc aaccaggtat    720
acatcatcga ctttggtctt gcaagaagt acagagataa cactactcat cagcacattc    780
cttaccgaga aacaagaat ctcactggaa ctgcaagata tgctagtatg aacactcact    840
tgggaattga acaaagcaga agggatgact tagaatctct tggttacatt ctcatgtatt    900
tccttaaagg aagtcttcca tggcaagggc ttaaagctgg aaccaagaaa caaaatatg    960 agagaatcag cgaaaagaaa gtctctacat ccattgagtc cttatgccgt ggctacccat   1020
ctgagttcgc atcctacttc cattactgcc gctccctccg gtttgatgat aaaccagatt   1080
acggttacct caaaagaata ttcagagatc tcttcatccg cgaagggttt caattcgatt   1140
atgtctttga ctggaccata ctgaagtacc aacagtcaca gctaacagct cctccaacac   1200
gtggccctgc ggctggaacc agttcgggtt tgtctccagg attgaccagc actgatagat   1260
acggagagga agatggaggg agaccaccga tggattcatc aagaaggaga acatcaggag   1320
ctctcgagaa ctcatcagct gctgttagag ctccaatgat gccaagctcg tcgctgttcg   1380
gacaatcagc aggatcatcg aggagagtaa cgtctgagga gctgcagaga agccgtacgg   1440
gcagtggatt gagaaactct gggatggttt caacgtcgga gaggaagaga tcttcttcca   1500
ctaggaaaca atatgattct gctatcaaag gcattgagac tctccatgtc tctgacgaaa   1560
ggtatcacca ccattgatct atcggttaga aagagaaaaa acatgtcatg tttgtattaa   1620
tcatataaag attcgactct atatattaga gaaaccagta ttttttgtgt tgtttttaat   1680
cttctcattt tttacgtgaa aaaaaaaaaa aaaaaa                              1716
```

<210> SEQ ID NO 14
<211> LENGTH: 430
<212> TYPE: PRT
<213> ORGANISM: Brassica napus

<400> SEQUENCE: 14

```
Met Glu Ala Arg Val Gly Asn Lys Phe Arg Leu Gly Arg Lys Ile Gly
 1               5                  10                  15

Ser Gly Ser Phe Gly Glu Ile His Leu Gly Thr His Leu Gln Thr Asn
            20                  25                  30

Glu Glu Val Ala Ile Lys Leu Glu Asn Ala Lys Thr Lys His Pro Gln
        35                  40                  45

Leu Leu Tyr Glu Ser Lys Leu Tyr Arg Leu Leu Gln Gly Gly Thr Gly
    50                  55                  60

Val Pro Asn Leu Lys Trp Phe Gly Val Glu Gly Asp Tyr Asn Val Leu
65                  70                  75                  80

Val Met Asp Leu Leu Gly Pro Ser Leu Glu Asp Leu Phe Asn Phe Cys
                85                  90                  95

Ser Arg Lys Leu Ser Leu Lys Ser Val Leu Met Leu Ala Asp Gln Met
            100                 105                 110

Ile Asn Arg Val Glu Tyr Phe His Ser Lys Ser Phe Leu His Arg Asp
        115                 120                 125
```

```
Leu Lys Pro Asp Asn Phe Leu Met Gly Leu Gly Arg Arg Ala Asn Gln
    130                 135                 140

Val Tyr Ile Ile Asp Phe Gly Leu Ala Lys Lys Tyr Arg Asp Asn Thr
145                 150                 155                 160

Thr His Gln His Ile Pro Tyr Arg Glu Asn Lys Asn Leu Thr Gly Thr
                165                 170                 175

Ala Arg Tyr Ala Ser Met Asn Thr His Leu Gly Ile Glu Gln Ser Arg
            180                 185                 190

Arg Asp Asp Leu Glu Ser Leu Gly Tyr Ile Leu Met Tyr Phe Leu Lys
        195                 200                 205

Gly Ser Leu Pro Trp Gln Gly Leu Lys Ala Gly Thr Lys Lys Gln Lys
    210                 215                 220

Tyr Glu Arg Ile Ser Glu Lys Lys Val Ser Thr Ser Ile Glu Ser Leu
225                 230                 235                 240

Cys Arg Gly Tyr Pro Ser Glu Phe Ala Ser Tyr Phe His Tyr Cys Arg
                245                 250                 255

Ser Leu Arg Phe Asp Asp Lys Pro Asp Tyr Gly Tyr Leu Lys Arg Ile
            260                 265                 270

Phe Arg Asp Leu Phe Ile Arg Glu Gly Phe Gln Phe Asp Tyr Val Phe
        275                 280                 285

Asp Trp Thr Ile Leu Lys Tyr Gln Gln Ser Gln Leu Thr Ala Pro Pro
    290                 295                 300

Thr Arg Gly Pro Ala Ala Gly Thr Ser Ser Gly Leu Ser Pro Gly Leu
305                 310                 315                 320

Thr Ser Thr Asp Arg Tyr Gly Glu Glu Asp Gly Arg Pro Pro Met
                325                 330                 335

Asp Ser Ser Arg Arg Thr Ser Gly Ala Leu Glu Asn Ser Ser Ala
            340                 345                 350

Ala Val Arg Ala Pro Met Met Pro Ser Ser Ser Leu Phe Gly Gln Ser
        355                 360                 365

Ala Gly Ser Ser Arg Arg Val Thr Ser Glu Glu Leu Gln Arg Ser Arg
    370                 375                 380

Thr Gly Ser Gly Leu Arg Asn Ser Gly Met Val Ser Thr Ser Glu Arg
385                 390                 395                 400

Lys Arg Ser Ser Ser Thr Arg Lys Gln Tyr Asp Ser Ala Ile Lys Gly
                405                 410                 415

Ile Glu Thr Leu His Val Ser Asp Glu Arg Tyr His His His
            420                 425                 430

<210> SEQ ID NO 15
<211> LENGTH: 1830
<212> TYPE: DNA
<213> ORGANISM: Brassica napus

<400> SEQUENCE: 15
cggcgattca actcttcttc cacggcggca ttgatggtt  ccttctctga cgcaggagag       60
aaagagagaa agaattttga acaggtgtt  tagggttctt gtctgaatgg acttgaaaat      120
ggataatgta atcggtggca agtttaagct tggtcggaag atcggcggtg gctcttttgg      180
agagcttttt cttggagtaa gtgtgcaaac cggagaagag gtcgctgtaa agctggagcc      240
tgcgaaaact aagcatccac aacttcatta tgagtccaag atttatatgc ttctacaagg      300
aggaactggc atccccagcc tcaagtggtt tggggttcag ggagactaca atgcgatggt      360
cattgatctc cttggtccga gtttggaaga tttgttcaac tattgtaata gaaagctcac      420
```

```
tttgaaggca gttctgatgc ttgcggatca actgattagc agagttgagt atatgcattc   480
aagaggattt ctacaccgag acataaaacc agacaatttc ttgatgggac ttggtcgcaa   540
agcaaaccag gtgtatgtca ttgatttggg ccttgcaaag aagtataggg atctccaaac   600
acatagacac atcccctaca gagaaaacaa gaaccttacg ggcacagctc ggtatgctag   660
cgtcaacact caccttggtg ttgagcaaag tcgaagggat gatctggagt ctcttggtta   720
cgtgctcatg tatttcctca gaggaagcct gccatggcag ggactaaaag ctggcacaaa   780
gaagcagaag tatgacagaa tcagtgagaa gaaagtttca actcctatag aggtcttgtg   840
caagtcctat ccacaagaat tcgtatcata ctttcaatac tgcaggtcct tgcgattcga   900
agacaaacca gactactcgt atctaaagag gctattccgg gatttgttta ccgcgaagg    960
ctatcagttt gactatgtat ttgactggac tgcactgaaa cacctcaga gtagttctag   1020
ctcccggtcc agctcacacg gaaggcatcg tacgggtaaa ccagttgcgg ccgcaggacc   1080
gtctgctgag aaacctgaaa ggatctcagt tgggagggaa atccgcgaca gattctctgg   1140
tgcagttgaa gcattcgcga gaaggaacgc tacaggagcc actccccatc aaaaccaaac   1200
caagcatcga actcttgacg atgttcctcc accaatgaaa cctgctgtga atatggtatc   1260
tgagaaagga agaaacactt ccggatacgg cagtgcttca aggagagcgg tggcctcagg   1320
gagtagacca agctcatcag gtgaacaagg ggacagccgc ggttcaagcc gtgtggcctc   1380
tagtggaggt ggtgttcgac cttctgtttt ccagagagct caagcggcag ctggtgtgag   1440
tggatatgag tcgaagacag cctctgcctt taaccgcaac agagtggctg cttctaggac   1500
tgcacgtgac gatgctctca gaagctttga gcttcttttct atccgcaaat gagaaagtta   1560
gtaagaacaa acgaaagtta ctatcaactc tttttctgta aattggattc ttctttacac   1620
gtgtgttgtt tggtcctcac gtttccacga aactaccaaa ttttcatgt attatgaatg    1680
taacgtttct ctggattttt gtattaaatt gttacgctct tgtactgtaa tcacgacaag   1740
ttgttactcg tatatcttaa ttttttgtgta aaaaaaaaa aaaaaaaaaa aaaaaaaaaa    1800
aaaaaaaaaa ataaaaaaaa aaaaaaaaaa                                    1830
```

<210> SEQ ID NO 16
<211> LENGTH: 481
<212> TYPE: PRT
<213> ORGANISM: Brassica napus

<400> SEQUENCE: 16

```
Met Asp Leu Lys Met Asp Asn Val Ile Gly Gly Lys Phe Lys Leu Gly
  1               5                  10                  15

Arg Lys Ile Gly Gly Gly Ser Phe Gly Glu Leu Phe Leu Gly Val Ser
             20                  25                  30

Val Gln Thr Gly Glu Glu Val Ala Val Lys Leu Glu Pro Ala Lys Thr
         35                  40                  45

Lys His Pro Gln Leu His Tyr Glu Ser Lys Ile Tyr Met Leu Leu Gln
     50                  55                  60

Gly Gly Thr Gly Ile Pro Ser Leu Lys Trp Phe Gly Val Gln Gly Asp
 65                  70                  75                  80

Tyr Asn Ala Met Val Ile Asp Leu Leu Gly Pro Ser Leu Glu Asp Leu
                 85                  90                  95

Phe Asn Tyr Cys Asn Arg Lys Leu Thr Leu Lys Ala Val Leu Met Leu
            100                 105                 110

Ala Asp Gln Leu Ile Ser Arg Val Glu Tyr Met His Ser Arg Gly Phe
        115                 120                 125
```

Leu His Arg Asp Ile Lys Pro Asp Asn Phe Leu Met Gly Leu Gly Arg
    130                 135                 140

Lys Ala Asn Gln Val Tyr Val Ile Asp Phe Gly Leu Ala Lys Lys Tyr
145                 150                 155                 160

Arg Asp Leu Gln Thr His Arg His Ile Pro Tyr Arg Glu Asn Lys Asn
                165                 170                 175

Leu Thr Gly Thr Ala Arg Tyr Ala Ser Val Asn Thr His Leu Gly Val
            180                 185                 190

Glu Gln Ser Arg Arg Asp Asp Leu Glu Ser Leu Gly Tyr Val Leu Met
        195                 200                 205

Tyr Phe Leu Arg Gly Ser Leu Pro Trp Gln Gly Leu Lys Ala Gly Thr
    210                 215                 220

Lys Lys Gln Lys Tyr Asp Arg Ile Ser Glu Lys Lys Val Ser Thr Pro
225                 230                 235                 240

Ile Glu Val Leu Cys Lys Ser Tyr Pro Gln Glu Phe Val Ser Tyr Phe
                245                 250                 255

Gln Tyr Cys Arg Ser Leu Arg Phe Glu Asp Lys Pro Asp Tyr Ser Tyr
            260                 265                 270

Leu Lys Arg Leu Phe Arg Asp Leu Phe Ile Arg Glu Gly Tyr Gln Phe
        275                 280                 285

Asp Tyr Val Phe Asp Trp Thr Ala Leu Lys His Pro Gln Ser Ser Ser
    290                 295                 300

Ser Ser Arg Ser Ser Ser His Gly Arg His Arg Thr Gly Lys Pro Val
305                 310                 315                 320

Ala Ala Ala Gly Pro Ser Ala Glu Lys Pro Glu Arg Ile Ser Val Gly
                325                 330                 335

Arg Glu Ile Arg Asp Arg Phe Ser Gly Ala Val Glu Ala Phe Ala Arg
            340                 345                 350

Arg Asn Ala Thr Gly Ala Thr Pro His Gln Asn Gln Thr Lys His Arg
        355                 360                 365

Thr Leu Asp Asp Val Pro Pro Pro Met Lys Pro Ala Val Asn Met Val
    370                 375                 380

Ser Glu Lys Gly Arg Asn Thr Ser Gly Tyr Gly Ser Ala Ser Arg Arg
385                 390                 395                 400

Ala Val Ala Ser Gly Ser Arg Pro Ser Ser Ser Gly Glu Gln Gly Asp
                405                 410                 415

Ser Arg Gly Ser Ser Arg Val Ala Ser Ser Gly Gly Val Arg Pro
            420                 425                 430

Ser Val Phe Gln Arg Ala Gln Ala Ala Gly Val Ser Gly Tyr Glu
        435                 440                 445

Ser Lys Thr Ala Ser Ala Phe Asn Arg Asn Arg Val Ala Ala Ser Arg
    450                 455                 460

Thr Ala Arg Asp Asp Ala Leu Arg Ser Phe Glu Leu Leu Ser Ile Arg
465                 470                 475                 480

Lys

<210> SEQ ID NO 17
<211> LENGTH: 1887
<212> TYPE: DNA
<213> ORGANISM: Brassica napus

<400> SEQUENCE: 17
ttcgccgagg ctatttcacc ggaagtcaaa cgaaatccac cgctactcct accttcaatc        60

-continued

```
cgattgattc ccttccgctg tagctatctc atacgcctta agtacgctgc tccagtagct    120
tcttgtggtg gctagtagta tagaggtagt tctagggttt cgatttgatg gagccgcgag    180
tcggaaacaa gtttcggctg gggcggaaga tcggaagtgg atcattcgga gagatctatc    240
ttggtactga tatacagact aatgaagaag ttgccattaa actcgaaaat gtgaaaacta    300
agcatcctca gttactgtat gaatcaaaat tatataaagt attacaagga ggaaccggcg    360
ttccaaacat taaatggtat ggtgttgaag gggaatataa cgtccttgtg atagacttgt    420
ttgggcctag ccttgaagat ctattcaatt tctgtagtag gaaactctca ctaaagactg    480
tactgatgct tgccgatcaa atgatcaatc gcattgaatt tgttcatcag aggtcatttc    540
tacaccggga catcaagcct gacaactttc tgatgggtct cgggaggcgc gcaaatcagg    600
tatacatcat cgactttggt ctagcgaaga agtacagaga ctcgaatcat cagcatattc    660
cgtacaggga aaacaaaaac ttaactggaa ctgctagata cgccagcatg aacactcacc    720
ttggcattga acaaagccgt agggatgatt tggagtcact tggatttgtt ctcatgtact    780
ttttaaaagg aagtcttcct tggcaaggac tgaaagctgg taataagaag caaaagtatg    840
agaggattag tgaaaagaaa gtatcgacat ctattgagtc tttatgccga ggatatccat    900
ctgaatttgc ttcttacttc cattattgcc ggtccctgag attcgatgac aagccagact    960
atgcctacct gaaacggctt ttccgtgacc tgtttattcg cgaaggcttc cagtttgatt   1020
atgtatttga ctggactatc ttgaagtatc agcaatcaca gctttctact cctccccgtc   1080
ccaatgtccc tggagttggg caaagctctg gccttccccc tgctattgct agtgctgaga   1140
ggccatcagg tggcgaggaa gctagaactt ctggctggcc atcaggaaac gctaggcgga   1200
tttctggaca aatatttaat tcaggcaact tagctaaaca aaaagcacca gtttcaagtg   1260
atcctgcaat ctctaaaaat gtaatgttat ctagctctag ctttctccgc gcaactgggt   1320
catcaagacg tgctgctgtc tccggtagtc gcgaggctgc agttcctgga actgattctg   1380
agccatcaaa ccctcaaatc attgaagctg gaacaagctc caacccaaag attcatggtg   1440
gtcgaagctc acctatagtc tcatctgaga acaagaagct atcatctcca tcaaggggaa   1500
atacttcagt tatgaagaac tatgagtcca atcttaataa agggatcgag ggtctgcact   1560
tttagccgct gggtacccac tgaccagtga atgatgtttg taaatttaaa gaccaaagaa   1620 aaccttttctt aggccctccc caggttttag agggagggag acttttgattg tgcttgtaag   1680 cactctcaaa taacgaagaa taaagtaaag actctggaag aagtgattcc agaggaatac   1740
aaactcagaa gtgagtcaag gagtcaaaag actgttgtgt atgtctcgtt tggtactgca   1800
aagttaattt cgagtctcaa agggatttga agtgtaagcg ataattgtac tgtttttttt   1860
aaaaaaaaaa aaaaaaaaaa aaaaaaa                                      1887
```

<210> SEQ ID NO 18
<211> LENGTH: 465
<212> TYPE: PRT
<213> ORGANISM: Brassica napus

<400> SEQUENCE: 18

```
Met Glu Pro Arg Val Gly Asn Lys Phe Arg Leu Gly Arg Lys Ile Gly
 1               5                  10                  15

Ser Gly Ser Phe Gly Glu Ile Tyr Leu Gly Thr Asp Ile Gln Thr Asn
            20                  25                  30

Glu Glu Val Ala Ile Lys Leu Glu Asn Val Lys Thr Lys His Pro Gln
        35                  40                  45
```

```
Leu Leu Tyr Glu Ser Lys Leu Tyr Lys Val Leu Gln Gly Gly Thr Gly
    50                  55                  60

Val Pro Asn Ile Lys Trp Tyr Gly Val Glu Gly Glu Tyr Asn Val Leu
 65                  70                  75                  80

Val Ile Asp Leu Phe Gly Pro Ser Leu Glu Asp Leu Phe Asn Phe Cys
                 85                  90                  95

Ser Arg Lys Leu Ser Leu Lys Thr Val Leu Met Leu Ala Asp Gln Met
            100                 105                 110

Ile Asn Arg Ile Glu Phe Val His Gln Arg Ser Phe Leu His Arg Asp
            115                 120                 125

Ile Lys Pro Asp Asn Phe Leu Met Gly Leu Gly Arg Arg Ala Asn Gln
    130                 135                 140

Val Tyr Ile Ile Asp Phe Gly Leu Ala Lys Lys Tyr Arg Asp Ser Asn
145                 150                 155                 160

His Gln His Ile Pro Tyr Arg Glu Asn Lys Asn Leu Thr Gly Thr Ala
                165                 170                 175

Arg Tyr Ala Ser Met Asn Thr His Leu Gly Ile Glu Gln Ser Arg Arg
            180                 185                 190

Asp Asp Leu Glu Ser Leu Gly Phe Val Leu Met Tyr Phe Leu Lys Gly
            195                 200                 205

Ser Leu Pro Trp Gln Gly Leu Lys Ala Gly Asn Lys Lys Gln Lys Tyr
    210                 215                 220

Glu Arg Ile Ser Glu Lys Lys Val Ser Thr Ser Ile Glu Ser Leu Cys
225                 230                 235                 240

Arg Gly Tyr Pro Ser Glu Phe Ala Ser Tyr Phe His Tyr Cys Arg Ser
                245                 250                 255

Leu Arg Phe Asp Asp Lys Pro Asp Tyr Ala Tyr Leu Lys Arg Leu Phe
            260                 265                 270

Arg Asp Leu Phe Ile Arg Glu Gly Phe Gln Phe Asp Tyr Val Phe Asp
            275                 280                 285

Trp Thr Ile Leu Lys Tyr Gln Gln Ser Gln Leu Ser Thr Pro Pro Arg
    290                 295                 300

Pro Asn Val Pro Gly Val Gly Gln Ser Ser Gly Leu Pro Pro Ala Ile
305                 310                 315                 320

Ala Ser Ala Glu Arg Pro Ser Gly Gly Glu Glu Ala Arg Thr Ser Gly
                325                 330                 335

Trp Pro Ser Gly Asn Ala Arg Arg Ile Ser Gly Gln Ile Phe Asn Ser
            340                 345                 350

Gly Asn Leu Ala Lys Gln Lys Ala Pro Val Ser Ser Asp Pro Ala Ile
            355                 360                 365

Ser Lys Asn Val Met Leu Ser Ser Ser Phe Leu Arg Ala Thr Gly
    370                 375                 380

Ser Ser Arg Arg Ala Ala Val Ser Gly Ser Arg Glu Ala Ala Val Pro
385                 390                 395                 400

Gly Thr Asp Ser Glu Pro Ser Asn Pro Gln Ile Ile Glu Ala Gly Thr
                405                 410                 415

Ser Ser Asn Pro Lys Ile His Gly Gly Arg Ser Ser Pro Ile Val Ser
            420                 425                 430

Ser Glu Asn Lys Lys Leu Ser Ser Pro Ser Arg Gly Asn Thr Ser Val
            435                 440                 445

Met Lys Asn Tyr Glu Ser Asn Leu Asn Lys Gly Ile Glu Gly Leu His
    450                 455                 460

Phe
```

<210> SEQ ID NO 19
<211> LENGTH: 2276
<212> TYPE: DNA
<213> ORGANISM: Brassica napus

<400> SEQUENCE: 19

```
ggagaagagg tggtggtggt ggtagaggaa gaggaaccgc tgcagcttta gccaaagccg      60
ccgcacctcc aagaccgact ggtgctaccg gtagggtcg aggcatcagg ttaatagatt     120
tagaagcaga gcctataggt gagcctgctt ttaatcaagt ccaaggggta gctgataagg     180
gtatcgccat ggaaggtggt agcccggaga agatagttgg tgtgggagaa gatccaagca     240
cagctccagt ccctgaaagg gtacaagttg gaagctctcc tgtttataag actgagagga     300
aactcggtaa aggaggcttt ggtcaagttt tgttggtag aagggtgagt ggtggcagcg      360
ataggattgg ccctgatgca gttgaggtgg ctctgaaatt tgagcacaaa aatagcaaag     420
gatgcaattt tggtccacct tacgagtggc aagtgtacag taatctcaac ggttgctatg     480
gagttcctgc ggtacattat aagggtcgtc aaggagattt ttacatcctt gtcatggaca     540
tgcttggtcc gagtctctgg gatgtttgga actcttcagg gcaatcgatg tcaccaaaca     600
tggtagcgtg cattgcagtt gagtctatat ctattcttga gaacttcac atgaaagggt      660
ttgtccatgg agatgtgaag cctgaaaact ttttactcgg tcaacccgga acagcagatg     720
agaaaaaact ctaccttatc gatcttggtc tagcatcaaa atggaaagaa gctcactcag     780
gcctgcatgt tgaatatgat caaagacctg atgtgttcag ggggactgta aggtatgcaa     840
gtgttcatgc acatctagga cgtactggaa gtcgaagaga tgatcttgag tcattggctt     900
atactctaat ttttctattg aaaggaagat tgccatggca aggttaccag ggtgataaca     960
agagctttct tgtttgcaag aaaaagatgt caacttctcc tgaagtgatg tgctgttttct    1020
gtccaccacc gtttaagcta ttccttgagg cagttactaa tctgaagttt gacgaggagc    1080
ctaattatgc aaagcttatt tcgattttcg atactttaat tgagccgtgc gctctatcta    1140
gaccagttag aatcgatggg gctctcaagg ttgacaaaa gcgtggaaga ctggttctca    1200
atttggaaga ggatgaacaa ccgaagaaga agatcagaat aggcactcct gccactcaat    1260
ggatttcagt ttataatgct cgtcgtccca tgaaacagag atatcactac aatgttgcag    1320
agacaagact gagccagcat gtacagaagg gtaatgaaga tggtcttttg attagctgtg    1380
tagcatcagc agcgaatctc tgggcccctta ttatggatgc tggaactgga tttacctctc    1440
aagtttatga attgtcaaag gtcttcctgc acaaggattg gattatggaa caatgggaaa    1500
agaactacta tataagttcc atagctggtg cagataacgg gagctcctta gttgttatgt    1560
caaaaggaac tacttatact cagcagtcat acaaagtgag cgactcgttt ccattcaagt    1620
ggataaacaa gaaatggaaa gaagattttc atgtgacgtc catgacaact gctggtaatc    1680
gttggggtgt ggtaatgtcg aggaactctg gcttctctga tcaggtggtg gagcttggac    1740
ttttttgtacc caagcgatgg aatacatagg acctgggaga gtgggtatag aatcacatca    1800
atggcagcaa ctgcagatca agcagccttc atattaagca taccaaaacg taaaatgatg    1860
gatgaaactc aggagactct tcggaccacc gcctttccaa gtactcatgt caaggagaaa    1920
tgggcgaaaa atctgcacat tgcatcagta tgctatggca ggacagtgtg ctgaactgct    1980
gatactacat ttaacatcat atgttcagtt agaaagccaa agacaattag agctgcttat    2040
ggatcgtcat aatacccaa tcaaaagagg taaaaacgag acgcagcctg tttggctggt    2100
```

```
tgaatgtaat gaatagatgt cttggtaatg tatgtaacaa gttacaaaag cgaagatgga      2160
attaggaatt agagaaaaga tttgagggct tttgaagcct taagtgtgtg cttacttatt      2220
gttatcgttt tacttgcttg aaataatgtg agaaacgcaa aaaaaaaaaa aaaaaa          2276

<210> SEQ ID NO 20
<211> LENGTH: 526
<212> TYPE: PRT
<213> ORGANISM: Brassica napus

<400> SEQUENCE: 20

Met Glu Gly Gly Ser Pro Glu Lys Ile Val Gly Val Gly Glu Asp Pro
1               5                   10                  15

Ser Thr Ala Pro Val Pro Glu Arg Val Gln Val Gly Ser Ser Pro Val
            20                  25                  30

Tyr Lys Thr Glu Arg Lys Leu Gly Lys Gly Phe Gly Gln Val Phe
        35                  40                  45

Val Gly Arg Arg Val Ser Gly Gly Ser Asp Arg Ile Gly Pro Asp Ala
    50                  55                  60

Val Glu Val Ala Leu Lys Phe Glu His Lys Asn Ser Lys Gly Cys Asn
65                  70                  75                  80

Phe Gly Pro Pro Tyr Glu Trp Gln Val Tyr Ser Asn Leu Asn Gly Cys
                85                  90                  95

Tyr Gly Val Pro Ala Val His Tyr Lys Gly Arg Gln Gly Asp Phe Tyr
            100                 105                 110

Ile Leu Val Met Asp Met Leu Gly Pro Ser Leu Trp Asp Val Trp Asn
        115                 120                 125

Ser Ser Gly Gln Ser Met Ser Pro Asn Met Val Ala Cys Ile Ala Val
    130                 135                 140

Glu Ser Ile Ser Ile Leu Glu Lys Leu His Met Lys Gly Phe Val His
145                 150                 155                 160

Gly Asp Val Lys Pro Glu Asn Phe Leu Leu Gly Gln Pro Gly Thr Ala
                165                 170                 175

Asp Glu Lys Lys Leu Tyr Leu Ile Asp Leu Gly Leu Ala Ser Lys Trp
            180                 185                 190

Lys Glu Ala His Ser Gly Leu His Val Glu Tyr Asp Gln Arg Pro Asp
        195                 200                 205

Val Phe Arg Gly Thr Val Arg Tyr Ala Ser Val His Ala His Leu Gly
    210                 215                 220

Arg Thr Gly Ser Arg Arg Asp Asp Leu Glu Ser Leu Ala Tyr Thr Leu
225                 230                 235                 240

Ile Phe Leu Leu Lys Gly Arg Leu Pro Trp Gln Gly Tyr Gln Gly Asp
                245                 250                 255

Asn Lys Ser Phe Leu Val Cys Lys Lys Met Ser Thr Ser Pro Glu
            260                 265                 270

Val Met Cys Cys Phe Cys Pro Pro Phe Lys Leu Phe Leu Glu Ala
        275                 280                 285

Val Thr Asn Leu Lys Phe Asp Glu Glu Pro Asn Tyr Ala Lys Leu Ile
    290                 295                 300

Ser Ile Phe Asp Thr Leu Ile Glu Pro Cys Ala Leu Ser Arg Pro Val
305                 310                 315                 320

Arg Ile Asp Gly Ala Leu Lys Val Gly Gln Lys Arg Gly Arg Leu Val
                325                 330                 335

Leu Asn Leu Glu Glu Asp Glu Gln Pro Lys Lys Lys Ile Arg Ile Gly
```

-continued

```
                340                 345                 350
Thr Pro Ala Thr Gln Trp Ile Ser Val Tyr Asn Ala Arg Arg Pro Met
        355                 360                 365
Lys Gln Arg Tyr His Tyr Asn Val Ala Glu Thr Arg Leu Ser Gln His
    370                 375                 380
Val Gln Lys Gly Asn Glu Asp Gly Leu Leu Ile Ser Cys Val Ala Ser
385                 390                 395                 400
Ala Ala Asn Leu Trp Ala Leu Ile Met Asp Ala Gly Thr Gly Phe Thr
                405                 410                 415
Ser Gln Val Tyr Glu Leu Ser Lys Val Phe Leu His Lys Asp Trp Ile
            420                 425                 430
Met Glu Gln Trp Glu Lys Asn Tyr Tyr Ile Ser Ser Ile Ala Gly Ala
                435                 440                 445
Asp Asn Gly Ser Ser Leu Val Val Met Ser Lys Gly Thr Thr Tyr Thr
            450                 455                 460
Gln Gln Ser Tyr Lys Val Ser Asp Ser Phe Pro Phe Lys Trp Ile Asn
465                 470                 475                 480
Lys Lys Trp Lys Glu Asp Phe His Val Thr Ser Met Thr Thr Ala Gly
                485                 490                 495
Asn Arg Trp Gly Val Val Met Ser Arg Asn Ser Gly Phe Ser Asp Gln
                500                 505                 510
Val Val Glu Leu Gly Leu Phe Val Pro Lys Arg Trp Asn Thr
            515                 520                 525

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
caggaaacag ctatgacc                                                   18

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ctaaagggaa caaaagctg                                                  19

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgtaaaacga cggccagt                                                   18

<210> SEQ ID NO 24
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 24
cgaccgcagc ccatgaggaa gttat                                              25

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
atcccgggct cacgtagtgc actgaactct gtc                                     33

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcgttaacat gcccatcttc tcatactcag acc                                     33

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ctcgcctacc aagcccaatt agaaa                                              25

<210> SEQ ID NO 28
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
atcccgggtt gtcgaggacg gagagagaag ag                                      32

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gcgttaacct taggaatcgt atggcagaga gct                                     33

<210> SEQ ID NO 30
<211> LENGTH: 25
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 30
tgtgtctacg tgtcgcgggg tcgat                                            25

<210> SEQ ID NO 31
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
atcccgggag gcattgaact acctggagtg ag                                    32

<210> SEQ ID NO 32
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gcgatatcgt tgaactagta atctgtgtta actt                                  34

<210> SEQ ID NO 33
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggaattccag ctgaccacca tgtcccaacg atcttcacaa cac                        43

<210> SEQ ID NO 34
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gatccccggg aattgccatg tcaaaaaaaa aaaggaaaaa gagaaaag                   48

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gcgctgcaga tttcatttgg agaggacacg                                       30

<210> SEQ ID NO 36
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
cgcggccggc tcagaagaa ctcgtcaaga aggcg                            35

<210> SEQ ID NO 37
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ggaattccag ctgaccacca tggcaattcc cggggatc                        38

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gctgacacgc caagcctcgc tagtc                                      25

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gcgttaacat gcccatcttc tcatactcag acc                             33

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gctgacacgc caagcctcgc tagtc                                      25

<210> SEQ ID NO 41
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gcgttaacct taggaatcgt atggcagaga gct                             33

<210> SEQ ID NO 42
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 42
atcccgggag gcattgaact acctggagtg ag                                   32

<210> SEQ ID NO 43
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gcgatatcgt tgaactagta atctgtgtta actttatc                             38

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gcctgcctag ccccatcaag aaatt                                           25

<210> SEQ ID NO 45
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
atcccgggcg cagcatgtga ctcgtcacct g                                    31

<210> SEQ ID NO 46
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gcgttaacag ctactacttg ctctaggaag ctg                                  33

<210> SEQ ID NO 47
<211> LENGTH: 538
<212> TYPE: PRT
<213> ORGANISM: Saccharomyces cerevisiae

<400> SEQUENCE: 47

Met Ser Met Pro Ile Ala Ser Thr Thr Leu Ala Val Asn Asn Leu Thr
1               5                   10                  15

Asn Ile Asn Gly Asn Ala Asn Phe Asn Val Gln Ala Asn Lys Gln Leu
            20                  25                  30

His His Gln Ala Val Asp Ser Pro Ala Arg Ser Ser Met Thr Ala Thr
        35                  40                  45

Thr Ala Ala Asn Ser Asn Ser Asn Ser Ser Arg Asp Asp Ser Thr Ile
    50                  55                  60

Val Gly Leu His Tyr Lys Ile Gly Lys Lys Ile Gly Glu Gly Ser Phe
65                  70                  75                  80
```

```
Gly Val Leu Phe Glu Gly Thr Asn Met Ile Asn Gly Val Pro Val Ala
                85                  90                  95

Ile Lys Phe Glu Pro Arg Lys Thr Glu Ala Pro Gln Leu Arg Asp Glu
            100                 105                 110

Tyr Lys Thr Tyr Lys Ile Leu Asn Gly Thr Pro Asn Ile Pro Tyr Ala
            115                 120                 125

Tyr Tyr Phe Gly Gln Gly Leu His Asn Ile Leu Val Ile Asp Leu
            130                 135                 140

Leu Gly Pro Ser Leu Glu Asp Leu Phe Asp Trp Cys Gly Arg Lys Phe
145                 150                 155                 160

Ser Val Lys Thr Val Val Gln Val Ala Val Gln Met Ile Thr Leu Ile
                165                 170                 175

Glu Asp Leu His Ala His Asp Leu Ile Tyr Arg Asp Ile Lys Pro Asp
                180                 185                 190

Asn Phe Leu Ile Gly Arg Pro Gly Gln Pro Asp Ala Asn Asn Ile His
            195                 200                 205

Leu Ile Asp Phe Gly Met Ala Lys Gln Tyr Arg Asp Pro Lys Thr Lys
210                 215                 220

Gln His Ile Pro Tyr Arg Glu Lys Lys Ser Leu Ser Gly Thr Ala Arg
225                 230                 235                 240

Tyr Met Ser Ile Asn Thr His Leu Gly Arg Glu Gln Ser Arg Arg Asp
                245                 250                 255

Asp Met Glu Ala Leu Gly His Val Phe Phe Tyr Phe Leu Arg Gly His
            260                 265                 270

Leu Pro Trp Gln Gly Leu Lys Ala Pro Asn Asn Lys Gln Lys Tyr Glu
            275                 280                 285

Lys Ile Gly Glu Lys Lys Arg Ser Thr Asn Val Tyr Asp Leu Ala Gln
            290                 295                 300

Gly Leu Pro Val Gln Phe Gly Arg Tyr Leu Glu Ile Val Arg Ser Leu
305                 310                 315                 320

Ser Phe Glu Glu Cys Pro Asp Tyr Glu Gly Tyr Arg Lys Leu Leu Leu
                325                 330                 335

Ser Val Leu Asp Asp Leu Gly Glu Thr Ala Asp Gly Gln Tyr Asp Trp
            340                 345                 350

Met Lys Leu Asn Asp Gly Arg Gly Trp Asp Leu Asn Ile Asn Lys Lys
            355                 360                 365

Pro Asn Leu His Gly Tyr Gly His Pro Asn Pro Pro Asn Glu Lys Ser
            370                 375                 380

Arg Lys His Arg Asn Lys Gln Leu Gln Met Gln Gln Leu Gln Met Gln
385                 390                 395                 400

Gln Leu Gln Gln Gln Gln Gln Gln Gln Gln Tyr Ala Gln Lys Thr Glu
                405                 410                 415

Ala Asp Met Arg Asn Ser Gln Tyr Lys Pro Lys Leu Asp Pro Thr Ser
            420                 425                 430

Tyr Glu Ala Tyr Gln His Gln Thr Gln Gln Lys Tyr Leu Gln Glu Gln
            435                 440                 445

Gln Lys Arg Gln Gln Gln Lys Leu Gln Glu Gln Gln Leu Gln Glu
            450                 455                 460

Gln Gln Leu Gln Gln Gln Gln Gln Gln Gln Gln Leu Arg Ala Thr
465                 470                 475                 480

Gly Gln Pro Pro Ser Gln Pro Gln Ala Gln Thr Gln Ser Gln Gln Phe
                485                 490                 495
```

```
Gly Ala Arg Tyr Gln Pro Gln Gln Pro Ser Ala Ala Leu Arg Thr
            500                 505                 510

Pro Glu Gln His Pro Asn Asp Asn Ser Ser Leu Ala Ala Ser His
            515                 520                 525

Lys Gly Phe Phe Gln Lys Leu Gly Cys Cys
            530                 535

<210> SEQ ID NO 48
<211> LENGTH: 546
<212> TYPE: PRT
<213> ORGANISM: Saccharomyces cerevisiae

<400> SEQUENCE: 48

Met Ser Gln Val Gln Ser Pro Leu Thr Ala Thr Asn Ser Gly Leu Ala
  1               5                  10                  15

Val Asn Asn Asn Thr Met Asn Ser Gln Met Pro Asn Arg Ser Asn Val
                 20                  25                  30

Arg Leu Val Asn Gly Thr Leu Pro Pro Ser Leu His Val Ser Ser Asn
             35                  40                  45

Leu Asn His Asn Thr Gly Asn Ser Ser Ala Ser Tyr Ser Gly Ser Gln
         50                  55                  60

Ser Arg Asp Asp Ser Thr Ile Val Gly Leu His Tyr Lys Ile Gly Lys
 65                  70                  75                  80

Lys Ile Gly Glu Gly Ser Phe Gly Val Leu Phe Gly Thr Asn Met
                 85                  90                  95

Ile Asn Gly Leu Pro Val Ala Ile Lys Phe Glu Pro Arg Lys Thr Glu
            100                 105                 110

Ala Pro Gln Leu Lys Asp Glu Tyr Arg Thr Tyr Lys Ile Leu Ala Gly
            115                 120                 125

Thr Pro Gly Ile Pro Gln Glu Tyr Tyr Phe Gly Gln Glu Gly Leu His
            130                 135                 140

Asn Ile Leu Val Ile Asp Leu Leu Gly Pro Ser Leu Glu Asp Leu Phe
145                 150                 155                 160

Asp Trp Cys Gly Arg Arg Phe Ser Val Lys Thr Val Gln Val Ala
                165                 170                 175

Val Gln Met Ile Thr Leu Ile Glu Asp Leu His Ala His Asp Leu Ile
                180                 185                 190

Tyr Arg Asp Ile Lys Pro Asp Asn Phe Leu Ile Gly Arg Pro Gly Gln
            195                 200                 205

Pro Asp Ala Asn Lys Val His Leu Ile Asp Phe Gly Met Ala Lys Gln
            210                 215                 220

Tyr Arg Asp Pro Lys Thr Lys Gln His Ile Pro Tyr Arg Glu Lys Lys
225                 230                 235                 240

Ser Leu Ser Gly Thr Ala Arg Tyr Met Ser Ile Asn Thr His Leu Gly
                245                 250                 255

Arg Glu Gln Ser Arg Arg Asp Asp Met Glu Ala Met Gly His Val Phe
            260                 265                 270

Phe Tyr Phe Leu Arg Gly Gln Leu Pro Trp Gln Gly Leu Lys Ala Pro
            275                 280                 285

Asn Asn Lys Gln Lys Tyr Glu Lys Ile Gly Glu Lys Lys Arg Leu Thr
            290                 295                 300

Asn Val Tyr Asp Leu Ala Gln Gly Leu Pro Ile Gln Phe Gly Arg Tyr
305                 310                 315                 320

Leu Glu Ile Val Arg Asn Leu Ser Phe Glu Glu Thr Pro Asp Tyr Glu
                325                 330                 335
```

```
Gly Tyr Arg Met Leu Leu Leu Ser Val Leu Asp Asp Leu Gly Glu Thr
                340                 345                 350

Ala Asp Gly Gln Tyr Asp Trp Met Lys Leu Asn Gly Gly Arg Gly Trp
            355                 360                 365

Asp Leu Ser Ile Asn Lys Lys Pro Asn Leu His Gly Tyr Gly His Pro
        370                 375                 380

Asn Pro Pro Asn Glu Lys Ser Lys Arg His Arg Ser Lys Asn His Gln
385                 390                 395                 400

Tyr Ser Ser Pro Asp His His His Tyr Asn Gln Gln Gln Gln Gln Gln
                405                 410                 415

Gln Gln Ala Gln Ala Gln Ala Gln Ala Gln Ala Gln Ala Lys Val Gln
            420                 425                 430

Gln Gln Gln Leu Gln Gln Ala Gln Ala Gln Gln Gln Ala Asn Arg Tyr
                435                 440                 445

Gln Leu Gln Pro Asp Asp Ser His Tyr Asp Glu Glu Arg Glu Ala Ser
        450                 455                 460

Lys Leu Asp Pro Thr Ser Tyr Glu Ala Tyr Gln Gln Gln Thr Gln Gln
465                 470                 475                 480

Lys Tyr Ala Gln Gln Gln Lys Gln Met Gln Gln Lys Ser Lys Gln
                485                 490                 495

Phe Ala Asn Thr Gly Ala Asn Gly Gln Thr Asn Lys Tyr Pro Tyr Asn
                500                 505                 510

Ala Gln Pro Thr Ala Asn Asp Glu Gln Asn Ala Lys Asn Ala Ala Gln
            515                 520                 525

Asp Arg Asn Ser Asn Lys Ser Ser Lys Gly Phe Phe Ser Lys Leu Gly
        530                 535                 540

Cys Cys
545

<210> SEQ ID NO 49
<211> LENGTH: 416
<212> TYPE: PRT
<213> ORGANISM: Homo sapiens

<400> SEQUENCE: 49

Met Glu Leu Arg Val Gly Asn Lys Tyr Arg Leu Gly Arg Lys Ile Gly
 1               5                  10                  15

Ser Gly Ser Phe Gly Asp Ile Tyr Leu Gly Ala Asn Ile Ala Ser Gly
            20                  25                  30

Glu Glu Val Ala Ile Lys Leu Glu Cys Val Lys Thr Lys His Pro Gln
        35                  40                  45

Leu His Ile Glu Ser Lys Phe Tyr Lys Met Met Gln Gly Gly Val Gly
    50                  55                  60

Ile Pro Ser Ile Lys Trp Cys Gly Ala Glu Gly Asp Tyr Asn Val Met
65                  70                  75                  80

Val Met Glu Leu Leu Gly Pro Ser Leu Glu Asp Leu Phe Asn Phe Cys
                85                  90                  95

Ser Arg Lys Phe Ser Leu Lys Thr Val Leu Leu Leu Ala Asp Gln Met
                100                 105                 110

Ile Ser Arg Ile Glu Tyr Ile His Ser Lys Asn Phe Ile His Arg Asp
            115                 120                 125

Val Lys Pro Asp Asn Phe Leu Met Gly Leu Gly Lys Lys Gly Asn Leu
        130                 135                 140

Val Tyr Ile Ile Asp Phe Gly Leu Ala Lys Lys Tyr Arg Asp Ala Arg
```

```
                145                 150                 155                 160
Thr His Gln His Ile Pro Tyr Arg Glu Asn Lys Asn Leu Thr Gly Thr
                165                 170                 175
Ala Arg Tyr Ala Ser Ile Asn Thr His Leu Gly Ile Glu Gln Ser Arg
                180                 185                 190
Arg Asp Asp Leu Glu Ser Leu Gly Tyr Val Leu Met Tyr Phe Asn Leu
                195                 200                 205
Gly Ser Leu Pro Trp Gln Gly Leu Lys Ala Ala Thr Lys Arg Gln Lys
            210                 215                 220
Tyr Glu Arg Ile Ser Glu Lys Lys Met Ser Thr Pro Ile Glu Val Leu
225                 230                 235                 240
Cys Lys Gly Tyr Pro Ser Glu Phe Ser Thr Tyr Leu Asn Phe Cys Arg
                245                 250                 255
Ser Leu Arg Phe Asp Asp Lys Pro Asp Tyr Ser Tyr Leu Arg Gln Leu
                260                 265                 270
Phe Arg Asn Leu Phe His Arg Gln Gly Phe Ser Tyr Asp Tyr Val Phe
            275                 280                 285
Asp Trp Asn Met Leu Lys Phe Gly Ala Ala Arg Asn Pro Glu Asp Val
            290                 295                 300
Asp Arg Glu Arg Arg Glu His Glu Arg Glu Arg Met Gly Gln Leu
305                 310                 315                 320
Arg Gly Ser Ala Thr Arg Ala Leu Pro Pro Gly Pro Thr Gly Ala
                325                 330                 335
Thr Ala Asn Arg Leu Arg Ser Ala Ala Glu Pro Val Ala Ser Thr Pro
            340                 345                 350
Ala Ser Arg Ile Gln Pro Ala Gly Asn Thr Ser Pro Arg Ala Ile Ser
            355                 360                 365
Arg Val Asp Arg Glu Arg Lys Val Ser Met Arg Leu His Arg Gly Ala
            370                 375                 380
Pro Ala Asn Val Ser Ser Ser Asp Leu Thr Gly Arg Gln Glu Val Ser
385                 390                 395                 400
Arg Ile Pro Ala Ser Gln Thr Ser Val Pro Phe Asp His Leu Gly Lys
                405                 410                 415

<210> SEQ ID NO 50
<211> LENGTH: 415
<212> TYPE: PRT
<213> ORGANISM: Homo sapiens

<400> SEQUENCE: 50

Met Glu Leu Arg Val Gly Asn Arg Tyr Arg Leu Gly Arg Lys Ile Gly
1               5                   10                  15
Ser Gly Ser Phe Gly Asp Ile Tyr Leu Gly Thr Asp Ile Ala Ala Gly
            20                  25                  30
Glu Glu Val Ala Ile Lys Leu Glu Cys Val Lys Thr Lys His Pro Gln
        35                  40                  45
Leu His Ile Glu Ser Lys Ile Tyr Lys Met Met Gln Gly Gly Val Gly
    50                  55                  60
Ile Pro Thr Ile Arg Trp Cys Gly Ala Glu Gly Asp Tyr Asn Val Met
65                  70                  75                  80
Val Met Glu Leu Leu Gly Pro Ser Leu Glu Asp Leu Phe Asn Phe Cys
                85                  90                  95
Ser Arg Lys Phe Ser Leu Lys Thr Val Leu Leu Leu Ala Asp Gln Met
            100                 105                 110
```

```
Ile Ser Arg Ile Glu Tyr Ile His Ser Lys Asn Phe Ile His Arg Asp
        115                 120                 125

Val Lys Pro Asp Asn Phe Leu Met Gly Leu Gly Lys Lys Gly Asn Leu
    130                 135                 140

Val Tyr Ile Ile Asp Phe Gly Leu Ala Lys Lys Tyr Arg Asp Ala Arg
145                 150                 155                 160

Thr His Gln His Ile Pro Tyr Arg Glu Asn Lys Asn Leu Thr Gly Thr
                165                 170                 175

Ala Arg Tyr Ala Ser Ile Asn Thr His Leu Gly Ile Glu Gln Ser Arg
                180                 185                 190

Arg Asp Asp Leu Glu Ser Leu Gly Tyr Val Leu Met Tyr Phe Asn Leu
            195                 200                 205

Gly Ser Leu Pro Trp Gln Gly Leu Lys Ala Ala Thr Lys Arg Gln Lys
        210                 215                 220

Tyr Glu Arg Ile Ser Glu Lys Lys Met Ser Thr Pro Ile Glu Val Leu
225                 230                 235                 240

Cys Lys Gly Tyr Pro Ser Glu Phe Ala Thr Tyr Leu Asn Phe Cys Arg
                245                 250                 255

Ser Leu Arg Phe Asp Asp Lys Pro Asp Tyr Ser Tyr Leu Arg Gln Leu
            260                 265                 270

Phe Arg Asn Leu Phe His Arg Gln Gly Phe Ser Tyr Asp Tyr Val Phe
        275                 280                 285

Asp Trp Asn Met Leu Lys Phe Gly Ala Ser Arg Ala Ala Asp Asp Ala
    290                 295                 300

Glu Arg Glu Arg Arg Asp Arg Glu Glu Arg Leu Arg His Ser Arg Asn
305                 310                 315                 320

Pro Ala Thr Arg Gly Leu Pro Ser Thr Ala Ser Gly Arg Leu Arg Gly
                325                 330                 335

Thr Gln Glu Val Ala Pro Pro Thr Pro Leu Thr Pro Thr Ser His Thr
            340                 345                 350

Ala Asn Thr Ser Pro Arg Pro Val Ser Gly Met Glu Arg Glu Arg Lys
        355                 360                 365

Val Ser Met Arg Leu His Arg Gly Ala Pro Val Asn Ile Ser Ser Ser
    370                 375                 380

Asp Leu Thr Gly Arg Gln Asp Thr Ser Arg Met Ser Thr Ser Gln Ile
385                 390                 395                 400

Pro Gly Arg Val Ala Ser Ser Gly Leu Gln Ser Val Val His Arg
                405                 410                 415

<210> SEQ ID NO 51
<211> LENGTH: 337
<212> TYPE: PRT
<213> ORGANISM: Homo sapiens

<400> SEQUENCE: 51

Met Ala Ser Ser Gly Ser Lys Ala Glu Phe Ile Val Gly Gly Lys
1               5                   10                  15

Tyr Lys Leu Val Arg Lys Ile Gly Ser Gly Ser Phe Gly Asp Ile Tyr
                20                  25                  30

Leu Ala Ile Asn Ile Thr Asn Gly Glu Glu Val Ala Val Lys Leu Glu
            35                  40                  45

Ser Gln Lys Ala Arg His Pro Gln Leu Leu Tyr Glu Ser Lys Leu Tyr
        50                  55                  60

Lys Ile Leu Gln Gly Gly Val Gly Ile Pro His Ile Arg Trp Tyr Gly
65                  70                  75                  80
```

```
Gln Glu Lys Asp Tyr Asn Val Leu Val Met Asp Leu Leu Gly Pro Ser
                85                  90                  95

Leu Glu Asp Leu Phe Asn Phe Cys Ser Arg Arg Phe Thr Met Lys Thr
            100                 105                 110

Val Leu Met Leu Ala Asp Gln Met Ile Ser Arg Ile Glu Tyr Val His
        115                 120                 125

Thr Lys Asn Phe Ile His Arg Asp Ile Lys Pro Asp Asn Phe Leu Met
    130                 135                 140

Gly Ile Gly Arg His Cys Asn Lys Leu Phe Leu Ile Asp Phe Gly Leu
145                 150                 155                 160

Ala Lys Lys Tyr Arg Asp Asn Arg Thr Arg Gln His Ile Pro Tyr Arg
                165                 170                 175

Glu Asp Lys Asn Leu Thr Gly Thr Ala Arg Tyr Ala Ser Ile Asn Ala
            180                 185                 190

His Leu Gly Ile Glu Gln Ser Arg Arg Asp Asp Met Glu Ser Leu Gly
        195                 200                 205

Tyr Val Leu Met Tyr Phe Asn Arg Thr Ser Leu Pro Trp Gln Gly Leu
    210                 215                 220

Lys Ala Ala Thr Lys Lys Gln Lys Tyr Glu Lys Ile Ser Glu Lys Lys
225                 230                 235                 240

Met Ser Thr Pro Val Glu Val Leu Cys Lys Gly Phe Pro Ala Glu Phe
                245                 250                 255

Ala Met Tyr Leu Asn Tyr Cys Arg Gly Leu Arg Phe Glu Glu Ala Pro
            260                 265                 270

Asp Tyr Met Tyr Leu Arg Gln Leu Phe Arg Ile Leu Phe Arg Thr Leu
        275                 280                 285

Asn His Gln Tyr Asp Tyr Thr Phe Asp Trp Thr Met Leu Lys Gln Lys
    290                 295                 300

Ala Ala Gln Gln Ala Ala Ser Ser Gly Gln Gly Gln Gln Ala Gln
305                 310                 315                 320

Thr Pro Thr Gly Lys Gln Thr Asp Lys Thr Lys Ser Asn Met Lys Gly
                325                 330                 335

Phe

<210> SEQ ID NO 52
<211> LENGTH: 447
<212> TYPE: PRT
<213> ORGANISM: Homo sapiens

<400> SEQUENCE: 52

Met Glu Asn Lys Lys Lys Asp Lys Asp Lys Ser Asp Asp Arg Met Ala
1               5                   10                  15

Arg Pro Ser Gly Arg Ser Gly His Asn Thr Arg Gly Thr Gly Ser Ser
                20                  25                  30

Ser Ser Gly Val Leu Met Val Gly Pro Asn Phe Arg Val Gly Lys Lys
            35                  40                  45

Ile Gly Cys Gly Asn Phe Gly Glu Leu Arg Leu Gly Lys Asn Leu Tyr
        50                  55                  60

Thr Asn Glu Tyr Val Ala Ile Lys Leu Glu Pro Met Lys Ser Arg Ala
65                  70                  75                  80

Pro Gln Leu His Leu Glu Tyr Arg Phe Tyr Lys Gln Leu Gly Ser Gly
                85                  90                  95

Asp Gly Ile Pro Gln Val Tyr Tyr Phe Gly Pro Cys Gly Lys Tyr Asn
            100                 105                 110
```

```
Ala Met Val Leu Glu Leu Leu Gly Pro Ser Leu Glu Asp Leu Phe Asp
            115                 120                 125

Leu Cys Asp Arg Thr Phe Ser Leu Lys Thr Val Leu Met Ile Ala Ile
        130                 135                 140

Gln Leu Ile Ser Arg Met Glu Tyr Val His Ser Lys Asn Leu Ile Tyr
145                 150                 155                 160

Arg Asp Val Lys Pro Glu Asn Phe Leu Ile Gly Arg Pro Arg Asn Lys
                165                 170                 175

Thr Gln Gln Val Ile His Ile Ile Asp Phe Gly Leu Ala Lys Glu Tyr
            180                 185                 190

Ile Asp Pro Glu Thr Lys Lys His Ile Pro Tyr Arg Glu His Lys Ser
        195                 200                 205

Leu Thr Gly Thr Ala Arg Tyr Met Ser Ile Asn Thr His Leu Gly Lys
    210                 215                 220

Glu Gln Ser Arg Arg Asp Asp Leu Glu Ala Leu Gly His Met Phe Met
225                 230                 235                 240

Tyr Phe Leu Arg Gly Ser Leu Pro Trp Gln Gly Leu Lys Ala Asp Thr
                245                 250                 255

Leu Lys Glu Arg Tyr Gln Lys Ile Gly Asp Thr Lys Arg Ala Thr Pro
            260                 265                 270

Ile Glu Val Leu Cys Glu Asn Phe Pro Glu Met Ala Thr Tyr Leu Arg
        275                 280                 285

Tyr Val Arg Arg Leu Asp Phe Phe Glu Lys Pro Asp Tyr Glu Tyr Leu
    290                 295                 300

Arg Lys Leu Phe Thr Asp Leu Phe Asp Arg Lys Gly Tyr Met Phe Asp
305                 310                 315                 320

Tyr Glu Tyr Asp Trp Ile Gly Lys Gln Leu Pro Thr Pro Val Gly Ala
                325                 330                 335

Val Gln Gln Asp Pro Ala Leu Ser Ser Asn Arg Glu Ala His Gln His
            340                 345                 350

Arg Asp Lys Met Gln Gln Ser Lys Asn Gln Ser Ala Asp His Arg Ala
        355                 360                 365

Ala Trp Asp Ser Gln Gln Ala Asn Pro His His Leu Arg Ala His Leu
    370                 375                 380

Ala Ala Asp Arg His Gly Gly Ser Val Gln Val Ser Ser Thr Asn
385                 390                 395                 400

Gly Glu Leu Asn Thr Asp Asp Pro Thr Ala Gly Arg Ser Asn Ala Pro
                405                 410                 415

Ile Thr Ala Pro Thr Glu Val Glu Val Met Asp Glu Thr Lys Cys Cys
            420                 425                 430

Cys Phe Phe Lys Arg Arg Lys Arg Lys Thr Ile Gln Arg His Lys
        435                 440                 445

<210> SEQ ID NO 53
<211> LENGTH: 463
<212> TYPE: PRT
<213> ORGANISM: Oryza sativa

<400> SEQUENCE: 53

Met Glu His Val Ile Gly Gly Lys Phe Lys Leu Gly Arg Lys Ile Gly
 1               5                  10                  15

Ser Gly Ser Phe Gly Glu Leu Tyr Leu Gly Val Asn Ile Gln Ser Ser
                20                  25                  30

Glu Glu Val Ala Ile Lys Leu Glu Ser Val Lys Ser Arg His Pro Gln
```

-continued

```
                35                  40                  45
Leu His Tyr Glu Ser Lys Leu Tyr Met Leu Leu Gln Gly Gly Thr Gly
 50                  55                  60

Ile Pro His Leu Lys Trp Phe Gly Val Glu Gly Tyr Asn Val Met
 65                  70                  75                  80

Val Ile Asp Leu Leu Gly Pro Ser Leu Glu Asp Leu Phe Asn Tyr Cys
                 85                  90                  95

Asn Arg Lys Phe Ser Leu Lys Thr Val Leu Met Leu Ala Asp Gln Met
                100                 105                 110

Ile Asn Arg Val Glu Tyr Met His Thr Arg Gly Phe Leu His Arg Asp
            115                 120                 125

Ile Lys Pro Asp Asn Phe Leu Met Gly Leu Gly Arg Lys Ala Ser Gln
        130                 135                 140

Val Tyr Val Ile Asp Tyr Val Leu Ala Lys Lys Tyr Arg Asp Leu Gln
145                 150                 155                 160

Thr His Lys His Ile Pro Tyr Arg Glu Asn Lys Asn Leu Thr Gly Thr
                165                 170                 175

Ala Arg Tyr Ala Ser Val Asn Thr His Leu Gly Val Glu Gln Ser Arg
            180                 185                 190

Arg Asp Asp Leu Glu Ser Leu Gly Tyr Val Leu Met Tyr Phe Leu Arg
        195                 200                 205

Gly Ser Leu Pro Trp Gln Gly Leu Lys Ala Gly Thr Lys Lys Gln Lys
210                 215                 220

Tyr Asp Lys Ile Ser Glu Lys Lys Met Leu Thr Pro Val Glu Val Leu
225                 230                 235                 240

Cys Lys Ser Tyr Pro Thr Glu Phe Ile Ser Tyr Phe His Tyr Cys Arg
                245                 250                 255

Ser Leu Arg Phe Glu Asp Lys Pro Asp Tyr Ser Tyr Leu Lys Arg Leu
            260                 265                 270

Phe Arg Asp Leu Phe Ile Arg Glu Gly Tyr Gln Leu Asp Tyr Ile Phe
        275                 280                 285

Asp Trp Thr Lys Gln Gly Ser Glu Ser Asn Arg Leu Arg Ser Ser Gly
290                 295                 300

Arg Thr Ser Gly Leu Val Gly Pro Ser Ala Glu Arg Thr Glu Arg Ala
305                 310                 315                 320

Ala Ala Arg Gln Asp Val Pro Asp Arg Phe Ser Gly Thr Val Asp Pro
                325                 330                 335

Phe Ala Arg Arg Thr Gly Ser Gly Ser Gly His Tyr Gly Glu His Thr
            340                 345                 350

Lys His Arg Asn Ile Leu Asp Ser Leu Leu Ala Pro Lys Thr Ala Val
        355                 360                 365

Asp Leu Asp Lys Arg Arg Pro Thr Ser Ser Ser Arg Asn Gly Ser Thr
370                 375                 380

Ser Arg Lys Ala Leu Leu Ser Ser Ser Arg Pro Ser Ser Gly Asp Pro
385                 390                 395                 400

Ile Asp Pro Asn Arg Ser Asn Leu Ile Pro Thr Ser Ser Gly Ser Ser
                405                 410                 415

Arg Pro Ser Thr Met Gln Arg Leu His Gln Ser Thr Gly Leu Glu Thr
            420                 425                 430

Arg Ser Ser Leu Thr Lys Thr Ala Arg Asn Val His Asp Asp Pro Thr
        435                 440                 445

Leu Arg Thr Phe Glu Arg Leu Ser Ile Ser Ala Asp Arg Arg Lys
450                 455                 460
```

<210> SEQ ID NO 54
<211> LENGTH: 2250
<212> TYPE: DNA
<213> ORGANISM: Hordeum vulgare

<400> SEQUENCE: 54

```
ggaaggccag ctccaaaggc tagaggaaag agggtcgagg ctattgattt ggctgaccag      60
ccttttgagg acatccctga agctattgtt ggagaggcag ttgcaggcac agcccagcag     120
gtccttggtt tgaacaaggt agctgacagg gccgccaact tcaaaatgga aggtgcaagc     180
ggtgacagac ttgcagcggc ggaggatgaa gccacgacga cgccagtgcc tgagagggtt     240
caagttggtg gctctccaga atatataact gataggaagt tgggcaaagg tggatttggc     300
caggtctatg ttggcagaag aataactggt ggggcttctc gtacaggccc agatgcatac     360
gaggttgcac tcaaacttga acatcgaaga agcaaaggat gtagttatgg ccccccgttt     420
gagtggcagg tttatcagtc tctcaatggt tgttatggca taccatcagt ccactacaag     480
ggtcgccagg gagactacta cattcttgtc atggatatgc ttggtcctag cctctgggat     540
gtttggaatt caatgggaca ggcgatgtct tctcatatgg tggcttgcat tgccgtggag     600
tccatatcaa tccttgagaa gcttcattcc aaaggctttg tccatggaga tgtaaagcca     660
gaaaactttc tgcttggtca acctggatca cctgatgaga agaagctttt cctaattgat     720
cttggtttag catccaagtg gaaaaaagca tcatccagtc agcatgttga atatgaccag     780
aggccagaca tctttagggg aacaattaga tatgctagtg tccatgctca tttaggccgg     840
acaggcagta gaagggatga tttggagtca ctagcgtaca cccttatttt tttaataaga     900
ggaagattac cttggcaagg ttttcaggga acaacaaga gctttcttgt ttgtaagaag     960
aagatggcta cctctgcgga tgttctgagt tgcttttgtc cacctccatt caagcatttt    1020
cttgagatgg tcactaatat gaaatttgat gaagagccaa attacgcaaa actcatttct    1080
ctctttgata gtttgattga agtgcctgct tcaagaccca tcagaattga tggggctcta    1140
aaggttgggc agaaacgtgg aagaatggtt gtaaatcttg aagaagagga acagcctaag    1200
aagaaagttc ggttggggag cccagcaact caatggattt cggtttataa tgctaggcgg    1260
cccatgaagc agcgatacca ctacaatgta gccgattcaa ggttgcacca gcatatagaa    1320
aaaggcaatg aagatggctt gtatattagt tgcgtagctt cttcagcaaa ttttttgggct    1380
ctcataatgg acgctgggac cggttttggt tctcaagtgt atgagctttc acaaattttc    1440
ctgcacaagg attggattat ggagcaatgg gaaaagaact tctatataac agcaatagct    1500
ggagcaacca atggaagctc actggttgtg atgtccaaag gaactccgta cacgcagcag    1560
tcatacaaag tcagcgaatc ttttccttat aagtggatta ataaaaagtg gaaagaaggt    1620
tttcatgtaa catccatggg tactgctggg aaccgttggg gagttgtcat gtcgaggaat    1680
gctggctact ctgaccaggt tgtggagttg gattttctgt atccaagtga aggactgcat    1740
cggcgatggg agagtggcta cagaataact tcatccgcag gcacacctga ccaagctgct    1800
tttatcttga gcataccaaa gaggaagcca ctggacgaga cccaggaaac ccttcgaact    1860
tctgccttcc ctagtaacca tgtgaaggag aagtgggcga agaacctgta catcgcctcg    1920
atctgctacg gacgaactgc gtgttgatgc cgtacttgag cttgagggcg aaatcacctg    1980
agttttacca ctggagccag aagagagttc gagacggaac aaaactccgc gtcaaccttat   2040
tacctaggtt tcaagcgcaa ttggctggca ctggcactgg gctggcctct ttcggttggc    2100
```

```
ggcatgctat tctaattgta aagaatctcg tgaagatcat cggtgttgta tcagtcagtc    2160
ctcatcggat ggatatgaac ctgttgataa gataaggtca tattattggc agatttgctg    2220
ttgttcattc cgaaaaaaaa aaaaaaaaa                                      2250
```

<210> SEQ ID NO 55
<211> LENGTH: 593
<212> TYPE: PRT
<213> ORGANISM: Hordeum vulgare

<400> SEQUENCE: 55

```
Met Glu Gly Ala Ser Gly Asp Arg Leu Ala Ala Glu Asp Glu Ala
 1               5                  10                  15

Thr Thr Thr Pro Val Pro Glu Arg Val Gln Val Gly Gly Ser Pro Glu
            20                  25                  30

Tyr Ile Thr Asp Arg Lys Leu Gly Lys Gly Gly Phe Gly Gln Val Tyr
         35                  40                  45

Val Gly Arg Arg Ile Thr Gly Gly Ala Ser Arg Thr Gly Pro Asp Ala
 50                  55                  60

Tyr Glu Val Ala Leu Lys Leu Glu His Arg Arg Ser Lys Gly Cys Ser
65                  70                  75                  80

Tyr Gly Pro Pro Phe Glu Trp Gln Val Tyr Gln Ser Leu Asn Gly Cys
                85                  90                  95

Tyr Gly Ile Pro Ser Val His Tyr Lys Gly Arg Gln Gly Asp Tyr Tyr
            100                 105                 110

Ile Leu Val Met Asp Met Leu Gly Pro Ser Leu Trp Asp Val Trp Asn
         115                 120                 125

Ser Met Gly Gln Ala Met Ser Ser His Met Val Ala Cys Ile Ala Val
130                 135                 140

Glu Ser Ile Ser Ile Leu Glu Lys Leu His Ser Lys Gly Phe Val His
145                 150                 155                 160

Gly Asp Val Lys Pro Glu Asn Phe Leu Leu Gly Gln Pro Gly Ser Pro
                165                 170                 175

Asp Glu Lys Lys Leu Phe Leu Ile Asp Leu Gly Leu Ala Ser Lys Trp
            180                 185                 190

Lys Lys Ala Ser Ser Ser Gln His Val Glu Tyr Asp Gln Arg Pro Asp
         195                 200                 205

Ile Phe Arg Gly Thr Ile Arg Tyr Ala Ser Val His Ala His Leu Gly
210                 215                 220

Arg Thr Gly Ser Arg Arg Asp Asp Leu Glu Ser Leu Ala Tyr Thr Leu
225                 230                 235                 240

Ile Phe Leu Ile Arg Gly Arg Leu Pro Trp Gln Gly Phe Gln Gly Asp
                245                 250                 255

Asn Lys Ser Phe Leu Val Cys Lys Lys Met Ala Thr Ser Ala Asp
            260                 265                 270

Val Leu Ser Cys Phe Cys Pro Pro Phe Lys His Phe Leu Glu Met
         275                 280                 285

Val Thr Asn Met Lys Phe Asp Glu Glu Pro Asn Tyr Ala Lys Leu Ile
290                 295                 300

Ser Leu Phe Asp Ser Leu Ile Glu Val Pro Ala Ser Arg Pro Ile Arg
305                 310                 315                 320

Ile Asp Gly Ala Leu Lys Val Gly Gln Lys Gly Arg Met Val Val
                325                 330                 335

Asn Leu Glu Glu Glu Gln Pro Lys Lys Lys Val Arg Leu Gly Ser
            340                 345                 350
```

```
Pro Ala Thr Gln Trp Ile Ser Val Tyr Asn Ala Arg Arg Pro Met Lys
            355                 360                 365

Gln Arg Tyr His Tyr Asn Val Ala Asp Ser Arg Leu His Gln His Ile
        370                 375                 380

Glu Lys Gly Asn Glu Asp Gly Leu Tyr Ile Ser Cys Val Ala Ser Ser
385                 390                 395                 400

Ala Asn Phe Trp Ala Leu Ile Met Asp Ala Gly Thr Gly Phe Gly Ser
                405                 410                 415

Gln Val Tyr Glu Leu Ser Gln Ile Phe Leu His Lys Asp Trp Ile Met
            420                 425                 430

Glu Gln Trp Glu Lys Asn Phe Tyr Ile Thr Ala Ile Ala Gly Ala Thr
            435                 440                 445

Asn Gly Ser Ser Leu Val Val Met Ser Lys Gly Thr Pro Tyr Thr Gln
        450                 455                 460

Gln Ser Tyr Lys Val Ser Glu Ser Phe Pro Tyr Lys Trp Ile Asn Lys
465                 470                 475                 480

Lys Trp Lys Glu Gly Phe His Val Thr Ser Met Gly Thr Ala Gly Asn
                485                 490                 495

Arg Trp Gly Val Val Met Ser Arg Asn Ala Gly Tyr Ser Asp Gln Val
            500                 505                 510

Val Glu Leu Asp Phe Leu Tyr Pro Ser Glu Gly Leu His Arg Arg Trp
        515                 520                 525

Glu Ser Gly Tyr Arg Ile Thr Ser Ser Ala Gly Thr Pro Asp Gln Ala
530                 535                 540

Ala Phe Ile Leu Ser Ile Pro Lys Arg Lys Pro Leu Asp Glu Thr Gln
545                 550                 555                 560

Glu Thr Leu Arg Thr Ser Ala Phe Pro Ser Asn His Val Lys Glu Lys
                565                 570                 575

Trp Ala Lys Asn Leu Tyr Ile Ala Ser Ile Cys Tyr Gly Arg Thr Ala
            580                 585                 590

Cys

<210> SEQ ID NO 56
<211> LENGTH: 1999
<212> TYPE: DNA
<213> ORGANISM: Glycine max

<400> SEQUENCE: 56
agcaacgtgg ttgaatgtag caccagtcta gtcagttgca ggcttcctgc acgctactga    60
aaaagaaaga aaatccgttt ggatgaatgc gcgaggggaa gagagactct ctctcctctt   120
ccttctacac gtttagagag agaaagtgtg tctcattttt caatcttgcc cgcatctttt   180
tgcgatttct cattttctc ctgttccttt cctttccgtt tctctgctac tacttccaac    240
tccttccatt ctcaactttc tttcaatctc tagggtttaa ttcgccactc atcgaatgga   300
acctcgggtt gcgaacaagt tccgtcttgg ccgcaagatt ggtagcggat ccttcggcga   360
gatctatctc ggtacgaata ctcagacaaa tgaagaggtt gcagttaagc tcgaaaatgt   420
caaaactaag catcctcaat tgttgtacga atcaaagttg tataaaatac tgcaaggagg   480
aactgggatc ccaaatgtga gatggtttgg agttgaagga gattacaatg tccttgtgat   540
ggatttactg ggacctagtc ttgaggattt attcaatttc tgtacccgta aattgtccct   600
caaaactgtt ctcatgcttg ctgatcagat gataaatcga gttgaattta ttcattccaa   660 atcatttta cataggggaca tcaagccaga caacttccta atgggtttgg ggaggcgtgc   720
```

```
aaatcaagtt tatgccattg actttggtct tgctaagaag cacagagaca cctctaccca    780
tcaacatatt ccttacagag agaataagaa tttgactgga actgctagat atgctagtat    840
gaatactcat cttggaattg agcaaagccg tagggacgac ttagaatcac ttggatttgt    900
tcttatgtat tttttgagag gaagtctccc atggcaggga ttgaaagcag gtactaagaa    960
gcagaagtat gagagaatca gtgagaagaa agtttctact tctattgagt ctctgtgccg   1020
tagctacccc tcagagttcg cttcatactt tcattactgt cggtcactgc aatttgatga   1080
taaaccagat tatgcttatc tgaaaaggct tttccgtgac cttttcattc gtgaaggatt   1140
ccagtttgat tatgtctttg attggaccat tttgaaatat cagcaatctc aaattgccac   1200
acctcctgct cgtgctattg gtcctgctgc tggaccaagt tctgggctgc caccagctgt   1260
tgtaaatgct gatagacaga caggtgggga aaacagtagg catactggtt ggtcttcatc   1320
tgatcctgct cgaagaagaa actctggacc tattgcaaat gatggaatgt tgtcaagaca   1380
aaaagcccca tttccaagtg attcaactcg atctaaagat gttatgttgt ctagttctaa   1440
tttccgttca gtggatctaa caaggcgagg tgttgtatca agcagtcgtg atgcaactgt   1500
tggcaatgag actgagcctt ctcatcctct caccgtggat gctagtcaag gagcacttcg   1560
taaaatctcc ggtgctcaaa gaagttcacc tattatgcca tttgagcaca accgaacatc   1620
ctctggaaga aatacatcaa acatgaagaa ttacgagtca actatccggg gtattgagac   1680
cctaaatttc aatgacgaga ggttacagta ttagcagctt ccattctcga ctacctatca   1740
tagtaaattc ttaaaagaat tttataaact accgagtgga gtgtgttgtg ttgtctgtgc   1800
attttgttgg aggaaagctg caacaagatg gtaatggtca ctataaagtg ttaaagaaag   1860
atatgctcaa ccctgacaaa tctggccttg aaaaggcttt tgttaacaca gttgaccgtg   1920
ttggttctaa aaaaaaaaaa aaaaaaaaaa aaaaaaaaaa aaaaaaaaaa aaaaaaaaaa   1980
aaaaaaaaaa aaaaaaaaa                                                1999
```

<210> SEQ ID NO 57
<211> LENGTH: 472
<212> TYPE: PRT
<213> ORGANISM: Glycine max

<400> SEQUENCE: 57

```
Met Glu Pro Arg Val Ala Asn Lys Phe Arg Leu Gly Arg Lys Ile Gly
 1               5                  10                  15

Ser Gly Ser Phe Gly Glu Ile Tyr Leu Gly Thr Asn Thr Gln Thr Asn
            20                  25                  30

Glu Glu Val Ala Val Lys Leu Glu Asn Val Lys Thr Lys His Pro Gln
        35                  40                  45

Leu Leu Tyr Glu Ser Lys Leu Tyr Lys Ile Leu Gln Gly Gly Thr Gly
    50                  55                  60

Ile Pro Asn Val Arg Trp Phe Gly Val Glu Gly Asp Tyr Asn Val Leu
65                  70                  75                  80

Val Met Asp Leu Leu Gly Pro Ser Leu Glu Asp Leu Phe Asn Phe Cys
                85                  90                  95

Thr Arg Lys Leu Ser Leu Lys Thr Val Leu Met Leu Ala Asp Gln Met
            100                 105                 110

Ile Asn Arg Val Glu Phe Ile His Ser Lys Ser Phe Leu His Arg Asp
        115                 120                 125

Ile Lys Pro Asp Asn Phe Leu Met Gly Leu Gly Arg Arg Ala Asn Gln
    130                 135                 140
```

```
Val Tyr Ala Ile Asp Phe Gly Leu Ala Lys Lys His Arg Asp Thr Ser
145                 150                 155                 160

Thr His Gln His Ile Pro Tyr Arg Glu Asn Lys Asn Leu Thr Gly Thr
                165                 170                 175

Ala Arg Tyr Ala Ser Met Asn Thr His Leu Gly Ile Glu Gln Ser Arg
            180                 185                 190

Arg Asp Asp Leu Glu Ser Leu Gly Phe Val Leu Met Tyr Phe Leu Arg
        195                 200                 205

Gly Ser Leu Pro Trp Gln Gly Leu Lys Ala Gly Thr Lys Lys Gln Lys
    210                 215                 220

Tyr Glu Arg Ile Ser Glu Lys Lys Val Ser Thr Ser Ile Glu Ser Leu
225                 230                 235                 240

Cys Arg Ser Tyr Pro Ser Glu Phe Ala Ser Tyr Phe His Tyr Cys Arg
                245                 250                 255

Ser Leu Gln Phe Asp Asp Lys Pro Asp Tyr Ala Tyr Leu Lys Arg Leu
            260                 265                 270

Phe Arg Asp Leu Phe Ile Arg Glu Gly Phe Gln Phe Asp Tyr Val Phe
        275                 280                 285

Asp Trp Thr Ile Leu Lys Tyr Gln Gln Ser Gln Ile Ala Thr Pro Pro
    290                 295                 300

Ala Arg Ala Ile Gly Pro Ala Gly Pro Ser Ser Gly Leu Pro Pro
305                 310                 315                 320

Ala Val Val Asn Ala Asp Arg Gln Thr Gly Gly Glu Asn Ser Arg His
                325                 330                 335

Thr Gly Trp Ser Ser Ser Asp Pro Ala Arg Arg Asn Ser Gly Pro
            340                 345                 350

Ile Ala Asn Asp Gly Met Leu Ser Arg Gln Lys Ala Pro Phe Pro Ser
        355                 360                 365

Asp Ser Thr Arg Ser Lys Asp Val Met Leu Ser Ser Ser Asn Phe Arg
    370                 375                 380

Ser Ser Gly Ser Thr Arg Arg Gly Val Val Ser Ser Ser Arg Asp Ala
385                 390                 395                 400

Thr Val Gly Asn Glu Thr Glu Pro Ser His Pro Leu Thr Val Asp Ala
                405                 410                 415

Ser Gln Gly Ala Leu Arg Lys Ile Ser Gly Ala Gln Arg Ser Ser Pro
            420                 425                 430

Ile Met Pro Phe Glu His Asn Arg Thr Ser Ser Gly Arg Asn Thr Ser
        435                 440                 445

Asn Met Lys Asn Tyr Glu Ser Thr Ile Arg Gly Ile Glu Thr Leu Asn
450                 455                 460

Phe Asn Asp Glu Arg Leu Gln Tyr
465                 470

<210> SEQ ID NO 58
<211> LENGTH: 2035
<212> TYPE: DNA
<213> ORGANISM: Glycine max

<400> SEQUENCE: 58
cccatcactc ttacgctttc tttcttttt  tcttccaaat tctctctttc ttctaaccta    60
accctacaat tatgccccat taacacaaat cgcaattacc ccaaattcct caccctagcg   120
tagatcgatc tcttcttcct tcgtgaattc tggttcaggg tggctgccat gtatggcact   180 tagtatttc cctttttgaa gattaggggt gggtggttg tgtctcgctt agggttccaa     240
```

```
agtttgttgt tttgaatgga acctcgcgtt gggaataagt ttcgcctggg tcggaagatc    300
ggaagtggct cctttgggga gatctattta ggcactaata ttcagacaaa tgaagaggtt    360
gcaattaagc ttgaaaatgt caagacaaaa catcctcaat tgctgtatga gtccaagttg    420
tacagaattc tccagggagg aactggaatt ccaaatgtca gatggtttgg agtggaggga    480
gattacaatg ttttagtgat ggatctgctt ggaccgagtc ttgaagatct ttttaacttc    540
tgcagtagaa agctatcact aaagacagtt ctcatgcttg ctgatcaaat gatcaaccgt    600
gttgagttca ttcattcaaa atcgtttctg catcgggata tcaaaccgga taattttcta    660
atgggattag gaaggcgtgc aaaccaggtt tatgctattg attttggttt ggctaagaaa    720
tacagagata gttcaacaca tcaacacatt ccttacaggg aaaataagaa tttgactgga    780
actgcaaggt atgccagcat gaacactcac cttggcattg aacaaagcag aagagatgat    840
cttgagtctc ttggttatgt tttgatgtac ttcttgagag gaagtcttcc ttggcagggt    900
cttaaagcgg gaacaaagaa acagaagtat gagaaaatca gtgaaaaaaa ggtttctacc    960
tcgattgaag ccttgtgtcg aggttatcca acagaatttg catcttactt ccattactgc   1020
cgatcattga ggtttgatga taagccagat tatgcgtacc tcaaaaggat atttcgtgac   1080
ctgtttattc gtgaaggatt ccagtttgat tatgtctttg actggaccat tttgaagtat   1140
cagcaatcac agctagccac tcctccaaca cgggccattg gtcctagtgc tggaaccagc   1200
tctggaatgc cccccgctgt tactaatgct gataggcata caggagggga agaaggtaga   1260
cctcctgctt tggtttcagt ggattcctcg aggcgcagaa tgtcagggcc cattttaaat   1320
actttatcaa gtgccaatgc cttgggtcag tcaagtggat catctaggag ggttgctgtc   1380
tctagtagcc gtgatgcatt tgttggtgct gagtcagata tccgtactcg cactgctgag   1440
gctagccctg gagcagcaca tcgagctttg agtgggcaaa gaagttctcc aattggatct   1500
tctgatccta gagagttgt atcatcaggg agaaatgctt ctcatgtgaa aaattatgac   1560
actgcactta ggggcatgga aggtttgcaa ttagaaaatg atgagaggac ccattattaa   1620
tttcacaact tctctcctat taatttgtga gttgataggc actgccaacg ttgcttgtgt   1680
tgctaagttg agctgtgaga aaattcggat ctgaacttga aattctggct ttgtattgtt   1740
aacccatctg tcaaaccga tgaagctgtg aagctgaaat aatttgagcc aaaccaggga   1800
ttgtgcttgc tgtaaagctc agttttaatt ggttcttcta gctggaactc ctaagtttta   1860
taacatttt ctgagttatt atattggttt accagatgtt tacagtttca cgtggactgc   1920
aaatgtcaaa aactatcaaa taccagcaaa aatgtaatta gccattgtac tcttgttgga   1980
taagattccc ttggtttaca cgatgtaatt gtctggcaaa aaaaaaaaa aaaaa          2035
```

<210> SEQ ID NO 59
<211> LENGTH: 454
<212> TYPE: PRT
<213> ORGANISM: Glycine max

<400> SEQUENCE: 59

Met Glu Pro Arg Val Gly Asn Lys Phe Arg Leu Gly Arg Lys Ile Gly
  1               5                  10                  15

Ser Gly Ser Phe Gly Glu Ile Tyr Leu Gly Thr Asn Ile Gln Thr Asn
             20                  25                  30

Glu Glu Val Ala Ile Lys Leu Glu Asn Val Lys Thr Lys His Pro Gln
         35                  40                  45

Leu Leu Tyr Glu Ser Lys Leu Tyr Arg Ile Leu Gln Gly Gly Thr Gly

```
                50                  55                  60
Ile Pro Asn Val Arg Trp Phe Gly Val Glu Gly Asp Tyr Asn Val Leu
65                  70                  75                  80

Val Met Asp Leu Leu Gly Pro Ser Leu Glu Asp Leu Phe Asn Phe Cys
                85                  90                  95

Ser Arg Lys Leu Ser Leu Lys Thr Val Leu Met Leu Ala Asp Gln Met
            100                 105                 110

Ile Asn Arg Val Glu Phe Ile His Ser Lys Ser Phe Leu His Arg Asp
        115                 120                 125

Ile Lys Pro Asp Asn Phe Leu Met Gly Leu Gly Arg Arg Ala Asn Gln
    130                 135                 140

Val Tyr Ala Ile Asp Phe Gly Leu Ala Lys Lys Tyr Arg Asp Ser Ser
145                 150                 155                 160

Thr His Gln His Ile Pro Tyr Arg Glu Asn Lys Asn Leu Thr Gly Thr
                165                 170                 175

Ala Arg Tyr Ala Ser Met Asn Thr His Leu Gly Ile Glu Gln Ser Arg
            180                 185                 190

Arg Asp Asp Leu Glu Ser Leu Gly Tyr Val Leu Met Tyr Phe Leu Arg
        195                 200                 205

Gly Ser Leu Pro Trp Gln Gly Leu Lys Ala Gly Thr Lys Lys Gln Lys
    210                 215                 220

Tyr Glu Lys Ile Ser Glu Lys Lys Val Ser Thr Ser Ile Glu Ala Leu
225                 230                 235                 240

Cys Arg Gly Tyr Pro Thr Glu Phe Ala Ser Tyr Phe His Tyr Cys Arg
                245                 250                 255

Ser Leu Arg Phe Asp Asp Lys Pro Asp Tyr Ala Tyr Leu Lys Arg Ile
            260                 265                 270

Phe Arg Asp Leu Phe Ile Arg Glu Gly Phe Gln Phe Asp Tyr Val Phe
        275                 280                 285

Asp Trp Thr Ile Leu Lys Tyr Gln Gln Ser Gln Leu Ala Thr Pro Pro
    290                 295                 300

Thr Arg Ala Ile Gly Pro Ser Ala Gly Thr Ser Ser Gly Met Pro Pro
305                 310                 315                 320

Ala Val Thr Asn Ala Asp Arg His Thr Gly Gly Glu Glu Gly Arg Pro
                325                 330                 335

Pro Ala Leu Val Ser Val Asp Ser Ser Arg Arg Met Ser Gly Pro
            340                 345                 350

Ile Leu Asn Thr Leu Ser Ser Ala Asn Ala Leu Gly Gln Ser Ser Gly
        355                 360                 365

Ser Ser Arg Arg Val Ala Val Ser Ser Ser Arg Asp Ala Phe Val Gly
    370                 375                 380

Ala Glu Ser Asp Ile Arg Thr Arg Thr Ala Glu Ala Ser Pro Gly Ala
385                 390                 395                 400

Ala His Arg Ala Leu Ser Gly Gln Arg Ser Pro Ile Gly Ser Ser
                405                 410                 415

Asp Pro Lys Arg Val Val Ser Ser Gly Arg Asn Ala Ser His Val Lys
            420                 425                 430

Asn Tyr Asp Thr Ala Leu Arg Gly Met Glu Gly Leu Gln Leu Glu Asn
        435                 440                 445

Asp Glu Arg Thr His Tyr
    450

<210> SEQ ID NO 60
```

<211> LENGTH: 2560
<212> TYPE: DNA
<213> ORGANISM: Triticum aestivum

<400> SEQUENCE: 60

```
ctctctcgca gcgaacacac tccgcgtcta gccgatttgt atacatcagc accaccgcct        60
ccgccctcgg ccctcgctcc cattcccttc cctcaaatct gcgccggcac caccgctccc       120
gtcccgctcc ccgcactcgc caccgcacgc cgcgaccgga accttgccgc accgccccct       180
cccccttcgag atcggcgccg ttactgctgt ttggcggcgg aatctgaggg atcgacagcg      240
gcggggcgt gggccatggg gctcaatcgt tgacgatgcc tgtgctgcgt agtgcggctc        300
ggagggcccg tgaggcgcag gagaatccgg cggcggcggc ggcggcggcg gcggaagcac       360
cggttgtgcc accggcggcg aggaggcgca gggcggcgag aaggcaggag gcggaggcg        420
ttcgtgaggc cgccgcggcg gcggaggaga tcgcgcccgc ggaggactcg agtgaacgcg       480
ccggtgagga gccgatggat gaccaggaca gcgccgacaa acaggccggc gaggatgcct       540
ctccaatccc tgagacggtc caggtggcca attcacctag gtataaagtt gaaaggaagc       600
ttgggaaagg aggatttggc caagtatatg ttggccgccg catttcagct aatgctccag       660
gcgcagttga ggtggcgtta agtttgagc ataagaacag caaaggatgt aaccatgggc        720
ctccttatga gtggcaggtt tacgatatcc tcggtggcat tcacggggtt cctcgagtcc       780
actacaaagg gcgccaaggg gattacttca ttatggttat ggatatgctc ggtctcagtc      840
tgtgggatgc atgtagtaat aattcccaca caatgtcagt tgagatggtt gcttgcattg      900
ctatcgaagc tatctccata cttgagaaag tgcactcaaa aggatatgtc cacggggatg      960
tgaaacccga gaatttcttg ctaggacccc ctggaactcc tgaagagaaa aaactgtttc      1020
tcgtcgacct tggcttagct actaagtgga aggatagatc gacaggccat catgttgagt      1080
atgaccagcg acctgatatt ttcagggaa cgtttcgtta tgctagtgtt catgcacatc       1140
ttgggaggat aggcagcagg agggatgatt tagaatctct agcttataca ctagtctttc      1200
ttctacgggg acgtctacct tggcaaggct accaggtga aaacaagggt tttcttgttt       1260
gcaaaaagaa aatgtgcacc tctcctgaat ctctctgtag cttctgccct cagcccttta     1320
aggagtttgt agaatatgtg gtcaacttga gtttgatga agaacccaac tatgccaagt       1380
gtatctccct tttgatagt atagtgggcc caaatccaga tatcaggcca attaacacag       1440
atggtgctca gaagcttata caccaagttg gccaaaagag agggcgtata tcgttggaag       1500
gagagacaga tgagcaacca aagaagaaga tcaggatggg aatgcctgca acacagtgga      1560
taagtgttta taatgcaagg cggcctatga aacaaaggta ccactacaat gttgcagatt      1620
caaggcttgt acaacacatt gacaaaggga atgaagatgc actgtttatt agttgcatat      1680
catcttgtgc gaatctgtgg gcactaatca tggatgctgg cactgggttc tcttctcaag      1740
tttatgaact ttcaccacat ttccttcaca agaatggat aatggaccaa tgggatagga      1800
actactatat aactgcactt gctggagcaa acaatgggag ttccctggta gtgatgtcta      1860
aaggaacact gtatactcag cagtcctaca agtaagtga tacctttccc ttcaagtgga       1920
taaacaagaa atggcgtgat ggtttctatg tgacttccat ggcaactgct gggaataaat      1980
gggcgattgt tatgtcccgc aatgcagggt tttcggaaca ggttgttgag ctggacttct      2040
tgtacccctag tgagggagtc cataagaggt gggatagtgg ttaccgaata acagcagttg     2100
ctgcgacttg ggatcagact gcattgatct taagtgtacc aagaaggaag cctactgatg      2160
aaactcaaga gacactgaga acatctgctt tccccagtca gcatgtgaag gagaaatggt      2220
```

-continued

```
ccaagaatct ctaccttgct tcagtatgtt atgggcgtac cgtatcgtag aaatcctttg    2280
ccatgagagc tgaagcgtga gttaacctca tctttttgat ccagctcagc agtagttttc    2340
tgtttgtggg caagttgtga atgcggccta gtgtgttctt gtgaagatgt ttctgcctgt    2400
cgctgttaat tatagaaaaa tagtgtgtac agtagtaaat gttttgtagt cgtgttaatc    2460
ctttctgtag cggacgactc ttgactctag tgtaaggtga tacttagatg tgtaaacacc    2520
tgacttaatg ttttgtgctc cgaaaaaaaa aaaaaaaaa                           2560
```

<210> SEQ ID NO 61
<211> LENGTH: 664
<212> TYPE: PRT
<213> ORGANISM: Triticum aestivum

<400> SEQUENCE: 61

```
Met Pro Val Leu Arg Ser Ala Ala Arg Arg Ala Arg Glu Ala Gln Glu
  1               5                  10                  15

Asn Pro Ala Ala Ala Ala Ala Ala Glu Ala Pro Val Val Pro
             20                  25                  30

Pro Ala Ala Arg Arg Arg Ala Ala Arg Gln Glu Ala Gly Gly
         35                  40                  45

Val Arg Glu Ala Ala Ala Ala Glu Glu Ile Ala Pro Ala Glu Asp
     50                  55                  60

Ser Ser Glu Arg Ala Gly Glu Glu Pro Met Asp Asp Gln Asp Ser Ala
 65                  70                  75                  80

Asp Lys Gln Ala Gly Glu Asp Ala Ser Pro Ile Pro Glu Thr Val Gln
                 85                  90                  95

Val Ala Asn Ser Pro Arg Tyr Lys Val Glu Arg Lys Leu Gly Lys Gly
            100                 105                 110

Gly Phe Gly Gln Val Tyr Val Gly Arg Arg Ile Ser Ala Asn Ala Pro
        115                 120                 125

Gly Ala Val Glu Val Ala Leu Lys Phe Glu His Lys Asn Ser Lys Gly
    130                 135                 140

Cys Asn His Gly Pro Pro Tyr Glu Trp Gln Val Tyr Asp Ile Leu Gly
145                 150                 155                 160

Gly Ile His Gly Val Pro Arg Val His Tyr Lys Gly Arg Gln Gly Asp
                165                 170                 175

Tyr Phe Ile Met Val Met Asp Met Leu Gly Leu Ser Leu Trp Asp Ala
            180                 185                 190

Cys Ser Asn Asn Ser His Thr Met Ser Val Glu Met Ala Cys Ile
        195                 200                 205

Ala Ile Glu Ala Ile Ser Ile Leu Glu Lys Val His Ser Lys Gly Tyr
    210                 215                 220

Val His Gly Asp Val Lys Pro Glu Asn Phe Leu Leu Gly Pro Pro Gly
225                 230                 235                 240

Thr Pro Glu Glu Lys Lys Leu Phe Leu Val Asp Leu Gly Leu Ala Thr
                245                 250                 255

Lys Trp Lys Asp Arg Ser Thr Gly His His Val Glu Tyr Asp Gln Arg
            260                 265                 270

Pro Asp Ile Phe Arg Gly Thr Phe Arg Tyr Ala Ser Val His Ala His
        275                 280                 285

Leu Gly Arg Ile Gly Ser Arg Arg Asp Asp Leu Glu Ser Leu Ala Tyr
    290                 295                 300

Thr Leu Val Phe Leu Leu Arg Gly Arg Leu Pro Trp Gln Gly Tyr Gln
```

```
                305                 310                 315                 320
Gly Glu Asn Lys Gly Phe Leu Val Cys Lys Lys Met Cys Thr Ser
                325                 330                 335
Pro Glu Ser Leu Cys Ser Phe Cys Pro Gln Pro Phe Lys Glu Phe Val
            340                 345                 350
Glu Tyr Val Val Asn Leu Lys Phe Asp Glu Glu Pro Asn Tyr Ala Lys
            355                 360                 365
Cys Ile Ser Leu Phe Asp Ser Ile Val Gly Pro Asn Pro Asp Ile Arg
    370                 375                 380
Pro Ile Asn Thr Asp Gly Ala Gln Lys Leu Ile His Gln Val Gly Gln
385                 390                 395                 400
Lys Arg Gly Arg Ile Ser Leu Glu Gly Glu Thr Asp Glu Gln Pro Lys
                405                 410                 415
Lys Lys Ile Arg Met Gly Met Pro Ala Thr Gln Trp Ile Ser Val Tyr
                420                 425                 430
Asn Ala Arg Arg Pro Met Lys Gln Arg Tyr His Tyr Asn Val Ala Asp
                435                 440                 445
Ser Arg Leu Val Gln His Ile Asp Lys Gly Asn Glu Asp Gly Leu Phe
            450                 455                 460
Ile Ser Cys Ile Ser Ser Cys Ala Asn Leu Trp Ala Leu Ile Met Asp
465                 470                 475                 480
Ala Gly Thr Gly Phe Ser Ser Gln Val Tyr Glu Leu Ser Pro His Phe
                485                 490                 495
Leu His Lys Glu Trp Ile Met Asp Gln Trp Asp Arg Asn Tyr Tyr Ile
                500                 505                 510
Thr Ala Leu Ala Gly Ala Asn Asn Gly Ser Ser Leu Val Val Met Ser
                515                 520                 525
Lys Gly Thr Leu Tyr Thr Gln Gln Ser Tyr Lys Val Ser Asp Thr Phe
            530                 535                 540
Pro Phe Lys Trp Ile Asn Lys Lys Trp Arg Asp Gly Phe Tyr Val Thr
545                 550                 555                 560
Ser Met Ala Thr Ala Gly Asn Lys Trp Ala Ile Val Met Ser Arg Asn
                565                 570                 575
Ala Gly Phe Ser Glu Gln Val Val Glu Leu Asp Phe Leu Tyr Pro Ser
                580                 585                 590
Glu Gly Val His Lys Arg Trp Asp Ser Gly Tyr Arg Ile Thr Ala Val
                595                 600                 605
Ala Ala Thr Trp Asp Gln Thr Ala Leu Ile Leu Ser Val Pro Arg Arg
            610                 615                 620
Lys Pro Thr Asp Glu Thr Gln Glu Thr Leu Arg Thr Ser Ala Phe Pro
625                 630                 635                 640
Ser Gln His Val Lys Glu Lys Trp Ser Lys Asn Leu Tyr Leu Ala Ser
                645                 650                 655
Val Cys Tyr Gly Arg Thr Val Ser
                660

<210> SEQ ID NO 62
<211> LENGTH: 2269
<212> TYPE: DNA
<213> ORGANISM: Glycine max

<400> SEQUENCE: 62
gttcctgctt ccactccatc aaatccaaac cataataatc ataatgcatg agagagagat      60
ttcattcctc catttctct ctaaccatca ttttcttttc ttttagccta aaataattca     120
```

```
tccttctttt ttattatttc tatatttta tttatttatt ttttccatcg gagctgcatt      180
ttcctcttcc ttttttatg ttttttgaat ccgatcgatg aacgcggctt ctttgtttgt      240
agaattttg  gcattaaatg atcggaattc ggcgttggga tttgcttagg gtttcaaaaa     300
ctctctctct tttaaaaatt gttttttgaa tggaacctcg cgttgggaat aagtttcggc     360
ttggccgtaa gattggtagc ggatcgtttg gagagatcta tttaggtact aatattcaaa     420
ctaatgaaga ggttgcaatt aagcttgaaa atgtcaagac aaagcatcct cagttgctat     480
atgagtccaa gttgtacaga gttctccagg gaggaactgg aattccagat gttagatggt     540
ttggagtgga gggagattac aatgttctag tgatggatct gcttggacct agtcttgaag     600
atctatttaa cttctgcagt agaaagctct cactaaagac agttctcatg cttgctgatc     660
acatgatcaa ccgtgttgag tttgttcatt ctaaatcatt tcttcatcgg gatatcaaac     720
cagataattt cctcatgggc ttgggaaggc gggcaaacca ggtttactgt attgattttg     780
gtttggccaa gaaatataga gatagttcaa cccatcaaca cattccttac agggaaaaca     840
agaatttaac tgggactgct agatacgcga gtatgaatac ccaccttggc attgagcaaa     900
gtcgaagaga tgatttggag tctgttggtt ttgtcttgat gtatttcttg agaggaagtc     960
tcccttggca aggacttaaa gcaggaacaa agaaacacaa gtacgagaga atcagtgaaa    1020
aaaaggtttc tacctcaatt gaggccttgt gtcgaggtta tccaacagaa tttgcatcat    1080
acttccatta ctgccgctca ttaaggtttg atgataggcc agattatgct tacctcaaaa    1140
gaatattttg cgacttgttt attcgtgaag gattccagtt tgattatgtg tttgattgga    1200
caatcttgaa gtatcagcaa tcacagctag ctgctcctcc agcacgtgcc attggtccta    1260
atgttggaac tagttctgca atgccaccgg ctgtgactaa tgctgataga cagacaggag    1320
aggaagaagg gcgacctcct ggtctggttt cagggggattc cacaaggcga agaatgtcag   1380
ggcccatcac aaactctgta aatatttcaa agcagaaaaa tccagtcact acggatgctg    1440
cccttaataa ggaagccatg ttatcaaggc ccaatgtctt ggggcagtca agtggatcaa    1500
ggcgagctgc ggtttctagt aggcgtgatg catttgttgg ttcggatttg gatcttcgta    1560
ctcgttctac tgaggctaac cctggaacag caattaaaac atcatctgcg agaaatgctt    1620
ctcatgtcaa gaactatgaa actgcaatca gggcattga  gggtttgcaa ttagaaaatg    1680
atgagaaggc acattattga ttcctcacct tttcatgttg taaatataag ctttggttga    1740
cgggcactac aatagttgca tgttgccaag gtgagtcgcg aagggacgtg aatttgaact    1800
cagaagtctg ggcttgtgtt gtttaaccct tgtgctcatg ctgatcaagc atggaagctg    1860
aaaaaatttg agctaaatca gggattgttc ttgcttcgaa gctcagggtt tacgctggca    1920
ctagtcttct ggcgggaacc ctaaattttg taaccttttc ctgtgagtta ttattgattt    1980
accagatgtc taaagtgtca tgtggatcac attgttcaaa actatcaaat accagcaaaa    2040
atatctactc aagttttgga taagaccaaa gtttccaaga tgtttctgga gattactgcg    2100
gtatttagga atattcaagg ttcttgaaat gtttctacct tgtgaaattc ttataagctt    2160
gaatcctcgt atttctttag tttgtcttta atgttatctc gtaataatat ctgtaaattt    2220
ttattccaat aatttggaag gttttctttg caaaaaaaaa aaaaaaaa                 2269
```

<210> SEQ ID NO 63
<211> LENGTH: 456
<212> TYPE: PRT
<213> ORGANISM: Glycine max

<400> SEQUENCE: 63

```
Met Glu Pro Arg Val Gly Asn Lys Phe Arg Leu Gly Arg Lys Ile Gly
  1               5                  10                  15

Ser Gly Ser Phe Gly Glu Ile Tyr Leu Gly Thr Asn Ile Gln Thr Asn
             20                  25                  30

Glu Glu Val Ala Ile Lys Leu Glu Asn Val Lys Thr Lys His Pro Gln
         35                  40                  45

Leu Leu Tyr Glu Ser Lys Leu Tyr Arg Val Leu Gln Gly Gly Thr Gly
     50                  55                  60

Ile Pro Asp Val Arg Trp Phe Gly Val Glu Gly Asp Tyr Asn Val Leu
 65                  70                  75                  80

Val Met Asp Leu Leu Gly Pro Ser Leu Glu Asp Leu Phe Asn Phe Cys
                 85                  90                  95

Ser Arg Lys Leu Ser Leu Lys Thr Val Leu Met Leu Ala Asp His Met
             100                 105                 110

Ile Asn Arg Val Glu Phe Val His Ser Lys Ser Phe Leu His Arg Asp
         115                 120                 125

Ile Lys Pro Asp Asn Phe Leu Met Gly Leu Gly Arg Arg Ala Asn Gln
    130                 135                 140

Val Tyr Cys Ile Asp Phe Gly Leu Ala Lys Lys Tyr Arg Asp Ser Ser
145                 150                 155                 160

Thr His Gln His Ile Pro Tyr Arg Glu Asn Lys Asn Leu Thr Gly Thr
                165                 170                 175

Ala Arg Tyr Ala Ser Met Asn Thr His Leu Gly Ile Glu Gln Ser Arg
            180                 185                 190

Arg Asp Asp Leu Glu Ser Val Gly Phe Val Leu Met Tyr Phe Leu Arg
        195                 200                 205

Gly Ser Leu Pro Trp Gln Gly Leu Lys Ala Gly Thr Lys Lys His Lys
    210                 215                 220

Tyr Glu Arg Ile Ser Glu Lys Lys Val Ser Thr Ser Ile Glu Ala Leu
225                 230                 235                 240

Cys Arg Gly Tyr Pro Thr Glu Phe Ala Ser Tyr Phe His Tyr Cys Arg
                245                 250                 255

Ser Leu Arg Phe Asp Asp Arg Pro Asp Tyr Ala Tyr Leu Lys Arg Ile
            260                 265                 270

Phe Cys Asp Leu Phe Ile Arg Glu Gly Phe Gln Phe Asp Tyr Val Phe
        275                 280                 285

Asp Trp Thr Ile Leu Lys Tyr Gln Gln Ser Gln Leu Ala Ala Pro Pro
    290                 295                 300

Ala Arg Ala Ile Gly Pro Asn Val Gly Thr Ser Ser Ala Met Pro Pro
305                 310                 315                 320

Ala Val Thr Asn Ala Asp Arg Gln Thr Gly Glu Glu Gly Arg Pro
                325                 330                 335

Pro Gly Leu Val Ser Gly Asp Ser Thr Arg Arg Met Ser Gly Pro
            340                 345                 350

Ile Thr Asn Ser Val Asn Ile Ser Lys Gln Lys Asn Pro Val Thr Thr
    355                 360                 365

Asp Ala Ala Leu Asn Lys Glu Ala Met Leu Ser Arg Pro Asn Val Leu
    370                 375                 380

Gly Gln Ser Ser Gly Ser Arg Arg Ala Ala Val Ser Arg Arg Asp
385                 390                 395                 400

Ala Phe Val Gly Ser Asp Leu Asp Leu Arg Thr Arg Ser Thr Glu Ala
                405                 410                 415
```

```
Asn Pro Gly Thr Ala Ile Lys Thr Ser Ser Ala Arg Asn Ala Ser His
        420                 425                 430

Val Lys Asn Tyr Glu Thr Ala Ile Lys Gly Ile Glu Gly Leu Gln Leu
        435                 440                 445

Glu Asn Asp Glu Lys Ala His Tyr
        450                 455

<210> SEQ ID NO 64
<211> LENGTH: 1808
<212> TYPE: DNA
<213> ORGANISM: Linum usitatissimum

<400> SEQUENCE: 64
tgccccgtct ctctcgccat ccgttttagt tctagggttt actttggatc cccgatctaa     60
ccctaatttt ttgctgggtt tcttatcgag gaagatcgct gctttttata atctttcgtc    120
agggtttcga tctctttttt cgttgattcc ttttctcgcc tgtgagttgg aatatgtgaa    180
gttgggaaat ttgtttcagc ataagtaggc agtcagtgat ttaaagtttt gagcttctgc    240
tgtgttgaac gatggagaag atgaaggttg accatatcgt cggtggtaag tttaagcttg    300
ggaggaagat tgggagtgga tcttttggag agctctatct gggtgtaaat gtgcagactg    360
gagaagaagt tgctgttaag ctggaatctg tgaagaccaa gcatcctcag cttcagtatg    420
agtcaaagtt gtatatgctt ctccaaggag ggactggaat tcctcatctg aagtggtttg    480
gagttgaggt ggagtataat atcatggtta ttgatcttct tggaccgagt ttggaagatc    540
tattcaacta ctgtaatagg aaatttactt tgaaaacagt gctaatgctt gctgatcaac    600
tgattaatag ggttgaatat atgcattcaa gaggatttct tcaccgtgac ataaagcctg    660
ataacttctt gatgggccta ggtcgcaaag ccaatcaggt ctatgtaatt gattatggcc    720
ttgcaaagaa atacagggat ctccagactc acaagcacat tccatacaga gaaaataaga    780
acctaacagg cactgctcgt tatgcaagtg tcaacaccca cctcggagtt gagcaaagca    840
gaagggatga tttggagtca cttggatatg tgcttatgta tttcctccga ggaagcctcc    900
catggcaagg attaaaggct ggcacaaaaa agcagaaata tgacaggatc agtgaaagaa    960
aagtgcagac ttcaatagag tctctttgta aatcttatcc atccgagttt gtatcctact   1020
tccactactg tcgctcattg cgattcgaag ataaaccaga ttactcgtat ttgaagaggc   1080
ttttccggga cttatttatt cgggaaggtt atcaattcga ctatgtgttc gactggactg   1140
tactgaagta tcctcaagtt ggttccagct ctagagcacg agtaagtgtg aaaccaggtc   1200
ctgcactcgc ggcaggacca tctactgtaa gagtgcccga gagagtttct gttggcaaag   1260
agatccggga gagattctca ggcgctgttg aggcttttcc aatcaggaga atcactggtg   1320
ctagcccgct cgacaattcg agagccagga caaatgagac tcaacagcag cctgaggcgg   1380
agaaaggtcg cagcacgtct aggcatggaa gtagctcgag acgagccatc gttccgaacg   1440
gcaagccaag ttcctcaggt gatcacggag atggtcgcct gacgagaaca caccattctt   1500
ctggccatat ctcttccaca caaagaatcc tacctgcgta cgaacccatc aagtcatccg   1560
gtgctcgagc agctgctgcc aaatcccgcg aggaaaatct aaagagcttc gagttcctca   1620
ccctgaaccg acgatgaaag tagcggaaaa tgaatctgct ccttcataaa tcattgtcat   1680
gtttggttac acttgttggg atacaaagaa ttcgaaatcg taactctgaa gaaaccgagt   1740
ctccccactg ctgcatgtaa cacattgtga agaagagaaa tcagaaaccc aaaaaaaaaa   1800
aaaaaaaa                                                            1808
```

<210> SEQ ID NO 65
<211> LENGTH: 461
<212> TYPE: PRT
<213> ORGANISM: Linum usitatissimum

<400> SEQUENCE: 65

| | | | | | | | | | | | | | | |
|---|---|---|---|---|---|---|---|---|---|---|---|---|---|---|
| Met | Glu | Lys | Met | Lys | Val | Asp | His | Ile | Val | Gly | Gly | Lys | Phe | Lys | Leu |
| 1 | | | | 5 | | | | | 10 | | | | | 15 | |
| Gly | Arg | Lys | Ile | Gly | Ser | Gly | Ser | Phe | Gly | Glu | Leu | Tyr | Leu | Gly | Val |
| | | | 20 | | | | | 25 | | | | | 30 | | |
| Asn | Val | Gln | Thr | Gly | Glu | Glu | Val | Ala | Val | Lys | Leu | Glu | Ser | Val | Lys |
| | | | 35 | | | | | 40 | | | | | 45 | | |
| Thr | Lys | His | Pro | Gln | Leu | Gln | Tyr | Glu | Ser | Lys | Leu | Tyr | Met | Leu | Leu |
| | 50 | | | | | 55 | | | | | 60 | | | | |
| Gln | Gly | Gly | Thr | Gly | Ile | Pro | His | Leu | Lys | Trp | Phe | Gly | Val | Glu | Val |
| 65 | | | | | 70 | | | | | 75 | | | | | 80 |
| Glu | Tyr | Asn | Ile | Met | Val | Ile | Asp | Leu | Leu | Gly | Pro | Ser | Leu | Glu | Asp |
| | | | | 85 | | | | | 90 | | | | | 95 | |
| Leu | Phe | Asn | Tyr | Cys | Asn | Arg | Lys | Phe | Thr | Leu | Lys | Thr | Val | Leu | Met |
| | | | 100 | | | | | 105 | | | | | 110 | | |
| Leu | Ala | Asp | Gln | Leu | Ile | Asn | Arg | Val | Glu | Tyr | Met | His | Ser | Arg | Gly |
| | | | 115 | | | | | 120 | | | | | 125 | | |
| Phe | Leu | His | Arg | Asp | Ile | Lys | Pro | Asp | Asn | Phe | Leu | Met | Gly | Leu | Gly |
| | 130 | | | | | 135 | | | | | 140 | | | | |
| Arg | Lys | Ala | Asn | Gln | Val | Tyr | Val | Ile | Asp | Tyr | Gly | Leu | Ala | Lys | Lys |
| 145 | | | | | 150 | | | | | 155 | | | | | 160 |
| Tyr | Arg | Asp | Leu | Gln | Thr | His | Lys | His | Ile | Pro | Tyr | Arg | Glu | Asn | Lys |
| | | | | 165 | | | | | 170 | | | | | 175 | |
| Asn | Leu | Thr | Gly | Thr | Ala | Arg | Tyr | Ala | Ser | Val | Asn | Thr | His | Leu | Gly |
| | | | 180 | | | | | 185 | | | | | 190 | | |
| Val | Glu | Gln | Ser | Arg | Arg | Asp | Asp | Leu | Glu | Ser | Leu | Gly | Tyr | Val | Leu |
| | | | 195 | | | | | 200 | | | | | 205 | | |
| Met | Tyr | Phe | Leu | Arg | Gly | Ser | Leu | Pro | Trp | Gln | Gly | Leu | Lys | Ala | Gly |
| | 210 | | | | | 215 | | | | | 220 | | | | |
| Thr | Lys | Lys | Gln | Lys | Tyr | Asp | Arg | Ile | Ser | Glu | Lys | Lys | Val | Gln | Thr |
| 225 | | | | | 230 | | | | | 235 | | | | | 240 |
| Ser | Ile | Glu | Ser | Leu | Cys | Lys | Ser | Tyr | Pro | Ser | Glu | Phe | Val | Ser | Tyr |
| | | | | 245 | | | | | 250 | | | | | 255 | |
| Phe | His | Tyr | Cys | Arg | Ser | Leu | Arg | Phe | Glu | Asp | Lys | Pro | Asp | Tyr | Ser |
| | | | 260 | | | | | 265 | | | | | 270 | | |
| Tyr | Leu | Lys | Arg | Leu | Phe | Arg | Asp | Leu | Phe | Ile | Arg | Glu | Gly | Tyr | Gln |
| | | | 275 | | | | | 280 | | | | | 285 | | |
| Phe | Asp | Tyr | Val | Phe | Asp | Trp | Thr | Val | Leu | Lys | Tyr | Pro | Gln | Val | Gly |
| | 290 | | | | | 295 | | | | | 300 | | | | |
| Ser | Ser | Ser | Arg | Ala | Arg | Val | Ser | Val | Lys | Pro | Gly | Pro | Ala | Leu | Ala |
| 305 | | | | | 310 | | | | | 315 | | | | | 320 |
| Ala | Gly | Pro | Ser | Thr | Val | Arg | Val | Pro | Glu | Arg | Val | Ser | Val | Gly | Lys |
| | | | | 325 | | | | | 330 | | | | | 335 | |
| Glu | Ile | Arg | Glu | Arg | Phe | Ser | Gly | Ala | Val | Glu | Ala | Phe | Ser | Ile | Arg |
| | | | 340 | | | | | 345 | | | | | 350 | | |
| Arg | Ile | Thr | Gly | Ala | Ser | Pro | Leu | Asp | Asn | Ser | Arg | Ala | Arg | Thr | Asn |
| | | | 355 | | | | | 360 | | | | | 365 | | |
| Glu | Thr | Gln | Gln | Gln | Pro | Glu | Ala | Glu | Lys | Gly | Arg | Ser | Thr | Ser | Arg |

```
                370             375             380
His Gly Ser Ser Arg Arg Ala Ile Val Pro Asn Gly Lys Pro Ser
385                 390                 395                 400

Ser Ser Gly Asp His Gly Asp Gly Arg Leu Thr Arg Thr His His Ser
            405                 410                 415

Ser Gly His Ile Ser Ser Thr Gln Arg Ile Leu Pro Ala Tyr Glu Pro
            420                 425                 430

Ile Lys Ser Ser Gly Ala Arg Ala Ala Ala Lys Ser Arg Glu Glu
        435                 440                 445

Asn Leu Lys Ser Phe Glu Phe Leu Thr Leu Asn Arg Arg
        450                 455                 460

<210> SEQ ID NO 66
<211> LENGTH: 1383
<212> TYPE: DNA
<213> ORGANISM: Brassica napus

<400> SEQUENCE: 66
ttcttccaca ctatttgact ctccacaaaa cttttcctc agaactcaga tccgaatcct      60
actaaattcc cctttccttt caaactcttt tcctatattc ttcttcttct tgcttcctat    120
cctaaactta ctttctttt ctttgtctcg ttcttgcaac tttcaccatc aaaaccagct    180
tcaacaactg ttgcttgggt ggtttcggtt tagtgatgag attgccattt agtgggtaaa    240
tcggatagtg ggtatttcta aagtggtgat tttgaagcgg aaaaagagg atggaacgga    300 atcagaagaa gatggatcac gtcatcggcg gaaagtttaa gttgggtagg aaactcggca    360
gcggatcgtt cggtgaactt tatttaggga tcaatattca gactggagaa gaagtcgcag    420
ttaagctgga agctgtgaag acgaggcatc ctcaactgca gtatgagtcg aagatatata    480
tgcatctcca aggaggaact ggtgttcccc atctcaaatg gttcggagtc gggggtgact    540
acagttgcat ggttatcgac cttcttggcc ccagcttgga ggacttattc aattactgca    600
ctcgaaagtt tactttgaaa tctgttttaa tgcttgcaga tcagttgata tgcagagttg    660
agtacacgca ttcacggggc tttcttcacc gcgatattaa accggacaac tttttgatgg    720
gtcttgggcg caaagcaaac caggtttata tcatcgatta tggccttgct aaaaaataca    780
aggattttca aacacaaaag catataccat acagggaaaa caagaatcta acggaactg    840 cacggtatgc aagtgtcaac acgcaccttg gcattgagca agtagaaga gatgatctgg    900 agtcacttgg ttatgtgttg atgtattttc tacgaggaag tcttccgtgg caagggttaa    960
aaggtgggac aaagaagcag aagtatgaca agattagtga aaagaagatg cttactcctg    1020
tagaggtata gcttttgtaa tgaggatata atgttttcaa atatccaaat agattttgac    1080
ttagcttggt tttaatcttt tttttttctt tttggagatt ctgtgcaagt cacatccatc    1140
agagttcacc tcctatttcc attactgtcg atcactgaga tttgaggaca aaccagatta    1200
ttcatatctg agaagacttt tcagagacct tttcattcgt gaaggttacc agctggacta    1260 cgtgttgat tggacaacct tgaaatatcc tcagtctggc tctacttcga gaccaaggct    1320
gactccaaga ccagccttgg acccggaccc tccaggacca cctgcaaaaa aaaaaaaaaa    1380
aaa                                                                 1383

<210> SEQ ID NO 67
<211> LENGTH: 246
<212> TYPE: PRT
<213> ORGANISM: Brassica napus
```

<400> SEQUENCE: 67

```
Met Glu Arg Asn Gln Lys Lys Met Asp His Val Ile Gly Gly Lys Phe
1               5                   10                  15
Lys Leu Gly Arg Lys Leu Gly Ser Gly Ser Phe Gly Glu Leu Tyr Leu
            20                  25                  30
Gly Ile Asn Ile Gln Thr Gly Glu Glu Val Ala Val Lys Leu Glu Ala
        35                  40                  45
Val Lys Thr Arg His Pro Gln Leu Gln Tyr Glu Ser Lys Ile Tyr Met
    50                  55                  60
His Leu Gln Gly Gly Thr Gly Val Pro His Leu Lys Trp Phe Gly Val
65                  70                  75                  80
Gly Gly Asp Tyr Ser Cys Met Val Ile Asp Leu Leu Gly Pro Ser Leu
                85                  90                  95
Glu Asp Leu Phe Asn Tyr Cys Thr Arg Lys Phe Thr Leu Lys Ser Val
            100                 105                 110
Leu Met Leu Ala Asp Gln Leu Ile Cys Arg Val Glu Tyr Thr His Ser
        115                 120                 125
Arg Gly Phe Leu His Arg Asp Ile Lys Pro Asp Asn Phe Leu Met Gly
    130                 135                 140
Leu Gly Arg Lys Ala Asn Gln Val Tyr Ile Ile Asp Tyr Gly Leu Ala
145                 150                 155                 160
Lys Lys Tyr Lys Asp Phe Gln Thr Gln Lys His Ile Pro Tyr Arg Glu
                165                 170                 175
Asn Lys Asn Leu Thr Gly Thr Ala Arg Tyr Ala Ser Val Asn Thr His
            180                 185                 190
Leu Gly Ile Glu Gln Ser Arg Arg Asp Asp Leu Glu Ser Leu Gly Tyr
        195                 200                 205
Val Leu Met Tyr Phe Leu Arg Gly Ser Leu Pro Trp Gln Gly Leu Lys
    210                 215                 220
Gly Gly Thr Lys Lys Gln Lys Tyr Asp Lys Ile Ser Glu Lys Lys Met
225                 230                 235                 240
Leu Thr Pro Val Glu Val
                245
```

<210> SEQ ID NO 68
<211> LENGTH: 1475
<212> TYPE: DNA
<213> ORGANISM: Helianthus annuus

<400> SEQUENCE: 68

```
cctaataatt cactcctcta taatacgtta caattcaatt tctttatctt caaaaccctg      60
gaacatcttc atggagcctc gtgttgctaa taagtttcga ttaggtcgta agattggaag    120
cggatccttc ggagagatct atttaggtac taatgttcag acaaatgaag aagttgcaat    180
taagcttgaa atgttaaga caaaacatcc tcagctgctg tacgagtcca agttatacag    240
gattctacag ggaggaactg gtattccaaa tgtgagatgg tttggagtgg agggagatta    300
taatgttctc gtgatggatt tgctcgggcc tagtcttgag gatttattca atttctgtaa    360
cagaaaactt tctttaaaaa ccgttctcat gcttgcagat caaatgatca accgtattga    420
atttgtgcac tctaaatcat ttctacatcg cgatatcaag cctgacaatt ttcttatggg    480
cctgggacga cgtgcaaatc aagtctacat cattgatttt ggtctggcca agaaatacag    540
ggatactaca actcaccagc acattccgta cagagacaac aaaaacttga ccgggactgc    600
tagatacgca agcatgaata ctcatcttgg aattgaacaa agcaggaggg atgatttaga    660
```

```
atctcttgga tacgttctca tgtatttcct aagagggagc cttccttggc aagggctgaa      720
agcgggaaat aagaaacaga aatacgagaa aataagtgag aaaaaagttt ctacatcaat      780
tgaggcctta tgtcgcggtt atccaacaga gtttgcatca tacttccatt actgccgttc      840
gttgcggttt gaggacaaac ccgattatgc ttatctgaag aggatattcc gtgacctctt      900
tatccgtgaa gggtttcagt ttgattacgt ttttgattgg acgattttga agtatcagca      960
atcacagatt gctcctcctc cgacccgcgg tcctggtatg gatgctgggc aagctctgc     1020 tattccaaat ggcgagcaaa gtgggagaca ggtgggctta tcttcattgg atccttcgcg     1080
tagaagaaat tccggcaatt tactacctag ggaaaagagc ccggttgcta atgatgcaac     1140
aatcagcaca gatgccatga gagcaagtgg atcgacgagg catgtggact ccagtggtcg     1200
ggcccgcatc ccagacacta gaccgagaag ctcaccacga gacggatcct tgactcagaa     1260
tgcagctgcg gggacaaaca agtatgaaac cactcttaag ggaatggaaa gtctaaattt     1320
tgatgataat aaaagggttg gttaatctct tgtaaattgt gcaactttat tccataaaac     1380
aaagaaattg gccttgatag taattgtgat agttggtgac ccagtaatat gtaaatttgt     1440 agcttttat gactttcaaa aaaaaaaaaa aaaaa                                 1475
```

<210> SEQ ID NO 69
<211> LENGTH: 424
<212> TYPE: PRT
<213> ORGANISM: Helianthus annuus

<400> SEQUENCE: 69

```
Met Glu Pro Arg Val Ala Asn Lys Phe Arg Leu Gly Arg Lys Ile Gly
  1               5                  10                  15

Ser Gly Ser Phe Gly Glu Ile Tyr Leu Gly Thr Asn Val Gln Thr Asn
             20                  25                  30

Glu Glu Val Ala Ile Lys Leu Glu Asn Val Lys Thr Lys His Pro Gln
         35                  40                  45

Leu Leu Tyr Glu Ser Lys Leu Tyr Arg Ile Leu Gln Gly Gly Thr Gly
     50                  55                  60

Ile Pro Asn Val Arg Trp Phe Gly Val Glu Gly Asp Tyr Asn Val Leu
 65                  70                  75                  80

Val Met Asp Leu Leu Gly Pro Ser Leu Glu Asp Leu Phe Asn Phe Cys
                 85                  90                  95

Asn Arg Lys Leu Ser Leu Lys Thr Val Leu Met Leu Ala Asp Gln Met
            100                 105                 110

Ile Asn Arg Ile Glu Phe Val His Ser Lys Ser Phe Leu His Arg Asp
        115                 120                 125

Ile Lys Pro Asp Asn Phe Leu Met Gly Leu Gly Arg Arg Ala Asn Gln
    130                 135                 140

Val Tyr Ile Ile Asp Phe Gly Leu Ala Lys Lys Tyr Arg Asp Thr Thr
145                 150                 155                 160

Thr His Gln His Ile Pro Tyr Arg Asp Asn Lys Asn Leu Thr Gly Thr
                165                 170                 175

Ala Arg Tyr Ala Ser Met Asn Thr His Leu Gly Ile Glu Gln Ser Arg
            180                 185                 190

Arg Asp Asp Leu Glu Ser Leu Gly Tyr Val Leu Met Tyr Phe Leu Arg
        195                 200                 205

Gly Ser Leu Pro Trp Gln Gly Leu Lys Ala Gly Asn Lys Lys Gln Lys
    210                 215                 220
```

-continued

```
Tyr Glu Lys Ile Ser Glu Lys Val Ser Thr Ser Ile Glu Ala Leu
225                 230                 235                 240

Cys Arg Gly Tyr Pro Thr Glu Phe Ala Ser Tyr Phe His Tyr Cys Arg
                245                 250                 255

Ser Leu Arg Phe Glu Asp Lys Pro Asp Tyr Ala Tyr Leu Lys Arg Ile
            260                 265                 270

Phe Arg Asp Leu Phe Ile Arg Glu Gly Phe Gln Phe Asp Tyr Val Phe
        275                 280                 285

Asp Trp Thr Ile Leu Lys Tyr Gln Gln Ser Gln Ile Ala Pro Pro Pro
    290                 295                 300

Thr Arg Gly Pro Gly Met Asp Ala Gly Pro Ser Ser Ala Ile Pro Asn
305                 310                 315                 320

Gly Glu Gln Ser Gly Arg Gln Val Gly Leu Ser Ser Leu Asp Pro Ser
                325                 330                 335

Arg Arg Arg Asn Ser Gly Asn Leu Leu Pro Arg Glu Lys Ser Pro Val
            340                 345                 350

Ala Asn Asp Ala Thr Ile Ser Thr Asp Ala Met Arg Ala Ser Gly Ser
        355                 360                 365

Thr Arg His Val Asp Ser Ser Gly Arg Ala Arg Ile Pro Asp Thr Arg
    370                 375                 380

Pro Arg Ser Ser Pro Arg Asp Gly Ser Leu Thr Gln Asn Ala Ala Ala
385                 390                 395                 400

Gly Thr Asn Lys Tyr Glu Thr Thr Leu Lys Gly Met Glu Ser Leu Asn
                405                 410                 415

Phe Asp Asp Asn Lys Arg Val Gly
            420
```

<210> SEQ ID NO 70
<211> LENGTH: 1803
<212> TYPE: DNA
<213> ORGANISM: Glycine max

<400> SEQUENCE: 70

```
gtggctttga tttcggttcc gaagggacaa ccaacgacca ccctctcttc tgactcactt      60
ctcgaacctt ccaaacatgg aacgcatcgt tggcggcaag tacaagctcg ccgcaagat     120
cggaagtgga tccttcggcg aaatctacct cgcgacgcat attgataccT tcgagatcgt     180
cgccgtcaag atcgagaata gtaaaacaaa acatccacaa ctgctttacg aggcaaagct     240
atacaatatt cttcaaggag gaagtggcat tccgaacata aaatggtctg gcatagacgg     300
ggaggataat gtgcttgtta ttgatttgct tgggccgagt cttgaggatc tctttgtgta     360
ttgtggaagg aagttttcat tgaagacagt attaatgttg gctgatcaaa tgatcactag     420
aatagaatat gtgcattcta aaggattttt acacagggat attaaacctg ataactttct     480
catgggactt ggtcgaaagg ccaaccaggt ttacataatt gattttgggc ttgcaaaacg     540
atatcgggat tccactacca atcgccacat cccttacagg agaacaaaaa acttaacggg     600
tactgctcga tatgcaagtt gcaatactca tcttgggatt gagcaaagtc gccgggatga     660
tttgaatca ctaggatatg tacttctgta cttcctaaga ggaagccttc cttggcaagg     720
tctaaaggcg gctacaaaga aacagaagta tgataaaata tgccagaaga aattatcaac     780
tcctattgag gtactatgca aatctcatcc tgtagagttt gcttcgtact tccattactg     840
ccactctttg acatttgatc aacgacctga ttatggtttc ttgaagcgcc tatttcggga     900
cctatttgct cgtgatggtt atgatttga ttacgttttt gattggacca ttttgaagta     960
```

```
ccagcaatct caaaagaatc cagttccagg agcaagtaac agtcgtgcaa ttccaatgga    1020
tattgacaat catcaaggtc ttaattcata ttcagggcat gttaaagagc gtattagagc    1080
tggtgatgct actggttctg tgttaaaat tcagtttaaa tcaccagtgg gtaaaaattt     1140
gagttatgag aaaccacttg acaaaaatat ttttggagaa gcaaatattc cctctacttc    1200
attttctcct gctagtactt cacaaaggaa ctccttgaag caatccttgt ctgctgaagc    1260
ttccaaccct ggacatgcac aaggcagtaa aattggccct tcaagtagct tgatgtcatc    1320
tctgcagcac atgtcttctg ctaaatgatt gcaaaatatg ctatgaagct tgaagaaga    1380 ttctgtgcat tgtttcccct attatttggt caagaatatt caagtcatta ttaattcatg    1440
gagactgcaa atgtgccaga aagttgacaa attgcatagc tcctattttg aggccattta    1500
gtgttgcttc tttcctgagg tgactacaaa tgcttgtgcg gtataaaaca gacttcccag    1560
gcttggctcc tgtgctgtac atagatgtca aatttggcac acagcaatat tttgtattca    1620
tgttttcatg taacattaat gtgtgtagta gccctgttac tccgatatgt tacttgatga    1680
tgattatcat tgtgccatac aataaatggt gacagagtgt tttaaaactt ctaaattatt    1740
tgtcaatatt ataaattgca aatgtatttt cagtttctcc taaaaaaga gagaccgaca    1800 cgc                                                                 1803

<210> SEQ ID NO 71
<211> LENGTH: 423
<212> TYPE: PRT
<213> ORGANISM: Glycine max

<400> SEQUENCE: 71

Met Glu Arg Ile Val Gly Gly Lys Tyr Lys Leu Gly Arg Lys Ile Gly
  1               5                  10                  15

Ser Gly Ser Phe Gly Glu Ile Tyr Leu Ala Thr His Ile Asp Thr Phe
             20                  25                  30

Glu Ile Val Ala Val Lys Ile Glu Asn Ser Lys Thr Lys His Pro Gln
         35                  40                  45

Leu Leu Tyr Glu Ala Lys Leu Tyr Asn Ile Leu Gln Gly Gly Ser Gly
     50                  55                  60

Ile Pro Asn Ile Lys Trp Ser Gly Ile Asp Gly Glu Asp Asn Val Leu
 65                  70                  75                  80

Val Ile Asp Leu Leu Gly Pro Ser Leu Glu Asp Leu Phe Val Tyr Cys
                 85                  90                  95

Gly Arg Lys Phe Ser Leu Lys Thr Val Leu Met Leu Ala Asp Gln Met
            100                 105                 110

Ile Thr Arg Ile Glu Tyr Val His Ser Lys Gly Phe Leu His Arg Asp
        115                 120                 125

Ile Lys Pro Asp Asn Phe Leu Met Gly Leu Gly Arg Lys Ala Asn Gln
    130                 135                 140

Val Tyr Ile Ile Asp Phe Gly Leu Ala Lys Arg Tyr Arg Asp Ser Thr
145                 150                 155                 160

Thr Asn Arg His Ile Pro Tyr Arg Glu Asn Lys Asn Leu Thr Gly Thr
                165                 170                 175

Ala Arg Tyr Ala Ser Cys Asn Thr His Leu Gly Ile Glu Gln Ser Arg
            180                 185                 190

Arg Asp Asp Leu Glu Ser Leu Gly Tyr Val Leu Leu Tyr Phe Leu Arg
        195                 200                 205

Gly Ser Leu Pro Trp Gln Gly Leu Lys Ala Ala Thr Lys Lys Gln Lys
    210                 215                 220
```

Tyr Asp Lys Ile Cys Gln Lys Lys Leu Ser Thr Pro Ile Glu Val Leu
225                 230                 235                 240

Cys Lys Ser His Pro Val Glu Phe Ala Ser Tyr Phe His Tyr Cys His
            245                 250                 255

Ser Leu Thr Phe Asp Gln Arg Pro Asp Tyr Gly Phe Leu Lys Arg Leu
        260                 265                 270

Phe Arg Asp Leu Phe Ala Arg Asp Gly Tyr Asp Phe Asp Tyr Val Phe
            275                 280                 285

Asp Trp Thr Ile Leu Lys Tyr Gln Gln Ser Gln Lys Asn Pro Val Pro
        290                 295                 300

Gly Ala Ser Asn Ser Arg Ala Ile Pro Met Asp Ile Asp Asn His Gln
305                 310                 315                 320

Gly Leu Asn Ser Tyr Ser Gly His Val Lys Glu Arg Ile Arg Ala Gly
            325                 330                 335

Asp Ala Thr Gly Ser Gly Val Lys Ile Gln Phe Lys Ser Pro Val Gly
            340                 345                 350

Lys Asn Leu Ser Tyr Glu Lys Pro Leu Asp Lys Asn Ile Phe Gly Glu
        355                 360                 365

Ala Asn Ile Pro Ser Thr Ser Phe Ser Pro Ala Ser Thr Ser Gln Arg
370                 375                 380

Asn Ser Leu Lys Gln Ser Leu Ser Ala Glu Ala Ser Asn Pro Gly His
385                 390                 395                 400

Ala Gln Gly Ser Lys Ile Gly Pro Ser Ser Ser Leu Met Ser Ser Leu
            405                 410                 415

Gln His Met Ser Ser Ala Lys
            420

<210> SEQ ID NO 72
<211> LENGTH: 1628
<212> TYPE: DNA
<213> ORGANISM: Brassica napus

<400> SEQUENCE: 72
agagagagac attcctttg ttcccagatc gcgagaagga agatatatga caactgggtt      60
tctctgttct cagccctagt ttcccagaaa aatgggatct ttccttattt cattcggatt    120
tgcgctgatt ctggtgtgtt aaaagtttct ttcttggaaa agagagagag agggtaaagt    180
tgagattatc atcctagtta gggcttagga ggcatcgatg gagcatcttg tgggaaaaaa    240
gtttcggctg ggaaggaaaa ttggaagcgg ttcttttgga gagatccatc tcggtactca    300
tattcaaacc aacgaagaag tcgccatcaa gcttgaaaat gcaaagacaa aacatccaca    360
gctgctctac gaacccaagt tatacaaact tctacaggga ggaactggtg ttccaaatat    420
caagtggttt ggtgttgaaa gtgactacaa tgtgctggtc atggatttac ttggccctag    480
tcttgaagac ttgttcaatt tctgtagcag gaaactttct ctcaagtccg ttctcatgct    540
tgctgatcaa atgataaacc gtgttgagta tttccactct aagtctttcc ttcaccgaga    600
tctcaagcca gacaatttcc tcatggggct aggaagacgc gcaaaccagg tatacatcat    660
cgactttggt cttgctaaga agtacaggga taacactact catcagcaca ttccttacag    720
agaaaataag aatctcactg gaactgcaag atatgctagt atgaatactc acttgggaat    780
tgaacaaagc cgaagggatg atctcgaatc tcttggttac attctcatgt atttccttaa    840
aggaagtctt ccatggcaag gacttaaagc tggaaccaag aaacaaaagt acgagagaat    900
cagcgaaaag aaagtctcta cttccattga gtctttatac cgtggctacc atcagagtt    960

-continued

```
tgcttcttac ttccattact gccgctcgct tcggtttgat gacaaaccgg attacggtta    1020
tctcaaaaga atattcagag atctctttat ccgtgaaggg tttcagttcg attatgtctt    1080
tgactggacc atactgaagt accaacagtc acaactgaca gctcctccaa cccgtggcct    1140
cggaactcct gcagctggaa caagtgcggc tttgccccca ggattgacca ccatggatag    1200
atacgcaggg gaggaagaag gaggaaggcc accgatggat tcatcaagaa ggagaacgtc    1260
tggtgctctt gacaactctg gcaacttgag agccccaatg atgcatagct cgtcggtgtt    1320
cgcgcaatca gcaggatcat caaggagatt aacatcggag gagctacaga ggtcccgtac    1380
gggcagcgga ttaagaaaca caccggtggt acaacgtcg aagggaaga ggtcttcttc      1440 caccagaaaa cattacgatt ctgccatcaa aggcatcgag actcttcaag tctccagcga    1500
aaggtttcac caccattgat gatgatccat ctgttagaga aaacatgtc gtgtttattt     1560 gttcagaact cagaagttat tatttatatg tagttttcgg ctctatatcg aaaaaaaaaa    1620
aaaaaaaa                                                              1628
```

<210> SEQ ID NO 73
<211> LENGTH: 433
<212> TYPE: PRT
<213> ORGANISM: Brassica napus

<400> SEQUENCE: 73

```
Met Glu His Leu Val Gly Lys Lys Phe Arg Leu Gly Arg Lys Ile Gly
  1               5                  10                  15

Ser Gly Ser Phe Gly Glu Ile His Leu Gly Thr His Ile Gln Thr Asn
                 20                  25                  30

Glu Glu Val Ala Ile Lys Leu Glu Asn Ala Lys Thr Lys His Pro Gln
             35                  40                  45

Leu Leu Tyr Glu Pro Lys Leu Tyr Lys Leu Leu Gln Gly Gly Thr Gly
         50                  55                  60

Val Pro Asn Ile Lys Trp Phe Gly Val Glu Ser Asp Tyr Asn Val Leu
 65                  70                  75                  80

Val Met Asp Leu Leu Gly Pro Ser Leu Glu Asp Leu Phe Asn Phe Cys
                 85                  90                  95

Ser Arg Lys Leu Ser Leu Lys Ser Val Leu Met Leu Ala Asp Gln Met
            100                 105                 110

Ile Asn Arg Val Glu Tyr Phe His Ser Lys Ser Phe Leu His Arg Asp
        115                 120                 125

Leu Lys Pro Asp Asn Phe Leu Met Gly Leu Gly Arg Arg Ala Asn Gln
    130                 135                 140

Val Tyr Ile Ile Asp Phe Gly Leu Ala Lys Lys Tyr Arg Asp Asn Thr
145                 150                 155                 160

Thr His Gln His Ile Pro Tyr Arg Glu Asn Lys Asn Leu Thr Gly Thr
                165                 170                 175

Ala Arg Tyr Ala Ser Met Asn Thr His Leu Gly Ile Glu Gln Ser Arg
            180                 185                 190

Arg Asp Asp Leu Glu Ser Leu Gly Tyr Ile Leu Met Tyr Phe Leu Lys
        195                 200                 205

Gly Ser Leu Pro Trp Gln Gly Leu Lys Ala Gly Thr Lys Lys Gln Lys
    210                 215                 220

Tyr Glu Arg Ile Ser Glu Lys Lys Val Ser Thr Ser Ile Glu Ser Leu
225                 230                 235                 240

Tyr Arg Gly Tyr Pro Ser Glu Phe Ala Ser Tyr Phe His Tyr Cys Arg
```

```
                     245                 250                 255
Ser Leu Arg Phe Asp Asp Lys Pro Asp Tyr Gly Tyr Leu Lys Arg Ile
                260                 265                 270

Phe Arg Asp Leu Phe Ile Arg Glu Gly Phe Gln Phe Asp Tyr Val Phe
            275                 280                 285

Asp Trp Thr Ile Leu Lys Tyr Gln Gln Ser Gln Leu Thr Ala Pro Pro
        290                 295                 300

Thr Arg Gly Leu Gly Thr Pro Ala Ala Gly Thr Ser Ala Ala Leu Pro
305                 310                 315                 320

Pro Gly Leu Thr Thr Met Asp Arg Tyr Ala Gly Glu Glu Glu Gly Gly
                325                 330                 335

Arg Pro Pro Met Asp Ser Ser Arg Arg Arg Thr Ser Gly Ala Leu Asp
                340                 345                 350

Asn Ser Gly Asn Leu Arg Ala Pro Met Met His Ser Ser Ser Val Phe
            355                 360                 365

Ala Gln Ser Ala Gly Ser Ser Arg Arg Leu Thr Ser Glu Glu Leu Gln
        370                 375                 380

Arg Ser Arg Thr Gly Ser Gly Leu Arg Asn Thr Pro Val Val Thr Thr
385                 390                 395                 400

Ser Glu Gly Lys Arg Ser Ser Ser Thr Arg Lys His Tyr Asp Ser Ala
                405                 410                 415

Ile Lys Gly Ile Glu Thr Leu Gln Val Ser Ser Glu Arg Phe His His
                420                 425                 430

His

<210> SEQ ID NO 74
<211> LENGTH: 1806
<212> TYPE: DNA
<213> ORGANISM: Brassica napus

<400> SEQUENCE: 74
gagaagcgtc taagaaacga cattccgttg agattggatt gtgttttctc cagatcgaga      60
cgaggaggat gaagatagct attgggtttt tttgattctt gttgggtcct tctttcttcc     120
cgcttttgaa tctgctttat ttttggggg ttgagattct aaattagggt ttcgtgggtt     180
atattgatgg aatctcgtgt tggaaacaag tttcgccttg ccggaagat cggtagcggt     240
tccttcgggg agatctatct gggtactaat attcaaacga atgaagaagt tgcaatcaag     300
cttgaaagtg tgaagacgaa acatcctcag ctgctttatg aattgaagtt atacaagatt     360
ctacaaggag gaactggtgt cccaaatgtg aaatggtacg gtgttgaagg ggactacaat     420
gttttggtga tcgatctact agggccgagt cttgaagatc tgttcaattt ctgtagcagg     480
aaactttcct tgaagtcggt cctcatgctt gctgatcaaa tgatcaaccg tgttgagttt     540
ttccattcaa aatctttcct tcaccgagat cccaagcctg acaatttcct catgggcctt     600
ggaaggcgtg ccaaccaggt ttacatcatc gactttggtc tagctaagaa gtacagagat     660
agtacaacac atcagcacat tccctacaga gaaataaga acctgacagg aactgcacgt     720
tacgctagta tgaacaccca cttgggaatt gaacaaagcc gaagggatga tctagagtct     780
cttggttata tccttatgta tttcctcaaa ggaagtcttc cttggcaagg actgaaagct     840
ggaaacaaga agcaaaagta cgagagaatt agcgaaaaga agtttccac atccattgag     900
gtcttatgtc ggggttaccc atcagaattt gcatcctatt ccactactg ccggtcgctt     960
cgttttgatg ataaaccaga ctacgcttat ctcaaacgga tattcagaga tctctttatc    1020
```

-continued

```
cgtgaaggat tcaatttga ttacgtgttt gactggacca tcttgaagta ccaacaatca    1080
caactaaccg ctcctccttc tcgtaatctc aaccctgcgg ttggaactag cgcagcattg    1140
ccacctggcg tttccaacat tgatagatac acaggcgagg aagaagggcg accggttggt    1200
tactcgcata tggaatcatc tcgacggaga gcttcaggca ctcttgacca ctcagggaat    1260
ctttcgaacc aacagacatc atcatttaac agagaatcca tgatgccgag ctcctcgatg    1320
tttgcacaat cagcaggatc atcgaggaga gtagcggcag tgagcagccg agacaatctt    1380
ctgagcgggg aagagtttca gagaagccac cgtacaggtg acgtaagccg cggaggagtg    1440
atctctagga actcccctgt ggaggctggg aagaggtctt cttcctcgag aagacactac    1500
gaatcagcca tcaaaggcat tgataatctt caagtctcct ccgacgacaa gtttcaccac    1560
caccactgat aataataata ataacaacat taattgtact tgcaccgtat tggtcaaacg    1620
acctcagaag tttcatatgt tttttcttct tcttaattac gcactacgaa agtttgaata    1680
caatcgagtt aatccacttt aaaaaaaaaa aaaaaaaaaa aaaaaaaaaa aaaaaaaaaa    1740
aaaaaaaaaa aaaaaaaaaa aaaaaaaaaa aaaaaaaaaa aaaaaaaaaa aaaaaaaaaa    1800
aaaaaa                                                               1806
```

<210> SEQ ID NO 75
<211> LENGTH: 460
<212> TYPE: PRT
<213> ORGANISM: Brassica napus

<400> SEQUENCE: 75

```
Met Glu Ser Arg Val Gly Asn Lys Phe Arg Leu Gly Arg Lys Ile Gly
1               5                   10                  15

Ser Gly Ser Phe Gly Glu Ile Tyr Leu Gly Thr Asn Ile Gln Thr Asn
            20                  25                  30

Glu Glu Val Ala Ile Lys Leu Glu Ser Val Lys Thr Lys His Pro Gln
        35                  40                  45

Leu Leu Tyr Glu Leu Lys Leu Tyr Lys Ile Leu Gln Gly Gly Thr Gly
    50                  55                  60

Val Pro Asn Val Lys Trp Tyr Gly Val Glu Gly Asp Tyr Asn Val Leu
65                  70                  75                  80

Val Ile Asp Leu Leu Gly Pro Ser Leu Glu Asp Leu Phe Asn Phe Cys
                85                  90                  95

Ser Arg Lys Leu Ser Leu Lys Ser Val Leu Met Leu Ala Asp Gln Met
            100                 105                 110

Ile Asn Arg Val Glu Phe Phe His Ser Lys Ser Phe Leu His Arg Asp
        115                 120                 125

Pro Lys Pro Asp Asn Phe Leu Met Gly Leu Gly Arg Arg Ala Asn Gln
    130                 135                 140

Val Tyr Ile Ile Asp Phe Gly Leu Ala Lys Lys Tyr Arg Asp Ser Thr
145                 150                 155                 160

Thr His Gln His Ile Pro Tyr Arg Glu Asn Lys Asn Leu Thr Gly Thr
                165                 170                 175

Ala Arg Tyr Ala Ser Met Asn Thr His Leu Gly Ile Glu Gln Ser Arg
            180                 185                 190

Arg Asp Asp Leu Glu Ser Leu Gly Tyr Ile Leu Met Tyr Phe Leu Lys
        195                 200                 205

Gly Ser Leu Pro Trp Gln Gly Leu Lys Ala Gly Asn Lys Lys Gln Lys
    210                 215                 220

Tyr Glu Arg Ile Ser Glu Lys Lys Val Ser Thr Ser Ile Glu Val Leu
```

```
                225                 230                 235                 240
Cys Arg Gly Tyr Pro Ser Glu Phe Ala Ser Tyr Phe His Tyr Cys Arg
                    245                 250                 255
Ser Leu Arg Phe Asp Asp Lys Pro Asp Tyr Ala Tyr Leu Lys Arg Ile
                260                 265                 270
Phe Arg Asp Leu Phe Ile Arg Glu Gly Phe Gln Phe Asp Tyr Val Phe
            275                 280                 285
Asp Trp Thr Ile Leu Lys Tyr Gln Gln Ser Gln Leu Thr Ala Pro Pro
        290                 295                 300
Ser Arg Asn Leu Asn Pro Ala Val Gly Thr Ser Ala Ala Leu Pro Pro
305                 310                 315                 320
Gly Val Ser Asn Ile Asp Arg Tyr Thr Gly Glu Glu Glu Gly Arg Pro
                325                 330                 335
Val Gly Tyr Ser His Met Glu Ser Ser Arg Arg Ala Ser Gly Thr
                340                 345                 350
Leu Asp His Ser Gly Asn Leu Ser Asn Gln Gln Thr Ser Ser Phe Asn
                355                 360                 365
Arg Glu Ser Met Met Pro Ser Ser Ser Met Phe Ala Gln Ser Ala Gly
            370                 375                 380
Ser Ser Arg Arg Val Ala Ala Val Ser Ser Arg Asp Asn Leu Leu Ser
385                 390                 395                 400
Gly Glu Glu Phe Gln Arg Ser His Arg Thr Gly Asp Val Ser Arg Gly
                    405                 410                 415
Gly Val Ile Ser Arg Asn Ser Pro Val Glu Ala Gly Lys Arg Ser Ser
                420                 425                 430
Ser Ser Arg Arg His Tyr Glu Ser Ala Ile Lys Gly Ile Asp Asn Leu
                435                 440                 445
Gln Val Ser Ser Asp Asp Lys Phe His His His
            450                 455                 460

<210> SEQ ID NO 76
<211> LENGTH: 2189
<212> TYPE: DNA
<213> ORGANISM: Triticum aestivum

<400> SEQUENCE: 76
ctgcttgctg cctcctccgg cgaaggccca gttttttgccc ccgtctctcc ggatctcctc      60
gcccgacccg ctcgcctcga ttcgtttcgt ttattcgatt tttgctcccc tgtcctgtac     120
atatctgctc ggtcggcgcc cggatttctc ggcggcgtgt ctggatctgg ccttgcgagg     180
cgcctcgcgg tccgaatcct tgctcgattc gcccaggccc cgcggcggcg ggtttggatc     240
tcgcggggga ttcgtcggga ggcaggcagc ggtaatcgga gatggatcac atcgtcggcg     300
gcaagttcaa gctcggcaag aagatcggga gcggatcctt cggggagctc ttcctcgctg     360
tgaatgtgca gaccggagag gaggtcgccg tcaaactgga aaatgtcaag accaagcacc     420
cgcagctcca ttacgagtcc aagctctaca tgcttctcca gggaggaact ggcattccgc     480
acctcaagtg gttcggtgtg agggggagt ataatgtgat ggtgattgat cttctcggac     540
ccagcctcga ggacctcttc aactactgca gtagaaagtt ctcgctcaag accgtgctca     600
tgctcgctga tcagatgata aaccgagttg agtacatgca tcagaaggga tttcttcatc     660
gtgacataaa acctgataat ttccttatgg gcctcggaag gaaagccaat caggtatata     720
taatagatta tggacttgca aagaaattca gagaccttca gactcataag cacatcccct     780 acaggggagaa caagaatctc actggaactg cacgctatgc tagtgtcaat acccaccttg     840
```

```
gcgttgagca aagcaggaga gatgatttag aatcacttgg ttatgtactt atgtacttcc   900
tcagaggcag tctgccatgg caggggctga agcgggcac taagaagcag aaatatgaca    960
aaattagtga agaagatg cttactcctg tggaggtact ctgcaagtct tacccttcag    1020
aattcatttc ttacttccac tactgtcgat cattgcggtt tgaagacaag ccagattatt  1080
cttacctaaa gagactattc cgtgatctct tcatccggga agggtaccaa ttcgattatg  1140
tgtttgactg gaccattttg aaatatcccc agataggctc caatccaagg atgaggccaa  1200
gtgaaagagt cagtggagct gctggaccctt ctatcgagaa gatagagaag cccccaggcg 1260
aagcatctgc tagaaggaat cccagtgctt ctctgaatca gagtgacaac cacgcaacca  1320
gaccacggga aactgtatcg atgtcattaa aggagattat gcatagcaca gaccggtccg  1380
gtgaaaggac tgtggagagg accgtggaga gacctcgtac atcctcccgt acaggcagcg  1440
catccaggag agcagttgca tcaagcagca ggccaggctc atccatggaa ccgagcgagc  1500
agcagtacag ccggacgagc aggttgttct ccagcagcaa taacggcggc agccgcccgt  1560
ccagcaccca gagagtcaat cctggagtgg gcgagtcacg ggccacgtcc ctctcacggg  1620
cggcggtcgc aagagggtcg cgtgatgagc ccctccaccg cagcctcgag ctcctgtccc  1680
tcggcaccgg caagaggaaa taacaggaag gaggggaca agggaacccg aacctgagaa  1740
cgaacgatga agaaggaac gacgccgttt gcgactctgt aaatgacagg ataccaccac  1800
cctattcgtc aacagcccgc ctggagcatc ccataatttc catggtgctc agcctgttg   1860
gtagtatcac caccaccatc attgtttgat agatagcaat aatttgctgc tgctgctgct  1920
gttggttgtt gttgtcgtcc tcgtcggcgt gtgcgtgtta gggccaagtc ctagctttgt  1980
ggtgattaat ttagaggtgg tcaagattca acatatttat gtttctttat taccttcccg  2040
ctgggacttg gcaaactttt ttccgagact ttgttgtatt ttctcttcct gtttgttgca  2100
acctctggat ctgcctgttc agcaacagaa agttgatgaa agtaacttcc agtataaaaa  2160
ttagagagag agagagagac cgacacgca                                    2189
```

<210> SEQ ID NO 77
<211> LENGTH: 473
<212> TYPE: PRT
<213> ORGANISM: Triticum aestivum

<400> SEQUENCE: 77

```
Met Asp His Ile Val Gly Gly Lys Phe Lys Leu Gly Lys Lys Ile Gly
  1               5                  10                  15
Ser Gly Ser Phe Gly Glu Leu Phe Leu Ala Val Asn Val Gln Thr Gly
                 20                  25                  30
Glu Glu Val Ala Val Lys Leu Glu Asn Val Lys Thr Lys His Pro Gln
             35                  40                  45
Leu His Tyr Glu Ser Lys Leu Tyr Met Leu Leu Gln Gly Gly Thr Gly
         50                  55                  60
Ile Pro His Leu Lys Trp Phe Gly Val Glu Gly Glu Tyr Asn Val Met
 65                  70                  75                  80
Val Ile Asp Leu Leu Gly Pro Ser Leu Glu Asp Leu Phe Asn Tyr Cys
                 85                  90                  95
Ser Arg Lys Phe Ser Leu Lys Thr Val Leu Met Leu Ala Asp Gln Met
                100                 105                 110
Ile Asn Arg Val Glu Tyr Met His Gln Lys Gly Phe Leu His Arg Asp
            115                 120                 125
```

```
Ile Lys Pro Asp Asn Phe Leu Met Gly Leu Gly Arg Lys Ala Asn Gln
130                 135                 140

Val Tyr Ile Ile Asp Tyr Gly Leu Ala Lys Lys Phe Arg Asp Leu Gln
145             150                 155                 160

Thr His Lys His Ile Pro Tyr Arg Glu Asn Lys Asn Leu Thr Gly Thr
                165                 170                 175

Ala Arg Tyr Ala Ser Val Asn Thr His Leu Gly Val Glu Gln Ser Arg
            180                 185                 190

Arg Asp Asp Leu Glu Ser Leu Gly Tyr Val Leu Met Tyr Phe Leu Arg
        195                 200                 205

Gly Ser Leu Pro Trp Gln Gly Leu Lys Ala Gly Thr Lys Lys Gln Lys
    210                 215                 220

Tyr Asp Lys Ile Ser Glu Lys Lys Met Leu Thr Pro Val Glu Val Leu
225             230                 235                 240

Cys Lys Ser Tyr Pro Ser Glu Phe Ile Ser Tyr Phe His Tyr Cys Arg
                245                 250                 255

Ser Leu Arg Phe Glu Asp Lys Pro Asp Tyr Ser Tyr Leu Lys Arg Leu
            260                 265                 270

Phe Arg Asp Leu Phe Ile Arg Glu Gly Tyr Gln Phe Asp Tyr Val Phe
        275                 280                 285

Asp Trp Thr Ile Leu Lys Tyr Pro Gln Ile Gly Ser Asn Pro Arg Met
    290                 295                 300

Arg Pro Ser Glu Arg Val Ser Gly Ala Ala Gly Pro Ser Ile Glu Lys
305             310                 315                 320

Ile Glu Lys Ala Pro Gly Glu Ala Ser Ala Arg Arg Asn Pro Ser Ala
                325                 330                 335

Ser Leu Asn Gln Ser Asp Asn His Ala Thr Arg Pro Arg Glu Thr Val
            340                 345                 350

Ser Met Ser Leu Lys Glu Ile Met His Ser Thr Asp Arg Ser Gly Glu
        355                 360                 365

Arg Thr Val Glu Arg Thr Val Glu Arg Pro Arg Thr Ser Ser Arg Thr
    370                 375                 380

Gly Ser Ala Ser Arg Arg Ala Val Ala Ser Ser Arg Pro Gly Ser
385             390                 395                 400

Ser Met Glu Pro Ser Glu Gln Gln Tyr Ser Arg Thr Ser Arg Leu Phe
                405                 410                 415

Ser Ser Ser Asn Asn Gly Gly Ser Arg Pro Ser Ser Thr Gln Arg Val
            420                 425                 430

Asn Pro Gly Val Gly Glu Ser Arg Ala Thr Ser Leu Ser Arg Ala Ala
        435                 440                 445

Val Ala Arg Gly Ser Arg Asp Glu Pro Leu His Arg Ser Leu Glu Leu
    450                 455                 460

Leu Ser Leu Gly Thr Gly Lys Arg Lys
465             470
```

CASEIN KINASE STRESS-RELATED POLYPEPTIDES AND METHODS OF USE IN PLANTS

CROSS-REFERENCE TO RELATED APPLICATIONS

This application is a divisional of U.S. patent application Ser. No. 11/667,820, filed May 15, 2007, which is a national phase application filed pursuant to 35 U.S.C. §371 of PCT/US2005/041522, filed Nov. 17, 2005, which claims the priority benefit of U.S. application Ser. No. 10/904,588, filed Nov. 17, 2004, as a continuation-in-part application of U.S. application Ser. No. 09/828,313, filed Apr. 6, 2001 claiming the priority benefit of U.S. Provisional Patent Application No. 60/196,001, filed Apr. 7, 2000. U.S. application Ser. No. 10/904,588 is also a continuation-in-part of U.S. application Ser. No. 10/292,408, filed Nov. 12, 2002, claiming the priority benefit of U.S. Provisional Patent Application No. 60/346,096, filed Nov. 9, 2001. The entire contents of the applications identified above are hereby incorporated by reference.

BACKGROUND OF THE INVENTION

1. Field of the Invention

This invention relates generally to nucleic acid sequences encoding polypeptides that are associated with abiotic stress responses and abiotic stress tolerance in plants. In particular, this invention relates to nucleic acid sequences encoding polypeptides that confer drought, cold, and/or salt tolerance to plants.

2. Background Art

Abiotic environmental stresses, such as drought stress, salinity stress, heat stress, and cold stress, are major limiting factors of plant growth and productivity. Crop losses and crop yield losses of major crops such as soybean, rice, maize (corn), cotton, and wheat caused by these stresses represent a significant economic and political factor and contribute to food shortages in many underdeveloped countries.

Plants are typically exposed during their life cycle to conditions of reduced environmental water content. Most plants have evolved strategies to protect themselves against these conditions of desiccation. However, if the severity and duration of the drought conditions are too great, the effects on development, growth, and yield of most crop plants are profound. Continuous exposure to drought conditions causes major alterations in the plant metabolism, which ultimately lead to cell death and consequently yield losses.

Developing stress-tolerant plants is a strategy that has the potential to solve or mediate at least some of these problems. However, traditional plant breeding strategies to develop new lines of plants that exhibit resistance (tolerance) to these types of stresses are relatively slow and require specific resistant lines for crossing with the desired line. Limited germplasm resources for stress tolerance and incompatibility in crosses between distantly related plant species represent significant problems encountered in conventional breeding. Additionally, the cellular processes leading to drought, cold, and salt tolerance in model drought- and/or salt-tolerant plants are complex in nature and involve multiple mechanisms of cellular adaptation and numerous metabolic pathways. This multi-component nature of stress tolerance has not only made breeding for tolerance largely unsuccessful, but has also limited the ability to genetically engineer stress tolerant plants using biotechnological methods.

Drought stresses, heat stresses, cold stresses, and salt stresses have a common theme important for plant growth and that is water availability. As discussed above, most plants have evolved strategies to protect themselves against conditions of desiccation; however, if the severity and duration of the drought conditions are too great, the effects on plant development, growth and yield of most crop plants are profound. Furthermore, most of the crop plants are very susceptible to higher salt concentrations in the soil. Because high salt content in some soils results in less water being available for cell intake, high salt concentration has an effect on plants similar to the effect of drought on plants. Additionally, under freezing temperatures, plant cells lose water as a result of ice formation that starts in the apoplast and withdraws water from the symplast. A plant's molecular response mechanisms to each of these stress conditions are common, and protein kinases, such as casein kinases, play an essential role in these molecular mechanisms.

Protein kinases represent a superfamily, and the members of this superfamily catalyze the reversible transfer of a phosphate group of ATP to serine, threonine, and tyrosine amino acid side chains on target polypeptides. Protein kinases are primary elements in signaling processes in plants and have been reported to play crucial roles in perception and transduction of signals that allow a cell (and the plant) to respond to environmental stimuli. In particular, casein kinase I proteins are monomeric serine/threonine type protein kinases that contain a highly conserved central kinase domain. Members of this family have divergent N-terminal and C-terminal extensions. The N-terminal region is responsible for substrate recognition and the C-terminal extension is important for the interaction of the kinase with substrates. The C-terminal extension also is thought to be important for mediating regulation through auto-phosphorylation (Gross and Anderson, 1998 Cell Signal 10:699-711; Graves and Roach, 1995, J Biol Chem 270:21689-21694).

Although some genes that are involved in stress responses and water use efficiency in plants have been characterized, the characterization and cloning of plant genes that confer stress tolerance and water use efficiency remains largely incomplete and fragmented. For example, certain studies have indicated that drought and salt stress in some plants may be due to additive gene effects, in contrast to other research that indicates specific genes are transcriptionally activated in vegetative tissue of plants under osmotic stress conditions. Although it is generally assumed that stress-induced proteins have a role in tolerance, direct evidence is still lacking, and the functions of many stress-responsive genes are unknown.

There is a fundamental physiochemically-constrained trade-off, in all terrestrial photosynthetic organisms, between $CO_2$ absorption and water loss (Taiz and Zeiger 1991 Plant Physiology, Benjamin/Cummings Publishing Co, p94). $CO_2$ needs to be in aqueous solution for the action of $CO_2$ fixation enzymes such as Rubisco (Ribulose 1,5-bisphosphate Carboxylase/Oxygenase) and PEPC (Phosphoenolpyruvate carboxylase). As a wet cell surface is required for $CO_2$ diffusion, evaporation will inevitably occur when the humidity is below 100% (Taiz and Zeiger 1991 Plant Physiology, Benjamin/Cummings Publishing Co p257). Plants have numerous physiological mechanisms to reduce water loss (e.g. waxy cuticles, stomatal closure, leaf hairs, sunken stomatal pits). As these barriers do not discriminate between water and $CO_2$ flux, these water conservation measures will also act to increase resistance to $CO_2$ uptake (Kramer 1983 Water Relations of Plants, Academic Press p305). Photosynthetic $CO_2$ uptake is absolutely required for plant growth and biomass accumulation in photoautotrophic plants. Water Use Efficiency (WUE) is a parameter frequently used to estimate the trade off between water consumption and $CO_2$ uptake/growth (Kramer 1983 Water Relations of Plants, Academic Press p405). WUE has been defined and measured in multiple ways. One approach is to calculate the ratio of whole plant dry weight, to the weight of water consumed by the plant throughout its life (Chu et al 1992 Oecologia 89:580). Another variation is to use a shorter time interval when biomass accumulation and water use are measured (Mian et al 1998 Crop Sci. 38:390). Often measurements from restricted parts of the plant are used, for example, measuring only aerial growth and water use (Nienhuis et al 1994 Amer J Bot 81:943). WUE has also been defined as the ratio of $CO_2$ uptake to water vapor loss from a leaf or portion of a leaf, often measured over a very short time period (seconds/minutes) (Kramer 1983 Water Relations of Plants, Academic Press p406). The ratio of $^{13}C/^{12}C$ fixed in plant tissue, and measured with an isotope ratio mass-spectrometer, has also been used to estimate WUE in plants using $C_3$ photo-synthesis (Martin et al 1999 Crop Sci. 1775).

An increase in WUE is informative about the relatively improved efficiency of growth and water consumption, but on its own it does not describe which of these two processes (or both) have changed. In selecting traits for improving crops, an increase in WUE due to a decrease in water use, without a change in growth would have particular merit in an irrigated agricultural system where the water input costs were high. An increase in WUE driven mainly by an increase in growth without a corresponding jump in water use would have applicability to all agricultural systems. In many agricultural systems where water supply is not limiting, an increase in growth, even if it came at the expense of an increased water use (i.e. no change in WUE), could also increase yield. Therefore new methods to increase both WUE and biomass accumulation are required to improve agricultural productivity. As WUE integrates many physiological processes relating to primary metabolism and water use, it is typically a highly polygenic trait with a large genotype by environment interaction (Richards et al 2002 Crop Sci 42:111). For these and other reasons few attempts to select for WUE changes in traditional breeding programs have been successful.

There is a need, therefore, to identify genes expressed in stress tolerant plants and plants that are efficient in water use that have the capacity to confer stress tolerance and water use efficiency to its host plant and to other plant species. Newly generated stress tolerant plants will have many advantages, such as an increased range in which the crop plants can be cultivated, by for example, decreasing the water requirements of a plant species. Other desirable advantages include increased resistance to lodging, the bending of shoots or stems in response to wind, rain, pests, or disease.

SUMMARY OF THE INVENTION

This invention fulfills in part the need to identify new, unique casein kinases capable of conferring stress tolerance to plants upon over-expression. The present invention describes a novel genus of Casein Kinase Stress-Related Polypeptides (CKSRPs) and CKSRP coding nucleic acids that are important for modulating a plant's response to an environmental stress. More particularly, overexpression of these CKSRP coding nucleic acids in a plant results in the plant's increased tolerance to an environmental stress.

Therefore, the present invention includes an isolated plant cell comprising a CKSRP coding nucleic acid, wherein expression of the nucleic acid sequence in the plant cell results in increased tolerance to environmental stress as compared to a wild type variety of the plant cell. Preferably, the CKSRP is from *P. patens*, *S. cerevisiae*, or *B. napus*. Namely, described herein are the *P. patens* Casein Kinase-4 (PpCK-4 or EST 289), *P. patens* Casein Kinase-1 (PpCK-1 or EST 194), *P. patens* Casein Kinase-2 (PpCK-2 or EST 263), *P. patens* Protein Kinase-4 (PpPK-4 or EST 142), *S. cerevisiae* Casein Kinase-1 (ScCK-1 or ORF 760), *B. napus* Casein Kinase-1 (BnCK-1), *B. napus* Casein Kinase-2 (BnCK-2). *B. napus* Casein Kinase-3 (BnCK-3), *B. napus* Casein Kinase-4 (BnCK-4), and *B. napus* Casein Kinase-5 (BnCK-5).

The invention provides in some embodiments that the CKSRP and coding nucleic acid are those that are found in members of the genus *Physcomitrella*, *Saccharomyces* or *Brassica*. In another preferred embodiment, the nucleic acid and polypeptide are from a *P. patens* or *B. napus* plant or a *S. cerevisiae* yeast. The invention provides that the environmental stress can be salinity, drought, temperature, metal, chemical, pathogenic and oxidative stresses, or combinations thereof. In preferred embodiments, the environmental stress can be selected from one or more of the group consisting of drought, high salt, and low temperature.

The invention further provides a seed produced by a transgenic plant transformed by a CKSRP coding nucleic acid, wherein the plant is true breeding for increased tolerance to environmental stress as compared to a wild type variety of the plant.

The invention further provides an agricultural product produced by any of the below-described transgenic plants, plant parts, or seeds. The invention further provides an isolated CKSRP as described below. The invention further provides an isolated CKSRP coding nucleic acid, wherein the CKSRP coding nucleic acid codes for a CKSRP as described below.

The invention further provides an isolated recombinant expression vector comprising a CKSRP coding nucleic acid as described below, wherein expression of the vector in a host cell results in increased tolerance to environmental stress as compared to a wild type variety of the host cell. The invention further provides a host cell containing the vector and a plant containing the host cell.

The invention further provides a method of producing a transgenic plant with a CKSRP coding nucleic acid, wherein expression of the nucleic acid in the plant results in increased tolerance to environmental stress as compared to a wild type variety of the plant comprising: (a) transforming a plant cell with an expression vector comprising a CKSRP coding nucleic acid, and (b) generating from the plant cell a transgenic plant with an increased tolerance to environmental stress as compared to a wild type variety of the plant. In preferred embodiments, the CKSRP and CKSRP coding nucleic acid are as described below.

The present invention further provides a method of identifying a novel CKSRP, comprising (a) raising a specific antibody response to a CKSRP, or fragment thereof, as described below; (b) screening putative CKSRP material with the antibody, wherein specific binding of the antibody to the material indicates the presence of a potentially novel CKSRP; and (c) identifying from the bound material a novel CKSRP in comparison to known CKSRP. Alternatively, hybridization with nucleic acid probes as described below can be used to identify novel CKSRP nucleic acids.

The present invention also provides methods of modifying stress tolerance of a plant comprising, modifying the expression of a CKSRP nucleic acid in the plant, wherein the CKSRP is as described below. The invention provides that this method can be performed such that the stress tolerance is either increased or decreased. Preferably, stress tolerance is increased in a plant via increasing expression of a CKSRP nucleic acid.

BRIEF DESCRIPTION OF THE DRAWINGS

FIG. 5A-5C shows an alignment of the amino acid sequences of the five disclosed *P. patens* and *S. cerevisiae* casein kinases with the amino acid sequences of other known casein kinases (SEQ ID NOS 10, 47-48, 6, 4, 2, 49-52, 8, and 53, respectively in order of appearance). Amino acid residues that are conserved among each of the sequences, and those amino acid residues that are either identical or similar over some or all of the sequences, are indicated with shading.

FIG. 7A-7E shows an alignment of the amino acid sequence of the five disclosed *P. patens* and *S. cerevisiae* casein kinases with the disclosed *B. napus*, linseed, wheat, barley, sunflower and soybean casein kinases. Amino acid residues that are conserved among each of the sequences, and those amino acid residues that are either identical or similar over some or all of the sequences, are indicated with shading.

FIG. 8: PpPK-4, PpCK-4, PpCK-2 or PpCK-1 were over-expressed in *A. thaliana* under the control of a constitutive promoter. The transgenic lines were assayed for relative water use efficiency (WUE), dry weight (DW), and plant water use (E) (% difference from controls).

DETAILED DESCRIPTION OF THE INVENTION

Figure 1:
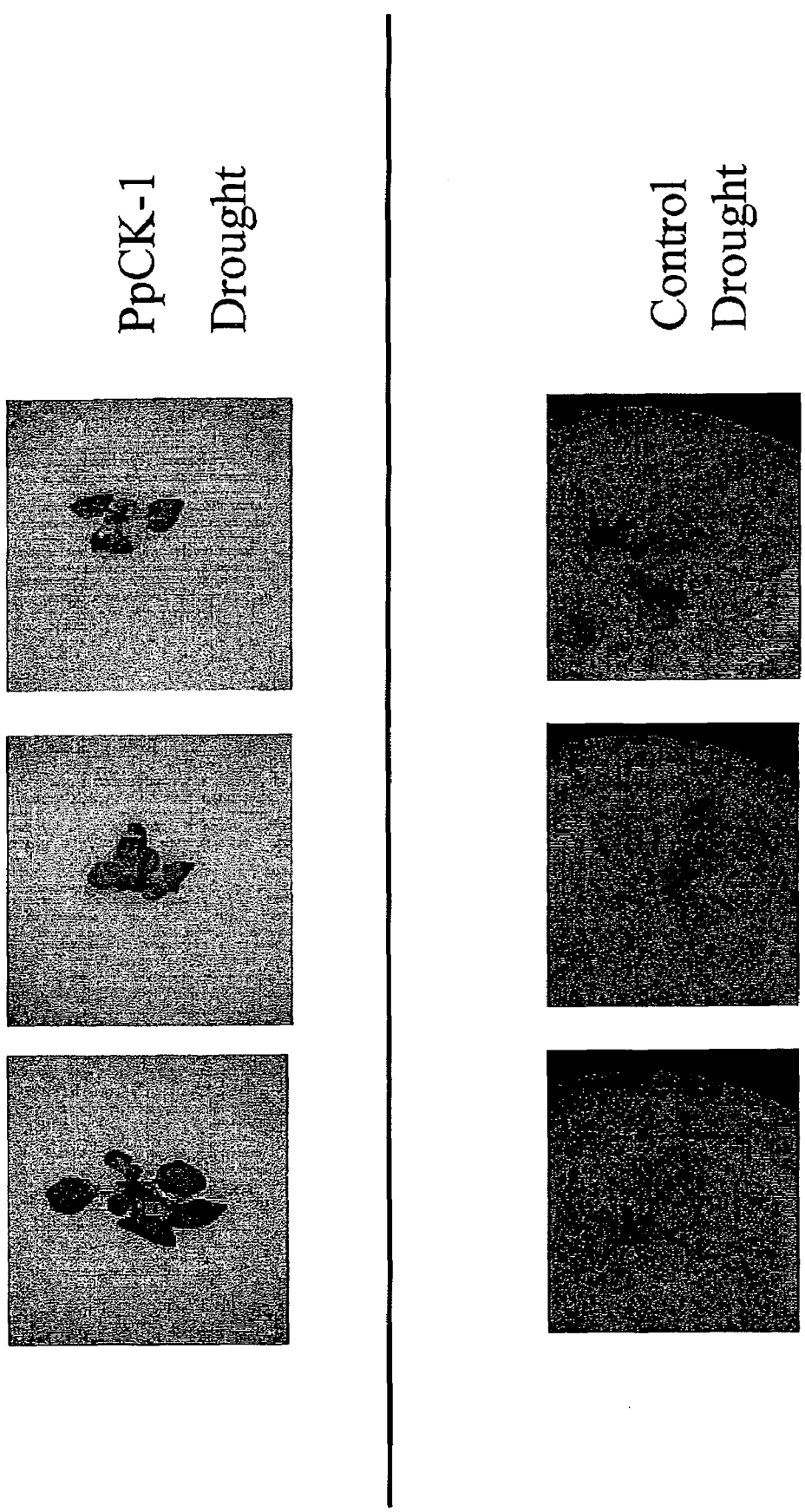
FIG. 1 shows the results of a drought stress test with over-expressing PpCK-1 transgenic plants and wild-type *Arabidopsis* lines. The transgenic lines display a tolerant phenotype. Individual transformant lines are shown.
Figure 2:
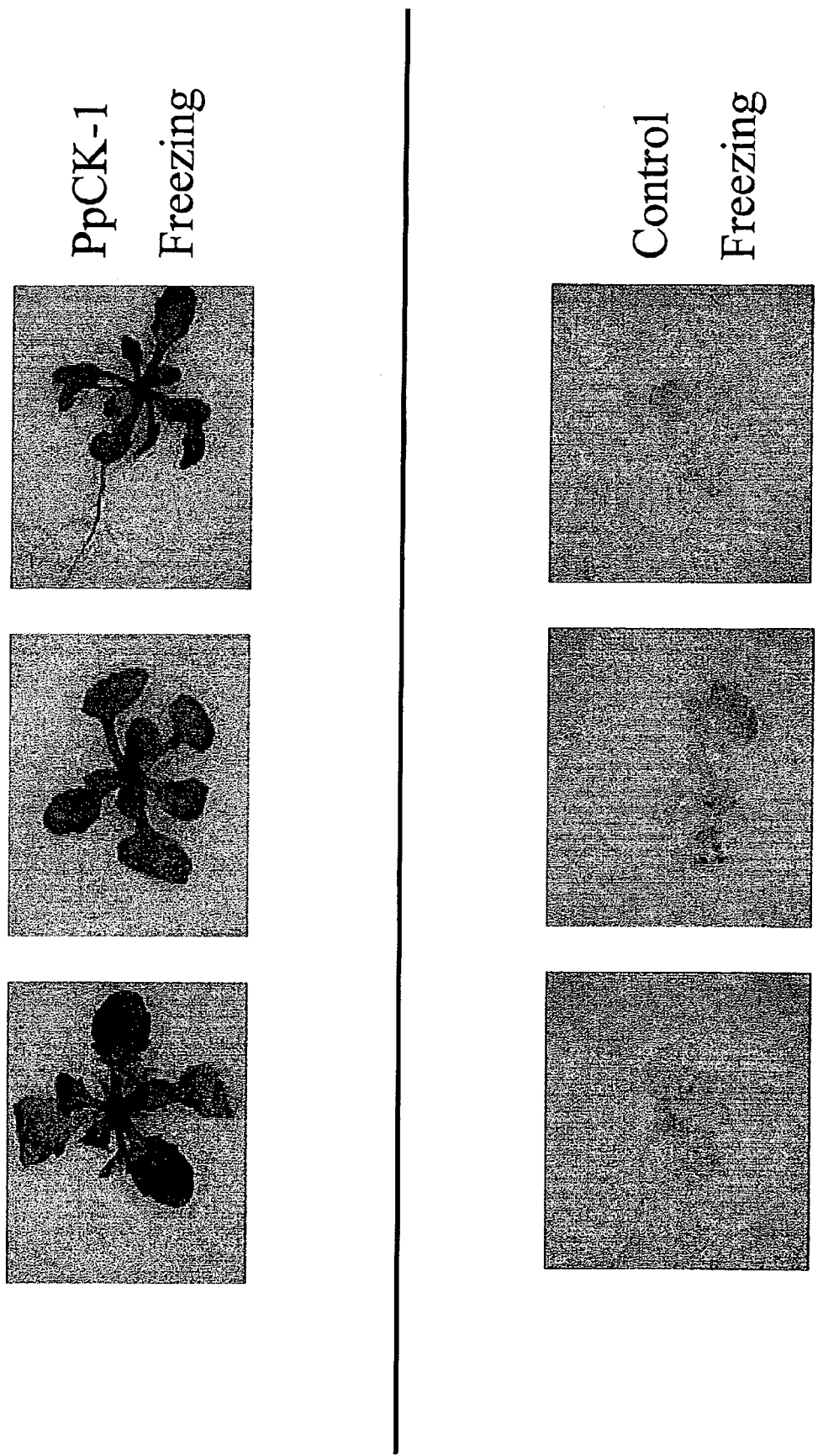
FIG. 2 shows the results of a freezing stress test with over-expressing PpCK-1 transgenic plants and wild-type *Arabidopsis* lines. The transgenic lines display a tolerant phenotype. Individual transformant lines are shown.
Figure 3:
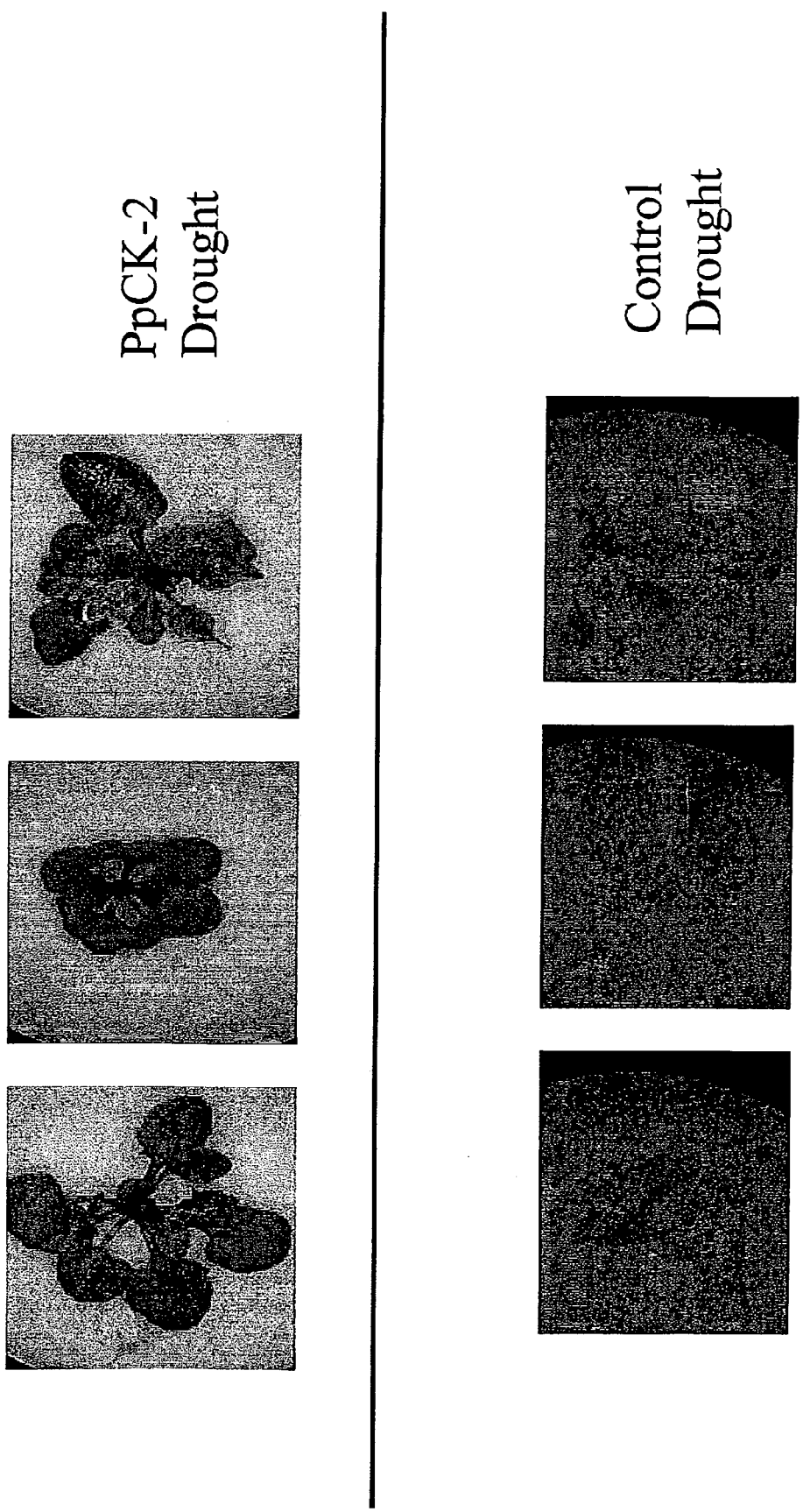
FIG. 3 shows the results of a drought stress test with over-expressing PpCK-2 transgenic plants and wild-type *Arabidopsis* lines. The transgenic lines display a tolerant phenotype. Individual transformant lines are shown.
Figure 4:
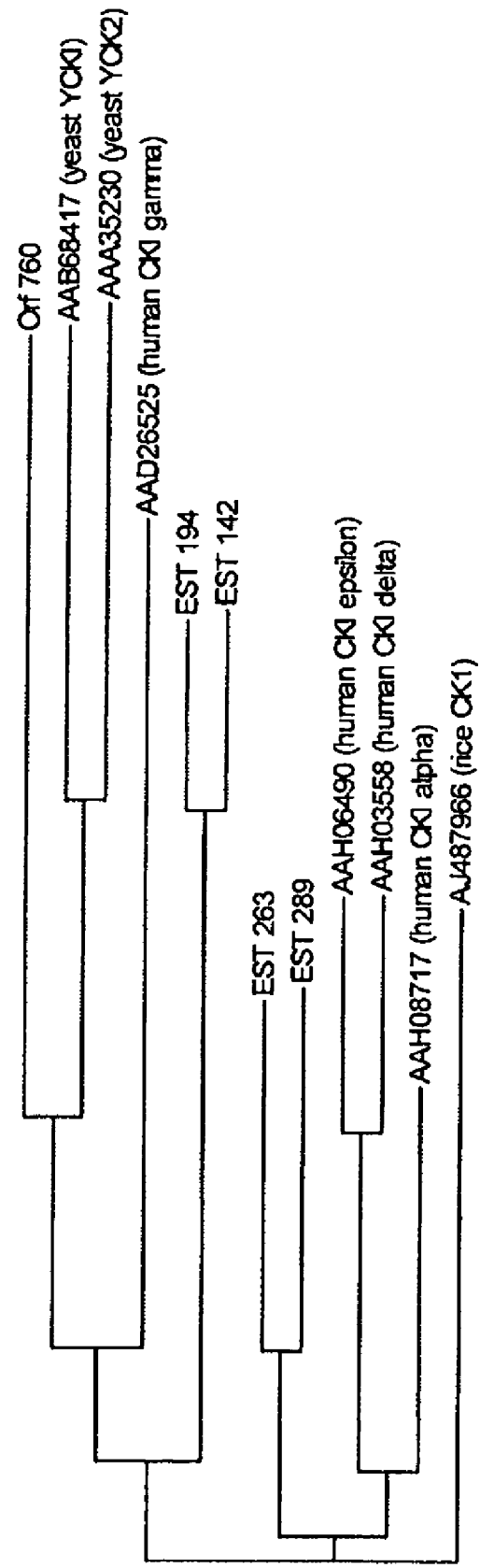
FIG. 4 shows a diagram illustrating the relative homology of the disclosed *P. patens* and *S. cerevisiae* casein kinases and other known casein kinases.
Figure 6:
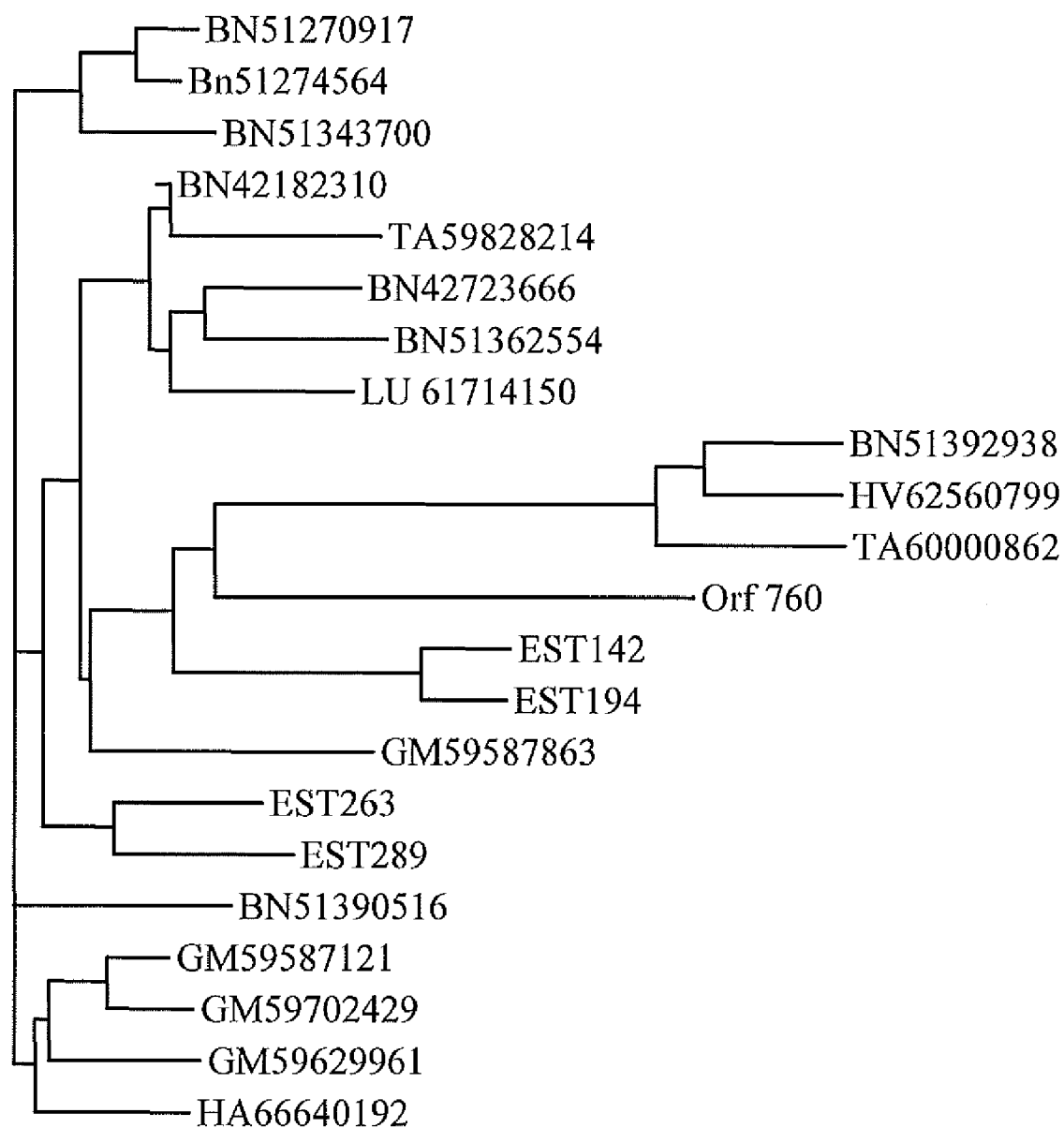
FIG. 6 shows a diagram illustrating the relative homology of the five disclosed *P. patens* and *S. cerevisiae* casein kinases with the disclosed *B. napus*, linseed, wheat, barley, sunflower and soybean casein kinases.

The present invention may be understood more readily by reference to the following detailed description of the preferred embodiments of the invention and the Examples included herein. However, before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting. In particular, the designation of the amino acid sequences as polypeptide "Casein Kinase Stress-Related Polypeptides" (CKSRPs), in no way limits the functionality of those sequences.

The present invention describes a novel genus of CKSRPs and CKSRP coding nucleic acids that are important for modulating a plant's response to an environmental stress. More particularly, over-expression of these CKSRP coding nucleic acids in a plant results in the plant's increased tolerance to an environmental stress. Representative members of the CKSRP genus include, but are not limited to, PpCK-1, PpCK-2, PpCK-4, PpPK-4, ScCK-1, BnCK-1, BnCK-2, BnCK-3, BnCK-4, and BnCK-5. In a preferred embodiment, all members of the genus are biologically active casein kinases.

Accordingly, the present invention encompasses CKSRP polynucleotide and polypeptide sequences and their use for increasing a plant's tolerance to an environmental stress. In one embodiment, the CKSRP sequences are from a plant, preferably a *Physcomitrella* plant or a *Brassica* plant, and more preferably a *P. patens* plant or a *B. napus* plant. In another embodiment, the CKSRP sequences include PpCK-1 (SEQ ID NOS:3 and 4), PpCK-2 (SEQ ID NOS:5 and 6), PpCK-4 (SEQ ID NOS:1 and 2), PpPK-4 (SEQ ID NOS:7 and 8), ScCK-1 (SEQ ID NOS:9 and 10), BnCK-1 (SEQ ID NOS:1 and 12), BnCK-2 (SEQ ID NOS:13 and 14), BnCK-3 (SEQ ID NOS:15 and 16), BnCK-4 (SEQ ID NOS:17 and 18), and BnCK-5 (SEQ ID NOS:19 and 20). The disclosed *P. patens* CKSRP sequences and the disclosed *S. cerevisiae* CKSRP sequence have significant percent identity to known casein kinases as is indicated in Table 1.

TABLE 1

| | ORF 760 Sim (%) | ORF 760 Iden (%) | EST 142 Sim (%) | EST 142 Iden (%) | EST 194 Sim (%) | EST 194 Iden (%) | EST 263 Sim (%) | EST 263 Iden (%) | EST 289 Sim (%) | EST 289 Iden (%) |
|---|---|---|---|---|---|---|---|---|---|---|
| ORF 760 | | | 32.9 | 25.4 | 33.4 | 24.7 | 43.3 | 34.5 | 42.0 | 32.4 |
| AAB68417 | 50.9 | 41.2 | 36.3 | 26.0 | 36.8 | 26.5 | 42.7 | 32.8 | 41.9 | 31.4 |
| AAA35230 | 48.8 | 39.4 | 36.2 | 25.8 | 36.9 | 26.1 | 42.3 | 31.3 | 43.2 | 31.1 |
| EST 263 | 43.3 | 34.5 | 40.4 | 32.5 | 40.5 | 33.2 | | | 80.8 | 74.0 |
| EST 194 | 33.4 | 24.7 | 90.2 | 86.9 | | | 40.5 | 33.2 | 42.0 | 32.4 |
| EST 289 | 42.0 | 32.4 | 41.3 | 33.3 | 41.7 | 33.7 | 80.8 | 74.0 | | |
| AAH06490 | 43.7 | 33.4 | 44.2 | 34.6 | 43.0 | 33.8 | 63.7 | 53.8 | 63.9 | 53.4 |
| AAH03558 | 42.4 | 33.0 | 43.7 | 34.5 | 44.1 | 34.9 | 63.2 | 54.5 | 65.0 | 54.2 |
| AAH08717 | 39.7 | 31.5 | 50.7 | 40.0 | 51.7 | 40.7 | 53.3 | 45.8 | 54.1 | 46.7 |
| AAD26525 | 41.6 | 32.8 | 43.6 | 32.3 | 42.5 | 31.9 | 48.9 | 38.4 | 49.0 | 38.0 |
| EST 142 | 32.9 | 25.4 | | | 90.2 | 86.9 | 40.4 | 32.5 | 41.3 | 33.3 |
| AJ487966 | 44.8 | 33.6 | 40.1 | 30.7 | 40.5 | 30.9 | 72.0 | 58.6 | 68.7 | 55.9 |

The present invention provides a transgenic plant cell transformed by a CKSRP coding nucleic acid, wherein expression of the nucleic acid sequence in the plant cell results in increased tolerance to an environmental stress as compared to a wild type variety of the plant cell. The invention further provides transgenic plant parts and transgenic plants containing the plant cells described herein. Plant parts include, but are not limited to, stems, roots, ovules, stamens, leaves, embryos, meristematic regions, callus tissue, gametophytes, sporophytes, pollen, microspores, and the like. In one embodiment, the transgenic plant is male sterile. Also provided is a plant seed produced by a transgenic plant transformed by a CKSRP coding nucleic acid, wherein the seed contains the CKSRP coding nucleic acid, and wherein the plant is true breeding for increased tolerance to environmental stress as compared to a wild type variety of the plant. The invention further provides a seed produced by a transgenic plant expressing a CKSRP, wherein the seed contains the CKSRP, and wherein the plant is true breeding for increased tolerance to environmental stress as compared to a wild type variety of the plant. The invention also provides an agricultural product produced by any of the below-described transgenic plants, plant parts, and plant seeds. Agricultural products include, but are not limited to, plant extracts, proteins, amino acids, carbohydrates, fats, oils, polymers, vitamins, and the like.

As used herein, the term "variety" refers to a group of plants within a species that share constant characters that separate them from the typical form and from other possible varieties within that species. While possessing at least one distinctive trait, a variety is also characterized by some variation between individuals within the variety, based primarily on the Mendelian segregation of traits among the progeny of succeeding generations. A variety is considered "true breeding" for a particular trait if it is genetically homozygous for that trait to the extent that, when the true-breeding variety is self-pollinated, a significant amount of independent segregation of the trait among the progeny is not observed. In the present invention, the trait arises from the transgenic expression of one or more DNA sequences introduced into a plant variety.

The present invention describes for the first time that the *P. patens* CKSRPs, PpCK-1, PpCK-2, PpCk-4, and PpPK-4; *S. cerevisiae* CKSRP ScCK-1; and *B. napus* CKSRPs, BnCK-1, BnCK-2, BnCK-3, BnCK-4, and BnCK-5 are useful for increasing a plant's tolerance to environmental stress. As used herein, the term polypeptide refers to a chain of at least four amino acids joined by peptide bonds. The chain may be linear, branched, circular, or combinations thereof. Accordingly, the present invention provides isolated CKSRPs selected from PpCK-1, PpCK-2, PpCK-4, PpPK-4, ScCK-1, BnCK-1, BnCK-2, BnCK-3, BnCK-4, and BnCK-5, and homologs thereof. In preferred embodiments, the CKSRP is selected from: 1) *P. patens* Casein Kinase-1 (PpCK-1) polypeptide as defined in SEQ ID NO:4) *P. patens* Casein Kinase-2 (PpCK-2) polypeptide as defined in SEQ ID NO:6) *P. patens* Casein Kinase-4 (PpCK-4) polypeptide as defined in SEQ ID NO:1) *P. patens* Protein Kinase-4 (PpPK-4) polypeptide as defined in SEQ ID NO:8) *S. cerevisiae* Casein Kinase-1 (ScCK-1) polypeptide as defined in SEQ ID NO:10) *B. napus* Casein Kinase-1 (BnCK-1) polypeptide as defined in SEQ ID NO:12; *B. napus* Casein Kinase-2 (BnCK-2) polypeptide as defined in SEQ ID NO:14; *B. napus* Casein Kinase-3 (BnCK-4) polypeptide as defined in SEQ ID NO:16; *B. napus* Casein Kinase-4 (BnCK-4) polypeptide as defined in SEQ ID NO:18; *B. napus* Casein Kinase-5 (BnCK-5) polypeptide as defined in SEQ ID NO:20; and homologs and orthologs thereof. Homologs and orthologs of the amino acid sequences are defined below.

The CKSRPs of the present invention are preferably produced by recombinant DNA techniques. For example, a nucleic acid molecule encoding the polypeptide is cloned into an expression vector (as described below), the expression vector is introduced into a host cell (as described below), and the CKSRP is expressed in the host cell. The CKSRP can then be isolated from the cells by an appropriate purification scheme using standard polypeptide purification techniques. For the purposes of the invention, the term "recombinant polynucleotide" refers to a polynucleotide that has been altered, rearranged, or modified by genetic engineering. Examples include any cloned polynucleotide, and polynucleotides that are linked or joined to heterologous sequences. The term "recombinant" does not refer to alterations to polynucleotides that result from naturally occurring events, such as spontaneous mutations. Alternative to recombinant expression, a CKSRP, or peptide thereof, can be synthesized chemically using standard peptide synthesis techniques. Moreover, native CKSRP can be isolated from cells (e.g., *P. patens*, *S. cerevisiae*, or *B. napus* cells), for example using an anti-CKSRP antibody, which can be produced by standard techniques utilizing a CKSRP or fragment thereof.

As used herein, the term "environmental stress" refers to sub-optimal conditions associated with salinity, drought, temperature, metal, chemical, pathogenic, and oxidative stresses, or combinations thereof. In preferred embodiments, the environmental stress can be selected from one or more of the group consisting of salinity, drought, or temperature, or combinations thereof, and in particular, can be selected from one or more of the group consisting of high salinity, low water content, or low temperature. It is also to be understood that as used in the specification and in the claims, "a" or "an" can mean one or more, depending upon the context in which it is used. Thus, for example, reference to "a cell" can mean that at least one cell can be utilized. As also used herein, the term "water use efficiency" refers to the amount of organic matter produced by a plant divided by the amount of water used by the plant in producing it, i.e. the dry weight of a plant in relation to the plant's water use.

As also used herein, the term "nucleic acid" and "polynucleotide" refer to RNA or DNA that is linear or branched, single or double stranded, or a hybrid thereof. The term also encompasses RNA/DNA hybrids, These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine, and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

An "isolated" nucleic acid molecule is one that is substantially separated from other nucleic acid molecules, which are present in the natural source of the nucleic acid (i.e., sequences encoding other polypeptides). Preferably, an "isolated" nucleic acid is free of some of the sequences, which naturally flank the nucleic acid (i.e. sequences located at the 5' and 3' ends of the nucleic acid) in its naturally occurring replicon. For example, a cloned nucleic acid is considered isolated. In various embodiments, the isolated CKSRP nucleic acid molecule can contain less than about 5 kb, 4 kb, 3 kb, 2 kb, 1 kb, 0.5 kb, or 0.1 kb of nucleotide sequences which naturally flank the nucleic acid molecule in genomic DNA of the cell from which the nucleic acid is derived (e.g., a *P. patens* cell, a *S. cerevisiase* cell, or a *B. napus* cell). A nucleic acid is also considered isolated if it has been altered by human intervention, or placed in a locus or location that is not its natural site, or if it is introduced into a cell by agroinfection. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

Specifically excluded from the definition of "isolated nucleic acids" are: naturally-occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified nucleic acid makes up less than 5% of the number of nucleic acid inserts in the vector molecules. Further specifically excluded are whole cell genomic DNA or whole cell RNA preparations (including whole cell preparations that are mechanically sheared or enzymatically digested). Even further specifically excluded are the whole cell preparations found as either an in vitro preparation or as a heterogeneous mixture separated by electrophoresis wherein the nucleic acid of the invention has not further been separated from the heterologous nucleic acids in the electrophoresis medium (e.g., further separating by excising a single band from a heterogeneous band population in an agarose gel or nylon blot).

A nucleic acid molecule of the present invention, e.g., a nucleic acid molecule having a nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, or a portion thereof, can be isolated using standard molecular biology techniques and the sequence information provided herein. For example, a *P. patens* CKSRP cDNA can be isolated from a *P. patens* library using all or a portion of one of the sequences disclosed herein. Moreover, a nucleic acid molecule encompassing all or a portion of one of the sequences of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, and SEQ ID NO:19, can be isolated by the polymerase chain reaction using oligonucleotide primers designed based upon this sequence. For example, mRNA can be isolated from plant cells (e.g., by the guanidinium-thiocyanate extraction procedure of Chirgwin et al., 1979, Biochemistry 18:5294-5299), and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, and SEQ ID NO:19. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to a CKSRP nucleotide sequence can be prepared by standard synthetic techniques, e.g., using an automated DNA synthesizer.

In a preferred embodiment, an isolated nucleic acid molecule of the invention comprises one of the nucleotide sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19. These cDNAs may comprise sequences encoding the CKSRPs, (i.e., the "coding region"), as well as 5' untranslated sequences and 3' untranslated sequences. Alternatively, the nucleic acid molecules of the present invention can comprise only the coding region of any of the sequences in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, or can contain whole genomic fragments isolated from genomic DNA. The present invention also includes CKSRP coding nucleic acids that encode CKSRPs as described herein. Preferred is a CKSRP coding nucleic acid that encodes a CKSRP selected from the group consisting of PpCK-1 (SEQ ID NO:4), PpCK-2 (SEQ ID NO:6), PpCK-4 (SEQ ID NO:2), PpPK-4 (SEQ ID NO:8), ScCK-1 (SEQ ID NO:10), BnCK-1 (SEQ ID NO:12), BnCK-2 (SEQ ID NO:14), BnCK-3 (SEQ ID NO:16), BnCK-4 (SEQ ID NO:18), and BnCK-5 (SEQ ID NO:20).

Moreover, the nucleic acid molecule of the invention can comprise a portion of the coding region of one of the sequences in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, and SEQ ID NO:19, for example, a fragment that can be used as a probe or primer or a fragment encoding a biologically active portion of a CKSRP. The nucleotide sequences determined from the cloning of the CKSRP genes from *P. patens, S. cerevisiae*, and *B. napus* allow for the generation of probes and primers designed for use in identifying and/or cloning CKSRP homologs in other cell types and organisms, as well as CKSRP homologs from other mosses and related species The portion of the coding region can also encode a biologically active fragment of a CKSRP.

As used herein, the term "biologically active portion of" a CKSRP is intended to include a portion, e.g., a domain/motif, of a CKSRP that participates in modulation of stress tolerance in a plant, and more preferably, drought tolerance or salt tolerance. For the purposes of the present invention, modulation of stress tolerance refers to at least a 10% increase or decrease in the stress tolerance of a transgenic plant comprising a CKSRP expression cassette (or expression vector) as compared to the stress tolerance of a non-transgenic control plant. Methods for quantitating stress tolerance are provided at least in Example 7 below. In a preferred embodiment, the biologically active portion of a CKSRP increases a plant's tolerance to an environmental stress.

Figure 5A:
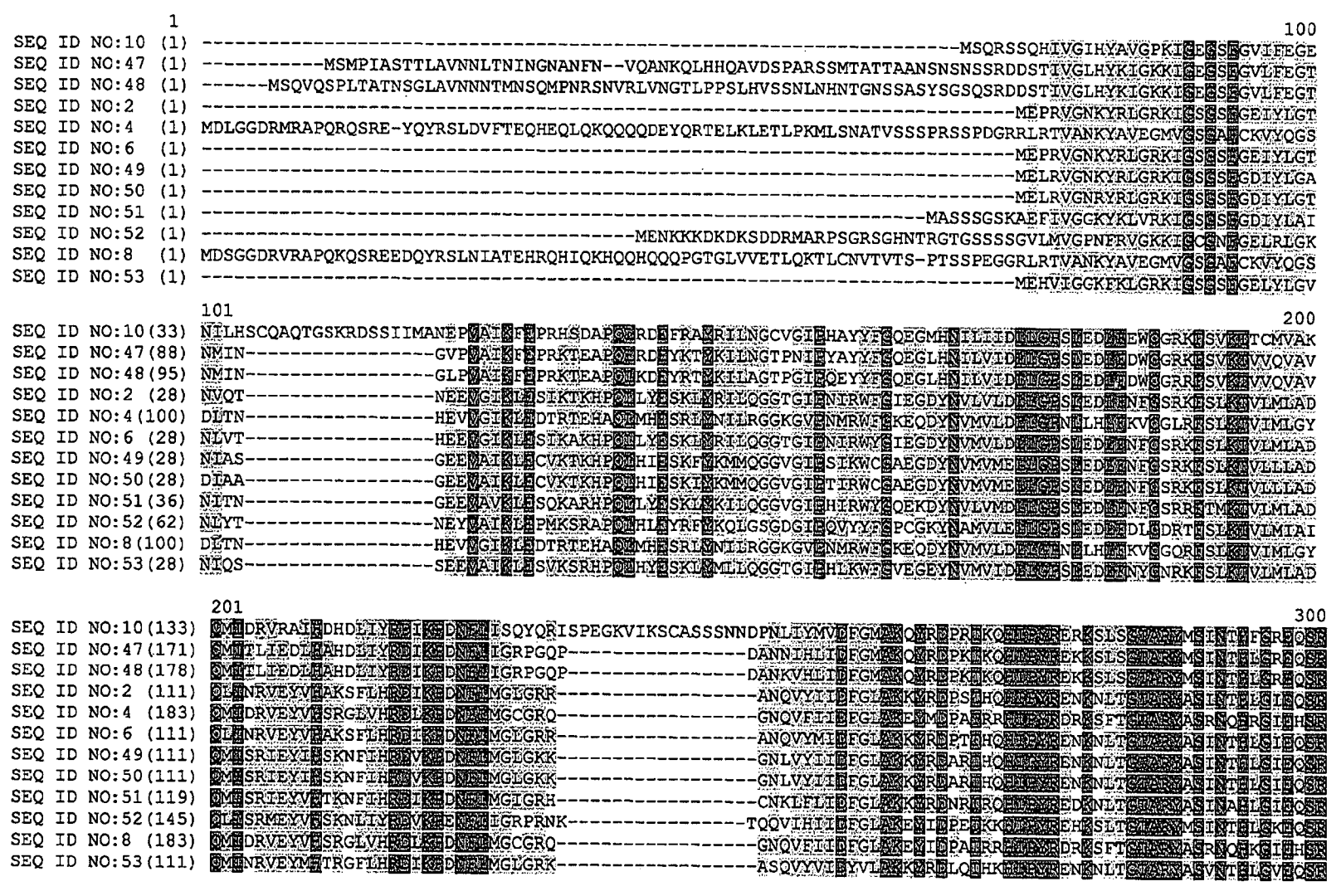
Figure 7A:
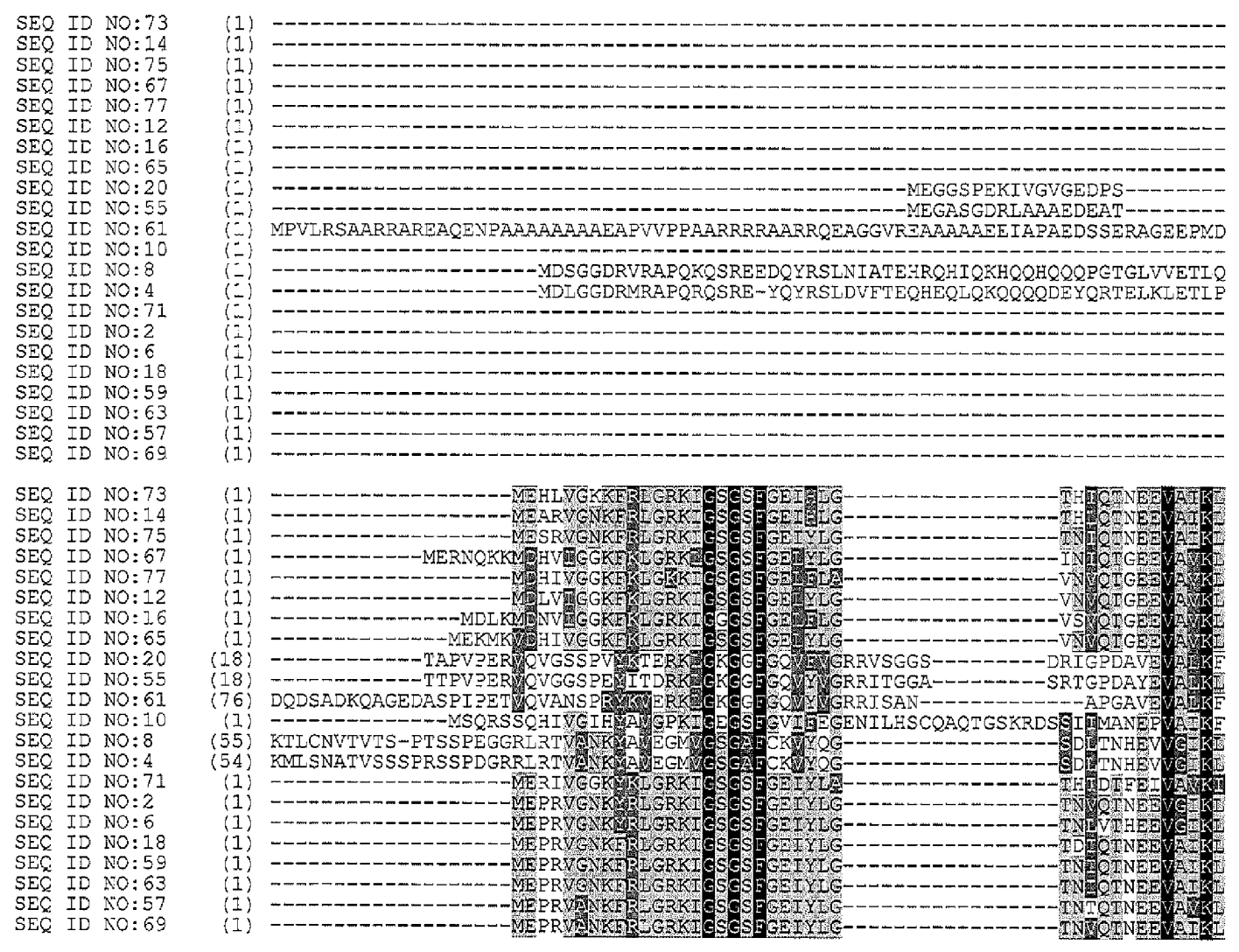
Figure 7B:
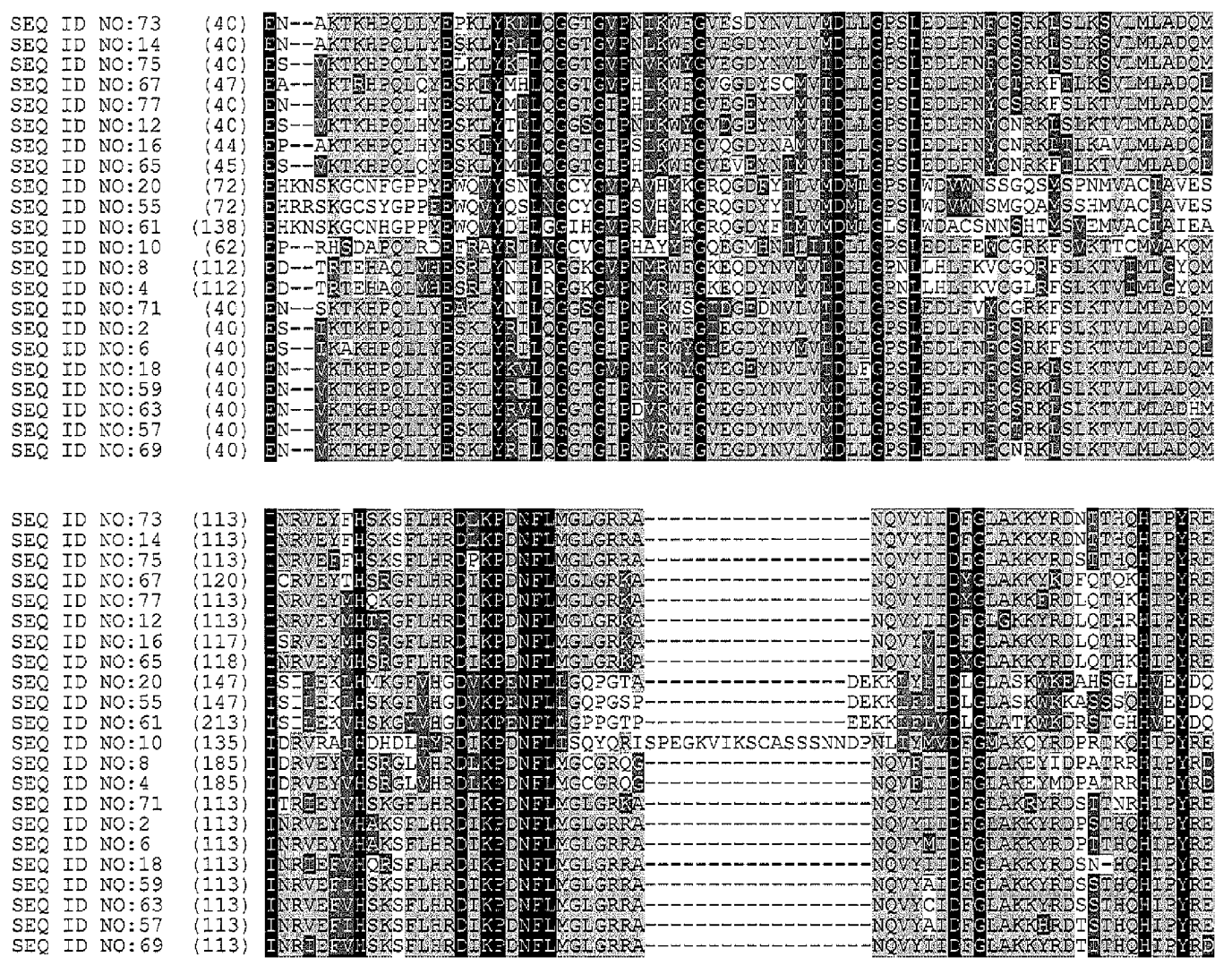
Figure 7C:
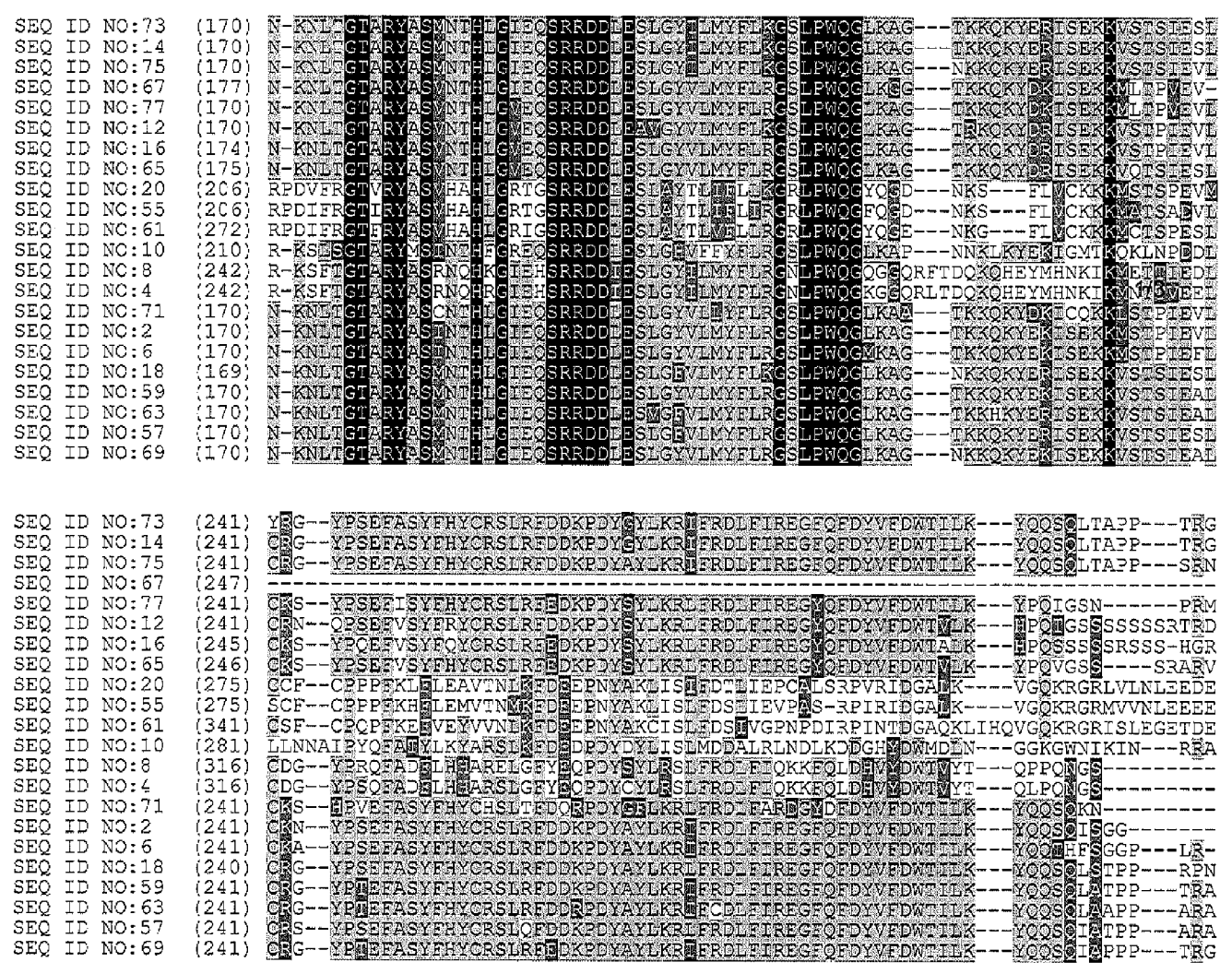
Figure 7D:
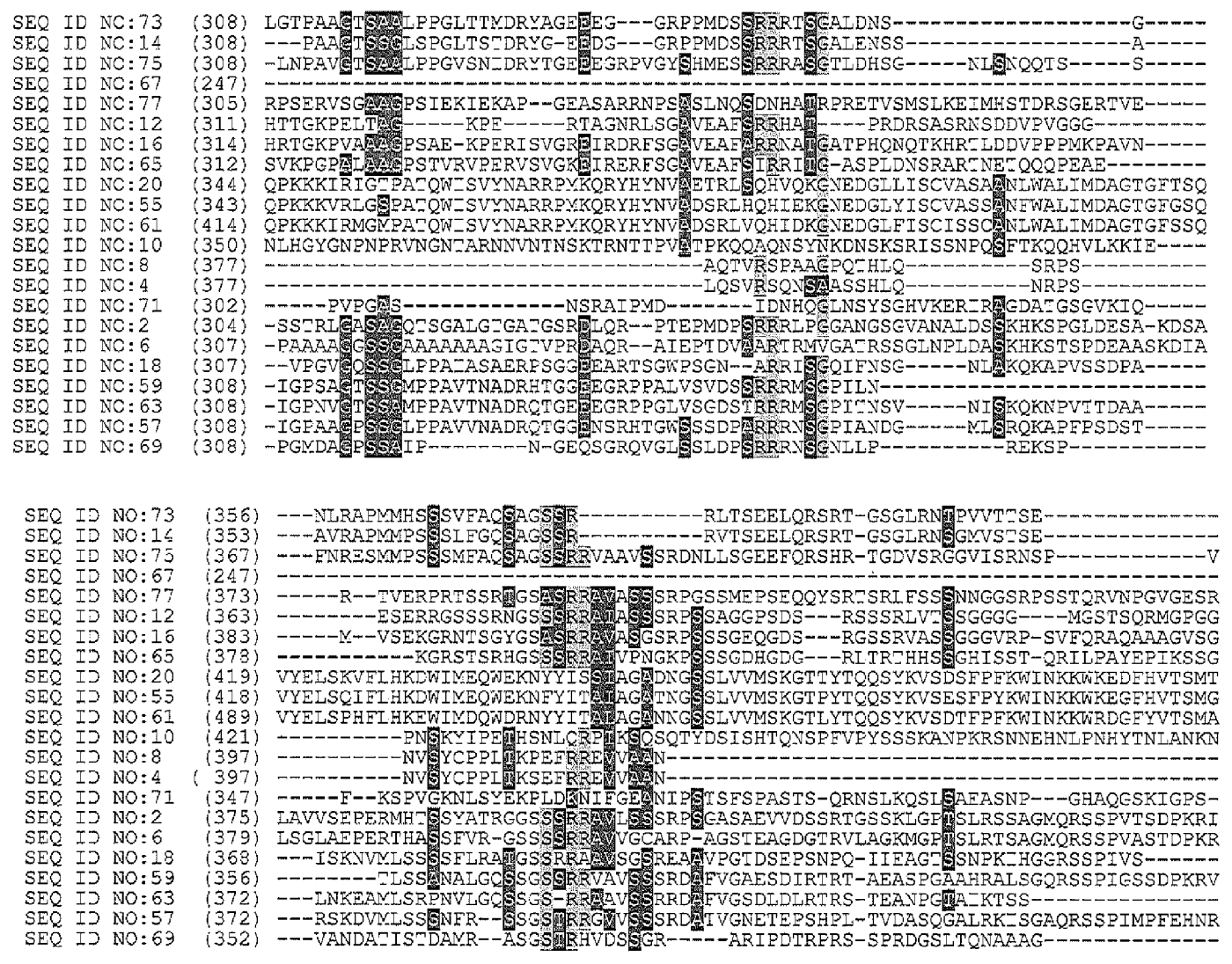

Biologically active portions of a CKSRP include peptides comprising amino acid sequences derived from the amino acid sequence of a CKSRP, e.g., an amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, or the amino acid sequence of a polypeptide identical to a CKSRP, which include fewer amino acids than a full length CKSRP or the full length polypeptide which is identical to a CKSRP, and exhibit at least one activity of a CKSRP. Typically, biologically active portions (e.g., peptides which are, for example, 5, 10, 15, 20, 30, 35, 36, 37, 38, 39, 40, 50, 100, or more amino acids in length) comprise a domain or motif with at least one activity of a CKSRP. Moreover, other biologically active portions, in which other regions of the polypeptide are deleted, can be prepared by recombinant techniques and evaluated for one or more of the activities described herein. Preferably, the biologically active portion of a CKSRP includes one or more selected domains/motifs, or portions thereof, having biological activity such as the conserved central kinase domain, as is shown in FIGS. 5 and 7. In a preferred embodiment, the conserved central kinase domain comprises four conserved regions, wherein the first region commences with a glycine residue at position 1 and has a glycine at position 3 and a phenylalanine residue at position 5; the second region is downstream from the first region, commences with a valine residue at position 1, and has a lysine at position 4, a glutamate residue at position 6, a glutamine residue at position 14, a leucine residue at position 15, a glutamate residue at position 18, a tyrosine residue at position 22, a proline residue at position 32, a glycine residue at position 38, a asparagine residue at position 44, a leucine residue at positions 50 and 51, a glycine residue at position 52, a proline residue at position 53, a leucine residue at position 55, a leucine residue at position 58, a phenylalanine residue at position 59, a cysteine residue at position 62, a phenylalanine residue at position 66, a lysine residue at position 69, a threonine residue at position 70, a glutamine residue at position 77, a isoleucine residue at position 79, a histidine residue at position 86, an arginine residue at position 93, an aspartic acid residue at position 94, a lysine residue at position 96, a proline residue at position 97, a asparagine residue at position 99, a phenylalanine residue at position 100, and a leucine residue at position 101; the third region is downstream from the second region, commences with an aspartic acid residue at position 1, and has an alanine residue at position 5, a lysine residue at position 6, a tyrosine residue at position 8, an aspartic acid residue at position 10, a threonine residue at position 13, a histidine residue at position 16, a isoleucine residue at position 17, a proline residue at position 18, a tyrosine residue at position 19, an arginine residue at position 20, a lysine residue at position 23, a glycine residue at position 27, a threonine residue at position 28, a alanine residue at position 29, a arginine residue at position 30, a tyrosine residue at position 31, a serine residue at position 33, an asparagines residue at position 35, a histidine residue at position 37, a glycine residue at position 39, a glutamate residue at position 41, a serine residue at position 43, an arginine residue at position 44, an arginine residue at position 45, an aspartic acid residue at position 46, an aspartic acid residue at position 47, a glutamate residue at position 49, a glycine residue at position 52, a tyrosine residue at position 57, a phenylalanine residue at position 58, a leucine residue at position 63, a proline residue at position 64, a tryptophan residue at position 65, a glutamine residue at position 66, and a glycine residue at position 67, and the fourth region is downstream from the third region, commences with a proline residue at position 1, and has an arginine residue at position 12, a leucine residue at position 14, a phenylalanine residue at position 16, a proline residue at position 20, an aspartic acid residue at position 21, a tyrosine residue at position 22, an aspartic acid residue at position 41, an aspartic acid residue at position 45, and a tryptophan residue at position 46.

The invention also provides CKSRP chimeric or fusion polypeptides. As used herein, a CKSRP "chimeric polypeptide" or "fusion polypeptide" comprises a CKSRP operatively linked to a non-CKSRP. A CKSRP refers to a polypeptide having an amino acid sequence corresponding to a CKSRP, whereas a nonCKSRP refers to a polypeptide having an amino acid sequence corresponding to a polypeptide which is not substantially identical to the CKSRP, e.g., a polypeptide that is different from the CKSRP and is derived from the same or a different organism. Within the fusion polypeptide, the term "operatively linked" is intended to indicate that the CKSRP and the non-CKSRP are fused to each other so that both sequences fulfill the proposed function attributed to the sequence used. The non-CKSRP can be fused to the N-terminus or C-terminus of the CKSRP. For example, in one embodiment, the fusion polypeptide is a GSTCKSRP fusion polypeptide in which the CKSRP sequences are fused to the C-terminus of the GST sequences. Such fusion polypeptides can facilitate the purification of recombinant CKSRPs. In another embodiment, the fusion polypeptide is a CKSRP containing a heterologous signal sequence at its No terminus. In certain host cells (e.g., mammalian host cells), expression and/or secretion of a CKSRP can be increased through use of a heterologous signal sequence.

Preferably, a CKSRP chimeric or fusion polypeptide of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and re-amplified to generate a chimeric gene sequence (See, for example, Current Protocols in Molecular Biology, Eds. Ausubel et al. John Wiley & Sons: 1992). Moreover, many expression vectors are commercially available that already encode a fusion moiety (e.g., a GST polypeptide). A CKSRP encoding nucleic acid can be cloned into such an expression vector such that the fusion moiety is linked in-frame to the CKSRP.

In addition to fragments and fusion polypeptides of the CKSRPs described herein, the present invention includes homologs and analogs of naturally occurring CKSRPs and CKSRP encoding nucleic acids in a plant. "Homologs" are defined herein as two nucleic acids or polypeptides that have similar, or "identical," nucleotide or amino acid sequences, respectively. Homologs include allelic variants, orthologs, paralogs, agonists, and antagonists of CKSRPs as defined hereafter. The term "homolog" further encompasses nucleic acid molecules that differ from one of the nucleotide sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, and SEQ ID NO:19 (and portions thereof) due to degeneracy of the genetic code and thus encode the same CKSRP as that encoded by the nucleotide sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17 or SEQ ID NO:19. For example homologs of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19 are described in SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74 and SEQ ID NO: 76.

As used herein, a "naturally occurring" CKSRP refers to a CKSRP amino acid sequence that occurs in nature. Preferably, a naturally occurring CKSRP comprises an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, and SEQ ID NO:20.

An agonist of the CKSRP can retain substantially the same, or a subset, of the biological activities of the CKSRP. An antagonist of the CKSRP can inhibit one or more of the activities of the naturally occurring form of the CKSRP. For example, the CKSRP antagonist can competitively bind to a downstream or up-stream member of the cell membrane component metabolic cascade that includes the CKSRP, or bind to a CKSRP that mediates transport of compounds across such membranes, thereby preventing translocation from taking place.

Nucleic acid molecules corresponding to natural allelic variants and analogs, orthologs, and paralogs of a CKSRP cDNA can be isolated based on their identity to the *P. patens, S. cerevisiae,* or *B. napus* CKSRP nucleic acids described herein using CKSRP cDNAs, or a portion thereof, as a hybridization probe according to standard hybridization techniques under stringent hybridization conditions. In an alternative embodiment, homologs of the CKSRP can be identified by screening combinatorial libraries of mutants, e.g., truncation mutants, of the CKSRP for CKSRP agonist or antagonist activity. In one embodiment, a variegated library of CKSRP variants is generated by combinatorial mutagenesis at the nucleic acid level and is encoded by a variegated gene library. A variegated library of CKSRP variants can be produced by, for example, enzymatically ligating a mixture of synthetic oligonucleotides into gene sequences such that a degenerate set of potential CKSRP sequences is expressible as individual polypeptides, or alternatively, as a set of larger fusion polypeptides (e.g., for phage display) containing the set of CKSRP sequences therein. There are a variety of methods that can be used to produce libraries of potential CKSRP homologs from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provision, in one mixture, of all of the sequences encoding the desired set of potential CKSRP sequences. Methods for synthesizing degenerate oligonucleotides are known in the art (See, e.g., Narang, S. A., 1983, Tetrahedron 39:3; Itakura et al., 1984, Annu, Rev. Biochem. 53:323; Itakura et al., 1984, Science 198:1056; Ike et al., 1983, Nucleic Acid Res. 11:477).

In addition, libraries of fragments of the CKSRP coding regions can be used to generate a variegated population of CKSRP fragments for screening and subsequent selection of homologs of a CKSRP. In one embodiment, a library of coding sequence fragments can be generated by treating a double stranded PCR fragment of a CKSRP coding sequence with a nuclease under conditions wherein nicking occurs only about once per molecule, denaturing the double stranded DNA, renaturing the DNA to form double stranded DNA, which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal, and internal fragments of various sizes of the CKSRP.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of CKSRP homologs. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify CKSRP homologs (Arkin and Yourvan, 1992, PNAS 89:7811-7815; Delgrave et al., 1993, Polypeptide Engineering 6(3):327-331). In another embodiment, cell based assays can be exploited to analyze a variegated CKSRP library, using methods well known in the art. The present invention further provides a method of identifying a novel CKSRP, comprising (a) raising a specific antibody response to a CKSRP, or a fragment thereof, as described herein; (b) screening putative CKSRP material with the antibody, wherein specific binding of the antibody to the material indicates the presence of a potentially novel CKSRP; and (c) analyzing the bound material in comparison to known CKSRP, to determine its novelty.

As stated above, the present invention includes CKSRPs and homologs thereof. To determine the percent sequence identity of two amino acid sequences (e.g., one of the sequences of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO: 18, and SEQ ID NO:20, and a mutant form thereof), the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence (e.g., one of the sequences of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, and SEQ ID NO:20) is occupied by the same amino acid residue as the corresponding position in the other sequence (e.g., a mutant form of the sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20), then the molecules are identical at that position. The same type of comparison can be made between two nucleic acid sequences.

The percent sequence identity between the two sequences is a function of the number of identical positions shared by the sequences (i.e., percent sequence identity=numbers of identical positions/total numbers of positions x 100). Preferably, the isolated amino acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to the core casein kinase domain containing the amino acid sequence shown as residues 2-304 of SEQ ID NO:2, residues 77-368 of SEQ ID NO:4, residues 2-294 of SEQ ID NO:6, residues 77-368 of SEQ ID NO:8, residues 77-336 of SEQ ID NO:10 residues 1-296 of SEQ ID NO:12, residues 1-296 of SEQ ID NO:14, residues 5-300 of SEQ ID NO:16, residues 1-295 of SEQ ID NO:18, or residues 25-327 of SEQ ID NO:20. In another embodiment, the isolated amino acid homolog of the present invention is encoded by a nucleic acid as defined by nucleotides at positions 4 to 912 of SEQ ID NO:1, nucleotides at positions 229 to 1104 of SEQ ID NO:3, nucleotides at positions 4 to 882 of SEQ ID NO:5, nucleotides at positions 229 to 1104 of SEQ ID NO:7, nucleotides at positions 229 to 1008 of SEQ ID NO:9, nucleotides at positions 1 to 888 of SEQ ID NO:11, nucleotides at positions 1 to 888 of SEQ ID NO:13, nucleotides at positions 13 to 900 of SEQ ID NO:15, nucleotides at positions 1 to 885 of SEQ ID NO:17, or nucleotides at positions 73 to 981 of SEQ ID NO:19.

Members of casein kinase I protein family have divergent N-terminal and C-terminal extensions. The N-terminal region is responsible for substrate recognition and the C-terminal region is important in the interaction with substrates and is thought to be important for mediating regulation through autophosphorylation (Gross and Anderson Cell Signal 1998 10:699-711; Graves and Roach J Biol Chem 1995 270:21689-21694), The amino acid sequence of Orf 760 (SEQ ID NO:10) contains two insertions not found in the other casein kinase I proteins, a 17 amino acid stretch from position 37 to 53 and a 16 amino acid stretch from position 165 to 180. The presence of these novel insertions could be important for function and the subsequent phenotype in transgenic lines overexpressing Orf 760. Casein kinase I proteins have been shown to modulate their activity by autophosphorylation of C-terminal serine and threonine residues (Graves and Roach J Biol Chem 1995 270:21 689-21694). The alignment in FIG. 5 demonstrates that C-terminal regions are found in Orf 760, EST 263, and EST 289 that are absent from EST 142 and EST 194. However, unlike Orf 760, EST 263, and EST 289, as demonstrated in the alignment in FIG. 5, EST 142 and EST 194 both contain N-terminal region of approximately 72 amino acids. The presence or absence of these N-terminal and C-terminal regions define at least six classes for these casein kinase I proteins that function in stress response. The N-terminal region, or the C-terminal region, or the core kinase domain, or combinations of core kinase a domains with different or homologous N-terminal and/or C-terminal extension regions or site-directed mutagenesis can be used to alter autophosphorylation sites to generate better agronomic phenotypes. For example, a chimeric or fusion polypeptide can comprise residues 1-72 of EST142 (the N-terminal region of SEQ ID NO:8) fused with any of the core kinase domains shown in FIG. 5, or with any of the C-terminal domains shown in FIG. 5, or with both the core kinase and C-terminal domains of any of the polypeptides shown in FIG. 5. In another embodiment, residues 295-473 of EST289 (the C-terminal region of SEQ ID NO:6) can be combined with the core kinase domain of any of the polypeptides shown in FIG. 5, or with any of the N-terminal domains shown in FIG. 5, or with both the core kinase and N-terminal domains of any of the polypeptides shown in FIG. 5 to generate a chimeric or fusion polypeptide which would confer better agronomic phenotypes.

In another embodiment, the isolated amino acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20. For example homologs of the amino acid sequences SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20 are described in SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75 and SEQ ID NO: 77.

In yet another embodiment, the isolated amino acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence encoded by a nucleic acid sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19or to their homologs e.g. as specified in SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74 or SEQ ID NO: 76.

In other embodiments, the CKSRP amino acid homologs have sequence identity over at least 15 contiguous amino acid residues, more preferably at least 25 contiguous amino acid residues, and most preferably at least 35 contiguous amino acid residues of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20 or with homologs of the amino acid sequences SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20 as described in SEQ ID NO: 55, SEQ ID NO: 57, SEQ ID NO: 59, SEQ ID NO: 61, SEQ ID NO:63, SEQ ID NO: 65, SEQ ID NO: 67, SEQ ID NO: 69, SEQ ID NO: 71, SEQ; ID NO: 73, SEQ ID NO: 75 and SEQ ID NO:77.

In another preferred embodiment, an isolated nucleic acid homolog of the invention comprises a nucleotide sequence which is at least about 40-60%, preferably at least about 60-70%, more preferably at least about 70-75%, 75-80%, 80-85%, 85-90%, or 90-95%, and even more preferably at least about 95%, 96%, 97%, 98%, 99%, or more identical to a nucleotide sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19, or to a portion comprising at least 60 consecutive nucleotides thereof. The preferable length of sequence comparison for nucleic acids is at least 75 nucleotides, more preferably at least 100 nucleotides, and most preferably the entire length of the coding region. It is even more preferable that the nucleic acid homologs encode proteins having homology with SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20 over the central kinase domain shown in FIGS. 5 and 7.

It is further preferred that the isolated nucleic acid homolog of the invention encodes a CKSRP, or portion thereof, that is at least 70% identical to an amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20 and that functions as a modulator of an environmental stress response in a plant. In a more preferred embodiment, overexpression of the nucleic acid homolog in a plant increases the tolerance of the plant to an environmental stress. In a further preferred embodiment, the nucleic acid homolog encodes a CKSRP that functions as a casein kinase.

For the purposes of the invention, the percent sequence identity between two nucleic acid or polypeptide sequences is determined using the Vector NTI 6.0 (PC) software package (InforMax, 7600 Wisconsin Ave., Bethesda, Md. 20814). A gap-opening penalty of 15 and a gap extension penalty of 6.66 are used for determining the percent identity of two nucleic acids. A gap-opening penalty of 10 and a gap extension penalty of 0.1 are used for determining the percent identity of two polypeptides. All other parameters are set at the default settings. For purposes of a multiple alignment (Clustal W algorithm), the gap-opening penalty is 10, and the gap extension penalty is 0.05 with blosum62 matrix. It is to be understood that for the purposes of determining sequence identity when comparing a DNA sequence to an RNA sequence, a thymidine nucleotide is equivalent to a uracil nucleotide.

In another aspect, the invention provides an isolated nucleic acid comprising a polynucleotide that hybridizes to the polynucleotide of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19 under stringent conditions. More particularly, an isolated nucleic acid molecule of the invention is at least 15 nucleotides in length and hybridizes under stringent conditions to the nucleic acid molecule comprising a nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19. In other embodiments, the nucleic acid is at least 30, 50, 110, 250, or more nucleotides in length. Preferably, an isolated nucleic acid homolog of the invention comprises a nucleotide sequence which hybridizes under highly stringent conditions to the nucleotide sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19 and functions as a modulator of stress tolerance in a plant. In a further preferred embodiment, overexpression of the isolated nucleic acid homolog in a plant increases a plant's tolerance to an environmental stress. In an even further preferred embodiment, the isolated nucleic acid homolog encodes a CKSRP that functions as a casein kinase.

As used herein with regard to hybridization for DNA to a DNA blot, the term "stringent conditions" refers to hybridization overnight at 60° C. in 10× Denhart's solution, 6×SSC, 0.5% SDS, and 100 µg/ml denatured salmon sperm DNA. Blots are washed sequentially at 62° C. for 30 minutes each time in 3×SSC/0.1% SDS, followed by 1×SSC/0.1% SDS, and finally 0.1×SSC/0.1% SDS. As also used herein, in a preferred embodiment, the phrase "highly stringent conditions" refers to hybridization in a 6×SSC solution at 65° C. In another embodiment, "highly stringent conditions" refers to hybridization overnight at 65° C. in 10×Denharts solution, 6×SSC, 0.5% SDS, and 100 µg/ml denatured salmon sperm DNA. Blots are washed sequentially at 65° C. for 30 minutes each time in 3×SSC/0.1% SDS, followed by 1×SSC/0.1% SDS, and finally 0.1×SSC/0.1% SDS. Methods for nucleic acid hybridizations are described in Mein koth and Wahl, 1984, Anal. Biochem. 138:267-284; Current Protocols in Molecular Biology, Chapter 2, Ausubel et al. Eds., Greene Publishing and Wiley-Interscience, New York, 1995; and Tijssen, 1993, Laboratory Techniques in Biochemistry and Molecular Biology: Hybridization with Nucleic Acid Probes, Part I, Chapter 2, Elsevier, N.Y., 1993. Preferably, an isolated nucleic acid molecule of the invention that hybridizes under stringent or highly stringent conditions to a sequence of SEQ ID NO:1, SEQ ID NO:3, SEQ ID NO:5, SEQ ID NO:7, SEQ ID NO:9, SEQ ID NO:1, SEQ ID NO:13, SEQ ID NO:15, SEQ ID NO:17, or SEQ ID NO:19 corresponds to a naturally occurring nucleic acid molecule. As used herein, a "naturally occurring" nucleic acid molecule refers to an RNA or DNA molecule having a nucleotide sequence that occurs in nature (e.g., end codes a natural polypeptide). In one embodiment, the nucleic acid encodes a naturally occurring *P. patens* CKSRP, a *S. cerevisiae* CKSRP or a *B. napus* CKSRP.

Using the above-described methods, and others known to those of skill in the art, one of ordinary skill in the art can isolate homologs of the CKSRPs comprising amino acid sequences shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20. Such homologs are specified for example in SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO. 73, SEQ ID NO: 75 and SEQ ID NO: 77.

Table A correlates the gene ID with the SEQ ID NO in the sequence listing.

TABLE A

| Gene ID | Sequence type | Sequence nature | SEQ ID NO | Organism |
|---|---|---|---|---|
| EST263 | DNA | Full-length | 1 | P. patens |
| EST263 | protein | Full-length | 2 | P. patens |
| EST194 | DNA | Full-length | 3 | P. patens |
| EST194 | protein | Full-length | 4 | P. patens |
| EST289 | DNA | Full-length | 5 | P. patens |
| EST289 | protein | Full-length | 6 | P. patens |
| EST142 | DNA | Full-length | 7 | P. patens |
| EST142 | protein | Full-length | 8 | P. patens |
| ORF760 | DNA | Full-length | 9 | yeast |
| ORF760 | protein | Full-length | 10 | yeast |
| BN42723666 | DNA | Full-length | 11 | canola |
| BN42723666 | protein | Full-length | 12 | canola |
| BN51274564 | DNA | Full-length | 13 | canola |
| BN51274564 | protein | Full-length | 14 | canola |
| BN51362554 | DNA | Full-length | 15 | canola |
| BN51362554 | protein | Full-length | 16 | canola |
| BN51390516 | DNA | Full-length | 17 | canola |
| BN51390516 | protein | Full-length | 18 | canola |
| BN51392938 | DNA | Full-length | 19 | canola |
| BN51392938 | protein | Full-length | 20 | canola |
| AAB68417 | protein | Full-length | 47 | yeast |
| AAA35230 | protein | Full-length | 48 | yeast |
| AAH06490 | protein | Full-length | 49 | human |
| AAH03558 | protein | Full-length | 50 | human |
| AAH08717 | protein | Full-length | 51 | human |
| AAD26525 | protein | Full-length | 52 | human |
| AJ487966 | protein | Full-length | 53 | rice |
| HV62560799 | DNA | Full-length | 54 | barley |
| HV62560799 | protein | Full-length | 55 | barley |
| GM59629961 | DNA | Full-length | 56 | soybean |
| GM59629961 | protein | Full-length | 57 | soybean |
| GM59587121 | DNA | Full-length | 58 | soybean |
| GM59587121 | protein | Full-length | 59 | soybean |
| TA60000862 | DNA | Full-length | 60 | wheat |
| TA60000862 | protein | Full-length | 61 | wheat |
| GM59702429 | DNA | Full-length | 62 | soybean |
| GMS9702429 | protein | Full-length | 63 | soybean |
| LU61714150 | DNA | Full-length | 64 | linseed |
| LU61714150 | protein | Full-length | 65 | linseed |
| BN42182310 | DNA | Full-length | 66 | canola |
| BN42182310 | protein | Full-length | 67 | canola |
| HA66640192 | DNA | Full-length | 68 | sunflower |
| HA66640192 | protein | Full-length | 69 | sunflower |
| GM59587863 | DNA | Full-length | 70 | soybean |
| GM59587863 | protein | Full-length | 71 | soybean |
| BN51270917 | DNA | Full-length | 72 | canola |
| BN51270917 | protein | Full-length | 73 | canola |
| BN51343700 | DNA | Full-length | 74 | canola |
| BN51343700 | protein | Full-length | 75 | canola |
| TA59828214 | DNA | Full-length | 76 | Wheat |
| TA59828214 | protein | Full-length | 77 | wheat |

One subset of these homologs is allelic variants. As used herein, the term "allelic variant" refers to a nucleotide sequence containing polymorphisms that lead to changes in the amino acid sequences of a CKSRP and that exist within a natural population (e.g., a plant species or variety). Such natural allelic variations can typically result in 1-5% variance in a CKSRP nucleic acid. Allelic variants can be identified by sequencing the nucleic acid sequence of interest in a number of different plants, which can be readily carried out by using hybridization probes to identify the same CKSRP genetic locus in those plants. Any and all such nucleic acid variations and resulting amino acid polymorphisms or variations in a CKSRP that are the result of natural allelic variation and that do not alter the functional activity of a CKSRP, are intended to be within the scope of the invention.

Moreover, nucleic acid molecules encoding CKSRPs from the same or other species such as CKSRP analogs, orthologs, and paralogs, are intended to be within the scope of the present invention. As used herein, the term "analogs" refers to two nucleic acids that have the same or similar function, but that have evolved separately in unrelated organisms. As used herein, the term "orthologs" refers to two nucleic acids from different species, but that have evolved from a common ancestral gene by specification. Normally, orthologs encode polypeptides having the same or similar functions. As also used herein, the term "paralogs" refers to two nucleic acids that are related by duplication within a genome. Paralogs usually have different functions, but these functions may be related (Tatusov, R. L. et al., 1997, Science 278(5338):631-637). Analogs, orthologs, and paralogs of a naturally occurring CKSRP can differ from the naturally occurring CKSRP by post-translational modifications, by amino acid sequence differences, or by both. Post-translational modifications include in vivo and in vitro chemical derivatization of polypeptides, erg., acetylation, carboxylation, phosphorylation, or glycosylation, and such modifications may occur during polypeptide synthesis or processing or following treatment with isolated modifying enzymes. In particular, orthologs of the invention will generally exhibit at least 80-85%, more preferably, 85-90% or 90-95%, and most preferably 95%, 96%, 97%, 98%, or even 99% identity, or 100% sequence identity, with all or part of a naturally occurring CKSRP amino acid sequence, and will exhibit a function similar to a CKSRP. Preferably, a CKSRP ortholog of the present invention functions as a modulator of an environmental stress response in a plant and/or functions as a casein kinase. More preferably, a CKSRP ortholog increases the stress tolerance of a plant. In one embodiment, the CKSRP orthologs maintain the ability to participate in the metabolism of compounds necessary for the construction of cellular membranes in a plant, or in the transport of molecules across these membranes.

In addition to naturally-occurring variants of a CKSRP sequence that may exist in the population, the skilled artisan will further appreciate that changes can be introduced by mutation into a nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19, thereby leading to changes in the amino acid sequence of the encoded CKSRP, without altering the functional activity of the CKSRP. For example, nucleotide substitutions leading to amino acid substitutions at "non-essential" amino acid residues can be made in a sequence of SEQ ID NO:1, SEQ ID NO:3, SEQ ID NOS, SEQ ID NO:7, SEQ ID NO:9, SEQ ID NO:11, SEQ ID NO:13, SEQ ID NO:15, SEQ ID NO:17, or SEQ ID NO:19. A "non-essential" amino acid residue is a residue that can be altered from the wild-type sequence of one of the CKSRPs without altering the activity of said CKSRP, whereas an "essential" amino acid residue is required for CKSRP activity. Other amino acid residues, however, (e.g., those that are not conserved or only semi-conserved in the domain having CKSRP activity) may not be essential for activity and thus are likely to be amenable to alteration without altering CKSRP activity.

Accordingly, another aspect of the invention pertains to nucleic acid molecules encoding CKSRPs that contain changes in amino acid residues that are not essential for CKSRP activity. Such CKSRPs differ in amino acid sequence from a sequence contained in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20, yet retain at least one of the CKSRP activities described herein. In one embodiment, the isolated nucleic acid molecule comprises a nucleotide sequence encoding a polypeptide, wherein the polypeptide comprises an amino acid sequence at least about 50% identical to the central protein kinase region of an amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20. Preferably, the polypeptide encoded by the nucleic acid molecule is at least about 50-60% identical to the central protein kinase region of one of the sequences of SEQ ID NO:2, SEQ ID NO:14, SEQ ID NO:6, SEQ ID NO:8, SEQ ID NO:10, SEQ ID NO:12, SEQ ID NO:14, SEQ ID NO:16, SEQ ID NO:18, or SEQ ID NO:20, more preferably at least about 60-70% identical to the central protein kinase region of one of the sequences of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20, even more preferably at least about 70-75%, 75-80%, 80-85%, 85-90%, or 90-95% identical to the central protein kinase region of one of the sequences of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20, and most preferably at least about 96%, 97%, 98%, or 99% identical to the central protein kinase region of one of the sequences of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20. In another embodiment, the polypeptide encoded by the nucleic acid molecule is at least about 50-60% identical to one of the sequences of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20, more preferably at least about 60-70% identical to one of the sequences of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20, even more preferably at least about 70-75%, 75-80%, 80-85%, 85-90%, or 90-95% identical to one of the sequences of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20, and most preferably at least about 96%, 97%, 98%, or 99% identical to one of the sequences of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20. The preferred CKSRP homologs of the present invention preferably participate in a stress tolerance response in a plant, or more particularly, participate in the transcription of a polypeptide involved in a stress tolerance response in a plant, and/or function as a casein kinase.

An isolated nucleic acid molecule encoding a CKSRP having sequence identity with a polypeptide sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20 can be created by introducing one or more nucleotide substitutions, additions or deletions into a nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19, respectively, such that one or more amino acid substitutions, additions, or deletions are introduced into the encoded polypeptide. Mutations can be introduced into one of the sequences of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19 by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain.

Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Thus, a predicted nonessential amino acid residue in a CKSRP is preferably replaced with another amino acid residue from the same side chain family. Alternatively, in another embodiment, mutations can be introduced randomly along all or part of a CKSRP coding sequence, such as by saturation mutagenesis, and the resultant mutants can be screened for a CKSRP activity described herein to identify mutants that retain CKSRP activity. Following mutagenesis of one of the sequences of SEQ ID NO:1, SEQ ID NO:3, SEQ ID NO:5, SEQ ID NO:7, SEQ ID NO:9, SEQ ID NO:11, SEQ ID NO:13, SEQ ID NO:5, SEQ ID NO:17, or SEQ ID NO:19, the encoded polypeptide can be expressed recombinantly and the activity of the polypeptide can be determined by analyzing the stress tolerance of a plant expressing the polypeptide as described in Example 7.

Additionally, optimized CKSRP nucleic acids can be created. Preferably, an optimized CKSRP nucleic acid encodes a CKSRP that binds to a phosphate group and/or modulates a plant's tolerance to an environmental stress, and more preferably increases a plant's tolerance to an environmental stress upon its overexpression in the plant. As used herein, "optimized" refers to a nucleic acid that is genetically engineered to increase its expression in a given plant or animal. To provide plant optimized CKSRP nucleic acids, the DNA sequence of the gene can be modified to 1) comprise codons preferred by highly expressed plant genes; 2) comprise an A+T content in nucleotide base composition to that substantially found in plants; 3) form a plant initiation sequence; or 4) to eliminate sequences that cause destabilization, inappropriate polyadenylation, degradation and termination of RNA, or that form secondary structure hairpins or RNA splice sites. Increased expression of CKSRP nucleic acids in plants can be achieved by utilizing the distribution frequency of codon usage in plants in general or in a particular plant. Methods for optimizing nucleic acid expression in plants can be found in EPA 0359472; EPA 0385962; PCT Application No. WO 91/16432; U.S. Pat. Nos. 5,380,831; 5,436,391; Perlack et al., 1991, Proc. Natl. Acad. Sci. USA 88:3324-3328; and Murray et al., 1989, Nucleic Acids Res. 17:477-498.

As used herein, "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable that this analysis be limited to genes that are highly expressed by the host cell. The percent deviation of the frequency of preferred codon usage for a synthetic gene from that employed by a host cell is calculated first by determining the percent deviation of the frequency of usage of a single codon from that of the host cell followed by obtaining the average deviation over all codons. As defined herein, this calculation includes unique codons (i.e., ATG and TGG). In general terms, the overall average deviation of the codon usage of an optimized gene from that of a host cell is calculated using the equation $1A = n-1 \ ZX_n - Y_n X_n$ times 100 Z where $X_n$=frequency of usage for codon n in the host cell; $Y_n$=frequency of usage for codon n in the synthetic gene; n represents an individual codon that specifies an amino acid; and the total number of codons is Z. The overall deviation of the frequency of codon usage, A, for all amino acids should preferably be less than about 25%, and more preferably less than about 10%.

Hence, a CKSRP nucleic acid can be optimized such that its distribution frequency of codon usage deviates, preferably, no rhore than 25% from that of highly expressed plant genes and, more preferably, no more than about 10%. In addition, consideration is given to the percentage C+C content of the degenerate third base (monocotyledons appear to favor G+C in this position, whereas dicotyledons do not). It is also recognized that the XCG (where X is A, T, C, or G) nucleotide is the least preferred codon in dicots whereas the XTA codon is avoided in both monocots and dicots. Optimized CKSRP nucleic acids of this invention also preferably have CG and TA doublet avoidance indices closely approximating those of the chosen host plant (e.g., *P. patens, B. napus, G. max*, or *O. sativa*). More preferably these indices deviate from that of the host by no more than about 10-15%.

In addition to the nucleic acid molecules encoding the CKSRPs described above, another aspect of the invention pertains to isolated nucleic acid molecules that are antisense thereto. Antisense polynucleotides are thought to inhibit gene expression of a target polynucleotide by specifically binding the target polynucleotide and interfering with transcription, splicing, transport, translation, and/or stability of the target polynucleotide. Methods are described in the prior art for targeting the antisense polynucleotide to the chromosomal DNA, to a primary RNA transcript, or to a processed mRNA. Preferably, the target regions include splice sites, translation initiation codons, translation termination codons, and other sequences within the open reading frame.

The term "antisense," for the purposes of the invention, refers to a nucleic acid comprising a polynucleotide that is sufficiently complementary to all or a portion of a gene, primary transcript, or processed mRNA, so as to interfere with expression of the endogenous gene. "Complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA.

It is understood that two polynucleotides may hybridize to each other even if they are not completely complementary to each other, provided that each has at least one region that is substantially complementary to the other. The term "antisense nucleic acid" includes single stranded RNA as well as double-stranded DNA expression cassettes that can be transcribed to produce an antisense RNA. "Active" antisense nucleic acids are antisense RNA molecules that are capable of selectively hybridizing with a primary transcript or mRNA encoding a polypeptide having at least 80% sequence identity with the polypeptide of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20.

The antisense nucleic acid can be complementary to an entire CKSRP coding strand, or to only a portion thereof. In one embodiment, an antisense nucleic acid molecule is antisense to a "coding region" of the coding strand of a nucleotide sequence encoding a CKSRP. The term "coding region" refers to the region of the nucleotide sequence comprising codons that are translated into amino acid residues. In another embodiment, the antisense nucleic acid molecule is antisense to a "noncoding region" of the coding strand of a nucleotide sequence encoding a CKSRP. The term "noncoding region" refers to 5' and 3' sequences that flank the coding region that are not translated into amino acids (i.e., also referred to as 5' and 3' untranslated regions). The antisense nucleic acid molecule can be complementary to the entire coding region of CKSRP mRNA, but more preferably is an oligonucleotide that is antisense to only a portion of the coding or noncoding region of CKSRP mRNA. For example, the antisense oligonucleotide can be complementary to the region surrounding the translation start site of CKSRP mRNA. An antisense oligonucleotide can be, for example, about 5, 10, 15, 20, 25, 30, 35, 40, 45' or 50 nucleotides in length. Typically, the antisense molecules of the present invention comprise an RNA having 60-100% sequence identity with at least 14 consecutive nucleotides of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19, or a polynucleotide encoding a polypeptide of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20. Preferably, the sequence identity will be at least 70%, more preferably at least 75%, 80%, 85%, 90%, 95%, or 98%, and most preferably 99%.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl) uracil, (acp3)w , and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., 1987, Nucleic Acids. Res. 15:6625-6641). The antisense nucleic acid molecule can also comprise a 2'-o-methylribonucleotide (Inoue et al., 1987, Nucleic Acids Res. 15:6131-6148) or a chimeric RNA-DNA analogue (Inoue et al., 1987, FEBS Lett. 215:327-330).

The antisense nucleic acid molecules of the invention are typically administered to a cell or generated in situ such that they hybridize with or bind to cellular mRNA and/or genomic DNA encoding a CKSRP to thereby inhibit expression of the polypeptide, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic (including plant) promoter are preferred.

As an alternative to antisense polynucleotides, ribozymes, sense polynucleotides, or double stranded RNA (dsRNA) can be used to reduce expression of a CKSRP polypeptide. As used herein, the term "ribozyme" refers to a catalytic RNA-based enzyme with ribonuclease activity that is capable of cleaving a single-stranded nucleic acid, such as an mRNA, to which it has a complementary region. Ribozymes (e.g., hammerhead ribozymes described in Haselhoff and Gerlach, 1988, Nature 334:585-591) can be used to catalytically cleave CKSRP mRNA transcripts to thereby inhibit translation of CKSRP mRNA. A ri-bozyme having specificity for a CKSRP-encoding nucleic acid can be designed based upon the nucleotide sequence of a CKSRP cDNA, as disclosed herein (i.e., SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19) or on the basis of a heterologous sequence to be isolated according to methods taught in this invention. For example, a derivative of a Tetrahymena L-19 IVS RNA can be constructed in which the nucleotide sequence of the active site is complementary to the nucleotide sequence to be cleaved in a CKSRP-encoding mRNA. See, e.g., U.S. Pat. Nos. 4,987,071 and 5,116,742 to Cech et al. Alternatively, CKSRP mRNA can be used to select a catalytic RNA having a specific ribonuclease activity from a pool of RNA molecules. See, e.g., Bartel, D. and Szostak, J. W., 1993, Science 261:1411-1418. In preferred embodiments, the ribozyme will contain a portion having at least 7, 8, 9, 10, 12, 14, 16, 18, or nucleotides, and more preferably 7 or 8 nucleotides, that have 100% complementarity to a portion of the target RNA. Methods for making ribozymes are known to those skilled in the art. See, e.g., U.S. Pat. Nos. 6,025,167; 5,773,260; and 5,496,698.

The term "dsRNA," as used herein, refers to RNA hybrids comprising two strands of RNA. The dsRNAs can be linear or circular in structure. In a preferred embodiment, dsRNA is specific for a polynucleotide encoding either the polypeptide of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20, or a polypeptide having at least 80% sequence identity with a polypeptide of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20 over the central protein kinase domain. The hybridizing RNAs may be substantially or completely complementary. By "substantially complementary," is meant that when the two hybridizing RNAs are optimally aligned using the BLAST program as described above, the hybridizing portions are at least 95% complementary. Preferably, the dsRNA will be at least 100 base pairs in length. Typically, the hybridizing RNAs will be of identical length with no over hanging 5' or 3' ends and no gaps. However, dsRNAs having 5' or 3' overhangs of up to 100 nucleotides may be used in the methods of the invention.

The dsRNA may comprise ribonucleotides, ribonucleotide analogs such as 2'-O-methyl ribosyl residues, or combinations thereof. See, e.g., U.S. Pat. Nos. 4,130,641 and 4,024,222. A dsRNA polyriboinosinic acid:polyribocytidylic acid is described in U.S. Pat. No. 4,283,393. Methods for making and using dsRNA are known in the art. One method comprises the simultaneous transcription of two complementary DNA strands, either in vivo, or in a single in vitro reaction mixture. See, e.g., U.S. Pat. No. 5,795,715. In one embodiment, dsRNA can be introduced into a plant or plant cell directly by standard transformation procedures. Alternatively, dsRNA can be expressed in a plant cell by transcribing two complementary RNAs.

Other methods for the inhibition of endogenous gene expression, such as triple helix formation (Moser et al., 1987, Science 238:645-650 and Cooney et al., 1988, Science 241: 456-459) and co-suppression (Napoli et al., 1990, The Plant Cell 2:279-289) are known in the art. Partial and full-length cDNAs have been used for the co-suppression of endogenous plant genes. See, e.g., U.S. Pat. Nos. 4,801,340, 5,034,323, 5,231,020, and 5,283,184; Van der Kroll et al., 1990, The Plant Cell 2:291-299; Smith et al., 1990, Mol. Gen. Genetics 224:477-481; and Napoli et al., 1990, The Plant Cell 2:279-289.

For sense suppression, it is believed that introduction of a sense polynucleotide blocks transcription of the corresponding target gene. The sense polynucleotide will have at least 65% sequence identity with the target plant gene or RNA. Preferably, the percent identity is at least 80%, 90%, 95%, or more. The introduced sense polynucleotide need not be full length relative to the target gene or transcript. Preferably, the sense polynucleotide will have at least 65% sequence identity with at least 100 consecutive nucleotides of SEQ ID NO:1, SEQ ID NO:3, SEQ ID NO:5, SEQ ID NO:7, SEQ ID NO:9, SEQ ID NO:11 SEQ ID NO:13, SEQ ID NO:15, SEQ ID NO:17, or SEQ ID NO:19. The regions of identity can comprise introns and/or exons and untranslated regions. The introduced sense polynucleotide may be present in the plant cell transiently, or may be stably integrated into a plant chromosome or extrachromosomal replicon.

Alternatively, CKSRP gene expression can be inhibited by targeting nucleotide sequences complementary to the regulatory region of a CKSRP nucleotide sequence (e.g., a CKSRP promoter and/or enhancer) to form triple helical structures that prevent transcription of a CKSRP gene in target cells. See generally, Helene, C., 1991, Anticancer Drug Des. 6(6):569-84; Helene, C. et al., 992, Ann. N.Y. Acad. Sci. 660:27-36; and Maher, Lj., 1992, Bioassays 14(12):807-15.

In addition to the CKSRP nucleic acids and polypeptides described above, the present invention encompasses these nucleic acids and polypeptides attached to a moiety. These moieties include, but are not limited to, detection moieties, hybridization moieties, purification moieties, delivery moieties, reaction moieties, binding moieties, and the like. A typical group of nucleic acids having moieties attached are probes and primers. Probes and primers typically comprise a substantially isolated oligonucleotide. The oligonucleotide typically comprises a region of nucleotide sequence that hybridizes under stringent conditions to at least about 12, preferably about 25, more preferably about 40, 50, or 75 consecutive nucleotides of a sense strand of one of the sequences set forth in SEQ ID NO:1, SEQ ID NO:3, SEQ ID NO:5, SEQ ID NO:7, SEQ ID NO:9, SEQ ID NO:1, SEQ ID NO:13, SEQ ID NO:15, SEQ ID NO:17, or SEQ ID NO:19; an anti-sense sequence of one of the sequences set forth in SEQ ID NO:1, SEQ ID NO:3, SEQ ID NO:5, SEQ ID NO:7, SEQ ID NO:9, SEQ ID NO:1, SEQ ID NO:13, SEQ ID NO:15, SEQ ID NO:17, or SEQ ID NO:19; or naturally occurring mutants thereof. Primers based on a nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19 can be used in PCR reactions to clone CKSRP homologs. Probes based on the CKSRP nucleotide sequences can be used to detect transcripts or genomic sequences encoding the same or substantially identical polypeptides. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express a CKSRP, such as by measuring a level of a CKSRP-encoding nucleic acid, in a sample of cells, e.g., detecting CKSRP mRNA levels or determining whether a genomic CKSRP gene has been mutated or deleted.

In particular, a useful method to ascertain the level of transcription of the gene (an indicator of the amount of mRNA available for translation to the gene product) is to perform a Northern blot (For reference, see, for example, Ausubel et al., 1988, Current Protocols in Molecular Biology, Wiley. New York). The information from a Northern blot at least partially demonstrates the degree of transcription of the transformed gene. Total cellular RNA can be prepared from cells, tissues, or organs by several methods, all well-known in the art, such as that described in Bormann, E. R. et al., 1992, Mol. Microbiol. 6:317-326. To assess the presence or relative quantity of polypeptide translated from this mRNA, standard techniques, such as a Western blot, may be employed. These techniques are well known to one of ordinary skill in the art. (See, for example, Ausubel et al., supra.

The invention further provides an isolated recombinant expression vector comprising a CKSRP nucleic acid as described above, wherein expression of the vector in a host cell results in increased tolerance to environmental stress as compared to a wild type variety of the host cell. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. As used herein with respect to a recombinant expression vector, "operatively linked" is intended to mean that the nucleotide sequence of interest is linked to the regulatory sequencers) in a manner which allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). Such regulatory sequences are described, for example, in Goeddel, Gene Expression Technology Methods in Enzymology 185, Academic Press, San Diego, Calif. (1990) and Cruber and Crosby, in: Methods in Plant Molecular Biology and Biotechnology, eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., CKSRPs, mutant forms of CKSRPs, fusion polypeptides, etc.).

The recombinant expression vectors of the invention can be designed for expression of CKSRPs in prokaryotic or eukaryotic cells. For example, CKSRP genes can be expressed in bacterial cells such as *C. glutamicum*, insect cells (using baculovirus expression vectors), yeast and other fungal cells (See Romanos, M. A. et al., 1992, Foreign gene expression in yeast: a review, Yeast 8:423-488; van den Hondel, C. A. M. J. J. et al., 1991, Heterologous gene expression in filamentous fungi, in: More Gene Manipulations in Fungi, J. W. Bennet & L. L. Lasure, eds., p. 396-428: Academic Press: San Diego; and van den Hondel, C. A. M. J. J. & Punt, P. J., 1991, Gene transfer systems and vector development for filamentous fungi, in: Applied Molecular Genetics of Fungi, Peberdy, J. F. et al., eds., p. 1-28, Cambridge University Press: Cambridge), algae (Falciatore et al., 1999, Marine Biotechnology 1(3): 239-251), ciliates of the types: Holotrichia, Peritrichia, Spirotrichia, Suctoria, Tetrahymena, Paramecium, Colpidium, Glau-coma, Platyophrya, Potomacus, Pseudocohnilembus, Euplotes, Engelmaniella, and *Stylonychia*, especially of the genus *Stylonychia lemnae* with vectors following a transformation method as described in PCT Application No. WO 98/01572, and multicellular plant cells (See Schmidt, R. and Willmitzer, L., 9881 High efficiency *Agrobacterium tumefaciens*-mediated transformation of *A. thaliana* leaf and cotyledon explants, Plant Cell Rep. 583-586; Plant Molecular Biology and Biotechnology, C Press, Boca Raton, Fla., chapter 6/7, 5.71-119 (1993); F. F. White, B. Jenes et al., Techniques for Gene Transfer, in: Transgenic Plants, Vol. 1, Engineering and Utilization, eds. Kung und R. Wu, 128-43, Academic Press: 1993; Potrykus, 1991, Annu. Rev. Plant Physiol. Plant Molec. Biol. 42:205-225 and references cited therein), or mammalian cells. Suitable host cells are discussed further in Goeddel, supra. Alternatively, the recombinant expression vector can be transcribed and translated in vitro, for example using T7 promoter regulatory sequences and T7 polymerase.

Expression of polypeptides in prokaryotes is most often carried out with vectors containing constitutive or inducible promoters directing the expression of either fusion or non-fusion polypeptides. Fusion vectors add a number of amino acids to a polypeptide encoded therein, usually to the amino terminus of the recombinant polypeptide but also to the C-terminus or fused within suitable regions in the polypeptides. Such fusion vectors typically serve three purposes: 1) to increase expression of a recombinant polypeptide; 2) to increase the solubility of a recombinant polypeptide; and 3) to aid in the purification of a recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin, and enterokinase.

Typical fusion expression vectors include pGEX (Pharmacia Biotech Inc; Smith, D. B. and Johnson, K. S., 1988, Gene 67:31-40), pMAL (New England Bio-labs, Beverly, Mass.), and pRIT5 (Pharmacia, Piscataway, N.J.) which fuse glutathione S-transferase (GST), maltose E binding polypeptide, or polypeptide A, respectively, to the target recombinant polypeptide. In one embodiment, the coding sequence of the CKSRP is cloned into a pGEX expression vector to create a vector encoding a fusion polypeptide comprising, from the N-terminus to the C-terminus, GST-thrombin cleavage site-X polypeptide. The fusion poly-peptide can be purified by affinity chromatography using glutathione-agarose resin. Recombinant CKSRP unfused to GST can be recovered by cleavage of the fusion polypeptide with thrombin.

Examples of suitable inducible non-fusion *E. coli* expression vectors include pTrc (Amann et al., 1988, Gene 69:301-315) and pET 11d (Studier et al., Gene Expression Technology: Methods in Enzymology 185, Academic Press, San Diego, Calif. (1990) 60-89) Target gene expression from the pTrc vector relies on host RNA polymerase transcription from a hybrid trp-lac fusion promoter. Target gene expression from the pET 11d vector relies on transcription from a T7 gn1

O-lac fusion promoter mediated by a co-expressed viral RNA polymerase (T7 gnI). This viral polymerase is supplied by host strains BL21 (DE3) or HMS174(DE3) from a resident γ prophage harboring a T7 gn1 gene under the transcriptional control of the lacUV 5 promoter.

One strategy to maximize recombinant polypeptide expression is to ex-press the polypeptide in a host bacteria with an impaired capacity to proteolytically cleave the recombinant polypeptide (Gottesman, S., Gene Expression Technology. Methods in Enzymology 185, Academic Press, San Diego, Calif. (1990) 119-128). Another strategy is to alter the sequence of the nucleic acid to be inserted into an expression vector so that the individual codons for each amino acid are those preferentially utilized in the bacterium chosen for expression, such as *C. glutamicum* (Wada et al., 1992, Nucleic Acids Res. 20:2111-2118). Such alteration of nucleic acid sequences of the invention can be carried out by standard DNA synthesis techniques.

In another embodiment, the CKSRP expression vector is a yeast expression vector. Examples of vectors for expression in yeast *S. cerevisiae* include pYep-Sec1 (Baldari, et al., 1987, EMBO J. 6:229-234), pMFa (Kurjan and Herskowitz, 1982, Cell 30:933-943), pJRY88 (Schultz et al.; 1987, Gene 54:113-123), and pYES2 (Invitrogen Corporation, San Diego, Calif.). Vectors and methods for the construction of vectors appropriate for use in other fungi, such as the filamentous fungi, include those detailed in: van den Hondel, C. A. M. J. J. & Punt, P. J., 1991, "Gene transfer systems and vector development for filamentous fungi," in: Applied Molecular Genetics of Fungi, J. F. Peberdy, et al., eds., p. 1-28, Cambridge University Press: Cambridge.

Alternatively, the CKSRPs of the invention can be expressed in insect cells using baculovirus expression vectors. Baculovirus vectors available for expression of polypeptides in cultured insect cells (e.g., Sf 9 cells) include the pAc series (Smith et al., 1983, Mol. Cell. Biol. 3:2156-2165) and the pVL series (Lucklow and Summers, 1989, Virology 170: 31-39).

In yet another embodiment, a CKSRP nucleic acid of the invention is ex-pressed in mammalian cells using a mammalian expression vector. Examples of mammalian expression vectors include pCDM8 (Seed, B., 1987, Nature 329:840) and pMT2PC (Kaufman et al., 1987, EMBO J. 6:187-195). When used in mammalian cells, the expression vector's control functions are often pro-vided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook, J., Fritsh, E. F., and Maniatis, T. Molecular Cloning: A Laboratory Manual. latest ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, Genes Dev. 1:268-277), lymphoid-specific promoters (Calame and Eaton, 1988, Adv. Immunol. 43.235-275), in particular promoters of T cell receptors (Winoto and Baltimore, 1989, EMBO J. 8:729-733), and immunoglobulins (Banerji et al., 1983, Cell 33:729-740; Queen and Baltimore, 1983, Cell 33:741-748), neuron-specific promoters (e.g., the neurofilament promoter; Byrne and Ruddle, 1989, PNAS 86:5473-5477), pancreas-specific promoters (Edlund et al., 1985, Science 230.912-916), and mammary gland-specific promoters (e.g., milk whey promoter; U.S. Pat. No. 4,873,316 and European Application Publication No. 264, 166). Developmentally-regulated promoters are also encompassed, for example, the murine hox promoters (Kessel and Gruss, 1990, Science 249:374-379) and the fetopolypeptide promoter (Campes and Tilghman, 1989, Genes Dev. 3:537-546).

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics or herbicides) is generally introduced into the host cells along with the gene of interest. Preferred selectable markers include those that confer resistance to drugs, such as G418, hygromycin, and methotrexate, or in plants that confer resistance towards an herbicide such as glyphosate, glufosinate, or imidazolinone. Nucleic acid molecules encoding a selectable marker can be introduced into a host cell on the same vector as that encoding a CKSRP or can be introduced on a separate vector. Cells stably transfected with the introduced nucleic acid molecule can be identified by, for example, herbicide selection (e.g., cells that have incorporated the selectable marker gene will survive, while the other cells die).

In a preferred embodiment of the present invention, the CKSRPs are ex-pressed in plants and plants cells such as unicellular plant cells (e.g. algae) (See Falciatore et al., 1999, Marine Biotechnology 1(3):239-251 and references therein) and plant cells from higher plants (e.g., the spermatophytes, such as crop plants). A CKSRP may be "introduced" into a plant cell by any means, including transfection, transformation or transduction, electroporation, particle bombardment, agroinfection, and the like. One transformation method known to those of skill in the art is the dipping of a flowering plant into an *Agrobacteria* solution, wherein the *Agrobacteria* contain the CKSRP nucleic acid, followed by breeding of the transformed gametes.

Other suitable methods for transforming or transfecting host cells including plant cells can be found in Sambrook, et al. supra, and other laboratory manuals such as Methods in Molecular Biology, 1995, Vol. 44, *Agrobacterium* protocols, ed: Gartland and Davey, Humana Press, Totowa, N.J. As biotic and abiotic stress tolerance is a general trait wished to be inherited into a wide variety of plants like maize, wheat, rye, oat, triticale, rice, barley, soybean, peanut, cotton, rapeseed and canola, *manihot*, pepper, sunflower and tagetes, solanaceous plants like potato, tobacco, eggplant, and tomato, *Vicia* species, pea, alfalfa, bushy plants (coffee, cacao, tea), *Salix* species, trees (oil palm, coconut), perennial grasses, and forage crops, these crop plants are also preferred target plants for a genetic engineering as one further embodiment of the present invention. Forage crops include, but are not limited to, Wheat-grass, Canarygrass, Bromegrass, Wildrye Grass, Bluegrass, Orchardgrass, Alfalfa, Salfoin, Birdsfoot Trefoil, Alsike Clover, Red Clover, and Sweet Clover.

In one embodiment of the present invention, transfection of a CKSRP into a plant is achieved by *Agrobacterium* mediated gene transfer. *Agrobacterium* mediated plant transformation can be performed using for example the GV3101 (pMP90) (Koncz and Schell, 1986, Mol. Gen. Cenet, 204.383-396) or LBA4404 (Clontech) *A. tumefaciens* strain. Transformation can be performed by standard transformation and regeneration techniques (Deblaere et al., 1994, Nucl. Acids. Res. 13:4777-4788; Gelvin, Stanton B. and Schilperoort, Robert A, Plant Molecular Biology Manual, 2$^{nd}$ Ed.—Dordrecht: Kluwer Academic Publ., 1995.—in Sect., Ringbuc Zentrale Signatur: BT11-P ISBN 0-7923-2731-4; Glick, Bernard R.; Thompson, John E., Methods in Plant Molecular Biology and Biotechnology, Boca Raton: CRC Press, 1993 360 S., ISBN 08493-5164-2). For example, rapeseed can be transformed via cotyledon or hypocotyl trans-formation (Moloney et al., 1989, Plant Cell Report 8:238-242; De Block et al., 1989, Plant Physiol. 91:694-701). Use of antibiotics for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., 1994, Plant Cell Report 13:282-285. Additionally, transformation of soybean can be performed using for example a technique described in European Patent No. 0424 047, U.S. Pat. No. 5,322,783, European Patent No. 0397 687, U.S. Pat. No. 5,376,543, or U.S. Pat. No. 5,169,770. Transformation of maize can be achieved by particle bombardment, polyethylene glycol mediated DNA uptake, or via the silicon carbide fiber technique. (See, for example, Freeling and Walbot "The maize handbook" Springer Verlag: New York (1993) ISBN 3-540-97826-7). A specific example of maize transformation is found in U.S. Patent No. 5,990,387, and a specific example of wheat transformation can be found in PCT Application No. WO 93/07256.

According to the present invention, the introduced CKSRP may be maintained in the plant cell stably if it is incorporated into a non-chromosomal autonomous replicon or integrated into the plant chromosomes. Alternatively, the introduced CKSRP may be present on an extra-chromosomal non-replicating vector and may be transiently expressed or transiently active.

In one embodiment, a homologous recombinant microorganism can be created wherein the CKSRP is integrated into a chromosome, a vector is prepared which contains at least a portion of a CKSRP gene into which a deletion, addition, or substitution has been introduced to thereby alter, e.g., functionally disrupt, the CKSRP gene. Preferably, the CKSRP gene is a *P. patens*, *S. napus*, *G. max*, or *O. sativa* CKSRP gene, but it can be a homolog from a related plant or even from a mammalian, yeast, or insect source. In one embodiment, the vector is designed such that, upon homologous recombination, the endogenous CKSRP gene is functionally disrupted (i.e., no longer encodes a functional polypeptide; also referred to as a knock-out vector). Alternatively, the vector can be designed such that, upon homologous recombination, the endogenous CKSRP gene is mutated or otherwise altered but still encodes a functional polypeptide (e.g., the upstream regulatory region can be altered to thereby alter the expression of the endogenous CKSRP). To create a point mutation via homologous recombination, DNA-RNA hybrids can be used in a technique known as chimeraplasty (Cole-Strauss et al., 1999, Nucleic Acids Research 27(5):1323-1330 and Kmiec, 1999, Gene Therapy American Scientist 87(3):240-247). Homologous recombination procedures in *P. patens* are also well known in the art and are contemplated for use herein.

Whereas in the homologous recombination vector, the altered portion of the CKSRP gene is flanked at its 5' and 3' ends by an additional nucleic acid molecule of the CKSRP gene to allow for homologous recombination to occur between the exogenous CKSRP gene carried by the vector and an endogenous CKSRP gene, in a microorganism or plant. The additional flanking CKSRP nucleic acid molecule is of sufficient length for successful homologous recombination with the endogenous gene. Typically, several hundreds of base pairs up to kilobases of flanking DNA (both at the 5' and 3' ends) are included in the vector (See e.g., Thomas, K. R., and Capecchil, M. R., 1987, Cell 51:503 for a description of homologous recombination vectors or Strepp et al., 1998, PNAS, 95(8):4368-4373 for cDNA based recombination in *P. patens*). The vector is introduced into a microorganism or plant cell (e.g., via polyethylene glycol mediated DNA), and cells in which the introduced CKSRP gene has homologously recombined with the endogenous CKSRP gene are selected using art-known techniques.

In another embodiment, recombinant microorganisms can be produced that contain selected systems that allow for regulated expression of the introduced gene. For example, inclusion of a CKSRP gene on a vector placing it under control of the lac operon permits expression of the CKSRP gene only in the presence of IPTG. Such regulatory systems are well known in the art.

Whether present in an extra-chromosomal non-replicating vector or a vector that is integrated into a chromosome, the CKSRP polynucleotide preferably resides in a plant expression cassette. A plant expression cassette preferably contains regulatory sequences capable of driving gene expression in plant cells that are operatively linked so that each sequence can fulfill its function, for example, termination of transcription by polyadenylation signals. Preferred polyadenylation signals are those originating from *A. tumefaciens* t-DNA such as the gene 3 known as octopine synthase of the Ti-plasmid pTiACH5 (Gielen et al., 1984, EMBO J. 3:835) or functional equivalents thereof, but also all other terminators functionally active in plants are suitable. As plant gene expression is very often not limited on transcriptional levels, a plant expression cassette preferably contains other operatively linked sequences like translational enhancers such as the overdrive-sequence containing the 5'-untranslated leader sequence from tobacco mosaic virus enhancing the polypeptide per RNA ratio (Gallie et al., 1987, Nucl. Acids Research 15:8693-8711). Examples of plant expression vectors include those detailed in: Becker, D., Kemper, E., Schell, J. and Masterson, R., 1992, New plant binary vectors with selectable markers located proximal to the left border, Plant Mol. Biol. 20: 1195-1197; and Bevan, M. W., 1984, Binary *Agrobacterium* vectors for plant transformation, Nucl. Acid. Res. 12:8711-8721; Vectors for Gene Transfer in Higher Plants; in: Transgenic Plants, Vol. 1, Engineering and Utilization, eds.: Kung and R. Wu, Academic Press, 1993, S. 15-38.

Plant gene expression should be operatively linked to an appropriate promoter conferring gene expression in a timely, cell specific, or tissue specific manner. Promoters useful in the expression cassettes of the invention include any promoter that is capable of initiating transcription in a plant cell. Such promoters include, but are not limited to, those that can be obtained from plants, plant viruses, and bacteria that contain genes that are expressed in plants, such as *Agrobacterium* and *Rhizobium*.

The promoter may be constitutive, inducible, developmental stage-preferred, cell type-preferred, tissue-preferred, or organ-preferred. Constitutive promoters are active under most conditions. Examples of constitutive promoters include the CaMV 19S and 35S promoters (Odell et al., 1985, Nature 313:810-812), the sX CaMV 35S promoter (Kay et al., 1987, Science 236:1299-1302) the Sep1 promoter, the rice actin promoter (McElroy et al., 1990, Plant Cell 2:163-171), the *Arabidopsis* actin promoter, the ubiquitan promoter (Christensen et al., 1989, Plant Molec. Biol. 18:675-689), pEmu (Last et al., 1991, Theor. Appl. Genet. 81:581-588), the figwort mosaic virus 35S promoter, the Smas promoter (Velten et al., 1984, EMBO J 3:2723-2730), the GRP1-8 promoter, the cinnamyl alcohol dehydrogenase promoter (U.S. Pat. No. 5,683,439), promoters from the T-DNA of *Agrobacterium*, such as manno-pine synthase, nopaline synthase, and octopine synthase, the small subunit of ribulose biphosphate carboxylase (ssuRUBISCO) promoter, and the like.

Inducible promoters are preferentially active under certain environmental conditions, such as the presence or absence of a nutrient or metabolite, heat or cold, light, pathogen attack, anaerobic conditions, and the like. For example, the hsp80 promoter from *Brassica* is induced by heat shock; the PPDK promoter is induced by light; the PR-1 promoter from tobacco, *Arabidopsis*, and maize are inducible by infection with a pathogen; and the Adh1 promoter is induced by hypoxia and cold stress. Plant gene expression can also be facilitated via an inducible promoter (For review, see Gatz, 1997, Annu. Rev. Plant Physiol. Plant Mol. Biol. 48:89-108). Chemically inducible promoters are especially suitable if gene expression is wanted to occur in a time specific manner. Examples of such promoters are a salicylic acid inducible promoter (PCT Application No. WO 95/19443), a tetracycline inducible promoter (Gatz et al., 1992, Plant J. 2:397-404), and an ethanol inducible promoter (PCT Application No. WO 93/21334).

In one preferred embodiment of the present invention, the inducible promoter is a stress-inducible promoter. For the purposes of the invention, stress inducible promoters are preferentially active under one or more of the following stresses: sub-optimal conditions associated with salinity, drought, temperature, metal, chemical, pathogenic, and oxidative stresses. Stress inducible promoters include, but are not limited to, Cor78 (Chak et al., 2000, Planta 210:875-883; Hovath et al., 1993, Plant Physiol. 103:1047-1053), Cor15a (Artus et al., 1996, PNAS 93(23):13404-09), Rci2A (Medina et al., 2001, Plant Physiol. 125:1655-66; Nylander et al., 2001, Plant Mol. Biol. 45:341-52; Navarre and Goffeau, 2000, EMBO J. 19:2515-24; Capel et al., 1997, Plant Physiol. 115: 569-76), Rd22 (Xiong et al., 2001, Plant Cell 13.2063-83; Abe et al., 1997, Plant Cell 9:1859-68; Iwasaki et al., 1995, Mol. Gen. Genet. 247:391-8), cDet6 (Lang and Palve, 1992, Plant Mol. Biol. 20.951-62), ADH1 (Hoeren et al., 1998, Genetics 149:479-90), KAT1 (Nakamura et al., 1995, Plant Physiol. 109:371-4), KST1 (Müller-Röber et al., 1995, EMBO 14:2409-16), Rhal (Terryn et al., 1993, Plant Cell 5:1761-9; Terryn et al., 1992, FEBS Lett. 299(3):287-90), ARSK1 (Atkinson et al., 1997, GenBank Accession # L22302, and PCT Application No. WO 97/20057), PtxA (Plesch et al., GenBank Accession # X67427), SbHRGP3 (Ahn et al, 1996, Plant Cell 8:1477-90), GH3 (Liu et al., 1994, Plant Cell 6:645-57), the pathogen inducible PRP1-gene promoter (Ward et al., 1993, Plant, Mol. Biol. 22:361-366), the heat inducible hsp80-promoter from tomato (U.S. Pat. No. 5,187, 267), cold inducible alpha-amylase promoter from potato (PCT Application No. WO 96/12814), or the wound-inducible pinil-promoter (European Patent No. 375091). For other examples of drought, cold, and salt-inducible promoters, such as the RD29A promoter, see Yamaguchi-Shinozalei et al., 1993, Mol. Gen. Genet. 236:331-340.

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, and leaf-preferred, stigma-preferred, pollen-preferred, anther-preferred, a petal-preferred, sepal-preferred, pedicel-preferred, silique-preferred, stem-preferred, root-preferred promoters, and the like. Seed preferred promoters are preferentially expressed during seed development and/or germination. For example, seed preferred promoters can be embryo-preferred, endosperm preferred, and seed coat-preferred. See Thompson et al., 1989, BioEssays 10:108. Examples of seed preferred promoters include, but are not limited to, cellulose synthase (celA), Cim1, gamma-zein, globulin-1, maize 19 kD zein (cZ19B1), and the like.

Other suitable tissue-preferred or organ-preferred promoters include the napin-gene promoter from rapeseed (U.S. Pat. No. 5,608,152), the USP-promoter from *Vicia faba* (Baeumlein et al., 1991, Mol. Gen. Genet. 225(3):459-67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980), or the legumin B4 promoter (LeB4; Baeumlein et al., 1992, Plant Journal, 2(2): 233-9), as well as promoters conferring seed specific expression in monocot plants like maize, barley, wheat, rye, rice, etc. Suitable promoters to note are the lpt2 or lpt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, *Sorghum* kasirin-gene, and rye secalin gene).

Other promoters useful in the expression cassettes of the invention include, but are not limited to, the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2, and bronze promoters, the Zm13 promoter (U.S. Pat. No. 5,086,169), the maize polygalacturonase promoters (PG) (U.S. Pat. Nos. 5,412,085 and 5,545,546), and the SGB6 promoter (U.S. Pat. No. 5,470,359), as well as synthetic or other natural promoters.

Additional flexibility in controlling heterologous gene expression in plants may be obtained by using DNA binding domains and response elements from heterologous sources (i.e., DNA binding domains from non-plant sources). An example of such a heterologous DNA binding domain is the LexA DNA binding domain (Brent and Ptashne, 1985, Cell 43:729-736).

The invention further provides a recombinant expression vector comprising a CKSRP DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to a CKSRP mRNA. Regulatory sequences operatively linked to a nucleic acid molecule cloned in the antisense orientation can be chosen which direct the continuous expression of the antisense RNA molecule in a variety of cell types. For instance, viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus wherein antisense nucleic acids are produced under the control of a high efficiency regulatory region. The activity of the regulatory region can be determined by the cell type, into which the vector is introduced. For a discussion of the regulation of gene expression using antisense genes, see Weintraub, H. et al., 1986, Antisense RNA as a molecular tool for genetic analysis, Reviews Trends in Genetics, Vol. 1(1), and Mol et al., 1990, FEBS Letters 268:427-430.

Another aspect of the invention pertains to host cells into which a recombinant expression vector of the invention has been introduced. The terms "host cell" and "recombinant host cell" are used interchangeably herein. It is under-stood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, a CKSRP can be expressed in bacterial cells such as *C. glutamicum*, insect cells, fungal cells, or mammalian cells (such as Chinese hamster ovary cells (CHO) or COS cells), algae, ciliates, plant cells, fungi, or other microorganisms like *C. glutamicum*. Other suitable host cells are known to those skilled in the art.

A host cell of the invention, such as a prokaryotic or eukaryotic host cell in culture, can be used to produce (i.e., express) a CKSRP. Accordingly, the invention further provides methods for producing CKSRPs using the host cells of the invention. In one embodiment, the method comprises culturing the host cell of invention (into which a recombinant expression vector encoding a CKSRP has been introduced, or into which genome has been introduced a gene encoding a wild-type or altered CKSRP) in a suitable medium until the CKSRP is produced. In another embodiment, the method further comprises isolating CKSRPs from the medium or the host cell.

Another aspect of the invention pertains to isolated CKSRPs, and biologically active portions thereof. An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of CKSRP in which the polypeptide is separated from some of the cellular components of the cells in which it is naturally or recombinantly produced. In one embodiment, the language "substantially free of cellular material" includes preparations of a CKSRP having less than about 30% (by dry weight) of non-CKSRP material (also referred to herein as a "contaminating polypeptide"), more preferably less than about 20% of non-CKSRP material, still more preferably less than about 10% of non-CKSRP material, and most preferably less than about 5% non-CKSRP material.

When the CKSRP or biologically active portion thereof is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of CKSRP in which the polypeptide is separated from chemical precursors or other chemicals that are involved in the syn-thesis of the polypeptide. In one embodiment, the language "substantially free of chemical precursors or other chemicals" includes preparations of a CKSRP having less than about 30% (by dry weight) of chemical precursors or non-CKSRP chemicals, more preferably less than about 20% chemical precursors or non-CKSRP chemicals, still more preferably less than about 10% chemical precursors or non-CKSRP chemicals, and most preferably less than about 5% chemical precursors or non-CKSRP chemicals. In preferred embodiments, isolated polypeptides, or biologically active portions thereof, lack contaminating polypeptides from the same organism from which the CKSRP is derived. Typically, such polypeptides are produced by recombinant expression of, for ex-ample, a *P. patens* or *B. napus* CKSRP in plants other than *P. patens* or *B. napus*, or microorganisms such as *C. glutamicum*, ciliates, algae, or fungi.

The nucleic acid molecules, polypeptides, polypeptide homologs, fusion polypeptides, primers, vectors, and host cells described herein can be used in one or more of the following methods: identification of *P. patens, S. cerevisiae* or *B. napus* and related organisms; mapping of genomes of organisms related to *P. patens*, S. cerevisiae or *B. napus*; identification and localization of *P. patens, S. cerevisiae* or *B. napus* sequences of interest; evolutionary studies; determination of CKSRP regions required for function; modulation of a CKSRP activity; modulation of the metabolism of one or more cell functions; modulation of the transmembrane transport of one or more compounds; modulation of stress resistance; and modulation of expression of CKSRP nucleic acids. In one embodiment of these methods, the CKSRP functions as an active potassium transport protein. In another embodiment of these methods, the CKSRP functions as a zinc transporter.

The moss *P. patens* is related to other mosses, such as *Ceratodon purpureus*, that are capable of growth in the absence of light. Mosses like *Ceratodon* and *Physcomitrella* share a high degree of sequence identity on the DNA sequence and polypeptide level allowing the use of heterologous screening of DNA molecules with probes evolving from other mosses or organisms, thus enabling the derivation of a consensus sequence suitable for heterologous screening or functional annotation and prediction of gene functions in third species. The ability to identify such functions can therefore have significant relevance, e.g., prediction of substrate specificity of enzymes. Further, these nucleic acid molecules may serve as reference points for the mapping of moss genomes, or of genomes of related organisms.

The CKSRP nucleic acid molecules of the invention have a variety of uses. Most importantly, the nucleic acid and amino acid sequences of the present invention can be used to transform plants, thereby inducing tolerance to stresses such as drought, high salinity, and cold. The present invention therefore provides a transgenic plant transformed by a CKSRP nucleic acid, wherein expression of the nucleic acid sequence in the plant results in increased tolerance to environmental stress as compared to a wild type variety of the plant. The transgenic plant can be a monocot or a dicot. The invention further provides that the transgenic plant can be selected from maize, wheat, rye, oat, triticale, rice, barley, soybean, peanut, cotton, rapeseed, canola, *manihot*, pepper, sunflower, tagetes, solanaceous plants, potato, tobacco, eggplant, tomato, *Vicia* species, pea, alfalfa, coffee, cacao, tea, *Salix* species, oil palm, coconut, perennial grass, and forage crops, for example.

Accordingly, the invention provides a method of producing a transgenic In particular, the present invention describes using the expression of PpCk-1, PpCK-2, PpCK-4, and PpPK-4 of *P. patens*; ScCK-1 of *S. cerevisiae*; and BnCK-1, BnCK-2, BnCK-3, BnCK-4, and BnCK-5 of *B. napus* to engineer drought-tolerant, salt-tolerant, and/or cold-tolerant plants. This strategy has herein been demonstrated for *A. thaliana*, Rapeseed/Canola, soybeans, corn, and wheat, but its application is not restricted to these plants. Accordingly, the invention provides a transgenic plant containing a CKSRP such as the PpCK-1 as defined in SEQ ID NO:4, PpCK-2 as defined in SEQ ID NO:6, PpCK-4 as de-fined in SEQ ID NO:2, PpPK-4 as defined in SEQ ID NO:8, ScCK-1 as defined in SEQ ID NO:10, BnCK-1 as defined in SEQ ID NO:12, BnCK-2 as defined in SEQ ID NO:14, BnCK-3 as defined in SEQ ID NO:16, BnCK-4 as defined in SEQ ID NO:18, and BnCK-5 as defined in SEQ ID NO:20, wherein the plant has an increased tolerance to an environmental stress selected from one or more of the group consisting of drought, increased salt, or decreased or increased temperature. In preferred embodiments, the environmental stress is drought or decreased temperature.

Plant with a CKSRP coding nucleic acid, wherein expression of the nucleic acid(s) in the plant results in increased tolerance to environmental stress as compared to a wild type variety of the plant comprising: (a) introducing into a plant cell an expression vector comprising a CKSRP nucleic acid, and (b) generating from the plant cell a transgenic plant with a increased tolerance to environmental stress as compared to a wild type variety of the plant. The plant cell includes, but is not limited to, a protoplast, gamete producing cell, and a cell that regenerates into a whole plant. As used herein, the term "transgenic" refers to any plant, plant cell, callus, plant tissue, or plant part, that contains all or part of at least one recombinant polynucleotide. In many cases, all or part of the recombinant polynucleotide is stably integrated into a chromosome or stable extra-chromosomal element, so that it is passed on to successive generations. In preferred embodiments, the CKSRP nucleic acid encodes a protein comprising the polypeptide of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20.

The present invention also provides a method of modulating a plant's tolerance to an environmental stress comprising, modifying the expression of a CKSRP coding nucleic acid in the plant. The plant's tolerance to the environ-mental stress can be increased or decreased as achieved by increasing or decreasing the expression of a CKSRP, respectively. Preferably, the plant's tolerance to the environmental stress is increased by increasing expression of a CKSRP. Expression of a CKSRP can be modified by any method known to those of skill in the art. The methods of increasing expression of CKSRPs can be used wherein the plant is either transgenic or not transgenic. In cases when the plant is transgenic, the plant can be transformed with a vector containing any of the above described CKSRP coding nucleic acids, or the plant can be transformed with a promoter that directs expression of native CKSRP in the plant, for example. The invention provides that such a promoter can be tissue preferred, developmentally regulated, stress inducible, or a combination thereof. Alternatively, non-transgenic plants can have native CKSRP expression modified by inducing a native promoter. The expression of PpCK-1 as defined in SEQ ID NO:4, PpCK-2 as defined in SEQ ID NO:6, PpCK-4 as defined in SEQ ID NO:2, PpPK-4 as defined in SEQ ID NO:8, ScCK-1 as defined in SEQ ID NO:10, BnCK-1 as defined in SEQ ID NO:12, BnCK-2 as defined in SEQ ID NO:14, BnCK-3 as defined in SEQ ID NO:16, BnCK-4 as defined in SEQ ID NO:18, or BnCK-5 as defined in SEQ ID NO:20 in target plants can be accomplished by, but is not limited to, one of the following examples: (a) constitutive promoter, (b) stress-inducible promoter, (c) chemical-induced promoter, and (d) engineered promoter overexpression with, for example, zinc-finger derived transcription factors (Greisman and Pabo, 1997, Science 275.657).

In a preferred embodiment, transcription of the CKSRP is modulated using zinc-finger derived transcription factors (ZFPs) as described in Greisman and Pabo, 1997, Science 275:657 and manufactured by Sangamo Biosciences, Inc. These ZFPs comprise both a DNA recognition domain and a functional domain that causes activation or repression of a target nucleic acid such as a CKSRP nucleic acid. Therefore, activating and repressing ZFPs can be created that specifically recognize the CKSRP promoters described above and used to increase or decrease CKSRP expression in a plant, thereby modulating the stress tolerance of the plant. The present invention also includes identification of the homologs of PpCK-1 as defined in SEQ ID NO:4, PpCK-2 as defined in SEQ ID NO:6, PpCK-4 as defined in SEQ ID NO:2, PpPK-4 as defined in SEQ ID NO:8, ScCK-1 as defined in SEQ ID NO:10, BnCK-1 as defined in SEQ ID NO:12, BnCK-2 as defined in SEQ ID NO:14, BnCK-3 as defined in SEQ ID NO:16, BnCK-4 as defined in SEQ ID NO:18, and BnCK-5 as defined in SEQ ID NO:20 in a target plant, as well as the homolog's promoter. The invention also provides a method of increasing expression of a gene of interest within a host cell as compared to a wild type variety of the host cell, wherein the gene of interest is transcribed in response to a CKSRP, comprising. (a) transforming the host cell with an expression vector comprising a CKSRP coding nucleic acid, and (b) ex-pressing the CKSRP within the host cell, thereby increasing the expression of the gene transcribed in response to the CKSRP, as compared to a wild type variety of the host cell.

In addition to introducing the CKSRP nucleic acid sequences into transgenic plants, these sequences can also be used to identify an organism as being *P. patens, B. napus, S. cerevisiae*, or a close relative thereof. Also, they may be used to identify the presence of *P. patens, B. napus, S. cerevisiae*, or a relative thereof in a mixed population of microorganisms. The invention provides the nucleic acid sequences of a number of *P. patens, S. napus*, and *S. cerevisiae* genes; by probing the extracted genomic DNA of a culture of a unique or mixed population of microorganisms under stringent conditions with a probe spanning a region of a *P. patens, B. napus*, or *S. cerevisiae* gene that is unique to this organism, one can ascertain whether this organism is present.

Further, the nucleic acid and polypeptide molecules of the invention may serve as markers for specific regions of the genome. This has utility not only in the mapping of the genome, but also in functional studies of *P. patens, B. napus*, or *S. cerevisiae* polypeptides. For example, to identify the region of the genome to which a particular *P. patens* DNA-binding polypeptide binds, the *P. patens* genome could be digested, and the fragments incubated with the DNA-binding polypeptide. Those fragments that bind the polypeptide may be additionally probed with the nucleic acid molecules of the invention, preferably with readily detectable labels. Binding of such a nucleic acid molecule to the genome fragment enables the localization of the fragment to the genome map of *P. patens*, and, when performed multiple times with different enzymes, facilitates a rapid determination of the nucleic acid sequence to which the poly-peptide binds. Further, the nucleic acid molecules of the invention may be sufficiently identical to the sequences of related species such that these nucleic acid molecules may serve as markers for the construction of a genomic map in related mosses.

The CKSRP nucleic acid molecules of the invention are also useful for evolutionary and polypeptide structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed.

Similarly, such a comparison permits an assessment of which regions of the sequence are conserved and which are not, which may aid in determining those regions of the polypeptide that are essential for the functioning of the enzyme. This type of determination is of value for polypeptide engineering studies and may give an indication of what the polypeptide can tolerate in terms of mutagenesis without losing function.

Manipulation of the CKSRP nucleic acid molecules of the invention may result in the production of CKSRPs having functional differences from the wild-type CKSRPs. These polypeptides may be improved in efficiency or activity, may be present in greater numbers in the cell than is usual, or may be decreased in efficiency or activity.

There are a number of mechanisms by which the alteration of a CKSRP of the invention may directly affect stress response and/or stress tolerance. In the case of plants expressing CKSRPs, increased transport can lead to improved salt and/or solute partitioning within the plant tissue and organs. By either increasing the number or the activity of transporter molecules that export ionic molecules from the cell, it may be possible to affect the salt tolerance of the cell.

The effect of the genetic modification in plants, *C. glutamicum*, fungi, algae, or ciliates on stress tolerance can be assessed by growing the modified microorganism or plant under less than suitable conditions and then analyzing the growth characteristics and/or metabolism of the plant. Such analysis techniques are well known to one skilled in the art, and include dry weight, wet weight, polypeptide synthesis, carbohydrate synthesis, lipid synthesis, evapotranspiration rates, general plant and/or crop yield, flowering, reproduction, seed setting, root growth, respiration rates, photosynthesis rates, etc. (Applications of HPLC in Biochemistry in: Laboratory Techniques in Biochemistry and Molecular Biology, vol. 17; Rehm et al., 1993 Biotechnology, vol. 3, Chapter III: Product recovery and purification, page 469-714, VCH: Weinheim; Belter, P. A. et al., 1988, Bioseparations: downstream processing for biotechnology, John Wiley and Sons; Kennedy, J. F. and Cabral, J. M. S., 1992, Recovery processes for biological materials, John Wiley and Sons; Shaeiwitz, J. A. and Henry, J. D., 1988, Biochemical separations, in: Ulmann's Encyclopedia of Industrial Chemistry, vol. B3, Chapter 11, page 1-27, VCH: Weinheim; and Dechow, F J., 1989, Separation and purification techniques in biotechnology, Noyes Publications).

For example, yeast expression vectors comprising the nucleic acids disclosed herein, or fragments thereof, can be constructed and transformed into *S. cerevisiae* using standard protocols. The resulting transgenic cells can then be assayed for fail or alteration of their tolerance to drought, salt, and temperature stresses. Similarly, plant expression vectors comprising the nucleic acids disclosed herein, or fragments thereof, can be constructed and transformed into an appropriate plant cell such as *Arabidopsis*, soy, rape, maize, wheat, *Medicago truncatula*, etc., using standard protocols. The resulting transgenic cells and/or plants derived there from can then be assayed for fail or alteration of their tolerance to drought, salt, and temperature stresses. The engineering of one or more CKSRP genes of the invention may also result in CKSRPs having altered activities, which indirectly impact the stress response and/or stress tolerance of algae, plants, ciliates, or fungi, or other microorganisms like *C. glutamicum*. For example, the normal biochemical processes of metabolism result in the production of a variety of products (e.g., hydrogen peroxide and other reactive oxygen species), which may actively interfere with these same metabolic processes. For example, peroxynitrite is known to nitrate tyrosine side chains, thereby inactivating some enzymes having tyrosine in the active site (Groves, J. T., 1999, Curr. Opin. Chem. Biol. 3(2):226-235). While these products are typically excreted, cells can be genetically altered to transport more products than is typical for a wild-type cell. By optimizing the activity of one or more CKSRPs of the invention that are involved in the export of specific molecules, such as salt molecules, it may be possible to improve the stress tolerance of the cell.

Additionally, the sequences disclosed herein, or fragments thereof can be used to generate knockout mutations in the genomes of various organisms, such as bacteria, mammalian cells, yeast cells, and plant cells (Girke, T., 1998, The Plant Journal 15:39-48). The resultant knockout cells can then be evaluated for their ability or capacity to tolerate various stress conditions, their response to various stress conditions, and the effect on the phenotype and/or genotype of the mutation. For other methods of gene inactivation, see U.S. Pat. No. 6,004,804 "Non-Chimeric Mutational Vectors" and Puttaraju et al., 1999, Spliceosome-mediated RNA trans-splicing as a tool for gene therapy, Nature Biotechnology 17:246-252.

The aforementioned mutagenesis strategies for CKSRPs resulting in increased stress resistance are not meant to be limiting; variations on these strategies will be readily apparent to one skilled in the art. Using such strategies, and incorporating the mechanisms disclosed herein, the nucleic acid and polypeptide molecules of the invention may be utilized to generate algae, ciliates, plants, fungi, or other microorganisms like *C. glutamicum* expressing mutated CKSRP nucleic acid and polypeptide molecules such that the stress tolerance is improved.

The present invention also provides antibodies that specifically bind to a CKSRP, or a portion thereof, as encoded by a nucleic acid described herein. Antibodies can be made by many well-known methods (See, e.g., Harlow and Lane, "Antibodies; A Laboratory Manual," Cold Spring Harbor Laboratory, Cold Spring Harbor, N.Y., (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. (See, for example, Kelly et al., 1992, Bio/Technology 10:163-167; Bebbington et al., 1992, Bio/Technology 10: 169-175).

The phrases "selectively binds" and "specifically binds" with the polypeptide refer to a binding reaction that is determinative of the presence of the polypeptide in a heterogeneous population of polypeptides and other biologics. Thus, under designated immunoassay conditions, the specified antibodies bound to a particular polypeptide do not bind in a significant amount to other polypeptides present in the sample. Selective binding of an antibody under such conditions may require an antibody that is selected for its specificity for a particular polypeptide. A variety of immunoassay formats may be used to select antibodies that selectively bind with a particular polypeptide. For example, solid-phase ELISA immunoassays are routinely used to select antibodies selectively immunoreactive with a polypeptide. See Harlow and Lane, "Antibodies, A Laboratory Manual" Cold Spring Harbor Publications, New York, (1988), for a description of immunoassay formats and conditions that could be used to determine selective binding.

In some instances, it is desirable to prepare monoclonal antibodies from various hosts. A description of techniques for preparing such monoclonal antibodies may be found in Sites et al., eds., "Basic and Clinical Immunology," (Lange Medical Publications, Los Altos, Calif., Fourth Edition) and references cited therein, and in Harlow and Lane, supra.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Growth of P. patens cultures. For this study, plants of the species P. patens (Hedw.) B. S. G. from the collection of the genetic studies section of the University of Hamburg were used. They originate from the strain 16/14 collected by H. L. K. Whitehouse in Gransden Wood, Huntingdonshire (England), which was subcultured from a spore by Engel (1968, Am. J. Bot. 55, 438-446). Proliferation of the plants was carried out by means of spores and by means of regeneration of the gametophytes. The protonema developed from the haploid spore as a chloroplast-rich chloronema and chloroplast-low caulonema, on which buds formed after approximately 12 days. These grew to give gameto-phores bearing antheridia and archegonia. After fertilization, the diploid sporophyte with a short seta and the spore capsule resulted, in which the meiospores matured.

Culturing was carried out in a climatic chamber at an air temperature of 25° C. and light intensity of 55 micromols $m^{-2}$ $s^{-1}$ (white light; Philips TL 65W/25 fluorescent tube) and a light/dark change of 16/8 hours. The moss was either modified in liquid culture using Knop medium according to Reski and Abel (1985, Planta 165:354-358) or cultured on Knop solid medium using 1% oxoid agar (Unipath, Basingstoke, England). The protonemas used for RNA and DNA isolation were cultured in aerated liquid cultures. The protonemas were comminuted every 9 days and transferred to fresh culture medium.

Example 2

Total DNA isolation from plants. The details for the isolation of total DNA relate to the working up of one gram fresh weight of plant material. The materials used include the following buffers: CTAB buffer: 2% (w/v) N-cethyl-N,N,N-trimethylammonium bromide (CTAB); 100 mM Tris HCl pH 8.0; 1.4 M NaCl; 20 mM EDTA; N-Laurylsarcosine buffer: 10% (w/v) N-laurylsarcosine; 100 mM Tris HCl pH 8.0; and 20 mM EDTA.

The plant material was triturated under liquid nitrogen in a mortar to give a fine powder and transferred to 2 ml Eppendorf vessels. The frozen plant material was then covered with a layer of 1 ml of decomposition buffer (1 ml CTAB buffer, 100 µl of N-laurylsarcosine buffer, 20 µl of β-mercaptoethanol, and 10 µl of proteinase K solution, 10 mg/ml) and incubated at 60° C. for one hour with continuous shaking. The homogenate obtained was distributed into two Eppendorf vessels (2 ml) and extracted twice by shaking with the same volume of chloroform/isoamyl alcohol (24:1). For phase separation, centrifugation was carried out at 8000×g and room temperature for 15 minutes in each case. The DNA was then precipitated at −70° C. for 30 minutes using ice-cold isopropanol. The precipitated DNA was sedimented at 4° C. and 10,000 g for 30 minutes and resuspended in 180 µl of TE buffer (Sambrook et al., supra. For further purification, the DNA was treated with NaCl (1.2 M final concentration) and precipitated again at −70° C. for 30 minutes using twice the volume of absolute ethanol. After a washing step with 70% ethanol, the DNA was dried and subsequently taken up in 50 µl of $H_2O$+RNAse (50 mg/ml final concentration) The DNA was dissolved overnight at 4° C., and the RNAse digestion was subsequently carried out at 37° C. for 1 hour. Storage of the DNA took place at 4° C.

Example 3 isolation of total RNA and poly-(A)+ RNA and cDNA library construction from P. patens. For the investigation of transcripts, both total RNA and poly-(A)+ RNA were isolated. The total RNA was obtained from wild-type 9 day old protonemata following the GTC-method (Reski et al., 1994, Mol. Gen. Genet., 244:352-359). The Poly(A)+ RNA was isolated using Dyna Beadso (Dynal, Oslo, Norway) following the instructions of the manufacturer's protocol. After determination of the concentration of the RNA or of the poly(A)+ RNA, the RNA was precipitated by addition of 1/10 volumes of 3 M sodium acetate pH 4.6 and 2 volumes of ethanol and stored at −70° C.

For cDNA library construction, first strand synthesis was achieved using Murine Leukemia Virus reverse transcriptase (Roche, Mannheim, Germany) and oligo-d(T)-primers, second strand synthesis by incubation with DNA polymerase 1, Klenow enzyme and RNAseH digestion at 12° C. (2 hours), 16° C. (1 hour), and 22° C. (1 hour). The reaction was stopped by incubation at 65° C. (I 0 minutes) and subsequently transferred to ice, Double stranded DNA molecules were blunted by T4-DNA-polymerase (Roche, Mannheim) at 37° C. (30 minutes). Nucleotides were removed by phenol/chloroform extraction and Sephadex G50 spin columns. EcoRI adapters (Pharmacia, Freiburg, Germany) were ligated to the cDNA ends by T4-DNA-ligase (Roche, 12° C., overnight) and phosphorylated by incubation with polynucleotide kinase (Roche, 37° C., 30 minutes). This mixture was subjected to separation on a low melting agarose gel, DNA molecules larger than 300 base pairs were eluted from the gel, phenol extracted, concentrated on Elutip-D-columns (Schleicher and Schuell, Dassel, Germany), and were ligated to vector arms and packed into lambda ZAPII phages or lambda ZAP-Express phages using the Gigapack Gold Kit (Stratagene, Amsterdam, Netherlands) using material and following the instructions of the manufacturer.

Example 4

Sequencing and function annotation of P. patens ESTs. cDNA libraries as described in Example 3 were used for DNA sequencing according to standard methods, and in particular, by the chain termination method using the ABI PRISM Big Dye Terminator Cycle Sequencing Ready Reaction Kit (Perkin-Elmer, Weiterstadt, Germany). Random sequencing was carried out subsequent to preparative plasmid recovery from cDNA libraries via in vivo mass excision, retransformation, and subsequent plating of DH10B on agar plates (material and protocol details from Stratagene, Amsterdam, Netherlands). Plasmid DNA was prepared from overnight grown *E. coli* cultures grown in Luria-Broth medium containing ampicillin (See Sambrook et al., supra, on a Qiagene DNA preparation robot (Qiagen, Hilden) according to the manufacturer's protocols. Sequencing primers with the following nucleotide sequences were used:

```
5'-CAGGAAACAGCTATGACC-3'     SEQ ID NO: 21
5'-CTAAAGGGAACAAAAGCTG-3'    SEQ ID NO: 22
5'-TGTAAAACGACGGCCAGT-3'     SEQ ID NO: 23
```

Sequences were processed and annotated using the software package EST-MAX commercially provided by Bio-Max (Munich, Germany). The program incorporates practically all bioinformatics methods important for functional and structural characterization of protein sequences. The most important algorithms incorporated in EST-MAX are: FASTA (Very sensitive sequence database searches with estimates of statistical significance; Pearson W. R., 1990, Rapid and sensitive sequence comparison with FASTP and FASTA. Methods Enzymol. 183:63-98); BLAST (Very sensitive sequence database searches with estimates of statistical significance. Altschul S. F. et al., Basic local alignment search tool, Journal of Molecular Biology 215:403-10); PREDATOR (High-accuracy secondary structure prediction from single and multiple sequences. Frishman, D. and Argos, P., 1997, 75% accuracy in protein secondary structure prediction. Proteins, 27:329-335); CLUSTALW: Multiple sequence alignment. Thompson, J. D. et al., 1994, CLUSTAL W (improving the sensitivity of progressive multiple sequence alignment through sequence weighting, positions-specific gap penalties and weight matrix choice, Nucleic Acids Research, 22:4673-4680); TMAP (Transmembrane region prediction from multiply aligned sequences. Persson, B. and Argos, P., 1994, Prediction of transmembrane segments in proteins utilizing multiple sequence alignments. J. Mol. Biol. 237:182-192); ALOM2 (Transmembrane region prediction from single sequences. Klein, P. et al., Prediction of protein function from sequence properties. A discriminate analysis of a database. Biochim. Biophys. Acta 787:221-226 (1984). Version 2 by Dr. K. Nakai); PROSEARCH (Detection of PROSITE protein sequence patterns. Kolan kowski L. F. Jr., Leunissen J. A. M., Smith J. E., 1992, ProSearch: fast searching of protein sequences with regular expression patterns related to protein structure and function. Biotechniques 13, 919-921); BLIMPS (Similarity searches against a database of ungapped blocks, J. C. Wallace and Henikoff S., 1992); PATMAT (a searching and extraction program for sequence, pattern and block queries and databases, CABIOS 8:249-254. Written by Bill Alford).

Example 5

Identification of *P. patens* ORFs corresponding to PpCK-7, PpCK-2, PpCK-4, and PpPK-4. The *P. patens* partial cDNAs (ESTs) for partial PpCK-1, PpCK-2, PpCK-4, and PpPK-4 were identified in the *P. patens* EST sequencing program using the program EST-MAX through BLAST analysis. These particular clones, which were found to encode Protein Kinases, were chosen for further analyses.

TABLE 2

Degree of Amino Acid Identity and Similarity of PpCK-1 and Other Kinases (Pairwise Comparison was used: gap penalty: 10; gap extension penalty: 0.1; score matrix: blosum62)

| | Swiss-Prot # | | | | |
|---|---|---|---|---|---|
| | Q8LR51 | T04265 | Q8VYK9 | B84577 | H96751 |
| Polypeptide name | Putative Casein Kinase I- | Probable Kasein Kinase | Putatitive Col-0 Casein Kinase I | Probable Casein Kinase I | Probable Casein Kinase I |
| Species | *O. sativa* | *A. thaliana* | *A. thaliana* | *A. thaliana* | *A. thaliana* |
| Identity % | 32.9 | 34.3 | 34.3 | 34.4 | 31.4 |
| Similarity % | 42.4 | 43.2 | 43.2 | 43.9 | 40.9 |

TABLE 3

Degree of Amino Acid Identity and Similarity of PpCK-2 and Other Kinases (Pairwise Comparison was used: gap penalty: 10; gap extension penalty: 0.1; score matrix: blosum62)

| | Swiss-Prot # | | | | |
|---|---|---|---|---|---|
| | Q8LR51 | T04265 | QBVYK9 | Q8S1A8 | H96751 |
| Polypeptide name | Putative Casein Kinase I- | Probable Kasein Kinase | Putatitive Col-0 Casein Kinase I | Putative Casein Kinase | Probable Casein Kinase I |
| Species | *O. sativa* | *A. thaliana* | *A. thaliana* | *O. sativa* | *A. thaliana* |
| Identity % | 67.6 | 63.9 | 63.9 | 61.7 | 64.3 |
| Similarity % | 76.6 | 73.3 | 73.3 | 71.0 | 73.8 |

TABLE 4

Degree of Amino Acid Identity and Similarity of PpCK-4 and Other Kinases (Pairwise Comparison was used: gap penalty: 10; gap extension penalty: 0.1; score matrix: blosum62)

| | Swiss-Prot # | | | | |
|---|---|---|---|---|---|
| | Q8LR51 | T04265 | Q8S1A8 | Q8VYK9 | H96751 |
| Polypeptide name | Putative Casein Kinase I- | Probable Kasein Kinase | Putative Casein Kinase | Putatitive Col-0 Casein Kinase I | Probable Casein Kinase I |
| Species | *O. sativa* | *A. thaliana* | *O. sativa* | *A. thaliana* | *A. thaliana* |
| Identity % | 62.8 | 62.1 | 59.4 | 62.1 | 62.6 |
| Similarity % | 72.9 | 71.7 | 68.3 | 71.7 | 71.5 |

TABLE 5

Degree of Amino Acid Identity and Similarity of PpPK-4 and Other Kinases (Pairwise Comparison was used: gap penalty: 10; gap extension penalty: 0.1; score matrix: blosum62)

| | Swiss-Prot # | | | | |
|---|---|---|---|---|---|
| | Q9SZI1 | Q9ZUP4 | P42158 | Q39050 | Q9LW62 |
| Polypeptide name | COL-0 Casein Kinase I-Like Protein | Putative Casein Kinase I | Casein Kinase I, Delta Isoform Like | Casein Kinase I | Casein Kinase |
| Species | *A. thaliana* | *A. thaliana* | *A. thaliana* | *A. thaliana* | *A. thaliana* |
| Identity % | 35% | 35% | 37% | 35% | 35% |
| Similarity % | 46% | 44% | 47% | 45% | 44% |

Example 6

Cloning of the full-length *P. patens* cDNA encoding for PpCK-1, PpCK-2, PpCK-4, and PpPK-4. To isolate the clones encoding PpCK-1 (SEQ ID NO:3), PpCK-2 (SEQ ID NO:5), PpCK-4 (SEQ ID NO:1), and PpPK-4 (SEQ ID NO:7) from *P. patens*, cDNA libraries were created with SMART RACE cDNA Amplification kit (Clontech Laboratories) following the manufacturer's instructions. Total RNA isolated as described in Example 3 was used as the template. The cultures were treated prior to RNA isolation as follows. Salt Stress; 2, 6, 12, 24, 48 hours with 1-M NaCl-supplemented medium; Cold Stress: 4° C. for the same time points as for salt; Drought Stress: cultures were incubated on dry filter paper for the same time points as for salt.

5' RACE Protocol. The EST sequences of PpCK-1, PpCK-2, PpCK-4, and PpPK-4 identified from the database search as described in Example 5 were used to design oligos for RACE (See Table 6). The extended sequence for these genes were obtained by performing Rapid Amplification of cDNA Ends polymerase chain reaction (RACE PCR) using the Advantage 2 PCR kit (Clontech Laboratories) and the SMART RACE cDNA amplification kit (Clontech Laboratories) using a Biometra T3 Thermocycler following the manufacturer's instructions. The sequences obtained from the RACE reactions corresponded to full-length coding region of PpCK-1, PpCK-2, PpCK-4, and PpPK-4 were used to design oligos for full-length cloning of the respective gene (See below Full-Length Amplification).

Full-length Amplification. Full-length clones corresponding to PpCK-1, PpCK-2, and PpCK-4 were obtained by performing polymerase chain reaction (PCR) with gene-specific primers (See Table 6) and the original EST as the tem-plate. The conditions for the reaction were standard conditions with PWO DNA polymerase (Roche). PCR was performed according to standard conditions and to manufacturer's protocols (Sambrook et al., supra, Biometra T3 Thermocycler). The parameters for the reaction were: five minutes at 94° C. followed by five cycles of one minute at 94° C., one minute at 50° C., and 1.5 minutes at 72° C. This was followed by 25 cycles of one minute at 94° C., one minute at 65° C., and 1.5 minutes at 72° C.

Full-length clones for PpPK-4 (SEQ ID NO:7) were isolated by repeating the RACE method but using the gene-specific primers as given in Table 6. The amplified fragments were extracted from agarose gel with a QIAquick Gel Extraction Kit (Qiagen) and ligated into the TOPO pCR 2.1 vector (Invitrogen) following manufacturer's instructions. Recombinant vectors were transformed into Top10 cells (Invitrogen) using standard conditions (Sambrook et al., supra. Transformed cells were selected for on LB agar containing 100 mg/ml carbenicillin, 0.8 mg X-gal (5-bromo-4-chloro-3-indolyl-β-D-galactoside), and 0.8 mg IPTG (isopropylthio-b-D-galactoside) grown overnight at 37° C. White colonies were selected and used to inoculate 3 ml of liquid LB containing 100 mg/ml ampicillin and grown overnight at 37® C. Plasmid DNA was extracted using the QIAprep Spin Miniprep Kit (Qiagen) following manufacturer's instructions. Analyses of subsequent clones and restriction mapping was performed according to standard molecular biology techniques (Sam brook et al., supra.

TABLE 6

Scheme and primers used for cloning of full-length clones

| Gene | Final product Sites | Isolation Method | Primers Race | Primers RT-PCR |
|------|---------------------|------------------|--------------|----------------|
| PpCK-1 | XmaI/ HpaI | 5' RACE and RT-PCR for Full-length clone | NVT: (SEQ ID NQ: 24) CGACCGCAGCCCAT GAGGAAGTTAT | RC614: (SEQ ID NO: 25) ATCCCGGGCTCACG- TAGTGCACTGAACTC TGTC RC615: (SEQ ID NO: 26) GCGTTAACATGCCCA TCTTCTCATACTCA GACC |
| PpCK-2 | XmaI/ HpaI | 5' RACE and RT-PCR for Full-length clone | NVT: (SEQ ID NO: 27) CTCGCCTAC- CAAGCCCCATTA- GAAA | RC1012: (SEQ ID NO: 28) ATCCCGGGTTGTCGA GGACGGAGAGAGAA- GAG RC1015: (SEQ ID NO: 29) GCGTTAACCTTAG- GAATCGTATGGCA- GAGAGCT |
| PpCK-4 | XmaI/ HpaI | 5' RACE and RT-PCR for Full-length clone | NVT: (SEQ ID NO: 44) GCCTGCCTAGCCCC ATCAAGAAATT | RC598: (SEQ ID NO: 45) ATCCCGGGCGCAG- CATGTGACTCGTCAC CTG RC599: (SEQ ID NO: 46) GCGTTAACAGCTAC- TACTTGCTCTAG- GAAGCTG |

TABLE 6-continued

Scheme and primers used for cloning of full-length clones

| Gene | Final product Sites | Isolation Method | Primers Race | Primers RT-PCR |
|---|---|---|---|---|
| PpPK-4 | XmaI/ EcoRV | 5' RACE and RT-PCR for Full-length clone | RC072: 5'TGTGTCTACGTGT CGCGGGGTCGAT3' (SEQ ID NO: 30) | RC133N: 5'ATCCCGGGAGGCA TTGAAC- TACCTGGAGTGAG3' (SEQ ID NO: 31) RC134N: 5'GCGATATCGTTGAA CTAG- TAATCTGTGTTAACT T3' (SEQ ID NO: 32) |

Example 7

Identification of S. cerevisiae ORF corresponding to ScCK-1. The ORF 760 gene from S. cerevisiae, encoding a casein kinase 1, was first de-scribed in European Patent Application No. 03022225.1 by Metanomics, Inc. filed Sep. 30, 2003. The Metanomics patent application is hereby incorporated by reference in its entirety. The ORF 760 gene was isolated using the standard protocol of Pfu DNA polymerase or a Pfu|Taq DNA polymerase mix (Herculase) for the amplification procedure. Amplified ORF fragments were analyzed by gel electrophoresis. Each primer consists of a universal 5' end and ORF specific 3' end whereby the universal sequences differ for the forward and reverse primers (Forward primer sequence contained an EcoRI for yeast or SmaI for E. coli and the reverse primer sequence a SmaI for yease or SacI for E. coli) allowing a unidirectional cloning. PCR reactions for the amplification included: 1×PCR buffer, 0.2 mM dNTP, 100 ng S. cerevisiae genomic DNA (S288C) or 60 ng genomic DNA Escherichia coli K-12 (MC1-655), 25 µmol reverse primer, 2.5 u Pfu or Herculase DNA polymerase. The conditions consisted of: 1 cycle for 3' at 94° C.; followed by 25 cycles of 30" at 94° C., 30" at 55° C., and 5-6' at 72° C.; followed by 1 cycle for 610' at 72° C., then at 4° C. indefinitely. The forward sequence for ScCK-1 (ORF 760) is 5'-GGAATTCCAGCT-GACCACCATGTCCCAACGATCTTCACAACAC-3' (SEQ ID NO:33). The reverse sequence for ScCK-1 (ORF 760) is 5'-GATCCCCGGGAATTGCCATGT-CAAAAAAAAAAAGGAAAAA GAGAAAAG-3' (SEQ ID NO:34).

Example 8

Identification of B. nappus ORFs corresponding to BnCK-1, BnCK-2, BnCK-3, BnCK-4, and BnCK-5: Tissue harvest, RNA isolation, and cDNA library construction. Canola plants were grown under a variety of conditions and treatments, and different tissues were harvested at various developmental stages. Plant growth and harvesting were done in a strategic manner such that the probability of harvesting all expressable genes in at least one or more of the resulting libraries is maximized. The mRNA was isolated as de-scribed in Example 3 from each of the collected samples, and cDNA libraries were constructed. No amplification steps were used in the library production process in order to minimize redundancy of genes within the sample and to retain expression information. All libraries were 3' generated from mRNA purified on oligo dT columns. Colonies from the transformation of the cDNA library into E. coli were randomly picked and placed into microtiter plates.

Probe Hybridization. Plasmid DNA was isolated from the E. Coli colonies and then spotted on membranes. A battery of 288 $^{33}$P radiolabeled 7-mer oligonucleotides were sequentially hybridized to these membranes. To increase throughput, duplicate membranes were processed. After each hybridization, a blot image was captured during a phosphorimage scan to generate a hybridization profile for each oligonucleotide. This raw data image was automatically transferred via LIMS to a computer. Absolute identity was maintained by bar-coding for the image cassette, filter, and orientation within the cassette. The filters were then treated using relatively mild conditions to strip the bound probes and returned to the hybridization chambers for another round of hybridization. The hybridization and imaging cycle was repeated until the set of 288 oligomers was completed.

After completion of the hybridizations, a profile was generated for each spot (representing a cDNA insert), as to which of the 288 $^{33}$P radiolabeled 7-mer oligonucleotides bound to that particular spot (cDNA insert), and to what degree. This profile is defined as the signature generated from that clone. Each clone's signature was compared with all other signatures generated from the same organism to identify clusters of related signatures. This process "sorts" all of the clones from an organism into clusters before sequencing.

Gene Isolation. The clones were sorted into various clusters based on their having identical or similar hybridization signatures. A cluster should be indicative of the expression of an individual gene or gene family. A by-product of this analysis is an expression profile for the abundance of each gene in a particular library. One-path sequencing from the 5' end was used to predict the function of the particular clones by similarity and motif searches in sequence databases.

The full-length DNA sequence of the S. cerevisiae ScCK-1 (SEQ ID NO:9) was blasted against proprietary contig databases of canola at E value of E-10. (Altschul, Stephen et al., Gapped BLAST and PSI_BLAST: a new generation of protein database search program, Nucleic Acids Res. 25: 3389-3402). All the contig hits were analyzed for the putative full-length sequences, and the longest clones representing the putative full-length contigs were fully sequenced. Five such contigs isolated from the proprietary contig databases are BnCK-1, BnCK-2, BnCK-3, BnCK-4, and BnCK-5. The homology of the BnCK-1, BnCK-2, BnCK-3, BnCK-4, and BnCK-5 amino acid sequences to the closest known prior art is indicated in Tables 8-12.

TABLE 8

Degree of Amino Acid Identity and Similarity of BnCK-1 and a Similar Protein (Pairwise Comparison was used: gap penalty: 10; gap extension penalty: 0.1; score matrix: blosum62)

| Gene Name | Public Database Sequence | Protein Name | Species | Sequence Identity (%) | Sequence Similarity (%) |
|---|---|---|---|---|---|
| BnCK-1 | Q93Z18 | Ser/Thr protein kinase | A. thaliana | 53.9 | 65.1 |

TABLE 9

Degree of Amino Acid Identity and Similarity of BnCK-2 and a Similar Protein (Pairwise Comparison was used: gap penalty: 10; gap extension penalty: 0.1; score matrix: blosum62)

| Gene Name | Public Database Sequence | Protein Name | Species | Sequence Identity (%) | Sequence Similarity (%) |
|---|---|---|---|---|---|
| BnCK-2 | NP_680447 | Putative casein kinase | A. thaliana | 91.3 | 94.7 |

TABLE 10

Degree of Amino Acid Identity and Similarity of BnCK-3 and a Similar Protein (Pairwise Comparison was used: gap penalty: 10; gap extension penalty: 0.1; score matrix: blosum62)

| Gene Name | Public Database Sequence | Protein Name | Species | Sequence Identity (%) | Sequence Similarity (%) |
|---|---|---|---|---|---|
| BnCK-3 | NP_567812 | Putative casein kinase | A. thaliana | 92.5 | 95.6 |

TABLE 11

Degree of Amino Acid Identity and Similarity of BnCK-4 and a Similar Protein (Pairwise Comparison was used: gap penalty: 10; gap extension penalty: 0.1; score matrix: blosum62)

| Gene Name | Public Database Sequence | Protein Name | Species | Sequence Identity (%) | Sequence Similarity (%) |
|---|---|---|---|---|---|
| BnCK-4 | Q9SE85 | Casein kinase I like protein | Brassica oleracea | 91.2 | 91.4 |

TABLE 12

Degree of Amino Acid Identity and Similarity of BnCK-5 and a Similar Protein (Pairwise Comparison was used: gap penalty: 10; gap extension penalty: 0.1; score matrix: blosum62)

| Gene Name | Public Database Sequence | Protein Name | Species | Sequence Identity (%) | Sequence Similarity (%) |
|---|---|---|---|---|---|
| BnCK-5 | NP_197320 | Protein kinase family protein | A. thaliana | 70.2 | 73.5 |

Example 9

Engineering stress-tolerant *Arabidopsis* plants by overexpressing the genes PpCK-1, PpCK-2, PpCK-4, PpPK-4, ScCK-1, BnCK-1, BnCK-2, BnCK-3, BnCK-4, and BnCK-5: Binary vector construction: DBPS-JH001. The plasmid construct pLMNC53 (Mankin, 2000, Ph.D. thesis, University of North Carolina) was digested with HindIII (Roche) and blunt-end filled with Klenow enzyme and 0.1 mM dNTPs according to manufacturer's instructions. This fragment was purified by agarose gel and extracted via the QIAquick Gel Extraction kit (Qiagen) according to manufacturer's instructions. The purified fragment was then digested with EcoRI (Roche), purified by agarose gel, and extracted via the QIAquick Gel Extraction kit (Qiagen) according to manufacturer's instructions. The resulting 1.4 kilobase fragment, the gentamycin cassette, included the nos promoter, aaccI gene, and the g7 terminator.

The vector pBlueScript was digested with EcoRI and SmaI (Roche) according to manufacturer's instructions, and the resulting fragment was extracted from agarose gel with a QIAquick Gel Extraction Kit (Qiagen) according to manufacturer's instructions. The digested pBlueScript vector and the gentamycin cassette fragments were ligated with T4 DNA Ligase (Roche) according to manufacturer's instructions, joining the two respective EcoRI sites and joining the blunt-ended HindIII site with the SmaI site.

The recombinant vector (pGMBS) was transformed into Top10 cells (Invitrogen) using standard conditions. Transformed cells were selected for on LB agar containing 100 μg/ml carbenicillin, 0.8 mg X-gal (5-bromo-4-chloro-3-indolyi-β-D-galactoside) and 0.8 mg IPTG (isopropylthio-β-D-galactoside), grown overnight at 37° C. White colonies were selected and used to inoculate 3 ml of liquid LB containing 100 μg/ml ampicillin and grown overnight at 37° C. Plasmid DNA was extracted using the QIAprep Spin Mini-prep Kit (Qiagen) following manufacturer's instructions. Analyses of subsequent clones and restriction mapping were performed according to standard molecular biology techniques (Sambrook et al., supra.

Both the pGMBS vector and p1bxSuperGUS vector were digested with XbaI and KpnI (Roche) according to manufacturer's instructions, excising the gentamycin cassette from pGMBS and producing the backbone from the p1bxSuperGUS vector. The resulting fragments were extracted from agarose gel with a QIAquick Gel Extraction Kit (Qiagen) according to manufacturer's instructions. These two fragments were ligated with T4 DNA ligase (Roche) according to manufacturer's instructions.

The resulting recombinant vector (pBPS-JH001) was transformed into Top10 cells (Invitrogen) using standard conditions. Transformed cells were selected for on LB agar containing 100 μg/ml carbenicillin, 0.8 mg X-gal (5-bromo-4-chloro-3-indolyl-β-D-galactoside) and 0.8 mg IPTG (isopropylthio-β-D-galactoside), grown overnight at 37° C. White colonies were selected and used to inoculate 3 ml of liquid LB containing 100 μg/ml ampicillin and grown overnight at 37° C. Plasmid DNA was extracted using the QIAprep Spin Mini-prep Kit (Qiagen) following manufacturer's instructions. Analyses of subsequent clones and restriction mapping were performed according to standard molecular biology techniques (Sambrook et al., supra.

Subcloning of PpCK-1, PpCK-2, PpCK-4, PDPK-4, ScCK-1, BnCK-1 BnCK-2, BnCK-3, BnCK-4, and BnCK-5 into the binary vector. The fragments containing the different *P. patens* casein kinases were excised from the recombinant PCR2.1 TOPO vectors by double digestion with restriction enzymes (See Table 13) according to manufacturer's instructions. The subsequent fragments were excised from agarose gel with a QIAquick Gel Extraction Kit (Qiagen) according to manufacturer's instructions, ligated into binary vectors, cleaved with appropriate enzymes (See Table 13), and dephosphorylated prior to ligation. The resulting recombinant vectors contained the corresponding casein kinase in the sense orientation under the control of the constitutive super-promoter.

TABLE 13

Listed are the names of the constructs of the
P. patens casein kinases used for plant transformation.

| Gene | Enzymes used to generate gene fragment | Enzymes used to restrict binary vector | Recombinant binary vector construct |
|------|----------------------------------------|----------------------------------------|-------------------------------------|
| PpCK-1 | XmaI/HpaI | XmaI/Ecl136 | pBPS-SY012 |
| PpCK-2 | XmaI/HpaI | XmaI/Ecl136 | pBPS-JYW034 |
| PpCK-4 | XmaI/HpaI | XmaI/Ecl136 | pBPS-SY018 |
| PpPK-4 | Xma/EcoRV | XmaI/Ecl136 | pBPS-LVM015 |

Subcloning of ScCK-1 into the binary vector. The ScCK-1 gene was sub-cloned into a binary vector containing the bar gene driven by the masi promoter on its T-DNA (Velten et al., 1984, EMBO J. 3: 2723-2730; Mengiste, et al., 1997, Plant J., 12: 945-948). The T-DNA contained a constitutive promoter in front of a cloning cassette which was followed by the nos terminator (Depicker et al., J. Mol. Appl. Gen. 1(6):561-573). The cloning cassette consisted of the sequence: 5'-GGAAT-TCCAGCTGACCACCATGGCAATTCCCGGGGATC-3' (SEQ ID NO:37). Other selection systems and promoters are known in the art and are similarly capable of use in the present invention (e.g. AHAS marker, ubiquitin promoter (Callis et al., J. Biol. Chem., 1990, 265:12486-12493; U.S. Pat. Nos. 5,510,474; 6,020,190; Kawalleck et al., 1993, Plant Mol. Biol. 21:673-684), 34S promoter (GenBank Accession Numbers M59930 and X16673).

The binary vector and the ORF 760 gene (100 nu) were digested with EcoRI and SmaI using the standard protocol provided by the supplier (MBI Fermentas, Germany). The ORF 760 gene was purified using a Qiagen column (Qiagen, Hilden, Germany), and was ligated with the restriction digested binary vector (30 ng) using standard procedures (Maniatis et al.). Agrobacterium Transformation. The recombinant vectors were transformed into A. tumefaciens C58C1 and PMP90 according to standard conditions (Hoefgen and Willmitzer, 1990; Koncz and Schell, 1986, Mol. Gen. Genet. 204:383-396).

Plant Transformation. A. thaliana ecotype C24 were grown and trans-formed according to standard conditions (Bechtold, 1993, Acad. Sci. Paris. 316:1194-1199; Bent et al., 1994, Science 265:1856-1860).

Screening of Transformed Plants Comprising Physcomitrella Genes. T1 seeds were sterilized according to standard protocols (Xiong et al., 1999, Plant Molecular Biology Reporter 17: 159-170). Seeds were selected on Y2 Murashige and Skoog media (MS) (Sigma-Aldrich), 0.6% agar and supplemented with 1% sucrose, and 2 µg/ml benomyl (Sigma-Aldrich). Seeds on plates were vernalized for four days at 4° C. The seeds were germinated in a climatic chamber at an air temperature of 22° C. and light intensity of 40 micromols $m^{-2} s^{-1}$ (white light; Philips TL 65W/25 fluorescent tube) and 16 hours light and 8 hours dark day length cycle. Transformed seedlings were selected after 14 days and transferred to ½ MS media supplemented with 0.6% agar, 1% sucrose, and allowed to recover for five to seven days.

Drought Tolerance Screening of Transformed Plants Comprising Physcomitrella Genes. T1 seedlings were transferred to dry, sterile filter paper in a petri dish and allowed to desiccate for two hours at 80% RH (relative humidity) in a Sanyo Growth Cabinet MLR-350H, micromols $m^{-2} s^{-1}$ (white light; Philips TL 65W/25 fluorescent tube). The RH was then decreased to 60%, and the seed-lings were desiccated further for eight hours. Seedlings were then removed and placed on ½ MS 0.6% agar plates supplemented with 2 µg/ml benomyl (Sigma-Aldrich) and scored after five days. The transgenic plants were then screened for their improved drought tolerance.

Under drought stress conditions, PpCK-1-overexpressing A. thaliana plants showed a 50% survival rate to the drought stress (5 survivors from 10 stressed plants), PpCK-2-overexpressing A. thaliana plants showed a 52% survival rate to the drought stress (16 survivors from 31 stressed plants), and PpCK-4-overexpression A. thaliana plants showed a 14% survival rate to the drought stress (1 survivors from 7 stressed plants), as compared to the 11% survival rate that was demonstrated by the untransformed control plants (1 survivor from 9 stressed plants).

Transgenic Arabidopsis plants comprising the ScCK-1 gene were screened for their tolerance to drought in three separate experiments. In the first experiment, the plants were subjected to a period of twelve days of drought conditions. After the twelve days, the transgenic plants were screened for their improved drought tolerance. Transgenic plants containing the ScCK-1 transgene (11 plants) retained viability, as shown by their turgid appearance and maintenance of green color, for an average of 2.2 days beyond the untransformed wild type control plant.

In the second experiment, one plant from several independent transgenic lines was used. Three-week-old transgenic plants containing the ScCK-1 transgene were subjected to drought stress conditions. Transgenic plants containing the ScCK-1 transgene (6 plants) retained viability, as shown by their turgid appearance and maintenance of green color, for an average of 0.3 days beyond the untransformed wild type control plant.

In the third experiment, several plants from one independent transgenic line were used. Three-week-old transgenic plants containing the ScCK-1 transgene were subjected to drought stress conditions. The results are shown in Table 14. Transgenic plants containing the ScCK-1 transgene retained a significantly higher photosynthetic yield than the untransformed wild type control plant, For ScCK-1, the average result of 5 replicate plants is listed; for the wild type plants, the average result of 20-25 plants is listed.

TABLE 14

|  | Photosynthetic yield (6 days after final watering) | Photosynthetic yield (10 days after final watering) | Photosynthetic yield (14 days after final watering) |
|---|---|---|---|
| ScCK-1 | 767 | 780 | 147 |
| Wild type | 757 | 610 | 16 |

Freezing Tolerance Screening of Transformed Plants Comprising Physcomitrella Genes. Seedlings were moved to petri dishes containing 2 MS 0.6% agar supplemented with 2% sucrose and 2 µg/ml benomyl. After four days, the seedlings were incubated at 4° C. for 1 hour and then covered with shaved ice, The seedlings were then placed in an Environmental Specialist ES2000 Environmental Chamber and incubated for 3.5 hours beginning at −1.0° C., and de-creasing −1° C. each hour. The seedlings were then incubated at −5.0° C. for 24 hours and then allowed to thaw at 5° C. for 12 hours. The water was poured off, and the seedlings were scored after 5 days.

The transgenic plants are screened for their improved cold tolerance, demonstrating that transgene expression confers cold tolerance. Under freezing stress conditions, PpCK-1-overexpressing *A. thaliana* plants showed a 100% survival rate to the freeze stress (14 survivors from 14 stressed plants), as compared to the 2% survival rate that was demonstrated by the untransformed control plants (1 survivor from 48 stressed plants).

Salt Tolerance Screening. Seedlings are transferred to filter paper soaked in ½ MS and placed on ½ MS 0.6% agar supplemented with 2 µg/ml benomyl the night before the salt tolerance screening. For the salt tolerance screening, the filter paper with the seedlings was moved to stacks of sterile filter paper, soaked in 50 mM NaCl, in a petri dish. After two hours, the filter paper with the seedlings was moved to stacks of sterile filter paper, soaked with 200 mM NaCl, in a petri dish. After two hours, the filter paper with the seedlings was moved to stacks of sterile filter paper, soaked in 600 mM NaCl, in a petri dish. After 10 hours, the seedlings were moved to petri dishes containing 2 MS 0.6% agar supplemented with 2 µg/ml benomyl. The seedlings were scored after 5 days.

Transgenic plants overexpressing the transgene are screened for their improved salt tolerance demonstrating that transgene expression confers salt tolerance. Under freezing stress conditions, PpCK-1-overexpressing *A. thaliana* plants showed a 0% survival rate to the freeze stress (0 survivors from 20 stressed plants), PpCK-2-overexpressing *A. thaliana* plants showed a 10% survival rate to the freeze stress (1 survivors from 10 stressed plants), and PpCK-4-overexpressing *A. thaliana* plants showed a 0% survival rate to the freeze stress (0 survivors from 6 stressed plants), as compared to the 13% survival rate that was demonstrated by the untransformed control plants (3 survivor from 23 stressed plants).

Growth screen under water-limited conditions. The PpCK-1, PpCK-2, PpCK-4, and PpPK-4 genes were overexpressed in *A. thaliana* under the control of a constitutive promoter. The transgenic lines were assayed for water use efficiency (WUE), and some of the lines were also assayed for biomass after drought cycling (FIG. 8). SC024 represents the empty vector control, and BPS C24 represents the *Arabidopsis* ecotype used for transformation. DW indicates dry weight, and E denotes plant water use. The letters under the Assay column represent independent experiments.

With a constitutive promoter driving expression and for the transgenic lines assayed, EST 289 (PpCK-4) transgenic lines had significant increases in dry weight. EST 142 (PpPK-4) transgenic lines had significant increases in WUE and biomass under drought cycling conditions. EST194 (PpCK-1) had a significant increase in biomass under drought cycling conditions. For all of the transgenes, the mean versus both of the controls for each parameter was increased, 5-8% for WUE, 11-19% for DW, and 6-9% for E. The variation in phenotype from gene to gene may be explained by variation in the level of trans-gene expression and the site of transgene insertion. A unique letter was assigned to each independent assay.

TABLE 15

ScCK-1 (ORF 760) was overexpressed in *A. thaliana* under the control of a constitutive promoter.

| Line | Experiment | Average # days transgenic/WT |
|---|---|---|
| 760-3 | 1 | 0.75 |
|  | 2 | 0.33 |
| 760-4 | 1 | 0.5 |
|  | 2 | 2.2 |
|  | 3 | 1.053 |
| Mean |  | 0.97 |

The transgenic lines were assayed for dessication tolerance, measuring the average number of days of survival after the wild type control was dead.

Example 10

Detection of the Transgenes in the Transgenic *Arabidopsis* Lines, To check for the presence of the transgenes in transgenic *Arabidopsis* lines, PCR was performed on genomic DNA which contaminates the RNA samples taken as exemplified below. Two and one half microliters of the RNA sample was used in a 50 µl PCR reaction using Taq DNA polymerase (Roche Molecular Biochemicals) according to the manufacturer's instructions.

Binary vector plasmid with each gene cloned in was used as positive control, and the wild-type C24 genomic DNA was used as negative control in the PCR reactions. Ten µl of the PCR reaction was analyzed on 0.8% agarose-ethidium bromide gel.

PpCK-1: The primers used in the reactions are:

GCTGACACGCCAAGCCTCGCTAGTC         (SEQ ID NO: 38)

GCGTTAACATGCCCATCTTCTCATACTCAGACC (SEQ ID NO: 39)

The PCR program was as following: 30 cycles of 1 minute at 94° C., 1 minute at 62° C. and 4 minutes at 72° C., followed by 10 minutes at 72° C. A 1.7 kb fragment was produced from the positive control and the transgenic plants.

PpCK-2: The primers used in the reactions are:

GCTGACACGCCAAGCCTCGCTAGTC         (SEQ ID NO: 40)

GCGTTAACCTTAGGAATCGTATGGCAGAGAGCT (SEQ ID NO: 41)

The PCR program was as following: 30 cycles of 1 minute at 94° C., 1 minute at 62° C. and 4 minutes at 72° C., followed by 10 minutes at 72° C. A 1.9 kb fragment was produced from the positive control and the transgenic plants.

PpPK-4: The primers used in the reactions were:

(SEQ ID NO: 42)
5'ATCCCGGGAGGCATTGAACTACCTGGAGTGAG3'

(SEQ ID NO: 43)
5'GCGATATCGTTGAACTAGTAATCTGTGTTAACTTTATC3'

The PCR program was as following: 30 cycles of 1 minute at 94° C., 1 minute at 62° C., and 4 minutes at 72° C., followed by 10 minutes at 72° C. A 1.7 kilo-base fragment was produced from the positive control and the transgenic plants.

The transgenes were successfully amplified from the T1 transgenic lines, but not from the wild type C24. This result indicates that the T1 transgenic plants contain at least one copy of the transgenes. There was no indication of existence of either identical or very similar genes in the untransformed *A. thaliana* control, which could be amplified by this method from the wild-type plants.

Example 11

Engineering stress-tolerant soybean plants by over-expressing the PpCK-1, PpCK-2, PpCK-4, PpPK-4, ScCK-1, BnCK-7, BnCK-2, BnCK-3, BnCK-4, or BnCK-5 gene. Seeds of soybean are surface sterilized with 70% ethanol for 4 minutes at room temperature with continuous shaking, followed by 20% (v/v) Clorox supplemented with 0.05% (v/v) Tween for 20 minutes with continuous shaking. Then, the seeds are rinsed 4 times with distilled water and placed on moistened sterile filter paper in a Petri dish at room temperature for 6 to 39 hours. The seed coats are peeled off, and cotyledons are detached from the embryo axis. The embryo axis is examined to make sure that the meristematic region is not damaged. The excised embryo axes are collected in a half-open sterile Petri dish and air-dried to a moisture content less than 20% (fresh weight) in a sealed Petri dish until further use.

*A. tumefaciens* culture is prepared from a single colony in LB solid medium plus appropriate selection agents followed by growth of the single colony in liquid LB medium to an optical density at 600 nm of 0.8. Then, the bacteria culture is pelleted at 7000 rpm for 7 minutes at room temperature, and resuspended in MS (Murashige and Skoog, 1962) medium supplemented with 100 μM acetosyringone. Bacteria cultures are incubated in this pre-induction medium for 2 hours at room temperature before use. The axis of soybean zygotic seed embryos at approximately 15% moisture content are imbibed for 2 hours at room temperature with the pre-induced *Agrobacterium* suspension culture. The embryos are removed from the imbibition culture and are transferred to Petri dishes containing solid MS medium supplemented with 2% sucrose and incubated for 2 days in the dark at room temperature. Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/L carbenicillin or 300 mg/L cefotaxime to kill the *Agrobacteria*. The liquid medium is used to moisten the sterile filter paper. The embryos are incubated during 4 weeks at 25° C., under 150 μmol m$^{-2}$sec$^{-1}$ and 12 hours photoperiod. Once the seedlings produce roots, they are transferred to sterile metromix soil. The medium of the in vitro plants is washed off before transferring the plants to soil. The plants are kept under a plastic cover for 1 week to favor the acclimatization process. Then the plants are transferred to a growth room where they are incubated at 25° C., under 150 μmol m$^{-2}$sec$^{-1}$ light intensity and 12 hours photoperiod for about 80 days. The transgenic plants are screened for their improved drought, salt, and/or cold tolerance according to the screening method described in Example 9, demonstrating that transgene expression confers stress tolerance and/or increased water use efficiency.

Example 12

Engineering stress-tolerant Rapeseed/Canola plants by over-expressing the PpCK-1, PpCK-2, PpCK-4, PpPK-4, ScCK-1, BnCK-1, BnCK-2, BnCK-3, SnCK-4, or BnCK-5 gene. The method of plant transformation described herein is also applicable to *Brassica* and other crops. Seeds of canola are surface sterilized with 70% ethanol for 4 minutes at room temperature with continuous shaking, followed by 20% (v/v) Clorox supplemented with 0.05% (v/v) Tween for 20 minutes, at room temperature with continuous shaking. Then, the seeds are rinsed 4 times with distilled water and placed on moistened sterile filter paper in a Petri dish at room temperature for 18 hours. Then the seed coats are removed, and the seeds are air dried overnight in a half-open sterile Petri dish, During this period, the seeds lose approximately 85% of their water content. The seeds are then stored at room temperature in a sealed Petri dish until further use. DNA constructs and embryo imbibition are as described in Example 10. Samples of the primary transgenic plants (T0) are analyzed by PCR to confirm the presence of T-DNA. These results are confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer.

The transgenic plants are screened for their improved stress tolerance according to the screening method described in Example 9, demonstrating that transgene expression confers stress tolerance and/or increased water use efficiency.

Example 13

Engineering stress-tolerant corn plants by over-expressing the PpCK-1, PpCK-2, PpCK-4, PpPK-4, ScCK-1, BnCK-7, BnCK-2, BnCK-3, BnCK-4, or BnCK-5 gene. Transformation of maize (*Zea Mays* L.) with the gene of interest is performed with the method described by Ishida et al., 1996, Nature Biotech. 14745-50. Immature embryos are co-cultivated with *Agrobacterium tumefaciens* that carry "super binary" vectors, and transgenic plants are recovered through organogenesis. This procedure provides a transformation efficiency of between 2.5% and 20%. The transgenic plants are screened for their improved drought, salt, and/or cold tolerance according to the screening method described in Example 9, demonstrating that transgene expression confers stress tolerance and/or increased water use efficiency.

Example 14

Engineering stress-tolerant wheat plants by over-expressing the PpCK-1, PpCK-2, PpCK-4, PpPK-4, ScCK-1, BnCK-1, BnCK-2, BnCK-3, BnCK-4, or BnCK-5 gene. Transformation of wheat with the gene of interest is performed with the method described by Ishida et al., 1996, Nature Biotech. 14745-50. Immature embryos are co-cultivated with *Agrobacterium tumefaciens* that carry "super binary" vectors, and transgenic plants are recovered through organogenesis. This procedure provides a transformation efficiency between 2.5% and 20%. The transgenic plants are screened for their improved stress tolerance according to the screening method described in Example 9, demonstrating that transgene expression confers stress tolerance and/or increased water use efficiency.

Example 15

Identification of Homologous and Heterologous Genes. Gene sequences can be used to identify homologous or heterologous genes from cDNA or genomic libraries. Homologous genes (e.g. full-length cDNA clones) can be isolated via nucleic acid hybridization using for example cDNA libraries. Depending on the abundance of the gene of interest, 100,000 up to 1,000,000 recombinant bacteriophages are plated and transferred to nylon membranes. After denaturation with alkali, DNA is immobilized on the membrane by, e.g., UV cross linking. Hybridization is carried out at high stringency conditions. In aqueous solution, hybridization and washing is performed at an ionic strength of 1 M NaCl and a temperature of 68° C. Hybridization probes are generated by, e.g., radioactive ($^{32}$P) nick transcription labeling (High Prime, Roche, Mannheim, Germany). Signals are detected by autoradiography.

Partially homologous or heterologous genes that are related but not identical can be identified in a manner analogous to the above-described procedure using low stringency hybridization and washing conditions. For aqueous hybridization, the ionic strength is normally kept at 1 M NaCl while the temperature is progressively lowered from 68 to 42° C.

Isolation of gene sequences with homologies (or sequence identity/similarity) only in a distinct domain of (for example 10-20 amino acids) can be carried out by using synthetic radio labeled oligonucleotide probes. Radiolabeled oligonucleotides are prepared by phosphorylation of the 5-prime end of two complementary oligonucleotides with T4 polynucleotide kinase. The complementary oligonucleotides are annealed and ligated to form concatemers. The double stranded concatemers are then radiolabeled by, for ex-ample, nick transcription. Hybridization is normally performed at low stringency conditions using high oligonucleotide concentrations.

Oligonucleotide hybridization solution:
6×SSC
0.01 M sodium phosphate
1 mM EDTA (pH 8)
0.5% SDS
100 µg/ml denatured salmon sperm DNA
0.1% nonfat dried milk During hybridization, the temperature is lowered stepwise to 5-10° C. below the estimated oligonucleotide $T_m$, or down to room temperature, followed by washing steps and autoradiography. Washing is performed with low stringency, such as 3 washing steps using 4×SSC. Further details are described by Sambrook, J. et al., supra, or Ausubel, F. M. et al., 1994, "Current Protocols in Molecular Biology", John Wiley & Sons.

Example 16

Identification of Homologous Genes by Screening Expression Libraries with Antibodies. c-DNA clones can be used to produce recombinant protein for example in *E. coli* (e.g. Qiagen QIAexpress pQE system). Recombinant proteins are then normally affinity purified via Ni-NTA affinity chromatography (Qiagen). Recombinant proteins are then used to produce specific anti-bodies for example by using standard techniques for rabbit immunization. Antibodies are affinity purified using a Ni-NTA column saturated with the recombinant antigen as described by Gu et al., 1994, BioTechniques 17:257-262. The antibody can be used to screen expression cDNA libraries to identify homologous or heterologous genes via an immunological screening (Sambrook, J. et al., supra or Ausubel, F. M. et al., supra.

Example 17

In vivo Mutagenesis. In vivo mutagenesis of microorganisms can be performed by passage of plasmid (or other vector) DNA through *E. coli* or other microorganisms (e.g. *Bacillus* spp. or yeasts such as *S. cerevisiae*), which are impaired in their capabilities to maintain the integrity of their genetic information. Typical mutator strains have mutations in the genes for the DNA repair system (e.g., mutHLS, mutD, mutT ietc.; for reference, see Rupp, W. D., 1996, DNA repair mechanisms, in: *Escherichia coli* and *Salmonella*, p. 2277-2294, ASM: Washington.) Such strains are well known to those skilled in the art. The use of such strains is illustrated, for example, in Greener, A. and Callahan, M., 1994, Strategies 7:32-34. Transfer of mutated DNA molecules into plants is preferably done after selection and testing in microorganisms. Transgenic plants are generated according to various examples within the exemplification of this document.

Example 18

In vitro Analysis of the Function of *Physcomitrella* Genes in Transgenic Organisms. The determination of activities and kinetic parameters of enzymes is well established in the art. Experiments to determine the activity of any given altered enzyme must be tailored to the specific activity of the wild-type enzyme, which is well within the ability of one skilled in the art. Overviews about enzymes in general, as well as specific details concerning structure, kinetics, principles, methods, applications, and examples for the determination of many enzyme activities may be found, for example, in the following references: Dixon, M., and Webb, E. C., 1979, Enzymes. Longmans: London; Fersht, 1985, Enzyme Structure and Mechanism. Freeman: New York; Walsh, 1979, Enzymatic Reaction Mechanisms. Freeman: San Francisco; Price, N. C., Stevens, L., 1982, Fundamentals of Enzymology. Oxford Univ. Press: Oxford; Boyer, P. D., ed., 1983, The Enzymes, 3rd ed. Academic Press: New York; Bisswanger, H., 1994, Enzymkinetik, $2^{nd}$ ed. VCH: Weinheim (ISBN 3527300325); Bergmeyer, H. U., Bergmeyer, J., Graol, M., eds., 1983-1986, Methods of Enzymatic Analysis, $3^{rd}$ ed., vol. I-XII, Verlag Chemie: Weinheim; and Ullmann's Encyclopedia of Industrial Chemistry, 1987, vol. A9, Enzymes. VCH: Weinheim, p. 352-363.

The activity of proteins, which bind to DNA, can be measured by several well-established methods, such as DNA band-shift assays (also called gel retardation assays). The effect of such proteins on the expression of other molecules can be measured using reporter gene assays (such as that described in Kolmar, H. et al., 1995, EMBO J. 14: 3895-3904 and references cited therein). Reporter gene test systems are well known and established for applications in both pro- and eukaryotic cells, using enzymes such as β-galactosidase, green fluorescent protein, and several others.

The determination of activity of membrane-transport proteins can be per-formed according to techniques such as those described in Gennis, R. B., 1989, Pores, Channels and Transporters, in Biomembranes, Molecular Structure and Function, pp. 85-137, 199-234 and 270-322, Springer: Heidelberg.

Example 19

Purification of the Desired Product from Transformed Organisms. Recovery of the desired product from plant material (i.e., *P. patens* or *A. thaliana*), fungi, algae, ciliates, *C. glutamicum* cells, or other bacterial cells transformed with the nucleic acid sequences described herein, or the supernatant of the above-described cultures can be performed by various methods well known in the art. If the desired product is not secreted from the cells, the cells can be harvested from the culture by low-speed centrifugation, and the cells can be lysed by standard techniques, such as mechanical force or sonification. Organs of plants can be separated mechanically from other tissue or organs. Following homogenization, cellular debris is removed by centrifugation, and the supernatant fraction containing the soluble proteins is retained for further purification of the desired compound. If the product is secreted from desired cells, then the cells are removed from the culture by low-speed centrifugation, and the supernate fraction is retained for further purification.

The supernatant fraction from either purification method is subjected to chromatography with a suitable resin, in which the desired molecule is either retained on a chromatography resin while many of the impurities in the sample are not, or where the impurities are retained by the resin, while the sample is not. Such chromatography steps may be repeated as necessary, using the same or different chromatography resins. One skilled in the art would be well-versed in the selection of appropriate chromatography resins and in their most efficacious application for a particular molecule to be purified. The purified product may be concentrated by filtration or ultrafiltration, and stored at a temperature at which the stability of the product is maximized.

There is a wide array of purification methods known to the art and the preceding method of purification is not meant to be limiting. Such purification techniques are described, for example, in Bailey, J. E. & Ollis, 1986, D. F. Bio-chemical Engineering Fundamentals, McGraw-Hill: New York. Additionally, the identity and purity of the isolated compounds may be assessed by techniques standard in the art. These include high-performance liquid chromatography (HPLC), spectroscopic methods, staining methods, thin layer chromatography, NIRS, enzymatic assay, or microbiologically. Such analysis methods are reviewed in: Patek et al., 1994, Appl. Environ. Microbiol. 60:133-140; Malakhova et al., 1996, Biotekhnologiya 11:27-32; and Schmidt et al., 1998, Bioprocess Engineer. 19:67-70; Ulmann's Encyclopedia of Industrial Chemistry, 1996, vol. A27, VCH: Weinheim, p. 89-90, p. 521-540, p. 540-547, pX 559-566, 575-581, and p. 581-587; Michal, C., 1999, Biochemical Pathways: An Atlas of Biochemistry and Molecular Biology, John Wiley and Sons; Fallon, A. et al., 1987, Applications of HPLC in Biochemistry in: Laboratory Techniques in Bio-chemistry and Molecular Biology, vol. 17.

The invention claimed is:

1. An isolated polynucleotide having a sequence selected from the group consisting of:
   a) a polynucleotide sequence comprising nucleotides 1 to 1999 of SEQ ID NO:56; and
   b) a polynucleotide encoding the polypeptide sequence comprising amino acids 1 to 472 of SEQ ID NO:57.

2. The polynucleotide of claim 1, having the sequence comprising nucleotides 1 to 1999 of SEQ ID NO:56.

3. The polynucleotide of claim 1, encoding the polypeptide having the sequence comprising amino acids 1 to 472 of SEQ ID NO:57.

* * * * *